United States Patent
Kehler et al.

(10) Patent No.: US 10,034,861 B2
(45) Date of Patent: Jul. 31, 2018

(54) 1H-PYRAZOLO[4,3-B]PYRIDINES AS PDE1 INHIBITORS

(71) Applicant: H. Lundbeck A/S, Valby (DK)

(72) Inventors: Jan Kehler, Valby (DK); Karsten Juhl, Valby (DK); Mauro Marigo, Valby (DK); Paulo Jorge Vieira Vital, Valby (DK); Mikkel Jessing, Valby (DK); Morten Langgård, Valby (DK); Lars Kyhn Rasmussen, Valby (DK); Carl Martin Sebastian Clementson, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 15/637,920

(22) Filed: Jun. 29, 2017

(65) Prior Publication Data

US 2018/0000786 A1    Jan. 4, 2018

(30) Foreign Application Priority Data

Jul. 4, 2016 (DK) ................................ 2016 00397
Oct. 11, 2016 (DK) ................................ 2016 00612
Apr. 4, 2017 (DK) ................................ 2017 00236

(51) Int. Cl.
| | |
|---|---|
| *C07D 401/14* | (2006.01) |
| *A61K 31/437* | (2006.01) |
| *A61K 31/4162* | (2006.01) |
| *A61K 31/4745* | (2006.01) |
| *C07D 413/04* | (2006.01) |
| *C07D 471/04* | (2006.01) |
| *C07D 305/06* | (2006.01) |
| *C07D 401/04* | (2006.01) |

(52) U.S. Cl.
CPC ...... *A61K 31/4162* (2013.01); *A61K 31/4745* (2013.01); *C07D 413/04* (2013.01); *C07D 471/04* (2013.01); *C07D 305/06* (2013.01); *C07D 401/04* (2013.01)

(58) Field of Classification Search
CPC ........................... C07D 401/14; A61K 31/437
USPC ........................................ 514/303; 546/119
See application file for complete search history.

(56) References Cited

U.S. PATENT DOCUMENTS

| | | |
|---|---|---|
| 2016/0083391 A1 | 3/2016 | Burdi et al. |
| 2016/0083400 A1 | 3/2016 | Burdi et al. |

FOREIGN PATENT DOCUMENTS

| | | |
|---|---|---|
| WO | 2006/044821 | 4/2006 |
| WO | WO 2008/070095 | 6/2008 |
| WO | 2008/111010 | 9/2008 |
| WO | WO 2010/065153 A1 | 6/2010 |
| WO | WO 2013/142307 | 9/2013 |
| WO | WO 2016/042775 A1 | 3/2016 |
| WO | WO 2016/055618 A1 | 4/2016 |
| WO | WO 2016/147659 A1 | 9/2016 |
| WO | WO 2016/170064 A1 | 10/2016 |
| WO | WO 2017/172795 A1 | 10/2017 |

OTHER PUBLICATIONS

Bernard, A., et al. (2012) "Transcriptional Architecture of the Primate Neocortex," Neuron 73:1083-1099.
International Search Report PCT/EP2017/066255 (2017) (5 pages).
Yamamoto, S., et al. (2006) "The Effects of a Novel Phosphodiesterase 7A and—4 Dual Inhibitor, YM-393059, on a T-cell-related Cytokine Production in Vitro and in Vivo," Eur. J. Pharmacol. 541:106-114.
Blokland, A., et al. (2012) "PDE Inhibition and Cognition Enhancement," Expert Opinion Thera. Patents 22(4):349-354.
Francis, S.H., et al. (2011) "Mammalian Cyclic Nucleotide Phosphodiesterases: Molecular Mechanisms and Physiological Functions," Physiol. Rev. 91:651-690.
Medina, A.E. (2011) "Therapeutic Utility of Phosphodiesterase Type I Inhibitors in Neurological Conditions," Frontiers Neurosci. 5: Article 21.
International Search Report and Written Opinion dated Aug. 25, 2017 for Application No. PCT/EP2017/066255.
U.S. Appl. No. 15/849,798, filed Dec. 21, 2017, Kehler et al.

*Primary Examiner* — Niloofar Rahmani
(74) *Attorney, Agent, or Firm* — Wolf, Greenfield & Sacks, P.C.

(57) ABSTRACT

The present invention provides 1H-pyrazolo[4,3-b]pyridin-7-amines of formula (I) as PDE1 inhibitors and their use as a medicament, in particular for the treatment of neurodegenerative disorders and psychiatric disorders.

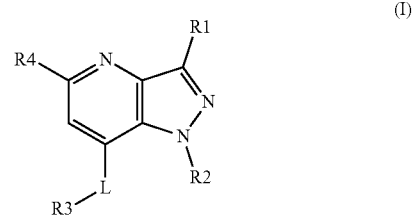

(I)

28 Claims, No Drawings

1H-PYRAZOLO[4,3-B]PYRIDINES AS PDE1 INHIBITORS

CROSS-REFERENCE TO RELATED APPLICATIONS

The present invention claims priority to Danish Patent Applications No. PA 2016 00397 (filed on Jul. 4, 2016), PA 2016 00612 (filed on Oct. 11, 2016), and PA 2017 00236 (filed on Apr. 4, 2017), each of which applications is incorporated by reference herein in its entirety.

FIELD OF THE INVENTION

The present invention provides compounds that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of cN-concentrations in all cells, and their varied regulatory mechanisms provide for integration and crosstalk with myriads of signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, PDE1 represents an interesting regulatory link between cyclic nucleotides and intracellular $Ca^{2+}$. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain that contains two $Ca^{2+}$/CaM binding domains and two phosphorylation sites differentiate their corresponding proteins and modulate their biochemical functions. PDE1 is a dual substrate PDE and the PDE1C-subtype has equal activity towards cAMP and cGMP (Km≈1-3 µM), whereas the subtypes PDE1A and PDE1B have a preference for cGMP (Km for cGMP≈1-3 µM and for cAMP≈10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messengers cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5(February), 21) has suggested the potential for the therapeutic use of PDE1 inhibitors in neurological disorders, like e.g. Alzheimer's, Parkinson's and Huntington's Diseases and in psychiatric disorders like e.g. Attention Deficit hyperactivity Disorder (ADHD), depression, anxiety, narcolepsy, cognitive impairment and cognitive impairment associated with schizophrenia (CIAS) and in restless leg syndrome. There have also been patent applications claiming that PDE1 inhibitors are useful in diseases that may be alleviated by the enhancement of progesterone-signalling such as female sexual dysfunction (e.g. WO 2008/070095).

The compounds of the invention may offer alternatives to current marketed treatments for neurodegenerative and/or psychiatric disorders, treatments which are not efficacious in all patients. Hence, there remains a need for alternative methods of treatment of such diseases.

SUMMARY OF THE INVENTION

PDE1 enzymes are expressed in the Central Nervous System (CNS), making this gene family an attractive source of new targets for the treatment of psychiatric and neurodegenerative disorders.

Accordingly, the present invention relates to compounds of formula (I)

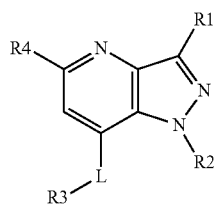

wherein
L is selected from the group consisting of NH, $CH_2$, S and O;
R1 is selected from the group consisting of hydrogen, linear or branched $C_1$-$C_5$ alkyl, $C_1$-$C_5$ fluoroalkyl and saturated monocyclic $C_3$-$C_5$ cycloalkyl;
R2 is selected from the group consisting of linear or branched $C_1$-$C_8$ alkyl, saturated monocyclic $C_3$-$C_8$ cycloalkyl, oxetanyl, tetrahydrofuranyl, and tetrahydropyranyl; all of which can be optionally substituted one or more times with one or more substituents selected from the group consisting of methyl, fluorine, hydroxy, cyano and methoxy;
R3 is methyl substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is methyl substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is ethyl substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is ethyl substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy; or
L is $CH_2$ and R3 is NH which is substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
L is $CH_2$ and R3 is NH which is substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy;
R4 is phenyl, pyridinyl or pyridonyl all of which can be optionally substituted one or more times with one or more substituents selected from the group consisting of halogen, cyano, $C_1$-$C_4$ alkyl, $C_1$-$C_4$ fluoroalkyl, $C_1$-$C_4$ deutereoalkyl, $C_1$-$C_3$ fluoroalkoxy, cyclopropyloxy, $C_1$-$C_3$ alkoxy, $C_1$-$C_3$ deutereoalkoxy and —N—R5R6 wherein R5 and R6 are each independently selected from H, $C_1$-$C_3$ alkyl and $C_1$-$C_3$ deutereoalkyl; or
R4 is a 5-membered heteroaryl which is optionally substituted with one or more substituents selected from halogen, cyano, $C_1$-$C_4$ alkyl, $C_1$-$C_4$ fluoroalkyl, $C_1$-$C_4$ deutereoalkyl, $C_1$-$C_3$ fluoroalkoxy, cyclopropyloxy, $C_1$-$C_3$ alkoxy, $C_1$-$C_3$ deutereoalkoxy and —N—R5R6 wherein R5 and R6 are each independently selected from H, $C_1$-$C_3$ alkyl and $C_1$-$C_3$ deutereoalkyl; or
R4 is a 4, 5 or 6 membered saturated heterocycle all of which can be optionally substituted with one or more substituents selected from oxo, $C_1$-$C_4$ alkyl and $C_1$-$C_4$ fluoroalkyl;
and pharmaceutically acceptable salts thereof.

Reference to Compound I includes the free base of Compound I, pharmaceutically acceptable salts of Compound I, such as acid addition salts of Compound I, racemic mixtures of Compound I, or the corresponding enantiomer and/or optical isomer of Compound I, and polymorphic and amorphous forms of Compound I as well as tautomeric forms of Compound I. Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

In one embodiment, the invention relates to a compound according to formula (I) for use in therapy.

In one embodiment, the invention relates to a pharmaceutical composition comprising a compound according formula (I), and one or more pharmaceutically acceptable carrier or excipients.

In one embodiment, the invention relates to a compound according to formula (I), for use in the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome.

In one embodiment, the invention relates to a method for the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to formula (I) to a patient in need thereof.

In one embodiment, the invention relates to the use of a compound according to formula (I), for the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome.

Definitions

PDE1 Enzymes:
The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.

PDE1 Inhibitors:

In the context of the present invention, a compound is considered to be a PDE1 inhibitor if the amount required to reach the $IC_{50}$ level of any of the three PDE1 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less.

In general, compounds of the invention exhibits selectivity towards the PDE1B isoform meaning that said compounds are stronger as PDE1B inhibitors than as PDE1A and/or PDE1C inhibitors. In preferred embodiments, said compounds are at least two fold stronger, five-fold stronger or ten-fold stronger as PDE1B inhibitors than as PDE1A and/or PDE1C inhibitors. In more preferred embodiments, said compounds are at least fifteen-fold stronger or twenty-fold stronger as PDE1B inhibitors than as PDE1A and/or PDE1C inhibitors.

In preferred embodiments the required amount of PDE1 inhibitor required to reach the $IC_{50}$ level of PDE1B is 400 nM or less, such as 300 nM or less, 200 nM or less, 100 nM or less, or even 80 nM or less, such as 50 nM or less, for example 25 nM or less. Selectivity towards the PDE1B isoform may prevent potentially unwanted effects associated with PDE1A and/or PDE1C inhibition. For example potentially unwanted peripheral effects.

Substituents:

In the present context, "optionally substituted" means that the indicated moiety may or may not be substituted, and when substituted is mono-, di-, or tri-substituted. It is understood that where no substituents are indicated for an "optionally substituted" moiety, then the position is held by a hydrogen atom.

As used in the context of the present invention, the terms "halo" and "halogen" are used interchangeably and refer to fluorine, chlorine, bromine or iodine.

A given range may interchangeably be indicated with "-" (dash) or "to", e.g. the term "$C_1$-$C_3$ alkyl" is equivalent to "$C_1$ to $C_3$ alkyl".

The terms "$C_1$-$C_3$ alkyl", "$C_1$-$C_4$ alkyl", "$C_1$-$C_5$ alkyl", "$C_1$-$C_6$ alkyl", "$C_1$-$C_7$ alkyl" and "$C_1$-$C_8$ alkyl" refer to a linear (i.e. unbranched) or branched saturated hydrocarbon having from one up to eight carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, n-hexyl, n-heptyl and n-octyl.

The term "$C_1$-$C_3$ fluoroalkyl" refers to a $C_1$-$C_3$ alkyl substituted with one or more fluorine.

The terms, "$C_1$-$C_4$ deutereoalkyl" and "$C_1$-$C_3$ deuteroalkyl" refer to a $C_1$-$C_4$ alkyl and a $C_1$-$C_3$ alkyl wherein one or more hydrogen atoms are designated as deuterium. Examples of "$C_1$-$C_3$ deutereoalkyl" include, but are not limited to, trideuteriomethyl, 1,1-dideuterioethyl, 2,2,2-trideuterioethyl and 1,1,2,2,2-pentadeuterioethyl.

The term saturated monocyclic $C_3$-$C_8$ cycloalkyl refers to cyclopropyl, cyclobutyl, cyclopentyl, cyclohexyl, cycloheptyl and cyclooctyl.

The term "5-membered heteroaryl" refers to a 5 membered aromatic monocyclic ring containing 1 to 4 carbon atoms and one or more heteroatoms selected from oxygen, nitrogen and sulfur. Examples include, but are not limited to thiazolyl, oxazolyl, isoxazolyl, triazolyl, pyrazolyl, tetrazolyl, imidazolyl, oxadiazolyl and thiadiazolyl and thiophenyl.

The term "$C_1$-$C_3$ alkoxy" refers to a moiety of the formula —OR', wherein R' indicates $C_1$-$C_3$ alkyl as defined above.

The term "$C_1$-$C_3$ fluoroalkoxy" refers to a moiety of the formula —OR', wherein R' indicates $C_1$-$C_3$ fluoroalkyl as defined above.

The term, "$C_1$-$C_3$ deutereoalkoxy" refers to a $C_1$-$C_3$ alkoxy wherein one or more hydrogen atoms are designated as deuterium. Examples include, but are not limited to, trideuteriomethoxy, 1,1-dideuterioethoxy, 2,2,2-trideuterioethoxy and 1,1,2,2,2-pentadeuterioethoxy.

The terms "4, 5 or 6 membered saturated heterocycle" refers to a saturated monocyclic ring containing 1 to 3, 4, or 5 carbon atoms and one or more heteroatoms selected from oxygen, nitrogen and sulfur, Examples include, but are not limited to oxazolidin-2-one, azetidin-2-one, imidazolidin-2-one, pyrrolidin-2-one, imidazolidine-2,4-dione, oxazolidine-2,4-dione or piperidin-2-one.

Isomeric and Tautomeric Forms:

Where compounds of the present invention contain one or more chiral centers reference to any of the compounds will, unless otherwise specified, cover the enantiomerically or diastereomerically pure compound as well as mixtures of the enantiomers or diastereomers in any ratio. For example, compound Example 15 is prepared as a racemate and covers both (R)-5-(2-ethoxypyridin-3-yl)-1-methyl-N-(1-(1-methyl-1H-pyrazol-4-yl)ethyl)-1H-pyrazolo[4,3-b]pyridin-7-amine and (S)-5-(2-ethoxypyridin-3-yl)-1-methyl-N-(1-(1-methyl-1H-pyrazol-4-yl)ethyl)-1H-pyrazolo[4,3-b]pyridin-7-amine as well as mixtures of these two enantiomers in any ratio, including the racemic mixture. The R-enantiomer of compound Example 15 has been designated as "15a" while the S-enantiomer has been designated as "15b".

When a compound of the invention is denoted with the suffix "enantiomer 1" or "enantiomer 2" it is understood that said enantiomer could be either the S-enantiomer or the R-enantiomer. I.e. "enantiomer 1" could be either the S-enantiomer or the R-enantiomer and "enantiomer 2" could be either the S-enantiomer or the R-enantiomer. When both enantiomer 1 and enantiomer 2 have been exemplified for a compound it follows that one is the S-enantiomer and the other is the R-enantiomer. For example compound Example 123 is 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, enantiomer 1; and compound Example 124 is 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, enantiomer 2. It follows that if for example compound Example 123 can be determined to be the R-enantiomer, then compound Example 124 will be the S-enantiomer and vice versa.

Some compounds of the invention have been exemplified in only one enantiomeric form, like for example compound Example 125: 5-(2-ethoxy-3-pyridyl)-N-[(5-methoxy-3-pyridyl)methyl]-3-methyl-1-[1-methylpropyl]pyrazolo[4,3-b]pyridin-7-amine, enantiomer 2, which has been prepared from 1-(sec-butyl)-5-(2-ethoxypyridin-3-yl)-3-methyl-1H-pyrazolo[4,3-b]pyridin-7-amine, enantiomer 2. In such case it follows that the corresponding enantiomer ("enantiomer 1") can be prepared by a similar method from 1-(sec-butyl)-5-(2-ethoxypyridin-3-yl)-3-methyl-1H-pyrazolo[4,3-b]pyridin-7-amine, enantiomer 1. Thus, the corresponding enantiomer ("enantiomer 1") is also a compound of the invention that can be individually claimed. Example 125 thus covers both enantiomeric forms, which can each be individually claimed, although only "enantiomer 2" has been prepared and tested in the PDE1 assay. The R-enantiomer of compound Example 125 has been designated as "125a" while the S-enantiomer has been designated as "125b". The same principle applies for other exemplified compounds for which only one enantiomer has been prepared.

The absolute stereochemistry for a compound of the invention can be determined by X-ray crystallography or vibrational circular dichroism.

Furthermore, some of the compounds of the present invention may exist in different tautomeric forms and it is intended that any tautomeric forms that the compounds are able to form are included within the scope of the present invention.

Deuterated Compounds:

The present invention also comprises deuterated compounds. The term "deuterated compound" indicates a compound comprising one or more atoms that are designated as deuterium.

It is recognized that elements are present in natural isotopic abundances in most synthetic compounds, and result in inherent incorporation of deuterium. The natural isotopic abundance of hydrogen isotopes such as deuterium is about 0.015%. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan. Any atom not designated as deuterium is present at about its natural isotopic abundance.

In some embodiments, designation of a position as "D" in a compound has a minimum deuterium incorporation of greater than 50% at that position. In some embodiments, designation of a position as "D" in a compound has a minimum deuterium incorporation of greater than 60%, such as greater than 65%, such as greater than 70%, such as greater than 75%, such as greater than 80% at that position. In a preferred embodiment, designation of a position as "D" in a compound has a minimum deuterium incorporation of greater than 85%, such as greater than 90% at that position. In a more preferred embodiment, designation of a position as "D" in a compound has a minimum deuterium incorporation of greater than 95%, such as greater than 97%, such as greater than 99% at that position.

The deuterated compounds of the present invention are compounds wherein one or more atoms of the substituent in R4 position are designated a deuterium.

Pharmaceutically Acceptable Salts:

The compounds of this invention are generally utilized as the free substance or as a pharmaceutically acceptable salt thereof. When a compound of formula (I) contains a free base such salts are prepared in a conventional manner by treating a solution or suspension of a free base of formula (I) with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Therapeutically Effective Amount:

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting or delaying progress of the clinical manifestation of the disease, or curing the disease. The patient to be treated is preferably a mammal, in particular a human being.

Administration Routes:

The pharmaceutical compositions may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients:

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (I), such as one of the compounds disclosed in the Experimental Section herein. The present invention also provides a process for making a pharmaceutical composition comprising a compound of formula (I). The pharmaceutical compositions according to the invention may be formulated with pharmaceutically acceptable excipients in accordance with conventional techniques such as those disclosed in Remington, "The Science and Practice of Pharmacy", $22^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

DETAILED DESCRIPTION OF THE INVENTION

The present inventors have identified compounds that are PDE1 inhibitors, and as such are useful to treat neurodegenerative and psychiatric disorders. The present invention thus provides compounds of formula (I) that are effective in inhibiting PDE1 for use as a medicament in the treatment of a mammal, preferably a human.

The invention provides a compound of formula (I) or a pharmaceutically acceptable acid addition salt thereof, as well as a pharmaceutical composition containing such a compound, for use in the treatment of a brain disease which could be a neurodegenerative disorder or a psychiatric disorder. In a preferred embodiment the neurodegenerative disorder is selected from the group consisting of Alzheimer's Disease, Parkinson's Disease and Huntington's Disease. In another preferred embodiment the psychiatric disorder is selected from the group consisting of Attention Deficit hyperactivity Disorder (ADHD), depression, anxiety, narcolepsy, cognitive impairment and cognitive impairment associated with schizophrenia (CIAS). Other brain disorders could be e.g. restless leg syndrome.

This invention further provides a method of treating a brain disease which could be a neurodegenerative or a psychiatric disorder, which method comprises administering to said mammal a pharmaceutically effective amount of a compound of formula (I). Examples of neurodegenerative disorders that can be treated according to the present invention include Alzheimer's Disease, Parkinson's Disease and Huntington's Disease, which method comprises administering to the subject a therapeutically effective amount of a compound of formula (I). Examples of psychiatric disorders that can be treated according to the present invention include Attention Deficit hyperactivity Disorder (ADHD), depression, narcolepsy, cognitive impairment and cognitive impairment associated with schizophrenia (CIAS). Other brain disorders to be treated could be e.g. restless leg syndrome.

Embodiments of the Invention

In the following, embodiments of the invention are disclosed. The first embodiment is denoted E1, the second embodiment is denoted E2 and so forth In a first embodiment E1 the present invention relates to compounds of formula (I)

E1. A compound according to formula (I)

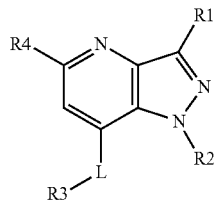

wherein
L is selected from the group consisting of NH, $CH_2$, S and O;
R1 is selected from the group consisting of hydrogen, linear or branched $C_1$-$C_5$ alkyl, $C_1$-$C_3$ fluoroalkyl and saturated monocyclic $C_3$-$C_5$ cycloalkyl;
R2 is selected from the group consisting of linear or branched $C_1$-$C_8$ alkyl, saturated monocyclic $C_3$-$C_8$ cycloalkyl, oxetanyl, tetrahydrofuranyl, and tetrahydropyranyl; all of which can be optionally substituted one or more times with one or more substituents selected from the group consisting of methyl, fluorine, hydroxy, cyano and methoxy;
R3 is methyl substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is methyl substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is ethyl substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is ethyl substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy; or
L is $CH_2$ and R3 is NH which is substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
L is $CH_2$ and R3 is NH which is substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy;
R4 is phenyl, pyridinyl or pyridonyl all of which can be optionally substituted one or more times with one or more substituents selected from the group consisting of halogen, cyano, $C_1$-$C_4$ alkyl, $C_1$-$C_4$ fluoroalkyl, $C_1$-$C_4$ deutereoalkyl, $C_1$-$C_3$ fluoroalkoxy, cyclopropyloxy, $C_1$-$C_3$ alkoxy, $C_1$-$C_3$ deutereoalkoxy and —N—R5R6 wherein R5 and R6 are each independently selected from H, $C_1$-$C_3$ alkyl and $C_1$-$C_3$ deutereoalkyl; or
R4 is a 5-membered heteroaryl which is optionally substituted with one or more substituents selected from halogen, cyano, $C_1$-$C_4$ alkyl, $C_1$-$C_4$ fluoroalkyl, $C_1$-$C_4$ deutereoalkyl, $C_1$-$C_3$ fluoroalkoxy, cyclopropyloxy, $C_1$-$C_3$ alkoxy, $C_1$-$C_3$ deutereoalkoxy and —N—R5R6 wherein R5 and R6 are each independently selected from H, $C_1$-$C_3$ alkyl and $C_1$-$C_3$ deutereoalkyl; or
R4 is a 4, 5 or 6 membered saturated heterocycle all of which can be optionally substituted with one or more substituents selected from oxo, $C_1$-$C_4$ alkyl and $C_1$-$C_4$ fluoroalkyl;
and pharmaceutically acceptable salts thereof.

E2. The compound according to embodiment 1, wherein
L is selected from the group consisting of NH, $CH_2$, S and O;
R1 is selected from the group consisting of hydrogen, linear or branched $C_1$-$C_5$ alkyl, $C_1$-$C_3$ fluoroalkyl and saturated monocyclic $C_3$-$C_5$ cycloalkyl;
R2 is selected from the group consisting of linear or branched $C_1$-$C_8$ alkyl, saturated monocyclic $C_3$-$C_8$ cycloalkyl, oxetanyl, tetrahydrofuranyl, and tetrahydropyranyl; all of which can be optionally substituted one or more times with one or more substituents selected from the group consisting of methyl, fluorine, hydroxy, cyano and methoxy;
R3 is methyl substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is methyl substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is ethyl substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
R3 is ethyl substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy;
R4 is phenyl, pyridinyl or pyridonyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ deutereoalkyl, $C_1$-$C_3$ fluoroalkoxy, cyclopropyloxy, $C_1$-$C_3$ alkoxy, $C_1$-$C_3$ deutereoalkoxy and —N—R5R6 wherein R5 and R6 are each independently selected from H, $C_1$-$C_3$ alkyl and $C_1$-$C_3$ deutereoalkyl; or
R4 is a 5-membered heteroaryl which is optionally substituted with one or more substituents selected from halogen, cyano, $C_1$-$C_3$ alkyl, $C_1$-$C_3$ fluoroalkyl, $C_1$-$C_3$ deutereoalkyl, $C_1$-$C_3$ fluoroalkoxy, cyclopropyloxy, $C_1$-$C_3$ alkoxy, $C_1$-$C_3$ deutereoalkoxy and —N—R5R6 wherein R5 and R6 are each independently selected from H, $C_1$-$C_3$ alkyl and $C_1$-$C_3$ deutereoalkyl; or
R4 is a 4, 5 or 6 membered saturated heterocycle all of which can be optionally substituted with one or more substituents selected from oxo, $C_1$-$C_4$ alkyl and $C_1$-$C_4$ fluoroalkyl;

E3. The compound according to any of embodiments 1 or 2, wherein L is NH.
E4. The compound according to any of embodiments 1 or 2, wherein L is $CH_2$.
E5. The compound according to any of embodiments 1 or 2, wherein L is S.
E6. The compound according to any of embodiments 1 or 2, wherein L is O.

E7. The compound according to embodiment 1, wherein
L is $CH_2$ and R3 is NH which is substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or
L is $CH_2$ and R3 is NH which is substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy.

E8. The compound according to anyone of embodiments 1-7, wherein R2 is selected from the group consisting of linear or branched $C_1$-$C_8$ alkyl, saturated monocyclic $C_3$-$C_8$ cycloalkyl, oxetanyl, tetrahydrofuranyl and tetrahydropyranyl, all of which are unsubstituted.

E9. The compound according to embodiment 8, wherein R2 is selected from the group consisting of linear or branched $C_1$-$C_4$ alkyl, cyclopropyl, oxetanyl, tetrahydrofuranyl and tetrahydropyranyl.

E10. The compound according to anyone of embodiments 1-9, wherein R3 is methyl substituted with phenyl, pyridonyl, pyridinyl, pyrimidinyl or pyrazinyl all of which can be optionally substituted with one or more methyl.

E11. The compound according to embodiment 10, wherein R3 is methyl substituted with phenyl, pyridonyl, pyridinyl, pyrimidinyl or pyrazinyl, all of which can be substituted with one methyl.

E12. The compound according to embodiment 10, wherein R3 is methyl substituted with phenyl, pyridonyl, pyridinyl, pyrimidinyl or pyrazinyl, all of which are unsubstituted.

E13. The compound according to anyone of embodiments 1-9, wherein R3 is ethyl substituted with phenyl, pyridonyl, pyridinyl, pyrimidinyl or pyrazinyl all of which can be optionally substituted with one or more methyl.

E14. The compound according to embodiment 13, wherein R3 is ethyl substituted with phenyl, pyridonyl, pyridinyl, pyrimidinyl or pyrazinyl all of which can be substituted with one methyl.

E15. The compound according to embodiment 13, wherein R3 is ethyl substituted with phenyl, pyridonyl, pyridinyl, pyrimidinyl or pyrazinyl all of which are unsubstituted.

E16. The compound according to anyone of embodiments 1-9, wherein R3 is methyl substituted with a 5-membered heteroaryl which is optionally substituted with one or more methyl.

E17. The compound according to anyone of embodiments 1-9, wherein R3 is ethyl substituted with a 5-membered heteroaryl which is optionally substituted with one or more methyl.

E18. The compound according to anyone of embodiments 16-17, wherein said 5-membered heteroaryl is substituted with one methyl.

E19. The compound according to anyone of embodiments 16-17, wherein said 5-membered heteroaryl is unsubstituted.

E20. The compound according to anyone of embodiments 16-19, wherein said 5-membered heteroaryl is selected from thiazolyl, oxazolyl, isoxazolyl, triazolyl, pyrazolyl, tetrazolyl, imidazolyl, oxadiazolyl and thiadiazolyl and thiophenyl.

E21. The compound according to anyone of embodiments 1-20, wherein R4 is phenyl, pyridinyl or pyridonyl all of which can be optionally substituted one time with a substituent selected from the group consisting of halogen, $C_1$-$C_3$ alkyl and $C_1$-$C_3$ alkoxy.

E22. The compound according to any of embodiments 1-20, wherein R4 is a 5-membered heteroaryl which is optionally substituted with one or more substituents selected from $C_1$-$C_3$ alkyl and $C_1$-$C_3$ fluoroalkyl.

E23. The compound according to embodiment 22, wherein R4 is a 5-membered heteroaryl which is optionally substituted with one or two methyl.

E24. The compound according to any of embodiments 22-23, wherein said 5-membered heteroaryl is selected from thiazolyl, oxazolyl, isoxazolyl, triazolyl, pyrazolyl, tetrazolyl, imidazolyl, oxadiazolyl and thiadiazolyl and thiophenyl.

E25. The compound according to any of embodiments 1-20, wherein R4 is a 4, 5 or 6 membered saturated heterocycle all of which can be optionally substituted one time with a substituent selected from oxo, $C_1$-$C_4$ alkyl and $C_1$-$C_4$ fluoroalkyl.

E26. The compound according any of embodiments 1-3 and 8-25 of formula (Ib)

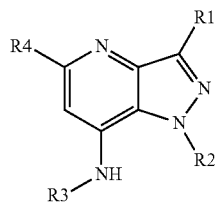

(Ib)

wherein
R1 is selected from the group consisting of hydrogen, linear or branched $C_1$-$C_5$ alkyl, and saturated monocyclic $C_3$-$C_5$ cycloalkyl;
R2 is selected from the group consisting of linear or branched $C_1$-$C_8$ alkyl, saturated monocyclic $C_3$-$C_8$ cycloalkyl, oxetanyl, tetrahydrofuranyl and tetrahydropyranyl, all of which can be optionally substituted one or more times with one or more substituents selected from the group consisting of methyl, fluorine, hydroxy, cyano and methoxy;
R3 is methyl substituted with phenyl, pyridonyl or pyridinyl, all of which can be optionally substituted one or more times with one or more substituents selected from the group consisting of halogen, $C_1$-$C_3$ alkyl and methoxy; or
R3 is methyl substituted with a 5-membered heteroaryl which is optionally substituted with one or more substituents selected from $C_1$-$C_3$ alkyl and $C_1$-$C_3$ fluoroalkyl; or
R3 is ethyl substituted with phenyl, pyridonyl or pyridinyl, all of which can be optionally substituted one or more times with one or more substituents selected from the group consisting of halogen, $C_1$-$C_3$ alkyl and methoxy; or
R3 is ethyl substituted with a 5-membered heteroaryl which is optionally substituted with one or more substituents selected from $C_1$-$C_3$ alkyl and $C_1$-$C_3$ fluoroalkyl;
R4 is phenyl, pyridinyl or pyridonyl, all of which can be optionally substituted one or more times with one or more substituents selected from the group consisting of halogen, $C_1$-$C_3$ alkyl and $C_1$-$C_3$ alkoxy; or
R4 is a 5-membered heteroaryl which is optionally substituted with one or more substituents selected from $C_1$-$C_3$ alkyl and $C_1$-$C_3$ fluoroalkyl;
and pharmaceutically acceptable salts thereof.

E27. The compound according to embodiment 1, wherein the compound is selected from the group consisting of:

1: 5-(2-ethoxy-3-pyridyl)-1-isopropyl-3-methyl-N-[(5-methyl-1,3,4-oxadiazol-2-yl)methyl]pyrazolo[4,3-b]pyridin-7-amine;
2: 5-(2-ethoxy-3-pyridyl)-1-isopropyl-3-methyl-N-[(5-methylthiazol-2-yl)methyl]pyrazolo[4,3-b]pyridin-7-amine;
3: 5-(2-ethoxy-3-pyridyl)-1-isopropyl-3-methyl-N-[(5-methylisoxazol-3-yl)methyl]pyrazolo[4,3-b]pyridin-7-amine;
4: 5-(2-ethoxy-3-pyridyl)-1-isopropyl-3-methyl-N-[(2-methyloxazol-5-yl)methyl]pyrazolo[4,3-b]pyridin-7-amine;
5: 5-(2-ethoxy-3-pyridyl)-1-isopropyl-3-methyl-N-[(2-methyltriazol-4-yl)methyl]pyrazolo[4,3-b]pyridin-7-amine;
6: 5-(2-ethoxy-3-pyridyl)-1-isopropyl-3-methyl-N-[(1-methyltriazol-4-yl)methyl]pyrazolo[4,3-b]pyridin-7-amine;
7: 5-(2-ethoxy-3-pyridyl)-1-isopropyl-3-methyl-N-(1H-pyrazol-4-ylmethyl)pyrazolo[4,3-b]pyridin-7-amine;
8: 5-(2-ethoxy-3-pyridyl)-1-isopropyl-3-methyl-N-[(2-methyltetrazol-5-yl)methyl]pyrazolo[4,3-b]pyridin-7-amine;
9: 5-(2-ethoxypyridin-3-yl)-1-isopropyl-3-methyl-N-((1-methyl-1H-pyrazol-4-yl)methyl)-1H-pyrazolo[4,3-b]pyridin-7-amine;
10: 5-(2-ethoxy-3-pyridyl)-1-isopropyl-3-methyl-N-[(3-methylisoxazol-5-yl)methyl]pyrazolo[4,3-b]pyridin-7-amine;
11: 5-(2-ethoxy-3-pyridyl)-1-isopropyl-3-methyl-N-[(2-methylthiazol-4-yl)methyl]pyrazolo[4,3-b]pyridin-7-amine;
12: 1-cyclopropyl-5-(2-ethoxy-3-pyridyl)-3-methyl-N-[(1-methyl pyrazol-4-yl)methyl]pyrazolo[4,3-b]pyridin-7-amine;
13: 5-(2-ethoxy-3-pyridyl)-N-[(1-methylpyrazol-4-yl)methyl]-1-propyl-pyrazolo[4,3-b]pyridin-7-amine;
14: 5-(2-ethoxypyridin-3-yl)-N-((1-methyl-1H-pyrazol-4-yl)methyl)-1-(oxetan-3-yl)-1H-pyrazolo[4,3-b]pyridin-7-amine;
15: 5-(2-ethoxypyridin-3-yl)-1-methyl-N-(1-(1-methyl-1H-pyrazol-4-yl)ethyl)-1H-pyrazolo[4,3-b]pyridin-7-amine;
16: 5-(2-ethoxypyridin-3-yl)-1-methyl-N-((1-methyl-1H-pyrazol-4-yl)methyl)-1H-pyrazolo[4,3-b]pyridin-7-amine;
17: 5-(2-ethoxy-3-pyridyl)-1-isopropyl-N-[(1-methylimidazol-2-yl)methyl]pyrazolo[4,3-b]pyridin-7-amine;
18: 5-(2-ethoxypyridin-3-yl)-1-isopropyl-N-((1-methyl-1H-pyrazol-5-yl)methyl)-1H-pyrazolo[4,3-b]pyridin-7-amine;
19: 5-(2-ethoxypyridin-3-yl)-1-isopropyl-N-((1-methyl-1H-pyrazol-3-yl)methyl)-1H-pyrazolo[4,3-b]pyridin-7-amine;
20: 5-(2-ethoxy-3-pyridyl)-1-isopropyl-N-(thiazol-2-ylmethyl)pyrazolo[4,3-b]pyridin-7-amine;
21: 5-(2-ethoxy-3-pyridyl)-1-isopropyl-N-[(1-methylimidazol-4-yl)methyl]pyrazolo[4,3-b]pyridin-7-amine;
22: 5-(2-ethoxy-3-pyridyl)-1-isopropyl-N-(4-pyridylmethyl)pyrazolo[4,3-b]pyridin-7-amine;
23: 5-(2-ethoxy-3-pyridyl)-1-isopropyl-N-(m-tolylmethyl)pyrazolo[4,3-b]pyridin-7-amine;
24: 5-(2-ethoxy-3-pyridyl)-1-isopropyl-N-(p-tolylmethyl)pyrazolo[4,3-b]pyridin-7-amine;
25: 5-(2-ethoxy-3-pyridyl)-1-isopropyl-N-[(1-methylpyrazol-4-yl)methyl]pyrazolo[4,3-b]pyridin-7-amine;
26: 5-(2-ethoxy-3-pyridyl)-1-ethyl-N-[(1-methylpyrazol-4-yl)methyl]pyrazolo[4,3-b]pyridin-7-amine;
27: 5-(2-ethoxy-3-pyridyl)-3-methyl-N-[(1-methylpyrazol-4-yl)methyl]-1-(oxetan-3-yl)pyrazolo[4,3-b]pyridin-7-amine;
28: 5-(2-ethoxy-3-pyridyl)-1,3-dimethyl-N-[(1-methylpyrazol-4-yl)methyl]pyrazolo[4,3-b]pyridin-7-amine;
29: 5-(2-ethoxy-3-pyridyl)-1-isopropyl-3-methyl-N-[(4-methylthiazol-2-yl)methyl]pyrazolo[4,3-b]pyridin-7-amine;
30: 5-(2-ethoxy-3-pyridyl)-1-isopropyl-3-methyl-N-[(3-methyl-1,2,4-oxadiazol-5-yl)methyl]pyrazolo[4,3-b]pyridin-7-amine;
31: 5-(2-ethoxy-3-pyridyl)-1-isopropyl-3-methyl-N-[(1-methyl-1,2,4-triazol-3-yl)methyl]pyrazolo[4,3-b]pyridin-7-amine;
32: 5-(2-ethoxy-3-pyridyl)-1-isopropyl-3-methyl-N-[(2-methylthiazol-5-yl)methyl]pyrazolo[4,3-b]pyridin-7-amine;
33: 5-(2-ethoxy-3-pyridyl)-1-isopropyl-3-methyl-N-[(5-methyl-1,3,4-thiadiazol-2-yl)methyl]pyrazolo[4,3-b]pyridin-7-amine;
34: 5-(2-ethoxy-3-pyridyl)-1-isopropyl-3-methyl-N-[(5-methyl-3-thienyl)methyl]pyrazolo[4,3-b]pyridin-7-amine;
35: 5-(2-ethoxy-3-pyridyl)-1-isopropyl-3-methyl-N-[(4-methyl-2-thienyl)methyl]pyrazolo[4,3-b]pyridin-7-amine;
36: 5-(2-ethoxy-3-pyridyl)-1-isopropyl-3-methyl-N-[(5-methyl-2-thienyl)methyl]pyrazolo[4,3-b]pyridin-7-amine;
37: 5-(2-ethoxy-3-pyridyl)-1-isopropyl-3-methyl-N-[(2-methyloxazol-4-yl)methyl]pyrazolo[4,3-b]pyridin-7-amine;
38: 5-(2-ethoxy-3-pyridyl)-1-isopropyl-3-methyl-N-[(5-methyloxazol-2-yl)methyl]pyrazolo[4,3-b]pyridin-7-amine;
39: 5-(2-ethoxy-3-pyridyl)-1-isopropyl-3-methyl-N-(1H-pyrazol-3-ylmethyl)pyrazolo[4,3-b]pyridin-7-amine;
40: 5-(2-ethoxy-3-pyridyl)-N-(1H-imidazol-4-ylmethyl)-1-isopropyl-3-methyl-pyrazolo[4,3-b]pyridin-7-amine;
41: N-benzyl-5-(2-ethoxy-3-pyridyl)-1-isopropyl-pyrazolo[4,3-b]pyridin-7-amine;
42: 5-(2-ethoxy-3-pyridyl)-1-isopropyl-N-[(3-methylisoxazol-5-yl)methyl]pyrazolo[4,3-b]pyridin-7-amine;
43: 5-(2-ethoxy-3-pyridyl)-1-isopropyl-N-[(5-methyl-1,2,4-oxadiazol-3-yl)methyl]pyrazolo[4,3-b]pyridin-7-amine;
44: N-[(1,5-dimethylpyrazol-3-yl)methyl]-5-(2-ethoxy-3-pyridyl)-1-isopropyl-pyrazolo[4,3-b]pyridin-7-amine;
45: 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one;
46: 5-(2-ethoxypyridin-3-yl)-1-isopropyl-3-methyl-N-((2-methyl-1H-imidazol-4-yl)methyl)-1H-pyrazolo[4,3-b]pyridin-7-amine;
47: 5-(2-ethoxypyridin-3-yl)-1-isopropyl-3-methyl-N-((5-methyl-1H-pyrazol-3-yl)methyl)-1H-pyrazolo[4,3-b]pyridin-7-amine;
48: 5-(2-ethoxypyridin-3-yl)-1-ethyl-3-methyl-N-((1-methyl-1H-pyrazol-4-yl)methyl)-1H-pyrazolo[4,3-b]pyridin-7-amine;
49: 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one;
50: 5-(2-ethoxypyridin-3-yl)-1-isopropyl-3-methyl-N-((4-methyloxazol-2-yl)methyl)-1H-pyrazolo[4,3-b]pyridin-7-amine;

51: N-((1,2-dimethyl-1H-imidazol-4-yl)methyl)-5-(2-ethoxypyridin-3-yl)-1-isopropyl-3-methyl-1H-pyrazolo[4,3-b]pyridin-7-amine;
52: 5-(2-ethoxy-3-pyridyl)-1-isopropyl-3-methyl-N-[(5-methyl-1,2,4-oxadiazol-3-yl)methyl]pyrazolo[4,3-b]pyridin-7-amine;
53: 5-(2-ethoxy-3-pyridyl)-1-isopropyl-3-methyl-N-(1,2,4-oxadiazol-3-ylmethyl)pyrazolo[4,3-b]pyridin-7-amine;
54: N-[(1,5-dimethylpyrazol-3-yl)methyl]-5-(2-ethoxy-3-pyridyl)-1-isopropyl-3-methyl-pyrazolo[4,3-b]pyridin-7-amine;
55: 5-(2-ethoxy-3-pyridyl)-1-isopropyl-3-methyl-N-[(5-methyl-1H-1,2,4-triazol-3-yl)methyl]pyrazolo[4,3-b]pyridin-7-amine;
56: 5-(2-ethoxy-3-pyridyl)-1-isopropyl-N-[(1-methyl-1,2,4-triazol-3-yl)methyl]pyrazolo[4,3-b]pyridin-7-amine;
57: 5-(2-ethoxy-3-pyridyl)-1-isopropyl-N-(1H-pyrazol-3-ylmethyl)pyrazolo[4,3-b]pyridin-7-amine;
58: 5-(2-ethoxypyridin-3-yl)-1-isopropyl-3-methyl-N-((1-methyl-1H-imidazol-4-yl)methyl)-1H-pyrazolo[4,3-b]pyridin-7-amine 2,2,2-trifluoroacetate;
59: 5-(2-ethoxy-3-pyridyl)-1-isopropyl-3-methyl-N-(1,3,4-oxadiazol-2-ylmethyl)pyrazolo[4,3-b]pyridin-7-amine;
60: 5-(2-ethoxy-3-pyridyl)-1-isopropyl-3-methyl-N-[(1-methylpyrazol-3-yl)methyl]pyrazolo[4,3-b]pyridin-7-amine;
61: 5-(1,3-dimethylpyrazol-4-yl)-1-isopropyl-3-methyl-N-[(1-methylpyrazol-4-yl)methyl]pyrazolo[4,3-b]pyridin-7-amine;
62: 1-isopropyl-5-(2-methoxy-3-pyridyl)-3-methyl-N-[(1-methylpyrazol-4-yl)methyl]pyrazolo[4,3-b]pyridin-7-amine;
63: 1-isopropyl-5-(2-methoxyphenyl)-3-methyl-N-[(1-methylpyrazol-4-yl)methyl]pyrazolo[4,3-b]pyridin-7-amine;
64: 1-isopropyl-3-methyl-N-[(1-methylpyrazol-4-yl)methyl]-5-phenyl-pyrazolo[4,3-b]pyridin-7-amine;
65: 1-isopropyl-3-methyl-N-[(1-methylpyrazol-4-yl)methyl]-5-(2-methyl-3-thienyl)pyrazolo[4,3-b]pyridin-7-amine;
66: 5-(1,5-dimethylpyrazol-4-yl)-1-isopropyl-3-methyl-N-[(1-methylpyrazol-4-yl)methyl]pyrazolo[4,3-b]pyridin-7-amine;
67: 5-(2-ethoxy-3-pyridyl)-3-methyl-1-[1-methylpropyl]-N-[(1-methylpyrazol-3-yl)methyl]pyrazolo[4,3-b]pyridin-7-amine, enantiomer 2;
68: 3-methyl-1-[1-methylpropyl]-N-[(2-methyltetrazol-5-yl)methyl]-5-(2-propoxy-3-pyridyl)pyrazolo[4,3-b]pyridin-7-amine, enantiomer 2;
69: 5-(2-ethoxy-3-pyridyl)-1-[1-methylpropyl]-N-[(1-methylpyrazol-4-yl)methyl]pyrazolo[4,3-b]pyridin-7-amine, enantiomer 1;
70: 5-(2-ethoxy-3-pyridyl)-1-[1-methylpropyl]-N-[(1-methylpyrazol-4-yl)methyl]pyrazolo[4,3-b]pyridin-7-amine, enantiomer 2;
71: 5-(2-ethoxy-3-pyridyl)-1-isopropyl-N-[(4-methylthiazol-5-yl)methyl]pyrazolo[4,3-b]pyridin-7-amine;
72: 5-[[5-(2-ethoxy-3-pyridyl)-1-isopropyl-3-methyl-pyrazolo[4,3-b]pyridin-7-yl]oxymethyl]-2-methyl-oxazole;
73: 5-(2-ethoxy-3-pyridyl)-1-isopropyl-3-methyl-N-(pyrimidin-4-ylmethyl)pyrazolo[4,3-b]pyridin-7-amine;
74: 5-(2-ethoxy-3-pyridyl)-1-isopropyl-3-methyl-N-(pyrimidin-2-ylmethyl)pyrazolo[4,3-b]pyridin-7-amine;
75: 5-(2-ethoxy-3-pyridyl)-1-isopropyl-3-methyl-N-[(4-methylpyrimidin-2-yl)methyl]pyrazolo[4,3-b]pyridin-7-amine;
76: 5-(2-ethoxy-3-pyridyl)-1-isopropyl-3-methyl-N-(pyrazin-2-ylmethyl)pyrazolo[4,3-b]pyridin-7-amine;
77: 5-(2-ethoxy-3-pyridyl)-1-isopropyl-3-methyl-N-[[2-(trifluoromethyl)-3-pyridyl]methyl]pyrazolo[4,3-b]pyridin-7-amine;
78: 4-[[[5-(2-ethoxy-3-pyridyl)-1-isopropyl-3-methyl-pyrazolo[4,3-b]pyridin-7-yl]amino]methyl]-1-methyl-pyridin-2-one;
79: 5-(2-(ethylamino)pyridin-3-yl)-1-isopropyl-3-methyl-N-((1-methyl-1H-pyrazol-4-yl)methyl)-1H-pyrazolo[4,3-b]pyridin-7-amine;
81: 5-(2-ethoxy-3-pyridyl)-1-isopropyl-N-[(4-methoxy-2-pyridyl)methyl]-3-methyl-pyrazolo[4,3-b]pyridin-7-amine;
82: 5-(2-ethoxy-3-pyridyl)-1-isopropyl-N-[(6-methoxypyrazin-2-yl)methyl]-3-methyl-pyrazolo[4,3-b]pyridin-7-amine;
83: 5-(2-ethoxy-3-pyridyl)-N-[(5-fluoropyrimidin-2-yl)methyl]-1-isopropyl-3-methyl-pyrazolo[4,3-b]pyridin-7-amine;
84: 5-(2-ethoxy-3-pyridyl)-1-isopropyl-3-methyl-N-[(2-methyl-3-pyridyl)methyl]pyrazolo[4,3-b]pyridin-7-amine;
85: 5-(2-ethoxy-3-pyridyl)-N-[(2-fluoro-3-pyridyl)methyl]-1-isopropyl-3-methyl-pyrazolo[4,3-b]pyridin-7-amine;
86: 5-(2-ethoxy-3-pyridyl)-1-isopropyl-N-[(2-methoxy-3-pyridyl)methyl]-3-methyl-pyrazolo[4,3-b]pyridin-7-amine;
87: 5-(2-ethoxy-3-pyridyl)-1-isopropyl-3-methyl-N-[(6-methyl-3-pyridyl)methyl]pyrazolo[4,3-b]pyridin-7-amine;
88: 5-(2-ethoxy-3-pyridyl)-1-isopropyl-N-[(2-methoxyphenyl)methyl]-3-methyl-pyrazolo[4,3-b]pyridin-7-amine;
89: 5-(2-ethoxy-3-pyridyl)-N-[(2-fluorophenyl)methyl]-1-isopropyl-3-methyl-pyrazolo[4,3-b]pyridin-7-amine;
90: 5-(2-ethoxy-3-pyridyl)-1-isopropyl-3-methyl-N-[[2-(trifluoromethyl)phenyl]methyl]pyrazolo[4,3-b]pyridin-7-amine;
91: 5-(2-ethoxy-3-pyridyl)-1-isopropyl-N-[(3-methoxypyrazin-2-yl)methyl]-3-methyl-pyrazolo[4,3-b]pyridin-7-amine;
92: 5-(2-ethoxy-3-pyridyl)-1-isopropyl-N-[(4-methoxy-3-pyridyl)methyl]-3-methyl-pyrazolo[4,3-b]pyridin-7-amine;
93: 1-isopropyl-3-methyl-N-[(2-methyltetrazol-5-yl)methyl]-5-(2-propoxy-3-pyridyl)pyrazolo[4,3-b]pyridin-7-amine;
94: 1-isopropyl-3-methyl-N-[(1-methylpyrazol-4-yl)methyl]-5-(2-propoxy-3-pyridyl)pyrazolo[4,3-b]pyridin-7-amine;
95: 1-isopropyl-5-(2-methoxy-3-pyridyl)-N-[(2-methoxy-3-pyridyl)methyl]-3-methyl-pyrazolo[4,3-b]pyridin-7-amine;
96: 1-isopropyl-5-(2-methoxy-3-pyridyl)-N-[(6-methoxy-3-pyridyl)methyl]-3-methyl-pyrazolo[4,3-b]pyridin-7-amine;
97: 5-(2-isopropoxy-3-pyridyl)-1-isopropyl-3-methyl-N-[(1-methylpyrazol-4-yl)methyl]pyrazolo[4,3-b]pyridin-7-amine;
98: 5-(2-ethoxy-3-pyridyl)-1-isopropyl-3-methyl-N-(1H-1,2,4-triazol-3-ylmethyl)pyrazolo[4,3-b]pyridin-7-amine;
99: 5-(2-ethoxy-3-pyridyl)-1-isopropyl-3-methyl-N-(2H-tetrazol-5-ylmethyl)pyrazolo[4,3-b]pyridin-7-amine;
100: 5-(2-ethoxy-3-pyridyl)-1-isopropyl-3-methyl-N-(2-pyridylmethyl)pyrazolo[4,3-b]pyridin-7-amine;

101: 5-(2-ethoxy-3-pyridyl)-1-isopropyl-3-methyl-N-[(6-methyl-2-pyridyl)methyl]pyrazolo[4,3-b]pyridin-7-amine;
102: 5-(2-ethoxy-3-pyridyl)-1-isopropyl-N-[(6-methoxy-2-pyridyl)methyl]-3-methyl-pyrazolo[4,3-b]pyridin-7-amine;
103: 5-(2-ethoxy-3-pyridyl)-1-isopropyl-3-methyl-N-[(2-methyl-4-pyridyl)methyl]pyrazolo[4,3-b]pyridin-7-amine;
104: 5-(2-ethoxy-3-pyridyl)-1-isopropyl-N-[(2-methoxy-4-pyridyl)methyl]-3-methyl-pyrazolo[4,3-b]pyridin-7-amine;
105: 5-(2-ethoxy-3-pyridyl)-1-isopropyl-3-methyl-N-[(2-methylpyrimidin-4-yl)methyl]pyrazolo[4,3-b]pyridin-7-amine;
106: 5-(2-ethoxy-3-pyridyl)-1-isopropyl-N-[(5-methoxy-2-pyridyl)methyl]-3-methyl-pyrazolo[4,3-b]pyridin-7-amine;
107: 5-(2-ethoxy-3-pyridyl)-1-isopropyl-3-methyl-N-[[6-(trifluoromethyl)-2-pyridyl]methyl]pyrazolo[4,3-b]pyridin-7-amine;
108: 3-[[[5-(2-ethoxy-3-pyridyl)-1-isopropyl-3-methyl-pyrazolo[4,3-b]pyridin-7-yl]amino]methyl]-1-methyl-pyridin-2-one;
109: 5-(2-ethoxy-3-pyridyl)-N-[(1-ethylpyrazol-4-yl)methyl]-1-isopropyl-3-methyl-pyrazolo[4,3-b]pyridin-7-amine;
110: 5-(2-ethoxy-3-pyridyl)-1-isopropyl-3-methyl-N-[(1-propylpyrazol-4-yl)methyl]pyrazolo[4,3-b]pyridin-7-amine;
111: 5-(2-ethoxy-3-pyridyl)-1-isopropyl-N-[(6-methoxy-3-pyridyl)methyl]-3-methyl-pyrazolo[4,3-b]pyridin-7-amine;
112: 5-(2-ethoxy-3-pyridyl)-1-isopropyl-N-[(5-methoxy-2-pyridyl)methyl]-3-methyl-pyrazolo[4,3-b]pyridin-7-amine;
113: 5-(2-ethoxy-3-pyridyl)-3-methyl-N-[(2-methylthiazol-4-yl)methyl]-1-(oxetan-3-yl)pyrazolo[4,3-b]pyridin-7-amine;
114: 5-(2-ethoxy-3-pyridyl)-1-isopropyl-N-[(5-methoxy-pyrazin-2-yl)methyl]-3-methyl-pyrazolo[4,3-b]pyridin-7-amine;
115: 5-(2-ethoxy-3-pyridyl)-1-isopropyl-3-methyl-N-(3-pyridylmethyl)pyrazolo[4,3-b]pyridin-7-amine;
116: 5-(2-ethoxy-3-pyridyl)-N-[(6-fluoro-3-pyridyl)methyl]-1-isopropyl-3-methyl-pyrazolo[4,3-b]pyridin-7-amine;
117: N-[[6-(difluoromethyl)-3-pyridyl]methyl]-5-(2-ethoxy-3-pyridyl)-1-isopropyl-3-methyl-pyrazolo[4,3-b]pyridin-7-amine;
118: 5-(2-ethoxy-3-pyridyl)-1-isopropyl-N-[(3-methoxy-2-pyridyl)methyl]-3-methyl-pyrazolo[4,3-b]pyridin-7-amine;
119: 5-(2-ethoxy-3-pyridyl)-3-methyl-1-[1-methylpropyl]-N-(1H-pyrazol-3-ylmethyl)pyrazolo[4,3-b]pyridin-7-amine, enantiomer 1;
120: 5-(2-ethoxy-3-pyridyl)-3-methyl-1-[1-methylpropyl]-N-(1H-pyrazol-3-ylmethyl)pyrazolo[4,3-b]pyridin-7-amine, enantiomer 2;
121: 5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine, enantiomer 1;
122: 5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine, enantiomer 2;
123: 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, enantiomer 1;
124: 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, enantiomer 2;
125: 5-(2-ethoxy-3-pyridyl)-N-[(5-methoxy-3-pyridyl)methyl]-3-methyl-1-[1-methylpropyl]pyrazolo[4,3-b]pyridin-7-amine, enantiomer 2;
126: 5-(2-ethoxy-3-pyridyl)-N-[(2-methoxy-4-pyridyl)methyl]-3-methyl-1-[1-methylpropyl]pyrazolo[4,3-b]pyridin-7-amine, enantiomer 2;
127: 5-(2-ethoxy-3-pyridyl)-3-methyl-1-[1-methylpropyl]-N-[(2-methyltetrazol-5-yl)methyl]pyrazolo[4,3-b]pyridin-7-amine, enantiomer 2;
128: 5-(2-ethoxy-3-pyridyl)-3-methyl-N-[(5-methyl-1,2,4-oxadiazol-3-yl)methyl]-1-[1-methylpropyl]pyrazolo[4,3-b]pyridin-7-amine, enantiomer 2;
129: 5-(2-ethoxy-3-pyridyl)-3-methyl-N-[(2-methyloxazol-4-yl)methyl]-1-[1-methylpropyl]pyrazolo[4,3-b]pyridin-7-amine, enantiomer 2;
130: 5-(2-ethoxy-3-pyridyl)-N-(1H-imidazol-4-ylmethyl)-3-methyl-1-[1-methylpropyl]pyrazolo[4,3-b]pyridin-7-amine, enantiomer 2;
131: 5-(2-ethoxy-3-pyridyl)-3-methyl-1-[1-methylpropyl]-N-[(5-methyl-1H-pyrazol-3-yl)methyl]pyrazolo[4,3-b]pyridin-7-amine, enantiomer 2;
132: 5-(2-ethoxy-3-pyridyl)-3-methyl-N-[(1-methylimidazol-4-yl)methyl]-1-[1-methylpropyl]pyrazolo[4,3-b]pyridin-7-amine, enantiomer 2;
133: 5-(2-ethoxy-3-pyridyl)-3-methyl-N-[(2-methyloxazol-5-yl)methyl]-1-[1-methylpropyl]pyrazolo[4,3-b]pyridin-7-amine, enantiomer 2;
134: 3-methyl-1-[1-methylpropyl]-N-[(1-methyl-1,2,4-triazol-3-yl)methyl]-5-(2-propoxy-3-pyridyl)pyrazolo[4,3-b]pyridin-7-amine, enantiomer 2;
135: 3-methyl-1-[1-methylpropyl]-5-(2-propoxy-3-pyridyl)-N-(1H-pyrazol-3-ylmethyl)pyrazolo[4,3-b]pyridin-7-amine, enantiomer 2;
136: 5-(2-ethoxy-3-pyridyl)-1-[1-methylpropyl]-N-(1H-pyrazol-3-ylmethyl)pyrazolo[4,3-b]pyridin-7-amine, enantiomer 1;
137: 5-(2-ethoxy-3-pyridyl)-1-[1-methylpropyl]-N-(1H-pyrazol-3-ylmethyl)pyrazolo[4,3-b]pyridin-7-amine, enantiomer 2;
138: 5-(2-ethoxy-3-pyridyl)-N-[(5-methyl-1,3,4-oxadiazol-2-yl)methyl]-1-[1-methylpropyl]pyrazolo[4,3-b]pyridin-7-amine, enantiomer 1;
139: 5-(2-ethoxy-3-pyridyl)-N-[(5-methyl-1,3,4-oxadiazol-2-yl)methyl]-1-[1-methylpropyl]pyrazolo[4,3-b]pyridin-7-amine, enantiomer 2;
140: 5-(2-ethoxy-3-pyridyl)-1-[1-methylpropyl]-N-[(1-methyl-1,2,4-triazol-3-yl)methyl]pyrazolo[4,3-b]pyridin-7-amine, enantiomer 1;
141: 5-(2-ethoxy-3-pyridyl)-1-[1-methylpropyl]-N-[(1-methyl-1,2,4-triazol-3-yl)methyl]pyrazolo[4,3-b]pyridin-7-amine, enantiomer 2;
142: 1-isopropyl-3-methyl-N-[(1-methylimidazol-4-yl)methyl]-5-(2-propoxy-3-pyridyl)pyrazolo[4,3-b]pyridin-7-amine;
143: 1-isopropyl-3-methyl-5-(2-propoxy-3-pyridyl)-N-(1H-pyrazol-3-ylmethyl)pyrazolo[4,3-b]pyridin-7-amine;
144: 5-(2-ethoxy-3-pyridyl)-3-methyl-1-[1-methylpropyl]-N-(1H-1,2,4-triazol-3-ylmethyl)pyrazolo[4,3-b]pyridin-7-amine, enantiomer 2;

145: 1-isopropyl-3-methyl-N-[(1-methyl-1,2,4-triazol-3-yl)methyl]-5-(2-propoxy-3-pyridyl)pyrazolo[4,3-b]pyridin-7-amine;
146: 1-isopropyl-3-methyl-5-(2-propoxy-3-pyridyl)-N-(1H-1,2,4-triazol-3-ylmethyl)pyrazolo[4,3-b]pyridin-7-amine;
147: 1-isopropyl-3-methyl-N-[(1-methylpyrazol-4-yl)methyl]-5-thiazol-2-yl-pyrazolo[4,3-b]pyridin-7-amine;
148: 1-isopropyl-3-methyl-N-[(1-methylpyrazol-4-yl)methyl]-5-(5-methylthiazol-2-yl)pyrazolo[4,3-b]pyridin-7-amine;
149: 1-isopropyl-3-methyl-N-[(1-methylpyrazol-4-yl)methyl]-5-(4-methylthiazol-2-yl)pyrazolo[4,3-b]pyridin-7-amine;
150: 3-[1-isopropyl-3-methyl-7-[(1-methylpyrazol-4-yl)methylamino]pyrazolo[4,3-b]pyridin-5-yl]-5-methyl-oxazolidin-2-one;
151: 3-[1-isopropyl-3-methyl-7-[(1-methylpyrazol-4-yl)methylamino]pyrazolo[4,3-b]pyridin-5-yl]oxazolidin-2-one;
152: 1-[1-isopropyl-3-methyl-7-[(1-methylpyrazol-4-yl)methylamino]pyrazolo[4,3-b]pyridin-5-yl]azetidin-2-one;
153: 1-tert-butyl-3-[1-isopropyl-3-methyl-7-[(1-methylpyrazol-4-yl)methylamino]pyrazolo[4,3-b]pyridin-5-yl]imidazolidin-2-one;
154: 1-[1-isopropyl-3-methyl-7-[(1-methylpyrazol-4-yl)methylamino]pyrazolo[4,3-b]pyridin-5-yl]pyrrolidin-2-one;
155: 3-[1-isopropyl-3-methyl-7-[(1-methylpyrazol-4-yl)methylamino]pyrazolo[4,3-b]pyridin-5-yl]-4-methyl-oxazolidin-2-one;
156: 4-ethyl-3-[1-isopropyl-3-methyl-7-[(1-methylpyrazol-4-yl)methylamino]pyrazolo[4,3-b]pyridin-5-yl]oxazolidin-2-one;
157: N-[[5-(2-ethoxy-3-pyridyl)-1-isopropyl-3-methyl-pyrazolo[4,3-b]pyridin-7-yl]methyl]-5-methoxy-pyridin-3-amine;
158: N-[[5-(2-ethoxy-3-pyridyl)-1-isopropyl-3-methyl-pyrazolo[4,3-b]pyridin-7-yl]methyl]-1-methyl-1,2,4-triazol-3-amine;
159: 5-(2-ethoxy-3-pyridyl)-1-isopropyl-7-[2-(5-methoxy-3-pyridyl)ethyl]-3-methyl-pyrazolo[4,3-b]pyridine;
160: 5-(2-ethoxy-3-pyridyl)-1-isopropyl-3-methyl-7-[2-(1-methyl-1,2,4-triazol-3-yl)ethyl]pyrazolo[4,3-b]pyridine;
161: 5-(2-ethoxy-3-pyridyl)-1-isopropyl-3-methyl-N-[(2-methyl-1,2,4-triazol-3-yl)methyl]pyrazolo[4,3-b]pyridin-7-amine;
162: 5-(2-ethoxy-3-pyridyl)-1-isopropyl-3-methyl-N-[(4-methyl-1,2,4-triazol-3-yl)methyl]pyrazolo[4,3-b]pyridin-7-amine;
163: 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine;
164: 5-(2-ethoxy-3-pyridyl)-1-isopropyl-3-methyl-7-[(1-methylpyrazol-4-yl)methylsulfanyl]pyrazolo[4,3-b]pyridine;
165: N-[[1-(difluoromethyl)pyrazol-4-yl]methyl]-5-(2-ethoxy-3-pyridyl)-1-isopropyl-3-methyl-pyrazolo[4,3-b]pyridin-7-amine;
166: 5-(2-ethoxy-3-pyridyl)-N-[[5-(fluoromethyl)isoxazol-3-yl]methyl]-1-isopropyl-3-methyl-pyrazolo[4,3-b]pyridin-7-amine;
167: 5-(2-ethoxy-3-pyridyl)-N-[[3-(fluoromethyl)isoxazol-5-yl]methyl]-1-isopropyl-3-methyl-pyrazolo[4,3-b]pyridin-7-amine;
168: 1-isopropyl-3-methyl-N-[(1-methylpyrazol-4-yl)methyl]-5-oxazol-2-yl-pyrazolo[4,3-b]pyridin-7-amine;
169: 1-isopropyl-3-methyl-N-[(1-methylpyrazol-4-yl)methyl]-5-(3-methyltriazol-4-yl)pyrazolo[4,3-b]pyridin-7-amine;
170: 1-isopropyl-5-(2-methoxy-3-pyridyl)-3-methyl-N-[[2-(trifluoromethyl)-3-pyridyl]methyl]pyrazolo[4,3-b]pyridin-7-amine;
171: 3-[1-isopropyl-7-[(2-methoxy-3-pyridyl)methylamino]-3-methyl-pyrazolo[4,3-b]pyridin-5-yl]-1H-pyridin-2-one;
172: 5-(2-ethoxy-3-pyridyl)-1-isopropyl-N-[(3-methoxy-4-pyridyl)methyl]-3-methyl-pyrazolo[4,3-b]pyridin-7-amine;
173: 1-isopropyl-5-(2-methoxy-3-pyridyl)-3-methyl-N-[(2-methylthiazol-5-yl)methyl]pyrazolo[4,3-b]pyridin-7-amine;
174: 5-(2-cyclopropoxypyridin-3-yl)-1-isopropyl-N-((2-methoxypyridin-3-yl)methyl)-3-methyl-1H-pyrazolo[4,3-b]pyridin-7-amine;
175: 1-isopropyl-N-((2-methoxypyridin-3-yl)methyl)-3-methyl-5-(1-methyl-1H-pyrazol-5-yl)-1H-pyrazolo[4,3-b]pyridin-7-amine;
176: 5-(2-ethoxy-3-pyridyl)-1-isopropyl-N-[(5-methoxypyrimidin-2-yl)methyl]-3-methyl-pyrazolo[4,3-b]pyridin-7-amine;
177: 3-[1-isopropyl-3-methyl-7-[(1-methyl pyrazol-4-yl)methylamino]pyrazolo[4,3-b]pyridin-5-yl]-1H-pyridin-2-one;
178: N-[[2-(difluoromethyl)-3-pyridyl]methyl]-5-(2-ethoxy-3-pyridyl)-1-isopropyl-3-methyl-pyrazolo[4,3-b]pyridin-7-amine;
179: 5-(2-ethoxy-3-pyridyl)-1-isopropyl-N-[(6-methoxypyrimidin-4-yl)methyl]-3-methyl-pyrazolo[4,3-b]pyridin-7-amine;
180: 5-(2-(ethoxy-1,1-d$_2$)pyridin-3-yl)-1-isopropyl-N-((2-methoxypyridin-3-yl)methyl)-3-methyl-1H-pyrazolo[4,3-b]pyridin-7-amine;
181: 5-(2-(ethoxy-d$_5$)pyridin-3-yl)-1-isopropyl-N-((2-methoxypyridin-3-yl)methyl)-3-methyl-1H-pyrazolo[4,3-b]pyridin-7-amine;
182: 5-(2-(ethoxy-2,2,2-d$_3$)pyridin-3-yl)-1-isopropyl-N-((2-methoxypyridin-3-yl)methyl)-3-methyl-1H-pyrazolo[4,3-b]pyridin-7-amine;
183: 1-isopropyl-N-((2-methoxypyridin-3-yl)methyl)-3-methyl-5-(2-(trifluoromethyl)pyridin-3-yl)-1H-pyrazolo[4,3-b]pyridin-7-amine;
184: 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine;
185: 1-isopropyl-3-methyl-N-((1-methyl-1H-pyrazol-4-yl)methyl)-5-(1H-1,2,4-triazol-1-yl)-1H-pyrazolo[4,3-b]pyridin-7-amine;
186: 3-[1-isopropyl-3-methyl-7-[(1-methyl-1,2,4-triazol-3-yl)methylamino]pyrazolo[4,3-b]pyridin-5-yl]-1H-pyridin-2-one;
187: 3-[1-isopropyl-3-methyl-7-(1H-pyrazol-3-ylmethylamino)pyrazolo[4,3-b]pyridin-5-yl]-1H-pyridin-2-one;
188: 5-[2-(difluoromethoxy)-3-pyridyl]-1-isopropyl-N-[(2-methoxy-3-pyridyl)methyl]-3-methyl-pyrazolo[4,3-b]pyridin-7-amine;
189: 5-(2-ethoxy-3-pyridyl)-1-isopropyl-N-[(4-methoxypyrimidin-2-yl)methyl]-3-methyl-pyrazolo[4,3-b]pyridin-7-amine;
190: 5-(2-ethoxy-3-pyridyl)-1-isopropyl-N-[(4-methoxypyrimidin-5-yl)methyl]-3-methyl-pyrazolo[4,3-b]pyridin-7-amine;

191: 5-(2-ethoxy-3-pyridyl)-N-[(2-ethoxy-3-pyridyl)methyl]-1-isopropyl-3-methyl-pyrazolo[4,3-b]pyridin-7-amine;
192: 5-[2-(dimethylamino)-3-pyridyl]-1-isopropyl-N-[(4-methoxyphenyl)methyl]-3-methyl-pyrazolo[4,3-b]pyridin-7-amine;
193: 3-[1-isopropyl-3-methyl-7-[[2-(trifluoromethyl)-3-pyridyl]methylamino]pyrazolo[4,3-b]pyridin-5-yl]-1H-pyridin-2-one;
194: 1-isopropyl-3-methyl-5-(3-methylisoxazol-4-yl)-N-[(1-methyl pyrazol-4-yl)methyl]pyrazolo[4,3-b]pyridin-7-amine;
195: 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine;
196: 1-isopropyl-3-methyl-5-(2-propoxy-3-pyridyl)-N-(1H-pyrazol-4-ylmethyl)pyrazolo[4,3-b]pyridin-7-amine;
197: 5-(2-ethoxy-3-pyridyl)-N-[(2-methoxy-3-pyridyl)methyl]-3-methyl-1-(oxetan-3-yl)pyrazolo[4,3-b]pyridin-7-amine;
198: 5-(2-(ethyl(methyl)amino)pyridin-3-yl)-1-isopropyl-N-(4-methoxybenzyl)-3-methyl-1H-pyrazolo[4,3-b]pyridin-7-amine;
199: 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine;
200: 1-isopropyl-3-methyl-N-((1-methyl-1H-pyrazol-4-yl)methyl)-5-(4-methyloxazol-5-yl)-1H-pyrazolo[4,3-b]pyridin-7-amine;
201: 5-[2-(dimethylamino)-3-pyridyl]-1-isopropyl-3-methyl-N-[(1-methylpyrazol-4-yl)methyl]pyrazolo[4,3-b]pyridin-7-amine;
202: 1-isopropyl-3-methyl-N-((1-methyl-1H-pyrazol-4-yl)methyl)-5-(4-methyloxazol-2-yl)-1H-pyrazolo[4,3-b]pyridin-7-amine;
203: 1-isopropyl-3-methyl-N-[(1-methylpyrazol-4-yl)methyl]-5-(4-methyl-1,2,4-triazol-3-yl)pyrazolo[4,3-b]pyridin-7-amine;
and pharmaceutically acceptable salts of any of these compounds.

E28. The compound according to embodiment 1, wherein the compound is selected from the group consisting of:
1: 5-(2-ethoxy-3-pyridyl)-1-isopropyl-3-methyl-N-[(5-methyl-1,3,4-oxadiazol-2-yl)methyl]pyrazolo[4,3-b]pyridin-7-amine;
2: 5-(2-ethoxy-3-pyridyl)-1-isopropyl-3-methyl-N-[(5-methylthiazol-2-yl)methyl]pyrazolo[4,3-b]pyridin-7-amine;
3: 5-(2-ethoxy-3-pyridyl)-1-isopropyl-3-methyl-N-[(5-methylisoxazol-3-yl)methyl]pyrazolo[4,3-b]pyridin-7-amine;
4: 5-(2-ethoxy-3-pyridyl)-1-isopropyl-3-methyl-N-[(2-methyloxazol-5-yl)methyl]pyrazolo[4,3-b]pyridin-7-amine;
5: 5-(2-ethoxy-3-pyridyl)-1-isopropyl-3-methyl-N-[(2-methyltriazol-4-yl)methyl]pyrazolo[4,3-b]pyridin-7-amine;
6: 5-(2-ethoxy-3-pyridyl)-1-isopropyl-3-methyl-N-[(1-methyltriazol-4-yl)methyl]pyrazolo[4,3-b]pyridin-7-amine;
7: 5-(2-ethoxy-3-pyridyl)-1-isopropyl-3-methyl-N-(1H-pyrazol-4-ylmethyl)pyrazolo[4,3-b]pyridin-7-amine;
8: 5-(2-ethoxy-3-pyridyl)-1-isopropyl-3-methyl-N-[(2-methyltetrazol-5-yl)methyl]pyrazolo[4,3-b]pyridin-7-amine;
9: 5-(2-ethoxypyridin-3-yl)-1-isopropyl-3-methyl-N-((1-methyl-1H-pyrazol-4-yl)methyl)-1H-pyrazolo[4,3-b]pyridin-7-amine;
10: 5-(2-ethoxy-3-pyridyl)-1-isopropyl-3-methyl-N-[(3-methylisoxazol-5-yl)methyl]pyrazolo[4,3-b]pyridin-7-amine;
11: 5-(2-ethoxy-3-pyridyl)-1-isopropyl-3-methyl-N-[(2-methylthiazol-4-yl)methyl]pyrazolo[4,3-b]pyridin-7-amine;
12: 1-cyclopropyl-5-(2-ethoxy-3-pyridyl)-3-methyl-N-[(1-methyl pyrazol-4-yl)methyl]pyrazolo[4,3-b]pyridin-7-amine;
13: 5-(2-ethoxy-3-pyridyl)-N-[(1-methylpyrazol-4-yl)methyl]-1-propyl-pyrazolo[4,3-b]pyridin-7-amine;
14: 5-(2-ethoxypyridin-3-yl)-N-((1-methyl-1H-pyrazol-4-yl)methyl)-1-(oxetan-3-yl)-1H-pyrazolo[4,3-b]pyridin-7-amine;
15: 5-(2-ethoxypyridin-3-yl)-1-methyl-N-(1-(1-methyl-1H-pyrazol-4-yl)ethyl)-1H-pyrazolo[4,3-b]pyridin-7-amine (racemic);
15a: (R)-5-(2-ethoxypyridin-3-yl)-1-methyl-N-(1-(1-methyl-1H-pyrazol-4-yl)ethyl)-1H-pyrazolo[4,3-b]pyridin-7-amine;
15b: (S)-5-(2-ethoxypyridin-3-yl)-1-methyl-N-(1-(1-methyl-1H-pyrazol-4-yl)ethyl)-1H-pyrazolo[4,3-b]pyridin-7-amine;
16: 5-(2-ethoxypyridin-3-yl)-1-methyl-N-((1-methyl-1H-pyrazol-4-yl)methyl)-1H-pyrazolo[4,3-b]pyridin-7-amine;
17: 5-(2-ethoxy-3-pyridyl)-1-isopropyl-N-[(1-methylimidazol-2-yl)methyl]pyrazolo[4,3-b]pyridin-7-amine;
18: 5-(2-ethoxypyridin-3-yl)-1-isopropyl-N-((1-methyl-1H-pyrazol-5-yl)methyl)-1H-pyrazolo[4,3-b]pyridin-7-amine;
19: 5-(2-ethoxypyridin-3-yl)-1-isopropyl-N-((1-methyl-1H-pyrazol-3-yl)methyl)-1H-pyrazolo[4,3-b]pyridin-7-amine;
20: 5-(2-ethoxy-3-pyridyl)-1-isopropyl-N-(thiazol-2-ylmethyl)pyrazolo[4,3-b]pyridin-7-amine;
21: 5-(2-ethoxy-3-pyridyl)-1-isopropyl-N-[(1-methylimidazol-4-yl)methyl]pyrazolo[4,3-b]pyridin-7-amine;
22: 5-(2-ethoxy-3-pyridyl)-1-isopropyl-N-(4-pyridylmethyl)pyrazolo[4,3-b]pyridin-7-amine;
23: 5-(2-ethoxy-3-pyridyl)-1-isopropyl-N-(m-tolylmethyl)pyrazolo[4,3-b]pyridin-7-amine;
24: 5-(2-ethoxy-3-pyridyl)-1-isopropyl-N-(p-tolylmethyl)pyrazolo[4,3-b]pyridin-7-amine;
25: 5-(2-ethoxy-3-pyridyl)-1-isopropyl-N-[(1-methylpyrazol-4-yl)methyl]pyrazolo[4,3-b]pyridin-7-amine;
26: 5-(2-ethoxy-3-pyridyl)-1-ethyl-N-[(1-methylpyrazol-4-yl)methyl]pyrazolo[4,3-b]pyridin-7-amine;
27: 5-(2-ethoxy-3-pyridyl)-3-methyl-N-[(1-methylpyrazol-4-yl)methyl]-1-(oxetan-3-yl)pyrazolo[4,3-b]pyridin-7-amine;
28: 5-(2-ethoxy-3-pyridyl)-1,3-dimethyl-N-[(1-methylpyrazol-4-yl)methyl]pyrazolo[4,3-b]pyridin-7-amine;
29: 5-(2-ethoxy-3-pyridyl)-1-isopropyl-3-methyl-N-[(4-methylthiazol-2-yl)methyl]pyrazolo[4,3-b]pyridin-7-amine;
30: 5-(2-ethoxy-3-pyridyl)-1-isopropyl-3-methyl-N-[(3-methyl-1,2,4-oxadiazol-5-yl)methyl]pyrazolo[4,3-b]pyridin-7-amine;
31: 5-(2-ethoxy-3-pyridyl)-1-isopropyl-3-methyl-N-[(1-methyl-1,2,4-triazol-3-yl)methyl]pyrazolo[4,3-b]pyridin-7-amine;

32: 5-(2-ethoxy-3-pyridyl)-1-isopropyl-3-methyl-N-[(2-methylthiazol-5-yl)methyl]pyrazolo[4,3-b]pyridin-7-amine;
33: 5-(2-ethoxy-3-pyridyl)-1-isopropyl-3-methyl-N-[(5-methyl-1,3,4-thiadiazol-2-yl)methyl]pyrazolo[4,3-b]pyridin-7-amine;
34: 5-(2-ethoxy-3-pyridyl)-1-isopropyl-3-methyl-N-[(5-methyl-3-thienyl)methyl]pyrazolo[4,3-b]pyridin-7-amine;
35: 5-(2-ethoxy-3-pyridyl)-1-isopropyl-3-methyl-N-[(4-methyl-2-thienyl)methyl]pyrazolo[4,3-b]pyridin-7-amine;
36: 5-(2-ethoxy-3-pyridyl)-1-isopropyl-3-methyl-N-[(5-methyl-2-thienyl)methyl]pyrazolo[4,3-b]pyridin-7-amine;
37: 5-(2-ethoxy-3-pyridyl)-1-isopropyl-3-methyl-N-[(2-methyloxazol-4-yl)methyl]pyrazolo[4,3-b]pyridin-7-amine;
38: 5-(2-ethoxy-3-pyridyl)-1-isopropyl-3-methyl-N-[(5-methyloxazol-2-yl)methyl]pyrazolo[4,3-b]pyridin-7-amine;
39: 5-(2-ethoxy-3-pyridyl)-1-isopropyl-3-methyl-N-(1H-pyrazol-3-ylmethyl)pyrazolo[4,3-b]pyridin-7-amine;
40: 5-(2-ethoxy-3-pyridyl)-N-(1H-imidazol-4-ylmethyl)-1-isopropyl-3-methyl-pyrazolo[4,3-b]pyridin-7-amine;
41: N-benzyl-5-(2-ethoxy-3-pyridyl)-1-isopropyl-pyrazolo[4,3-b]pyridin-7-amine;
42: 5-(2-ethoxy-3-pyridyl)-1-isopropyl-N-[(3-methylisoxazol-5-yl)methyl]pyrazolo[4,3-b]pyridin-7-amine;
43: 5-(2-ethoxy-3-pyridyl)-1-isopropyl-N-[(5-methyl-1,2,4-oxadiazol-3-yl)methyl]pyrazolo[4,3-b]pyridin-7-amine;
44: N-[(1,5-dimethylpyrazol-3-yl)methyl]-5-(2-ethoxy-3-pyridyl)-1-isopropyl-pyrazolo[4,3-b]pyridin-7-amine;
45: 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one;
46: 5-(2-ethoxypyridin-3-yl)-1-isopropyl-3-methyl-N-((2-methyl-1H-imidazol-4-yl)methyl)-1H-pyrazolo[4,3-b]pyridin-7-amine;
47: 5-(2-ethoxypyridin-3-yl)-1-isopropyl-3-methyl-N-((5-methyl-1H-pyrazol-3-yl)methyl)-1H-pyrazolo[4,3-b]pyridin-7-amine;
48: 5-(2-ethoxypyridin-3-yl)-1-ethyl-3-methyl-N-((1-methyl-1H-pyrazol-4-yl)methyl)-1H-pyrazolo[4,3-b]pyridin-7-amine;
49: 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one;
50: 5-(2-ethoxypyridin-3-yl)-1-isopropyl-3-methyl-N-((4-methyloxazol-2-yl)methyl)-1H-pyrazolo[4,3-b]pyridin-7-amine;
51: N-((1,2-dimethyl-1H-imidazol-4-yl)methyl)-5-(2-ethoxypyridin-3-yl)-1-isopropyl-3-methyl-1H-pyrazolo[4,3-b]pyridin-7-amine;
52: 5-(2-ethoxy-3-pyridyl)-1-isopropyl-3-methyl-N-[(5-methyl-1,2,4-oxadiazol-3-yl)methyl]pyrazolo[4,3-b]pyridin-7-amine;
53: 5-(2-ethoxy-3-pyridyl)-1-isopropyl-3-methyl-N-(1,2,4-oxadiazol-3-ylmethyl)pyrazolo[4,3-b]pyridin-7-amine;
54: N-[(1,5-dimethylpyrazol-3-yl)methyl]-5-(2-ethoxy-3-pyridyl)-1-isopropyl-3-methyl-pyrazolo[4,3-b]pyridin-7-amine;
55: 5-(2-ethoxy-3-pyridyl)-1-isopropyl-3-methyl-N-[(5-methyl-1H-1,2,4-triazol-3-yl)methyl]pyrazolo[4,3-b]pyridin-7-amine;
56: 5-(2-ethoxy-3-pyridyl)-1-isopropyl-N-[(1-methyl-1,2,4-triazol-3-yl)methyl]pyrazolo[4,3-b]pyridin-7-amine;
57: 5-(2-ethoxy-3-pyridyl)-1-isopropyl-N-(1H-pyrazol-3-ylmethyl)pyrazolo[4,3-b]pyridin-7-amine;
58: 5-(2-ethoxypyridin-3-yl)-1-isopropyl-3-methyl-N-((1-methyl-1H-imidazol-4-yl)methyl)-1H-pyrazolo[4,3-b]pyridin-7-amine 2,2,2-trifluoroacetate;
59: 5-(2-ethoxy-3-pyridyl)-1-isopropyl-3-methyl-N-(1,3,4-oxadiazol-2-ylmethyl)pyrazolo[4,3-b]pyridin-7-amine;
60: 5-(2-ethoxy-3-pyridyl)-1-isopropyl-3-methyl-N-[(1-methylpyrazol-3-yl)methyl]pyrazolo[4,3-b]pyridin-7-amine;
61: 5-(1,3-dimethylpyrazol-4-yl)-1-isopropyl-3-methyl-N-[(1-methylpyrazol-4-yl)methyl]pyrazolo[4,3-b]pyridin-7-amine;
62: 1-isopropyl-5-(2-methoxy-3-pyridyl)-3-methyl-N-[(1-methylpyrazol-4-yl)methyl]pyrazolo[4,3-b]pyridin-7-amine;
63: 1-isopropyl-5-(2-methoxyphenyl)-3-methyl-N-[(1-methylpyrazol-4-yl)methyl]pyrazolo[4,3-b]pyridin-7-amine;
64: 1-isopropyl-3-methyl-N-[(1-methylpyrazol-4-yl)methyl]-5-phenyl-pyrazolo[4,3-b]pyridin-7-amine;
65: 1-isopropyl-3-methyl-N-[(1-methylpyrazol-4-yl)methyl]-5-(2-methyl-3-thienyl)pyrazolo[4,3-b]pyridin-7-amine;
66: 5-(1,5-dimethylpyrazol-4-yl)-1-isopropyl-3-methyl-N-[(1-methylpyrazol-4-yl)methyl]pyrazolo[4,3-b]pyridin-7-amine;
67a: (R)-5-(2-ethoxy-3-pyridyl)-3-methyl-1-[1-methylpropyl]-N-[(1-methylpyrazol-3-yl)methyl]pyrazolo[4,3-b]pyridin-7-amine;
67b: (S)-5-(2-ethoxy-3-pyridyl)-3-methyl-1-[1-methylpropyl]-N-[(1-methylpyrazol-3-yl)methyl]pyrazolo[4,3-b]pyridin-7-amine;
68a: (R)-3-methyl-1-[1-methylpropyl]-N-[(2-methyltetrazol-5-yl)methyl]-5-(2-propoxy-3-pyridyl)pyrazolo[4,3-b]pyridin-7-amine;
68b: (S)-3-methyl-1-[1-methylpropyl]-N-[(2-methyltetrazol-5-yl)methyl]-5-(2-propoxy-3-pyridyl)pyrazolo[4,3-b]pyridin-7-amine;
69: (R)-5-(2-ethoxy-3-pyridyl)-1-[1-methylpropyl]-N-[(1-methylpyrazol-4-yl)methyl]pyrazolo[4,3-b]pyridin-7-amine or (S)-5-(2-ethoxy-3-pyridyl)-1-[1-methyl propyl]-N-[(1-methylpyrazol-4-yl)methyl]pyrazolo[4,3-b]pyridin-7-amine;
70: (R)-5-(2-ethoxy-3-pyridyl)-1-[1-methylpropyl]-N-[(1-methylpyrazol-4-yl)methyl]pyrazolo[4,3-b]pyridin-7-amine or (S)-5-(2-ethoxy-3-pyridyl)-1-[1-methylpropyl]-N-[(1-methylpyrazol-4-yl)methyl]pyrazolo[4,3-b]pyridin-7-amine;
71: 5-(2-ethoxy-3-pyridyl)-1-isopropyl-N-[(4-methylthiazol-5-yl)methyl]pyrazolo[4,3-b]pyridin-7-amine;
72: 5-[[5-(2-ethoxy-3-pyridyl)-1-isopropyl-3-methyl-pyrazolo[4,3-b]pyridin-7-yl]oxymethyl]-2-methyl-oxazole;
73: 5-(2-ethoxy-3-pyridyl)-1-isopropyl-3-methyl-N-(pyrimidin-4-ylmethyl)pyrazolo[4,3-b]pyridin-7-amine;
74: 5-(2-ethoxy-3-pyridyl)-1-isopropyl-3-methyl-N-(pyrimidin-2-ylmethyl)pyrazolo[4,3-b]pyridin-7-amine;
75: 5-(2-ethoxy-3-pyridyl)-1-isopropyl-3-methyl-N-[(4-methylpyrimidin-2-yl)methyl]pyrazolo[4,3-b]pyridin-7-amine;
76: 5-(2-ethoxy-3-pyridyl)-1-isopropyl-3-methyl-N-(pyrazin-2-ylmethyl)pyrazolo[4,3-b]pyridin-7-amine;
77: 5-(2-ethoxy-3-pyridyl)-1-isopropyl-3-methyl-N-[[2-(trifluoromethyl)-3-pyridyl]methyl]pyrazolo[4,3-b]pyridin-7-amine;

78: 4-[[[5-(2-ethoxy-3-pyridyl)-1-isopropyl-3-methyl-pyrazolo[4,3-b]pyridin-7-yl]amino]methyl]-1-methyl-pyridin-2-one;
79: 5-(2-(ethylamino)pyridin-3-yl)-1-isopropyl-3-methyl-N-((1-methyl-1H-pyrazol-4-yl)methyl)-1H-pyrazolo[4,3-b]pyridin-7-amine;
81: 5-(2-ethoxy-3-pyridyl)-1-isopropyl-N-[(4-methoxy-2-pyridyl)methyl]-3-methyl-pyrazolo[4,3-b]pyridin-7-amine;
82: 5-(2-ethoxy-3-pyridyl)-1-isopropyl-N-[(6-methoxy-pyrazin-2-yl)methyl]-3-methyl-pyrazolo[4,3-b]pyridin-7-amine;
83: 5-(2-ethoxy-3-pyridyl)-N-[(5-fluoropyrimidin-2-yl)methyl]-1-isopropyl-3-methyl-pyrazolo[4,3-b]pyridin-7-amine;
84: 5-(2-ethoxy-3-pyridyl)-1-isopropyl-3-methyl-N-[(2-methyl-3-pyridyl)methyl]pyrazolo[4,3-b]pyridin-7-amine;
85: 5-(2-ethoxy-3-pyridyl)-N-[(2-fluoro-3-pyridyl)methyl]-1-isopropyl-3-methyl-pyrazolo[4,3-b]pyridin-7-amine;
86: 5-(2-ethoxy-3-pyridyl)-1-isopropyl-N-[(2-methoxy-3-pyridyl)methyl]-3-methyl-pyrazolo[4,3-b]pyridin-7-amine;
87: 5-(2-ethoxy-3-pyridyl)-1-isopropyl-3-methyl-N-[(6-methyl-3-pyridyl)methyl]pyrazolo[4,3-b]pyridin-7-amine;
88: 5-(2-ethoxy-3-pyridyl)-1-isopropyl-N-[(2-methoxyphenyl)methyl]-3-methyl-pyrazolo[4,3-b]pyridin-7-amine;
89: 5-(2-ethoxy-3-pyridyl)-N-[(2-fluorophenyl)methyl]-1-isopropyl-3-methyl-pyrazolo[4,3-b]pyridin-7-amine;
90: 5-(2-ethoxy-3-pyridyl)-1-isopropyl-3-methyl-N-[[2-(trifluoromethyl)phenyl]methyl]pyrazolo[4,3-b]pyridin-7-amine;
91: 5-(2-ethoxy-3-pyridyl)-1-isopropyl-N-[(3-methoxy-pyrazin-2-yl)methyl]-3-methyl-pyrazolo[4,3-b]pyridin-7-amine;
92: 5-(2-ethoxy-3-pyridyl)-1-isopropyl-N-[(4-methoxy-3-pyridyl)methyl]-3-methyl-pyrazolo[4,3-b]pyridin-7-amine;
93: 1-isopropyl-3-methyl-N-[(2-methyltetrazol-5-yl)methyl]-5-(2-propoxy-3-pyridyl)pyrazolo[4,3-b]pyridin-7-amine;
94: 1-isopropyl-3-methyl-N-[(1-methylpyrazol-4-yl)methyl]-5-(2-propoxy-3-pyridyl)pyrazolo[4,3-b]pyridin-7-amine;
95: 1-isopropyl-5-(2-methoxy-3-pyridyl)-N-[(2-methoxy-3-pyridyl)methyl]-3-methyl-pyrazolo[4,3-b]pyridin-7-amine;
96: 1-isopropyl-5-(2-methoxy-3-pyridyl)-N-[(6-methoxy-3-pyridyl)methyl]-3-methyl-pyrazolo[4,3-b]pyridin-7-amine;
97: 5-(2-isopropoxy-3-pyridyl)-1-isopropyl-3-methyl-N-[(1-methylpyrazol-4-yl)methyl]pyrazolo[4,3-b]pyridin-7-amine;
98: 5-(2-ethoxy-3-pyridyl)-1-isopropyl-3-methyl-N-(1H-1,2,4-triazol-3-ylmethyl)pyrazolo[4,3-b]pyridin-7-amine;
99: 5-(2-ethoxy-3-pyridyl)-1-isopropyl-3-methyl-N-(2H-tetrazol-5-ylmethyl)pyrazolo[4,3-b]pyridin-7-amine;
100: 5-(2-ethoxy-3-pyridyl)-1-isopropyl-3-methyl-N-(2-pyridylmethyl)pyrazolo[4,3-b]pyridin-7-amine;
101: 5-(2-ethoxy-3-pyridyl)-1-isopropyl-3-methyl-N-[(6-methyl-2-pyridyl)methyl]pyrazolo[4,3-b]pyridin-7-amine;
102: 5-(2-ethoxy-3-pyridyl)-1-isopropyl-N-[(6-methoxy-2-pyridyl)methyl]-3-methyl-pyrazolo[4,3-b]pyridin-7-amine;
103: 5-(2-ethoxy-3-pyridyl)-1-isopropyl-3-methyl-N-[(2-methyl-4-pyridyl)methyl]pyrazolo[4,3-b]pyridin-7-amine;
104: 5-(2-ethoxy-3-pyridyl)-1-isopropyl-N-[(2-methoxy-4-pyridyl)methyl]-3-methyl-pyrazolo[4,3-b]pyridin-7-amine;
105: 5-(2-ethoxy-3-pyridyl)-1-isopropyl-3-methyl-N-[(2-methylpyrimidin-4-yl)methyl]pyrazolo[4,3-b]pyridin-7-amine;
106: 5-(2-ethoxy-3-pyridyl)-1-isopropyl-N-[(5-methoxy-3-pyridyl)methyl]-3-methyl-pyrazolo[4,3-b]pyridin-7-amine;
107: 5-(2-ethoxy-3-pyridyl)-1-isopropyl-3-methyl-N-[[6-(trifluoromethyl)-2-pyridyl]methyl]pyrazolo[4,3-b]pyridin-7-amine;
108: 3-[[[5-(2-ethoxy-3-pyridyl)-1-isopropyl-3-methyl-pyrazolo[4,3-b]pyridin-7-yl]amino]methyl]-1-methyl-pyridin-2-one;
109: 5-(2-ethoxy-3-pyridyl)-N-[(1-ethylpyrazol-4-yl)methyl]-1-isopropyl-3-methyl-pyrazolo[4,3-b]pyridin-7-amine;
110: 5-(2-ethoxy-3-pyridyl)-1-isopropyl-3-methyl-N-[(1-propylpyrazol-4-yl)methyl]pyrazolo[4,3-b]pyridin-7-amine;
111: 5-(2-ethoxy-3-pyridyl)-1-isopropyl-N-[(6-methoxy-3-pyridyl)methyl]-3-methyl-pyrazolo[4,3-b]pyridin-7-amine;
112: 5-(2-ethoxy-3-pyridyl)-1-isopropyl-N-[(5-methoxy-2-pyridyl)methyl]-3-methyl-pyrazolo[4,3-b]pyridin-7-amine;
113: 5-(2-ethoxy-3-pyridyl)-3-methyl-N-[(2-methylthiazol-4-yl)methyl]-1-(oxetan-3-yl)pyrazolo[4,3-b]pyridin-7-amine;
114: 5-(2-ethoxy-3-pyridyl)-1-isopropyl-N-[(5-methoxy-pyrazin-2-yl)methyl]-3-methyl-pyrazolo[4,3-b]pyridin-7-amine;
115: 5-(2-ethoxy-3-pyridyl)-1-isopropyl-3-methyl-N-(3-pyridylmethyl)pyrazolo[4,3-b]pyridin-7-amine;
116: 5-(2-ethoxy-3-pyridyl)-N-[(6-fluoro-3-pyridyl)methyl]-1-isopropyl-3-methyl-pyrazolo[4,3-b]pyridin-7-amine;
117: N-[[6-(difluoromethyl)-3-pyridyl]methyl]-5-(2-ethoxy-3-pyridyl)-1-isopropyl-3-methyl-pyrazolo[4,3-b]pyridin-7-amine;
118: 5-(2-ethoxy-3-pyridyl)-1-isopropyl-N-[(3-methoxy-2-pyridyl)methyl]-3-methyl-pyrazolo[4,3-b]pyridin-7-amine;
119: (R)-5-(2-ethoxy-3-pyridyl)-3-methyl-1-[1-methylpropyl]-N-(1H-pyrazol-3-ylmethyl)pyrazolo[4,3-b]pyridin-7-amine or (S)-5-(2-ethoxy-3-pyridyl)-3-methyl-1-[1-methylpropyl]-N-(1H-pyrazol-3-ylmethyl)pyrazolo[4,3-b]pyridin-7-amine;
120: (R)-5-(2-ethoxy-3-pyridyl)-3-methyl-1-[1-methylpropyl]-N-(1H-pyrazol-3-ylmethyl)pyrazolo[4,3-b]pyridin-7-amine or (S)-5-(2-ethoxy-3-pyridyl)-3-methyl-1-[1-methylpropyl]-N-(1H-pyrazol-3-ylmethyl)pyrazolo[4,3-b]pyridin-7-amine;
121: (R)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-3-methyl-1-[1-methyl propyl]-N-[(1-methyl-1,2,4-triazol-3-yl)methyl]pyrazolo[4,3-b]pyridin-7-amine;
122: (R)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-3-methyl-1-[1-methyl propyl]-N-[(1-methyl-1,2,4-triazol-3-yl)methyl]pyrazolo[4,3-b]pyridin-7-amine;

123: (R)-5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine or (S)-5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine;

124: (R)-5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine or (S)-5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine;

125a: (R)-5-(2-ethoxy-3-pyridyl)-N-[(5-methoxy-3-pyridyl)methyl]-3-methyl-1-[1-methylpropyl]pyrazolo[4,3-b]pyridin-7-amine;

125b: (S)-5-(2-ethoxy-3-pyridyl)-N-[(5-methoxy-3-pyridyl)methyl]-3-methyl-1-[1-methylpropyl]pyrazolo[4,3-b]pyridin-7-amine;

126a: (R)-5-(2-ethoxy-3-pyridyl)-N-[(2-methoxy-4-pyridyl)methyl]-3-methyl-1-[1-methylpropyl]pyrazolo[4,3-b]pyridin-7-amine;

126b: (S)-5-(2-ethoxy-3-pyridyl)-N-[(2-methoxy-4-pyridyl)methyl]-3-methyl-1-[1-methylpropyl]pyrazolo[4,3-b]pyridin-7-amine;

127a: (R)-5-(2-ethoxy-3-pyridyl)-3-methyl-1-[1-methylpropyl]-N-[(2-methyltetrazol-5-yl)methyl]pyrazolo[4,3-b]pyridin-7-amine;

127b: (S)-5-(2-ethoxy-3-pyridyl)-3-methyl-1-[1-methylpropyl]-N-[(2-methyltetrazol-5-yl)methyl]pyrazolo[4,3-b]pyridin-7-amine;

128a: (R)-5-(2-ethoxy-3-pyridyl)-3-methyl-N-[(5-methyl-1,2,4-oxadiazol-3-yl)methyl]-1-[1-methylpropyl]pyrazolo[4,3-b]pyridin-7-amine;

128b: (S)-5-(2-ethoxy-3-pyridyl)-3-methyl-N-[(5-methyl-1,2,4-oxadiazol-3-yl)methyl]-1-[1-methylpropyl]pyrazolo[4,3-b]pyridin-7-amine;

129a: (R)-5-(2-ethoxy-3-pyridyl)-3-methyl-N-[(2-methyloxazol-4-yl)methyl]-1-[1-methylpropyl]pyrazolo[4,3-b]pyridin-7-amine;

129b: (S)-5-(2-ethoxy-3-pyridyl)-3-methyl-N-[(2-methyloxazol-4-yl)methyl]-1-[1-methylpropyl]pyrazolo[4,3-b]pyridin-7-amine;

130a: (R)-5-(2-ethoxy-3-pyridyl)-N-(1H-imidazol-4-ylmethyl)-3-methyl-1-[1-methylpropyl]pyrazolo[4,3-b]pyridin-7-amine;

130b: (S)-5-(2-ethoxy-3-pyridyl)-N-(1H-imidazol-4-ylmethyl)-3-methyl-1-[1-methylpropyl]pyrazolo[4,3-b]pyridin-7-amine;

131a: (R)-5-(2-ethoxy-3-pyridyl)-3-methyl-1-[1-methylpropyl]-N-[(5-methyl-1H-pyrazol-3-yl)methyl]pyrazolo[4,3-b]pyridin-7-amine;

131 b: (S)-5-(2-ethoxy-3-pyridyl)-3-methyl-1-[1-methylpropyl]-N-[(5-methyl-1H-pyrazol-3-yl)methyl]pyrazolo[4,3-b]pyridin-7-amine;

132a: (R)-5-(2-ethoxy-3-pyridyl)-3-methyl-N-[(1-methylimidazol-4-yl)methyl]-1-[1-methylpropyl]pyrazolo[4,3-b]pyridin-7-amine;

132b: (S)-5-(2-ethoxy-3-pyridyl)-3-methyl-N-[(1-methylimidazol-4-yl)methyl]-1-[1-methylpropyl]pyrazolo[4,3-b]pyridin-7-amine;

133a: (R)-5-(2-ethoxy-3-pyridyl)-3-methyl-N-[(2-methyloxazol-5-yl)methyl]-1-[1-methylpropyl]pyrazolo[4,3-b]pyridin-7-amine;

133b: (S)-5-(2-ethoxy-3-pyridyl)-3-methyl-N-[(2-methyloxazol-5-yl)methyl]-1-[1-methylpropyl]pyrazolo[4,3-b]pyridin-7-amine;

134a: (R)-3-methyl-1-[1-methylpropyl]-N-[(1-methyl-1,2,4-triazol-3-yl)methyl]-5-(2-propoxy-3-pyridyl)pyrazolo[4,3-b]pyridin-7-amine;

134b: (S)-3-methyl-1-[1-methylpropyl]-N-[(1-methyl-1,2,4-triazol-3-yl)methyl]-5-(2-propoxy-3-pyridyl)pyrazolo[4,3-b]pyridin-7-amine;

135a: (R)-3-methyl-1-[1-methylpropyl]-5-(2-propoxy-3-pyridyl)-N-(1H-pyrazol-3-ylmethyl)pyrazolo[4,3-b]pyridin-7-amine;

135b: (S)-3-methyl-1-[1-methylpropyl]-5-(2-propoxy-3-pyridyl)-N-(1H-pyrazol-3-ylmethyl)pyrazolo[4,3-b]pyridin-7-amine;

136: (R)-5-(2-ethoxy-3-pyridyl)-1-[1-methylpropyl]-N-(1H-pyrazol-3-ylmethyl)pyrazolo[4,3-b]pyridin-7-amine or (S)-5-(2-ethoxy-3-pyridyl)-1-[1-methylpropyl]-N-(1H-pyrazol-3-ylmethyl)pyrazolo[4,3-b]pyridin-7-amine;

137: (R)-5-(2-ethoxy-3-pyridyl)-1-[1-methylpropyl]-N-(1H-pyrazol-3-ylmethyl)pyrazolo[4,3-b]pyridin-7-amine or (S)-5-(2-ethoxy-3-pyridyl)-1-[1-methylpropyl]-N-(1H-pyrazol-3-ylmethyl)pyrazolo[4,3-b]pyridin-7-amine;

138: (R)-5-(2-ethoxy-3-pyridyl)-N-[(5-methyl-1,3,4-oxadiazol-2-yl)methyl]-1-[1-methylpropyl]pyrazolo[4,3-b]pyridin-7-amine or (S)-5-(2-ethoxy-3-pyridyl)-N-[(5-methyl-1,3,4-oxadiazol-2-yl)methyl]-1-[1-methylpropyl]pyrazolo[4,3-b]pyridin-7-amine;

139: (R)-5-(2-ethoxy-3-pyridyl)-N-[(5-methyl-1,3,4-oxadiazol-2-yl)methyl]-1-[1-methylpropyl]pyrazolo[4,3-b]pyridin-7-amine or (S)-5-(2-ethoxy-3-pyridyl)-N-[(5-methyl-1,3,4-oxadiazol-2-yl)methyl]-1-[1-methylpropyl]pyrazolo[4,3-b]pyridin-7-amine;

140: (R)-5-(2-ethoxy-3-pyridyl)-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-1-[1-methyl propyl]-N-[(1-methyl-1,2,4-triazol-3-yl)methyl]pyrazolo[4,3-b]pyridin-7-amine;

141: (R)-5-(2-ethoxy-3-pyridyl)-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-1-[1-methylpropyl]-N-[(1-methyl-1,2,4-triazol-3-yl)methyl]pyrazolo[4,3-b]pyridin-7-amine;

142: 1-isopropyl-3-methyl-N-[(1-methylimidazol-4-yl)methyl]-5-(2-propoxy-3-pyridyl)pyrazolo[4,3-b]pyridin-7-amine;

143: 1-isopropyl-3-methyl-5-(2-propoxy-3-pyridyl)-N-(1H-pyrazol-3-ylmethyl)pyrazolo[4,3-b]pyridin-7-amine;

144a: (R)-5-(2-ethoxy-3-pyridyl)-3-methyl-1-[1-methylpropyl]-N-(1H-1,2,4-triazol-3-ylmethyl)pyrazolo[4,3-b]pyridin-7-amine;

144b: (S)-5-(2-ethoxy-3-pyridyl)-3-methyl-1-[1-methylpropyl]-N-(1H-1,2,4-triazol-3-ylmethyl)pyrazolo[4,3-b]pyridin-7-amine;

145: 1-isopropyl-3-methyl-N-[(1-methyl-1,2,4-triazol-3-yl)methyl]-5-(2-propoxy-3-pyridyl)pyrazolo[4,3-b]pyridin-7-amine;

146: 1-isopropyl-3-methyl-5-(2-propoxy-3-pyridyl)-N-(1H-1,2,4-triazol-3-ylmethyl)pyrazolo[4,3-b]pyridin-7-amine;

147: 1-isopropyl-3-methyl-N-[(1-methylpyrazol-4-yl)methyl]-5-thiazol-2-yl-pyrazolo[4,3-b]pyridin-7-amine;

148: 1-isopropyl-3-methyl-N-[(1-methylpyrazol-4-yl)methyl]-5-(5-methylthiazol-2-yl)pyrazolo[4,3-b]pyridin-7-amine;

149: 1-isopropyl-3-methyl-N-[(1-methylpyrazol-4-yl)methyl]-5-(4-methylthiazol-2-yl)pyrazolo[4,3-b]pyridin-7-amine;

150: 3-[1-isopropyl-3-methyl-7-[(1-methylpyrazol-4-yl)methylamino]pyrazolo[4,3-b]pyridin-5-yl]-5-methyl-oxazolidin-2-one;

151: 3-[1-isopropyl-3-methyl-7-[(1-methylpyrazol-4-yl)methylamino]pyrazolo[4,3-b]pyridin-5-yl]oxazolidin-2-one;

152: 1-[1-isopropyl-3-methyl-7-[(1-methylpyrazol-4-yl)methylamino]pyrazolo[4,3-b]pyridin-5-yl]azetidin-2-one;

153: 1-tert-butyl-3-[1-isopropyl-3-methyl-7-[(1-methylpyrazol-4-yl)methylamino]pyrazolo[4,3-b]pyridin-5-yl]imidazolidin-2-one;

154: 1-[1-isopropyl-3-methyl-7-[(1-methylpyrazol-4-yl)methylamino]pyrazolo[4,3-b]pyridin-5-yl]pyrrolidin-2-one;

155: 3-[1-isopropyl-3-methyl-7-[(1-methylpyrazol-4-yl)methylamino]pyrazolo[4,3-b]pyridin-5-yl]-4-methyl-oxazolidin-2-one;

156: 4-ethyl-3-[1-isopropyl-3-methyl-7-[(1-methylpyrazol-4-yl)methylamino]pyrazolo[4,3-b]pyridin-5-yl]oxazolidin-2-one;

157: N-[[5-(2-ethoxy-3-pyridyl)-1-isopropyl-3-methyl-pyrazolo[4,3-b]pyridin-7-yl]methyl]-5-methoxy-pyridin-3-amine;

158: N-[[5-(2-ethoxy-3-pyridyl)-1-isopropyl-3-methyl-pyrazolo[4,3-b]pyridin-7-yl]methyl]-1-methyl-1,2,4-triazol-3-amine;

159: 5-(2-ethoxy-3-pyridyl)-1-isopropyl-7-[2-(5-methoxy-3-pyridyl)ethyl]-3-methyl-pyrazolo[4,3-b]pyridine;

160: 5-(2-ethoxy-3-pyridyl)-1-isopropyl-3-methyl-7-[2-(1-methyl-1,2,4-triazol-3-yl)ethyl]pyrazolo[4,3-b]pyridine;

161: 5-(2-ethoxy-3-pyridyl)-1-isopropyl-3-methyl-N-[(2-methyl-1,2,4-triazol-3-yl)methyl]pyrazolo[4,3-b]pyridin-7-amine;

162: 5-(2-ethoxy-3-pyridyl)-1-isopropyl-3-methyl-N-[(4-methyl-1,2,4-triazol-3-yl)methyl]pyrazolo[4,3-b]pyridin-7-amine;

163: 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine;

164: 5-(2-ethoxy-3-pyridyl)-1-isopropyl-3-methyl-7-[(1-methylpyrazol-4-yl)methylsulfanyl]pyrazolo[4,3-b]pyridine;

165: N-[[1-(difluoromethyl)pyrazol-4-yl]methyl]-5-(2-ethoxy-3-pyridyl)-1-isopropyl-3-methyl-pyrazolo[4,3-b]pyridin-7-amine;

166: 5-(2-ethoxy-3-pyridyl)-N-[[5-(fluoromethyl)isoxazol-3-yl]methyl]-1-isopropyl-3-methyl-pyrazolo[4,3-b]pyridin-7-amine;

167: 5-(2-ethoxy-3-pyridyl)-N-[[3-(fluoromethyl)isoxazol-5-yl]methyl]-1-isopropyl-3-methyl-pyrazolo[4,3-b]pyridin-7-amine;

168: 1-isopropyl-3-methyl-N-[(1-methyl pyrazol-4-yl)methyl]-5-oxazol-2-yl-pyrazolo[4,3-b]pyridin-7-amine;

169: 1-isopropyl-3-methyl-N-[(1-methylpyrazol-4-yl)methyl]-5-(3-methyltriazol-4-yl)pyrazolo[4,3-b]pyridin-7-amine;

170: 1-isopropyl-5-(2-methoxy-3-pyridyl)-3-methyl-N-[[2-(trifluoromethyl)-3-pyridyl]methyl]pyrazolo[4,3-b]pyridin-7-amine;

171: 3-[1-isopropyl-7-[(2-methoxy-3-pyridyl)methylamino]-3-methyl-pyrazolo[4,3-b]pyridin-5-yl]-1H-pyridin-2-one;

172: 5-(2-ethoxy-3-pyridyl)-1-isopropyl-N-[(3-methoxy-4-pyridyl)methyl]-3-methyl-pyrazolo[4,3-b]pyridin-7-amine;

173: 1-isopropyl-5-(2-methoxy-3-pyridyl)-3-methyl-N-[(2-methylthiazol-5-yl)methyl]pyrazolo[4,3-b]pyridin-7-amine;

174: 5-(2-cyclopropoxypyridin-3-yl)-1-isopropyl-N-((2-methoxypyridin-3-yl)methyl)-3-methyl-1H-pyrazolo[4,3-b]pyridin-7-amine;

175: 1-isopropyl-N-((2-methoxypyridin-3-yl)methyl)-3-methyl-5-(1-methyl-1H-pyrazol-5-yl)-1H-pyrazolo[4,3-b]pyridin-7-amine;

176: 5-(2-ethoxy-3-pyridyl)-1-isopropyl-N-[(5-methoxypyrimidin-2-yl)methyl]-3-methyl-pyrazolo[4,3-b]pyridin-7-amine;

177: 3-[1-isopropyl-3-methyl-7-[(1-methyl pyrazol-4-yl)methylamino]pyrazolo[4,3-b]pyridin-5-yl]-1H-pyridin-2-one;

178: N-[[2-(difluoromethyl)-3-pyridyl]methyl]-5-(2-ethoxy-3-pyridyl)-1-isopropyl-3-methyl-pyrazolo[4,3-b]pyridin-7-amine;

179: 5-(2-ethoxy-3-pyridyl)-1-isopropyl-N-[(6-methoxypyrimidin-4-yl)methyl]-3-methyl-pyrazolo[4,3-b]pyridin-7-amine;

180: 5-(2-(ethoxy-1,1-$d_2$)pyridin-3-yl)-1-isopropyl-N-((2-methoxypyridin-3-yl)methyl)-3-methyl-1H-pyrazolo[4,3-b]pyridin-7-amine;

181: 5-(2-(ethoxy-$d_5$)pyridin-3-yl)-1-isopropyl-N-((2-methoxypyridin-3-yl)methyl)-3-methyl-1H-pyrazolo[4,3-b]pyridin-7-amine;

182: 5-(2-(ethoxy-2,2,2-$d_3$)pyridin-3-yl)-1-isopropyl-N-((2-methoxypyridin-3-yl)methyl)-3-methyl-1H-pyrazolo[4,3-b]pyridin-7-amine;

183: 1-isopropyl-N-((2-methoxypyridin-3-yl)methyl)-3-methyl-5-(2-(trifluoromethyl)pyridin-3-yl)-1H-pyrazolo[4,3-b]pyridin-7-amine;

184: 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine;

185: 1-isopropyl-3-methyl-N-((1-methyl-1H-pyrazol-4-yl)methyl)-5-(1H-1,2,4-triazol-1-yl)-1H-pyrazolo[4,3-b]pyridin-7-amine;

186: 3-[1-isopropyl-3-methyl-7-[(1-methyl-1,2,4-triazol-3-yl)methylamino]pyrazolo[4,3-b]pyridin-5-yl]-1H-pyridin-2-one;

187: 3-[1-isopropyl-3-methyl-7-(1H-pyrazol-3-ylmethylamino)pyrazolo[4,3-b]pyridin-5-yl]-1H-pyridin-2-one;

188: 5-[2-(difluoromethoxy)-3-pyridyl]-1-isopropyl-N-[(2-methoxy-3-pyridyl)methyl]-3-methyl-pyrazolo[4,3-b]pyridin-7-amine;

189: 5-(2-ethoxy-3-pyridyl)-1-isopropyl-N-[(4-methoxypyrimidin-2-yl)methyl]-3-methyl-pyrazolo[4,3-b]pyridin-7-amine;

190: 5-(2-ethoxy-3-pyridyl)-1-isopropyl-N-[(4-methoxypyrimidin-5-yl)methyl]-3-methyl-pyrazolo[4,3-b]pyridin-7-amine;

191: 5-(2-ethoxy-3-pyridyl)-N-[(2-ethoxy-3-pyridyl)methyl]-1-isopropyl-3-methyl-pyrazolo[4,3-b]pyridin-7-amine;

192: 5-[2-(dimethylamino)-3-pyridyl]-1-isopropyl-N-[(4-methoxyphenyl)methyl]-3-methyl-pyrazolo[4,3-b]pyridin-7-amine;

193: 3-[1-isopropyl-3-methyl-7-[[2-(trifluoromethyl)-3-pyridyl]methylamino]pyrazolo[4,3-b]pyridin-5-yl]-1H-pyridin-2-one;

194: 1-isopropyl-3-methyl-5-(3-methylisoxazol-4-yl)-N-[(1-methyl pyrazol-4-yl)methyl]pyrazolo[4,3-b]pyridin-7-amine;

195: 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine;

196: 1-isopropyl-3-methyl-5-(2-propoxy-3-pyridyl)-N-(1H-pyrazol-4-ylmethyl)pyrazolo[4,3-b]pyridin-7-amine;

197: 5-(2-ethoxy-3-pyridyl)-N-[(2-methoxy-3-pyridyl)methyl]-3-methyl-1-(oxetan-3-yl)pyrazolo[4,3-b]pyridin-7-amine;

198: 5-(2-(ethyl(methyl)amino)pyridin-3-yl)-1-isopropyl-N-(4-methoxybenzyl)-3-methyl-1H-pyrazolo[4,3-b]pyridin-7-amine;

199: 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine;
200: 1-isopropyl-3-methyl-N-((1-methyl-1H-pyrazol-4-yl)methyl)-5-(4-methyloxazol-5-yl)-1H-pyrazolo[4,3-b]pyridin-7-amine;
201: 5-[2-(dimethylamino)-3-pyridyl]-1-isopropyl-3-methyl-N-[(1-methylpyrazol-4-yl)methyl]pyrazolo[4,3-b]pyridin-7-amine;
202: 1-isopropyl-3-methyl-N-((1-methyl-1H-pyrazol-4-yl)methyl)-5-(4-methyloxazol-2-yl)-1H-pyrazolo[4,3-b]pyridin-7-amine;
203: 1-isopropyl-3-methyl-N-[(1-methylpyrazol-4-yl)methyl]-5-(4-methyl-1,2,4-triazol-3-yl)pyrazolo[4,3-b]pyridin-7-amine;
and pharmaceutically acceptable salts of any of these compounds.

E29. The compound according to embodiment 1, wherein the compound is selected from the group consisting of:
6: 5-(2-ethoxy-3-pyridyl)-1-isopropyl-3-methyl-N-[(1-methyltriazol-4-yl)methyl]pyrazolo[4,3-b]pyridin-7-amine;
7: 5-(2-ethoxy-3-pyridyl)-1-isopropyl-3-methyl-N-(1H-pyrazol-4-ylmethyl)pyrazolo[4,3-b]pyridin-7-amine;
21: 5-(2-ethoxy-3-pyridyl)-1-isopropyl-N-[(1-methylimidazol-4-yl)methyl]pyrazolo[4,3-b]pyridin-7-amine;
29: 5-(2-ethoxy-3-pyridyl)-1-isopropyl-3-methyl-N-[(4-methylthiazol-2-yl)methyl]pyrazolo[4,3-b]pyridin-7-amine;
32: 5-(2-ethoxy-3-pyridyl)-1-isopropyl-3-methyl-N-[(2-methylthiazol-5-yl)methyl]pyrazolo[4,3-b]pyridin-7-amine;
39: 5-(2-ethoxy-3-pyridyl)-1-isopropyl-3-methyl-N-(1H-pyrazol-3-ylmethyl)pyrazolo[4,3-b]pyridin-7-amine;
47: 5-(2-ethoxypyridin-3-yl)-1-isopropyl-3-methyl-N-((5-methyl-1H-pyrazol-3-yl)methyl)-1H-pyrazolo[4,3-b]pyridin-7-amine;
50: 5-(2-ethoxypyridin-3-yl)-1-isopropyl-3-methyl-N-((4-methyloxazol-2-yl)methyl)-1H-pyrazolo[4,3-b]pyridin-7-amine;
56: 5-(2-ethoxy-3-pyridyl)-1-isopropyl-N-[(1-methyl-1,2,4-triazol-3-yl)methyl]pyrazolo[4,3-b]pyridin-7-amine;
57: 5-(2-ethoxy-3-pyridyl)-1-isopropyl-N-(1H-pyrazol-3-ylmethyl)pyrazolo[4,3-b]pyridin-7-amine;
67a: (R)-5-(2-ethoxy-3-pyridyl)-3-methyl-1-[1-methylpropyl]-N-[(1-methylpyrazol-3-yl)methyl]pyrazolo[4,3-b]pyridin-7-amine;
67b: (S)-5-(2-ethoxy-3-pyridyl)-3-methyl-1-[1-methylpropyl]-N-[(1-methylpyrazol-3-yl)methyl]pyrazolo[4,3-b]pyridin-7-amine;
77: 5-(2-ethoxy-3-pyridyl)-1-isopropyl-3-methyl-N-[[2-(trifluoromethyl)-3-pyridyl]methyl]pyrazolo[4,3-b]pyridin-7-amine;
82: 5-(2-ethoxy-3-pyridyl)-1-isopropyl-N-[(6-methoxypyrazin-2-yl)methyl]-3-methyl-pyrazolo[4,3-b]pyridin-7-amine;
85: 5-(2-ethoxy-3-pyridyl)-N-[(2-fluoro-3-pyridyl)methyl]-1-isopropyl-3-methyl-pyrazolo[4,3-b]pyridin-7-amine;
86: 5-(2-ethoxy-3-pyridyl)-1-isopropyl-N-[(2-methoxy-3-pyridyl)methyl]-3-methyl-pyrazolo[4,3-b]pyridin-7-amine;
88: 5-(2-ethoxy-3-pyridyl)-1-isopropyl-N-[(2-methoxyphenyl)methyl]-3-methyl-pyrazolo[4,3-b]pyridin-7-amine;
89: 5-(2-ethoxy-3-pyridyl)-N-[(2-fluorophenyl)methyl]-1-isopropyl-3-methyl-pyrazolo[4,3-b]pyridin-7-amine;
90: 5-(2-ethoxy-3-pyridyl)-1-isopropyl-3-methyl-N-[[2-(trifluoromethyl)phenyl]methyl]pyrazolo[4,3-b]pyridin-7-amine;
92: 5-(2-ethoxy-3-pyridyl)-1-isopropyl-N-[(4-methoxy-3-pyridyl)methyl]-3-methyl-pyrazolo[4,3-b]pyridin-7-amine;
94: 1-isopropyl-3-methyl-N-[(1-methylpyrazol-4-yl)methyl]-5-(2-propoxy-3-pyridyl)pyrazolo[4,3-b]pyridin-7-amine;
100: 5-(2-ethoxy-3-pyridyl)-1-isopropyl-3-methyl-N-(2-pyridylmethyl)pyrazolo[4,3-b]pyridin-7-amine;
101: 5-(2-ethoxy-3-pyridyl)-1-isopropyl-3-methyl-N-[(6-methyl-2-pyridyl)methyl]pyrazolo[4,3-b]pyridin-7-amine;
107: 5-(2-ethoxy-3-pyridyl)-1-isopropyl-3-methyl-N-[[6-(trifluoromethyl)-2-pyridyl]methyl]pyrazolo[4,3-b]pyridin-7-amine;
111: 5-(2-ethoxy-3-pyridyl)-1-isopropyl-N-[(6-methoxy-3-pyridyl)methyl]-3-methyl-pyrazolo[4,3-b]pyridin-7-amine;
113: 5-(2-ethoxy-3-pyridyl)-3-methyl-N-[(2-methylthiazol-4-yl)methyl]-1-(oxetan-3-yl)pyrazolo[4,3-b]pyridin-7-amine;
118: 5-(2-ethoxy-3-pyridyl)-1-isopropyl-N-[(3-methoxy-2-pyridyl)methyl]-3-methyl-pyrazolo[4,3-b]pyridin-7-amine;
119: (R)-5-(2-ethoxy-3-pyridyl)-3-methyl-1-[1-methylpropyl]-N-(1H-pyrazol-3-ylmethyl)pyrazolo[4,3-b]pyridin-7-amine or (S)-5-(2-ethoxy-3-pyridyl)-3-methyl-1-[1-methylpropyl]-N-(1H-pyrazol-3-ylmethyl)pyrazolo[4,3-b]pyridin-7-amine;
120: (R)-5-(2-ethoxy-3-pyridyl)-3-methyl-1-[1-methylpropyl]-N-(1H-pyrazol-3-ylmethyl)pyrazolo[4,3-b]pyridin-7-amine or (S)-5-(2-ethoxy-3-pyridyl)-3-methyl-1-[1-methylpropyl]-N-(1H-pyrazol-3-ylmethyl)pyrazolo[4,3-b]pyridin-7-amine;
135a: (R)-3-methyl-1-[1-methylpropyl]-5-(2-propoxy-3-pyridyl)-N-(1H-pyrazol-3-ylmethyl)pyrazolo[4,3-b]pyridin-7-amine;
135b: (S)-3-methyl-1-[1-methylpropyl]-5-(2-propoxy-3-pyridyl)-N-(1H-pyrazol-3-ylmethyl)pyrazolo[4,3-b]pyridin-7-amine;
136: (R)-5-(2-ethoxy-3-pyridyl)-1-[1-methylpropyl]-N-(1H-pyrazol-3-ylmethyl)pyrazolo[4,3-b]pyridin-7-amine or (S)-5-(2-ethoxy-3-pyridyl)-1-[1-methylpropyl]-N-(1H-pyrazol-3-ylmethyl)pyrazolo[4,3-b]pyridin-7-amine;
137: (R)-5-(2-ethoxy-3-pyridyl)-1-[1-methylpropyl]-N-(1H-pyrazol-3-ylmethyl)pyrazolo[4,3-b]pyridin-7-amine or (S)-5-(2-ethoxy-3-pyridyl)-1-[1-methylpropyl]-N-(1H-pyrazol-3-ylmethyl)pyrazolo[4,3-b]pyridin-7-amine;
137: (R)-5-(2-ethoxy-3-pyridyl)-1-[1-methylpropyl]-N-(1H-pyrazol-3-ylmethyl)pyrazolo[4,3-b]pyridin-7-amine or (S)-5-(2-ethoxy-3-pyridyl)-1-[1-methylpropyl]-N-(1H-pyrazol-3-ylmethyl)pyrazolo[4,3-b]pyridin-7-amine;
140: (R)-5-(2-ethoxy-3-pyridyl)-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-1-[1-methyl propyl]-N-[(1-methyl-1,2,4-triazol-3-yl)methyl]pyrazolo[4,3-b]pyridin-7-amine;
141: (R)-5-(2-ethoxy-3-pyridyl)-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-1-[1-methyl propyl]-N-[(1-methyl-1,2,4-triazol-3-yl)methyl]pyrazolo[4,3-b]pyridin-7-amine;
180: 5-(2-(ethoxy-1,1-$d_2$)pyridin-3-yl)-1-isopropyl-N-((2-methoxypyridin-3-yl)methyl)-3-methyl-1H-pyrazolo[4,3-b]pyridin-7-amine;

181: 5-(2-(ethoxy-d)pyridin-3-yl)-1-isopropyl-N-((2-methoxypyridin-3-yl)methyl)-3-methyl-1H-pyrazolo[4,3-b]pyridin-7-amine;

182: 5-(2-(ethoxy-2,2,2-d$_3$)pyridin-3-yl)-1-isopropyl-N-((2-methoxypyridin-3-yl)methyl)-3-methyl-1H-pyrazolo[4,3-b]pyridin-7-amine;

191: 5-(2-ethoxy-3-pyridyl)-N-[(2-ethoxy-3-pyridyl)methyl]-1-isopropyl-3-methyl-pyrazolo[4,3-b]pyridin-7-amine;

and pharmaceutically acceptable salts of any of these compounds.

E30. A compound of any one of embodiments 1-29, wherein said compound has a PDE1A, PDE1B or PDE1C IC$_{50}$ value, determined as described in the section "PDE1 inhibition assay", of 10 micro molar or less, such as 5 micro molar or less, such as 4 micro molar or less, such as 3 micro molar or less, such as 2 micro molar or less, such as 1 micro molar or less, such as 500 nM or less, such as 400 nM or less, such as 300 nM or less, such as 200 nM or less, such as 100 nM or less.

E31. A compound of any one of embodiments 1-29 for use in therapy.

E32. A compound according to any of embodiments 1-29, for use as a medicament.

E33. A pharmaceutical composition comprising a therapeutically effective amount of a compound of any one of embodiments 1-29 and one or more pharmaceutically acceptable carriers, diluents and excipients.

E34. A compound according to any of embodiments 1-29 for use in the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome.

E35. A method for the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to any of embodiments 1-29 to a patient in need thereof.

E36. Use of a compound according to any of embodiments 1-29, for the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit hyperactivity Disorder (ADHD), depression, anxiety, narcolepsy, cognitive impairment and cognitive impairment associated with schizophrenia (CIAS), or another brain disease like restless leg syndrome.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Compounds of the Invention

TABLE 1

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 1 | 5-(2-ethoxy-3-pyridyl)-1-isopropyl-3-methyl-N-[(5-methyl-1,3,4-oxadiazol-2-yl)methyl]pyrazolo[4,3-b]pyridin-7-amine | 18 | 1.6 | 40 |
| 2 | 5-(2-ethoxy-3-pyridyl)-1-isopropyl-3-methyl-N-[(5-methylthiazol-2-yl)methyl]pyrazolo[4,3-b]pyridin-7-amine | 0.46 | 0.071 | 4.9 |
| 3 | 5-(2-ethoxy-3-pyridyl)-1-isopropyl-3-methyl-N-[(5-methylisoxazol-3-yl)methyl]pyrazolo[4,3-b]pyridin-7-amine | 0.8 | 0.11 | 3 |
| 4 | 5-(2-ethoxy-3-pyridyl)-1-isopropyl-3-methyl-N-[(2-methyloxazol-5-yl)methyl]pyrazolo[4,3-b]pyridin-7-amine | 8.6 | 0.86 | 19 |
| 5 | 5-(2-ethoxy-3-pyridyl)-1-isopropyl-3-methyl-N-[(2-methyltriazol-4-yl)methyl]pyrazolo[4,3-b]pyridin-7-amine | 11 | 1.8 | 28 |
| 6 | 5-(2-ethoxy-3-pyridyl)-1-isopropyl-3-methyl-N-[(1-methyltriazol-4-yl)methyl]pyrazolo[4,3-b]pyridin-7-amine | 4.8 | 0.22 | 5.6 |
| 7 | 5-(2-ethoxy-3-pyridyl)-1-isopropyl-3-methyl-N-(1H-pyrazol-4-ylmethyl)pyrazolo[4,3-b]pyridin-7-amine | 21 | 1.1 | 37 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 8 | 5-(2-ethoxy-3-pyridyl)-1-isopropyl-3-methyl-N-[(2-methyltetrazol-5-yl)methyl]pyrazolo[4,3-b]pyridin-7-amine | 2.9 | 0.34 | 8.9 |
| 9 | 5-(2-ethoxypyridin-3-yl)-1-isopropyl-3-methyl-N-((1-methyl-1H-pyrazol-4-yl)methyl)-1H-pyrazolo[4,3-b]pyridin-7-amine | 2.6 | 0.49 | 17 |
| 10 | 5-(2-ethoxy-3-pyridyl)-1-isopropyl-3-methyl-N-[(3-methylisoxazol-5-yl)methyl]pyrazolo[4,3-b]pyridin-7-amine | 4.1 | 0.47 | 14 |
| 11 | 5-(2-ethoxy-3-pyridyl)-1-isopropyl-3-methyl-N-[(2-methylthiazol-4-yl)methyl]pyrazolo[4,3-b]pyridin-7-amine | 9.6 | 0.72 | 30 |
| 12 | 1-cyclopropyl-5-(2-ethoxy-3-pyridyl)-3-methyl-N-[(1-methylpyrazol-4-yl)methyl]pyrazolo[4,3-b]pyridin-7-amine | 200 | 60 | 690 |
| 13 | 5-(2-ethoxy-3-pyridyl)-N-[(1-methylpyrazol-4-yl)methyl]-1-propyl-pyrazolo[4,3-b]pyridin-7-amine | 90 | 15 | 340 |
| 14 | 5-(2-ethoxypyridin-3-yl)-N-((1-methyl-1H-pyrazol-4-yl)methyl)-1-(oxetan-3-yl)-1H-pyrazolo[4,3-b]pyridin-7-amine | 450 | 38 | 300 |
| 15 | 5-(2-ethoxypyridin-3-yl)-1-methyl-N-(1-(1-methyl-1H-pyrazol-4-yl)ethyl)-1H-pyrazolo[4,3-b]pyridin-7-amine (racemic) | 820 | 200 | 36% inhibition at 10 μM |
| 16 | 5-(2-ethoxypyridin-3-yl)-1-methyl-N-((1-methyl-1H-pyrazol-4-yl)methyl)-1H-pyrazolo[4,3-b]pyridin-7-amine | 670 | 92 | 1800 |
| 17 | 5-(2-ethoxy-3-pyridyl)-1-isopropyl-N-[(1-methylimidazol-2-yl)methyl]pyrazolo[4,3-b]pyridin-7-amine | 700 | 54 | 970 |
| 18 | 5-(2-ethoxypyridin-3-yl)-1-isopropyl-N-((1-methyl-1H-pyrazol-5-yl)methyl)-1H-pyrazolo[4,3-b]pyridin-7-amine | 450 | 73 | 640 |
| 19 | 5-(2-ethoxypyridin-3-yl)-1-isopropyl-N-((1-methyl-1H-pyrazol-3-yl)methyl)-1H-pyrazolo[4,3-b]pyridin-7-amine | 66 | 4.6 | 150 |
| 20 | 5-(2-ethoxy-3-pyridyl)-1-isopropyl-N-(thiazol-2-ylmethyl)pyrazolo[4,3-b]pyridin-7-amine | 520 | 37 | 600 |
| 21 | 5-(2-ethoxy-3-pyridyl)-1-isopropyl-N-[(1-methylimidazol-4-yl)methyl]pyrazolo[4,3-b]pyridin-7-amine | 8.9 | 0.44 | 29 |
| 22 | 5-(2-ethoxy-3-pyridyl)-1-isopropyl-N-(4-pyridylmethyl)pyrazolo[4,3-b]pyridin-7-amine | 250 | 50 | 430 |
| 23 | 5-(2-ethoxy-3-pyridyl)-1-isopropyl-N-(m-tolylmethyl)pyrazolo[4,3-b]pyridin-7-amine | 240 | 38 | 750 |
| 24 | 5-(2-ethoxy-3-pyridyl)-1-isopropyl-N-(p-tolylmethyl)pyrazolo[4,3-b]pyridin-7-amine | 380 | 160 | 1200 |
| 25 | 5-(2-ethoxy-3-pyridyl)-1-isopropyl-N-[(1-methylpyrazol-4-yl)methyl]pyrazolo[4,3-b]pyridin-7-amine | 56 | 4.6 | 150 |
| 26 | 5-(2-ethoxy-3-pyridyl)-1-ethyl-N-[(1-methylpyrazol-4-yl)methyl]pyrazolo[4,3-b]pyridin-7-amine | 140 | 22 | 440 |
| 27 | 5-(2-ethoxy-3-pyridyl)-3-methyl-N-[(1-methylpyrazol-4-yl)methyl]-1-(oxetan-3-yl)pyrazolo[4,3-b]pyridin-7-amine | 94 | 6.6 | 170 |
| 28 | 5-(2-ethoxy-3-pyridyl)-1,3-dimethyl-N-[(1-methylpyrazol-4-yl)methyl]pyrazolo[4,3-b]pyridin-7-amine | 550 | 85 | 1900 |
| 29 | 5-(2-ethoxy-3-pyridyl)-1-isopropyl-3-methyl-N-[(4-methylthiazol-2-yl)methyl]pyrazolo[4,3-b]pyridin-7-amine | 27 | 1.1 | 44 |
| 30 | 5-(2-ethoxy-3-pyridyl)-1-isopropyl-3-methyl-N-[(3-methyl-1,2,4-oxadiazol-5-yl)methyl]pyrazolo[4,3-b]pyridin-7-amine | 15 | 1.3 | 31 |
| 31 | 5-(2-ethoxy-3-pyridyl)-1-isopropyl-3-methyl-N-[(1-methyl-1,2,4-triazol-3-yl)methyl]pyrazolo[4,3-b]pyridin-7-amine | 1.2 | 0.11 | 2.1 |
| 32 | 5-(2-ethoxy-3-pyridyl)-1-isopropyl-3-methyl-N-[(2-methylthiazol-5-yl)methyl]pyrazolo[4,3-b]pyridin-7-amine | 4.6 | 0.14 | 6.2 |
| 33 | 5-(2-ethoxy-3-pyridyl)-1-isopropyl-3-methyl-N-[(5-methyl-1,3,4-thiadiazol-2-yl)methyl]pyrazolo[4,3-b]pyridin-7-amine | 1.6 | 0.41 | 7.9 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 34 | 5-(2-ethoxy-3-pyridyl)-1-isopropyl-3-methyl-N-[(5-methyl-3-thienyl)methyl]pyrazolo[4,3-b]pyridin-7-amine | 8.1 | 1.8 | 21 |
| 35 | 5-(2-ethoxy-3-pyridyl)-1-isopropyl-3-methyl-N-[(4-methyl-2-thienyl)methyl]pyrazolo[4,3-b]pyridin-7-amine | 7.3 | 1.7 | 32 |
| 36 | 5-(2-ethoxy-3-pyridyl)-1-isopropyl-3-methyl-N-[(5-methyl-2-thienyl)methyl]pyrazolo[4,3-b]pyridin-7-amine | 24 | 5.2 | 41 |
| 37 | 5-(2-ethoxy-3-pyridyl)-1-isopropyl-3-methyl-N-[(2-methyloxazol-4-yl)methyl]pyrazolo[4,3-b]pyridin-7-amine | 5.9 | 0.43 | 18 |
| 38 | 5-(2-ethoxy-3-pyridyl)-1-isopropyl-3-methyl-N-[(5-methyloxazol-2-yl)methyl]pyrazolo[4,3-b]pyridin-7-amine | 1.1 | 0.24 | 13 |
| 39 | 5-(2-ethoxy-3-pyridyl)-1-isopropyl-3-methyl-N-(1H-pyrazol-3-ylmethyl)pyrazolo[4,3-b]pyridin-7-amine | 8.1 | 0.43 | 13 |
| 40 | 5-(2-ethoxy-3-pyridyl)-N-(1H-imidazol-4-ylmethyl)-1-isopropyl-3-methyl-pyrazolo[4,3-b]pyridin-7-amine | 14 | 1 | 32 |
| 41 | N-benzyl-5-(2-ethoxy-3-pyridyl)-1-isopropyl-pyrazolo[4,3-b]pyridin-7-amine | 500 | 45 | 500 |
| 42 | 5-(2-ethoxy-3-pyridyl)-1-isopropyl-N-[(3-methylisoxazol-5-yl)methyl]pyrazolo[4,3-b]pyridin-7-amine | 82 | 5.8 | 180 |
| 43 | 5-(2-ethoxy-3-pyridyl)-1-isopropyl-N-[(5-methyl-1,2,4-oxadiazol-3-yl)methyl]pyrazolo[4,3-b]pyridin-7-amine | 30 | 2.4 | 80 |
| 44 | N-[(1,5-dimethylpyrazol-3-yl)methyl]-5-(2-ethoxy-3-pyridyl)-1-isopropyl-pyrazolo[4,3-b]pyridin-7-amine | 19 | 1.4 | 70 |
| 45 | 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one | 8 | 0.62 | 16 |
| 46 | 5-(2-ethoxypyridin-3-yl)-1-isopropyl-3-methyl-N-((2-methyl-1H-imidazol-4-yl)methyl)-1H-pyrazolo[4,3-b]pyridin-7-amine | 5 | 0.42 | 9.7 |
| 47 | 5-(2-ethoxypyridin-3-yl)-1-isopropyl-3-methyl-N-((5-methyl-1H-pyrazol-3-yl)methyl)-1H-pyrazolo[4,3-b]pyridin-7-amine | 1.6 | 0.069 | 1.8 |
| 48 | 5-(2-ethoxypyridin-3-yl)-1-ethyl-3-methyl-N-((1-methyl-1H-pyrazol-4-yl)methyl)-1H-pyrazolo[4,3-b]pyridin-7-amine | 38 | 6.3 | 170 |
| 49 | 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one | 170 | 20 | 420 |
| 50 | 5-(2-ethoxypyridin-3-yl)-1-isopropyl-3-methyl-N-((4-methyloxazol-2-yl)methyl)-1H-pyrazolo[4,3-b]pyridin-7-amine 2,2,2-trifluoroacetate | 9 | 0.5 | 16 |
| 51 | N-((1,2-dimethyl-1H-imidazol-4-yl)methyl)-5-(2-ethoxypyridin-3-yl)-1-isopropyl-3-methyl-1H-pyrazolo[4,3-b]pyridin-7-amine 2,2,2-trifluoroacetate | 53 | 9.1 | 88 |
| 52 | 5-(2-ethoxy-3-pyridyl)-1-isopropyl-3-methyl-N-[(5-methyl-1,2,4-oxadiazol-3-yl)methyl]pyrazolo[4,3-b]pyridin-7-amine | 1.9 | 0.17 | 4.4 |
| 53 | 5-(2-ethoxy-3-pyridyl)-1-isopropyl-3-methyl-N-(1,2,4-oxadiazol-3-ylmethyl)pyrazolo[4,3-b]pyridin-7-amine | 9.3 | 0.89 | 17 |
| 54 | N-[(1,5-dimethylpyrazol-3-yl)methyl]-5-(2-ethoxy-3-pyridyl)-1-isopropyl-3-methyl-pyrazolo[4,3-b]pyridin-7-amine | 0.39 | 0.18 | 4.6 |
| 55 | 5-(2-ethoxy-3-pyridyl)-1-isopropyl-3-methyl-N-[(5-methyl-1H-1,2,4-triazol-3-yl)methyl]pyrazolo[4,3-b]pyridin-7-amine | 3.4 | 0.51 | 5.5 |
| 56 | 5-(2-ethoxy-3-pyridyl)-1-isopropyl-N-[(1-methyl-1,2,4-triazol-3-yl)methyl]pyrazolo[4,3-b]pyridin-7-amine | 16 | 1 | 45 |
| 57 | 5-(2-ethoxy-3-pyridyl)-1-isopropyl-N-(1H-pyrazol-3-ylmethyl)pyrazolo[4,3-b]pyridin-7-amine | 98 | 4.8 | 170 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 58 | 5-(2-ethoxypyridin-3-yl)-1-isopropyl-3-methyl-N-((1-methyl-1H-imidazol-4-yl)methyl)-1H-pyrazolo[4,3-b]pyridin-7-amine 2,2,2-trifluoroacetate | 1.1 | 0.17 | 2.1 |
| 59 | 5-(2-ethoxy-3-pyridyl)-1-isopropyl-3-methyl-N-(1,3,4-oxadiazol-2-ylmethyl)pyrazolo[4,3-b]pyridin-7-amine | 55 | 12 | 120 |
| 60 | 5-(2-ethoxy-3-pyridyl)-1-isopropyl-3-methyl-N-[(1-methylpyrazol-3-yl)methyl]pyrazolo[4,3-b]pyridin-7-amine | 6.5 | 0.59 | 12 |
| 61 | 5-(1,3-dimethylpyrazol-4-yl)-1-isopropyl-3-methyl-N-[(1-methylpyrazol-4-yl)methyl]pyrazolo[4,3-b]pyridin-7-amine | 550 | 120 | 680 |
| 62 | 1-isopropyl-5-(2-methoxy-3-pyridyl)-3-methyl-N-[(1-methylpyrazol-4-yl)methyl]pyrazolo[4,3-b]pyridin-7-amine | 16 | 2.4 | 21 |
| 63 | 1-isopropyl-5-(2-methoxyphenyl)-3-methyl-N-[(1-methylpyrazol-4-yl)methyl]pyrazolo[4,3-b]pyridin-7-amine | 64 | 9.4 | 20 |
| 64 | 1-isopropyl-3-methyl-N-[(1-methylpyrazol-4-yl)methyl]-5-phenyl-pyrazolo[4,3-b]pyridin-7-amine | 52 | 12 | 47 |
| 65 | 1-isopropyl-3-methyl-N-[(1-methylpyrazol-4-yl)methyl]-5-(2-methyl-3-thienyl)pyrazolo[4,3-b]pyridin-7-amine | 7.9 | 1.2 | 16 |
| 66 | 5-(1,5-dimethylpyrazol-4-yl)-1-isopropyl-3-methyl-N-[(1-methylpyrazol-4-yl)methyl]pyrazolo[4,3-b]pyridin-7-amine | 210 | 59 | 220 |
| 67 | 5-(2-ethoxy-3-pyridyl)-3-methyl-1-[1-methylpropyl]-N-[(1-methylpyrazol-3-yl)methyl]pyrazolo[4,3-b]pyridin-7-amine, enantiomer 2 | 9.6 | 0.64 | 27 |
| 68 | 3-methyl-1-[1-methylpropyl]-N-[(2-methyltetrazol-5-yl)methyl]-5-(2-propoxy-3-pyridyl)pyrazolo[4,3-b]pyridin-7-amine, enantiomer 2 | 0.79 | 0.14 | 1.3 |
| 69 | 5-(2-ethoxy-3-pyridyl)-1-[1-methylpropyl]-N-[(1-methylpyrazol-4-yl)methyl]pyrazolo[4,3-b]pyridin-7-amine, enantiomer 1 | 14 | 1.2 | 40 |
| 70 | 5-(2-ethoxy-3-pyridyl)-1-[1-methylpropyl]-N-[(1-methylpyrazol-4-yl)methyl]pyrazolo[4,3-b]pyridin-7-amine, enantiomer 2 | 140 | 14 | 360 |
| 71 | 5-(2-ethoxy-3-pyridyl)-1-isopropyl-N-[(4-methylthiazol-5-yl)methyl]pyrazolo[4,3-b]pyridin-7-amine | 170 | 18 | 180 |
| 72 | 5-[[5-(2-ethoxy-3-pyridyl)-1-isopropyl-3-methyl-pyrazolo[4,3-b]pyridin-7-yl]oxymethyl]-2-methyl-oxazole | 14 | 2.4 | 39 |
| 73 | 5-(2-ethoxy-3-pyridyl)-1-isopropyl-3-methyl-N-(pyrimidin-4-ylmethyl)pyrazolo[4,3-b]pyridin-7-amine | 81 | 9.2 | 140 |
| 74 | 5-(2-ethoxy-3-pyridyl)-1-isopropyl-3-methyl-N-(pyrimidin-2-ylmethyl)pyrazolo[4,3-b]pyridin-7-amine | 2.1 | 0.34 | 8.1 |
| 75 | 5-(2-ethoxy-3-pyridyl)-1-isopropyl-3-methyl-N-[(4-methylpyrimidin-2-yl)methyl]pyrazolo[4,3-b]pyridin-7-amine | 9.9 | 0.81 | 33 |
| 76 | 5-(2-ethoxy-3-pyridyl)-1-isopropyl-3-methyl-N-(pyrazin-2-ylmethyl)pyrazolo[4,3-b]pyridin-7-amine | 23 | 2.9 | 32 |
| 77 | 5-(2-ethoxy-3-pyridyl)-1-isopropyl-3-methyl-N-[[2-(trifluoromethyl)-3-pyridyl]methyl]pyrazolo[4,3-b]pyridin-7-amine | 21 | 0.22 | 64 |
| 78 | 4-[[[5-(2-ethoxy-3-pyridyl)-1-isopropyl-3-methyl-pyrazolo[4,3-b]pyridin-7-yl]amino]methyl]-1-methyl-pyridin-2-one | 27 | 3.2 | 44 |
| 79 | 5-(2-(ethylamino)pyridin-3-yl)-1-isopropyl-3-methyl-N-((1-methyl-1H-pyrazol-4-yl)methyl)-1H-pyrazolo[4,3-b]pyridin-7-amine | 230 | 31 | 260 |
| 81 | 5-(2-ethoxy-3-pyridyl)-1-isopropyl-N-[(4-methoxy-2-pyridyl)methyl]-3-methyl-pyrazolo[4,3-b]pyridin-7-amine | 1 | 0.26 | 4.7 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 82 | 5-(2-ethoxy-3-pyridyl)-1-isopropyl-N-[(6-methoxypyrazin-2-yl)methyl]-3-methyl-pyrazolo[4,3-b]pyridin-7-amine | 16 | 1 | 35 |
| 83 | 5-(2-ethoxy-3-pyridyl)-N-[(5-fluoropyrimidin-2-yl)methyl]-1-isopropyl-3-methyl-pyrazolo[4,3-b]pyridin-7-amine | 17 | 1.2 | 38 |
| 84 | 5-(2-ethoxy-3-pyridyl)-1-isopropyl-3-methyl-N-[(2-methyl-3-pyridyl)methyl]pyrazolo[4,3-b]pyridin-7-amine | 19 | 1.8 | 23 |
| 85 | 5-(2-ethoxy-3-pyridyl)-N-[(2-fluoro-3-pyridyl)methyl]-1-isopropyl-3-methyl-pyrazolo[4,3-b]pyridin-7-amine | 8.4 | 0.22 | 27 |
| 86 | 5-(2-ethoxy-3-pyridyl)-1-isopropyl-N-[(2-methoxy-3-pyridyl)methyl]-3-methyl-pyrazolo[4,3-b]pyridin-7-amine | 20 | 0.36 | 68 |
| 87 | 5-(2-ethoxy-3-pyridyl)-1-isopropyl-3-methyl-N-[(6-methyl-3-pyridyl)methyl]pyrazolo[4,3-b]pyridin-7-amine | 6.3 | 0.95 | 13 |
| 88 | 5-(2-ethoxy-3-pyridyl)-1-isopropyl-N-[(2-methoxyphenyl)methyl]-3-methyl-pyrazolo[4,3-b]pyridin-7-amine | 110 | 5.1 | 170 |
| 89 | 5-(2-ethoxy-3-pyridyl)-N-[(2-fluorophenyl)methyl]-1-isopropyl-3-methyl-pyrazolo[4,3-b]pyridin-7-amine | 61 | 1.5 | 93 |
| 90 | 5-(2-ethoxy-3-pyridyl)-1-isopropyl-3-methyl-N-[[2-(trifluoromethyl)phenyl]methyl]pyrazolo[4,3-b]pyridin-7-amine | 270 | 12 | 640 |
| 91 | 5-(2-ethoxy-3-pyridyl)-1-isopropyl-N-[(3-methoxypyrazin-2-yl)methyl]-3-methyl-pyrazolo[4,3-b]pyridin-7-amine | 27 | 2.3 | 70 |
| 92 | 5-(2-ethoxy-3-pyridyl)-1-isopropyl-N-[(4-methoxy-3-pyridyl)methyl]-3-methyl-pyrazolo[4,3-b]pyridin-7-amine | 47 | 2.7 | 110 |
| 93 | 1-isopropyl-3-methyl-N-[(2-methyltetrazol-5-yl)methyl]-5-(2-propoxy-3-pyridyl)pyrazolo[4,3-b]pyridin-7-amine | 4.3 | 0.96 | 17 |
| 94 | 1-isopropyl-3-methyl-N-[(1-methylpyrazol-4-yl)methyl]-5-(2-propoxy-3-pyridyl)pyrazolo[4,3-b]pyridin-7-amine | 1.4 | 0.065 | 4.9 |
| 95 | 1-isopropyl-5-(2-methoxy-3-pyridyl)-N-[(2-methoxy-3-pyridyl)methyl]-3-methyl-pyrazolo[4,3-b]pyridin-7-amine | 42 | 6.4 | 28 |
| 96 | 1-isopropyl-5-(2-methoxy-3-pyridyl)-N-[(6-methoxy-3-pyridyl)methyl]-3-methyl-pyrazolo[4,3-b]pyridin-7-amine | 18 | 3.8 | 5.3 |
| 97 | 5-(2-isopropoxy-3-pyridyl)-1-isopropyl-3-methyl-N-[(1-methylpyrazol-4-yl)methyl]pyrazolo[4,3-b]pyridin-7-amine | 1.4 | 0.6 | 9.1 |
| 98 | 5-(2-ethoxy-3-pyridyl)-1-isopropyl-3-methyl-N-(1H-1,2,4-triazol-3-ylmethyl)pyrazolo[4,3-b]pyridin-7-amine | 7.2 | 0.58 | 21 |
| 99 | 5-(2-ethoxy-3-pyridyl)-1-isopropyl-3-methyl-N-(2H-tetrazol-5-ylmethyl)pyrazolo[4,3-b]pyridin-7-amine | 0.73 | 0.31 | 3.8 |
| 100 | 5-(2-ethoxy-3-pyridyl)-1-isopropyl-3-methyl-N-(2-pyridylmethyl)pyrazolo[4,3-b]pyridin-7-amine | 6.3 | 0.39 | 21 |
| 101 | 5-(2-ethoxy-3-pyridyl)-1-isopropyl-3-methyl-N-[(6-methyl-2-pyridyl)methyl]pyrazolo[4,3-b]pyridin-7-amine | 20 | 0.9 | 43 |
| 102 | 5-(2-ethoxy-3-pyridyl)-1-isopropyl-N-[(6-methoxy-2-pyridyl)methyl]-3-methyl-pyrazolo[4,3-b]pyridin-7-amine | 8 | 0.73 | 34 |
| 103 | 5-(2-ethoxy-3-pyridyl)-1-isopropyl-3-methyl-N-[(2-methyl-4-pyridyl)methyl]pyrazolo[4,3-b]pyridin-7-amine | 5.4 | 2.9 | 17 |
| 104 | 5-(2-ethoxy-3-pyridyl)-1-isopropyl-N-[(2-methoxy-4-pyridyl)methyl]-3-methyl-pyrazolo[4,3-b]pyridin-7-amine | 2.2 | 0.16 | 6.3 |
| 105 | 5-(2-ethoxy-3-pyridyl)-1-isopropyl-3-methyl-N-[(2-methylpyrimidin-4-yl)methyl]pyrazolo[4,3-b]pyridin-7-amine | 54 | 12 | 150 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 106 | 5-(2-ethoxy-3-pyridyl)-1-isopropyl-N-[(5-methoxy-3-pyridyl)methyl]-3-methyl-pyrazolo[4,3-b]pyridin-7-amine | 2.1 | 0.45 | 3.9 |
| 107 | 5-(2-ethoxy-3-pyridyl)-1-isopropyl-3-methyl-N-[[6-(trifluoromethyl)-2-pyridyl]methyl]pyrazolo[4,3-b]pyridin-7-amine | 110 | 5.6 | 170 |
| 108 | 3-[[[5-(2-ethoxy-3-pyridyl)-1-isopropyl-3-methyl-pyrazolo[4,3-b]pyridin-7-yl]amino]methyl]-1-methyl-pyridin-2-one | 2.8 | 0.36 | 12 |
| 109 | 5-(2-ethoxy-3-pyridyl)-N-[(1-ethylpyrazol-4-yl)methyl]-1-isopropyl-3-methyl-pyrazolo[4,3-b]pyridin-7-amine | 4.9 | 0.66 | 11 |
| 110 | 5-(2-ethoxy-3-pyridyl)-1-isopropyl-3-methyl-N-[(1-propylpyrazol-4-yl)methyl]pyrazolo[4,3-b]pyridin-7-amine | 11 | 1.1 | 8.5 |
| 111 | 5-(2-ethoxy-3-pyridyl)-1-isopropyl-N-[(6-methoxy-3-pyridyl)methyl]-3-methyl-pyrazolo[4,3-b]pyridin-7-amine | 28 | 1.4 | 68 |
| 112 | 5-(2-ethoxy-3-pyridyl)-1-isopropyl-N-[(5-methoxy-2-pyridyl)methyl]-3-methyl-pyrazolo[4,3-b]pyridin-7-amine | 61 | 12 | 100 |
| 113 | 5-(2-ethoxy-3-pyridyl)-3-methyl-N-[(2-methylthiazol-4-yl)methyl]-1-(oxetan-3-yl)pyrazolo[4,3-b]pyridin-7-amine | 110 | 5.7 | 130 |
| 114 | 5-(2-ethoxy-3-pyridyl)-1-isopropyl-N-[(5-methoxypyrazin-2-yl)methyl]-3-methyl-pyrazolo[4,3-b]pyridin-7-amine | 24 | 3 | 46 |
| 115 | 5-(2-ethoxy-3-pyridyl)-1-isopropyl-3-methyl-N-(3-pyridylmethyl)pyrazolo[4,3-b]pyridin-7-amine | 15 | 2 | 31 |
| 116 | 5-(2-ethoxy-3-pyridyl)-N-[(6-fluoro-3-pyridyl)methyl]-1-isopropyl-3-methyl-pyrazolo[4,3-b]pyridin-7-amine | 21 | 2.4 | 46 |
| 117 | N-[[6-(difluoromethyl)-3-pyridyl]methyl]-5-(2-ethoxy-3-pyridyl)-1-isopropyl-3-methyl-pyrazolo[4,3-b]pyridin-7-amine | 18 | 2.3 | 26 |
| 118 | 5-(2-ethoxy-3-pyridyl)-1-isopropyl-N-[(3-methoxy-2-pyridyl)methyl]-3-methyl-pyrazolo[4,3-b]pyridin-7-amine | 13 | 0.42 | 88 |
| 119 | 5-(2-ethoxy-3-pyridyl)-3-methyl-1-[1-methylpropyl]-N-(1H-pyrazol-3-ylmethyl)pyrazolo[4,3-b]pyridin-7-amine, enantiomer 1 | 12 | 0.56 | 29 |
| 120 | 5-(2-ethoxy-3-pyridyl)-3-methyl-1-[1-methylpropyl]-N-(1H-pyrazol-3-ylmethyl)pyrazolo[4,3-b]pyridin-7-amine, enantiomer 2 | 4.6 | 0.27 | 7.6 |
| 121 | 5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine, enantiomer 1 | 4 | 0.47 | 10 |
| 122 | 5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine, enantiomer 2 | 2.2 | 0.15 | 3.5 |
| 123 | 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, enantiomer 1 | 54 | 7 | 130 |
| 124 | 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, enantiomer 2 | 9.7 | 1.1 | 21 |
| 125 | 5-(2-ethoxy-3-pyridyl)-N-[(5-methoxy-3-pyridyl)methyl]-3-methyl-1-[1-methylpropyl]pyrazolo[4,3-b]pyridin-7-amine, enantiomer 2 | 1 | 0.32 | 4.3 |
| 126 | 5-(2-ethoxy-3-pyridyl)-N-[(2-methoxy-4-pyridyl)methyl]-3-methyl-1-[1-methylpropyl]pyrazolo[4,3-b]pyridin-7-amine, enantiomer 2 | 5.4 | 0.51 | 8.4 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 127 | 5-(2-ethoxy-3-pyridyl)-3-methyl-1-[1-methylpropyl]-N-[(2-methyltetrazol-5-yl)methyl]pyrazolo[4,3-b]pyridin-7-amine, enantiomer 2 | 1.8 | 0.31 | 5.1 |
| 128 | 5-(2-ethoxy-3-pyridyl)-3-methyl-N-[(5-methyl-1,2,4-oxadiazol-3-yl)methyl]-1-[1-methylpropyl]pyrazolo[4,3-b]pyridin-7-amine, enantiomer 2 | 1.2 | 0.26 | 4.1 |
| 129 | 5-(2-ethoxy-3-pyridyl)-3-methyl-N-[(2-methyloxazol-4-yl)methyl]-1-[1-methylpropyl]pyrazolo[4,3-b]pyridin-7-amine, enantiomer 2 | 11 | 1.2 | 25 |
| 130 | 5-(2-ethoxy-3-pyridyl)-N-(1H-imidazol-4-ylmethyl)-3-methyl-1-[1-methylpropyl]pyrazolo[4,3-b]pyridin-7-amine, enantiomer 2 | 11 | 0.86 | 25 |
| 131 | 5-(2-ethoxy-3-pyridyl)-3-methyl-1-[1-methylpropyl]-N-[(5-methyl-1H-pyrazol-3-yl)methyl]pyrazolo[4,3-b]pyridin-7-amine, enantiomer 2 | 0.35 | 0.042 | 0.46 |
| 132 | 5-(2-ethoxy-3-pyridyl)-3-methyl-N-[(1-methylimidazol-4-yl)methyl]-1-[1-methylpropyl]pyrazolo[4,3-b]pyridin-7-amine, enantiomer 2 | 0.14 | 0.045 | 0.52 |
| 133 | 5-(2-ethoxy-3-pyridyl)-3-methyl-N-[(2-methyloxazol-5-yl)methyl]-1-[1-methylpropyl]pyrazolo[4,3-b]pyridin-7-amine, enantiomer 2 | 11 | 1.3 | 23 |
| 134 | 3-methyl-1-[1-methylpropyl]-N-[(1-methyl-1,2,4-triazol-3-yl)methyl]-5-(2-propoxy-3-pyridyl)pyrazolo[4,3-b]pyridin-7-amine, enantiomer 2 | 0.96 | 0.12 | 1.5 |
| 135 | 3-methyl-1-[1-methylpropyl]-5-(2-propoxy-3-pyridyl)-N-(1H-pyrazol-3-ylmethyl)pyrazolo[4,3-b]pyridin-7-amine, enantiomer 2 | 1.9 | 0.095 | 3.6 |
| 136 | 5-(2-ethoxy-3-pyridyl)-1-[1-methylpropyl]-N-(1H-pyrazol-3-ylmethyl)pyrazolo[4,3-b]pyridin-7-amine, enantiomer 1 | 62 | 3.2 | 100 |
| 137 | 5-(2-ethoxy-3-pyridyl)-1-[1-methylpropyl]-N-(1H-pyrazol-3-ylmethyl)pyrazolo[4,3-b]pyridin-7-amine, enantiomer 2 | 180 | 12 | 340 |
| 138 | 5-(2-ethoxy-3-pyridyl)-N-[(5-methyl-1,3,4-oxadiazol-2-yl)methyl]-1-[1-methylpropyl]pyrazolo[4,3-b]pyridin-7-amine, enantiomer 1 | 93 | 6.8 | 180 |
| 139 | 5-(2-ethoxy-3-pyridyl)-N-[(5-methyl-1,3,4-oxadiazol-2-yl)methyl]-1-[1-methylpropyl]pyrazolo[4,3-b]pyridin-7-amine, enantiomer 2 | 330 | 35 | 530 |
| 140 | 5-(2-ethoxy-3-pyridyl)-1-[1-methylpropyl]-N-[(1-methyl-1,2,4-triazol-3-yl)methyl]pyrazolo[4,3-b]pyridin-7-amine, enantiomer 1 | 32 | 1.7 | 52 |
| 141 | 5-(2-ethoxy-3-pyridyl)-1-[1-methylpropyl]-N-[(1-methyl-1,2,4-triazol-3-yl)methyl]pyrazolo[4,3-b]pyridin-7-amine, enantiomer 2 | 44 | 2.2 | 76 |
| 142 | 1-isopropyl-3-methyl-N-[(1-methylimidazol-4-yl)methyl]-5-(2-propoxy-3-pyridyl)pyrazolo[4,3-b]pyridin-7-amine | 0.26 | 0.1 | 0.8 |
| 143 | 1-isopropyl-3-methyl-5-(2-propoxy-3-pyridyl)-N-(1H-pyrazol-3-ylmethyl)pyrazolo[4,3-b]pyridin-7-amine | 3.8 | 0.26 | 9.2 |
| 144 | 5-(2-ethoxy-3-pyridyl)-3-methyl-1-[1-methylpropyl]-N-(1H-1,2,4-triazol-3-ylmethyl)pyrazolo[4,3-b]pyridin-7-amine, enantiomer 2 | 14 | 1.1 | 23 |
| 145 | 1-isopropyl-3-methyl-N-[(1-methyl-1,2,4-triazol-3-yl)methyl]-5-(2-propoxy-3-pyridyl)pyrazolo[4,3-b]pyridin-7-amine | 0.41 | 0.095 | 1.2 |
| 146 | 1-isopropyl-3-methyl-5-(2-propoxy-3-pyridyl)-N-(1H-1,2,4-triazol-3-ylmethyl)pyrazolo[4,3-b]pyridin-7-amine | 3.9 | 0.51 | 14 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 147 | 1-isopropyl-3-methyl-N-[(1-methylpyrazol-4-yl)methyl]-5-thiazol-2-yl-pyrazolo[4,3-b]pyridin-7-amine | 12 | 2.1 | 28 |
| 148 | 1-isopropyl-3-methyl-N-[(1-methylpyrazol-4-yl)methyl]-5-(5-methylthiazol-2-yl)pyrazolo[4,3-b]pyridin-7-amine | 110 | 58 | 86 |
| 149 | 1-isopropyl-3-methyl-N-[(1-methylpyrazol-4-yl)methyl]-5-(4-methylthiazol-2-yl)pyrazolo[4,3-b]pyridin-7-amine | 29 | 2.4 | 69 |
| 150 | 3-[1-isopropyl-3-methyl-7-[(1-methylpyrazol-4-yl)methylamino]pyrazolo[4,3-b]pyridin-5-yl]-5-methyl-oxazolidin-2-one | 44 | 33 | 13 |
| 151 | 3-[1-isopropyl-3-methyl-7-[(1-methylpyrazol-4-yl)methylamino]pyrazolo[4,3-b]pyridin-5-yl]oxazolidin-2-one | 10 | 4.7 | 12 |
| 152 | 1-[1-isopropyl-3-methyl-7-[(1-methylpyrazol-4-yl)methylamino]pyrazolo[4,3-b]pyridin-5-yl]azetidin-2-one | 48 | 32 | 61 |
| 153 | 1-tert-butyl-3-[1-isopropyl-3-methyl-7-[(1-methylpyrazol-4-yl)methylamino]pyrazolo[4,3-b]pyridin-5-yl]imidazolidin-2-one | 130 | 76 | 270 |
| 154 | 1-[1-isopropyl-3-methyl-7-[(1-methylpyrazol-4-yl)methylamino]pyrazolo[4,3-b]pyridin-5-yl]pyrrolidin-2-one | 26 | 3.6 | 49 |
| 155 | 3-[1-isopropyl-3-methyl-7-[(1-methylpyrazol-4-yl)methylamino]pyrazolo[4,3-b]pyridin-5-yl]-4-methyl-oxazolidin-2-one | 8.2 | 4.9 | 3.9 |
| 156 | 4-ethyl-3-[1-isopropyl-3-methyl-7-[(1-methylpyrazol-4-yl)methylamino]pyrazolo[4,3-b]pyridin-5-yl]oxazolidin-2-one | 31 | 31 | 5.1 |
| 157 | N-[[5-(2-ethoxy-3-pyridyl)-1-isopropyl-3-methyl-pyrazolo[4,3-b]pyridin-7-yl]methyl]-5-methoxy-pyridin-3-amine | 34 | 14 | 77 |
| 158 | N-[[5-(2-ethoxy-3-pyridyl)-1-isopropyl-3-methyl-pyrazolo[4,3-b]pyridin-7-yl]methyl]-1-methyl-1,2,4-triazol-3-amine | 23 | 4.9 | 50 |
| 159 | 5-(2-ethoxy-3-pyridyl)-1-isopropyl-7-[2-(5-methoxy-3-pyridyl)ethyl]-3-methyl-pyrazolo[4,3-b]pyridine | 270 | 70 | 1600 |
| 160 | 5-(2-ethoxy-3-pyridyl)-1-isopropyl-3-methyl-7-[2-(1-methyl-1,2,4-triazol-3-yl)ethyl]pyrazolo[4,3-b]pyridine | 23 | 3.9 | 56 |
| 161 | 5-(2-ethoxy-3-pyridyl)-1-isopropyl-3-methyl-N-[(2-methyl-1,2,4-triazol-3-yl)methyl]pyrazolo[4,3-b]pyridin-7-amine | 60 | 6.6 | 120 |
| 162 | 5-(2-ethoxy-3-pyridyl)-1-isopropyl-3-methyl-N-[(4-methyl-1,2,4-triazol-3-yl)methyl]pyrazolo[4,3-b]pyridin-7-amine | 100 | 13 | 180 |
| 163 | 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine | 120 | 14 | 120 |
| 164 | 5-(2-ethoxy-3-pyridyl)-1-isopropyl-3-methyl-7-[(1-methylpyrazol-4-yl)methylsulfanyl]pyrazolo[4,3-b]pyridine | 6.8 | 1.6 | 25 |
| 165 | N-[[1-(difluoromethyl)pyrazol-4-yl]methyl]-5-(2-ethoxy-3-pyridyl)-1-isopropyl-3-methyl-pyrazolo[4,3-b]pyridin-7-amine | 73 | 5.9 | 110 |
| 166 | 5-(2-ethoxy-3-pyridyl)-N-[[5-(fluoromethyl)isoxazol-3-yl]methyl]-1-isopropyl-3-methyl-pyrazolo[4,3-b]pyridin-7-amine | 2.1 | 0.16 | 7.2 |
| 167 | 5-(2-ethoxy-3-pyridyl)-N-[[3-(fluoromethyl)isoxazol-5-yl]methyl]-1-isopropyl-3-methyl-pyrazolo[4,3-b]pyridin-7-amine | 11 | 1 | 33 |
| 168 | 1-isopropyl-3-methyl-N-[(1-methylpyrazol-4-yl)methyl]-5-oxazol-2-yl-pyrazolo[4,3-b]pyridin-7-amine | 14 | 2.6 | 36 |
| 169 | 1-isopropyl-3-methyl-N-[(1-methylpyrazol-4-yl)methyl]-5-(3-methyltriazol-4-yl)pyrazolo[4,3-b]pyridin-7-amine | 610 | 85 | 170 |
| 170 | 1-isopropyl-5-(2-methoxy-3-pyridyl)-3-methyl-N-[[2-(trifluoromethyl)-3-pyridyl]methyl]pyrazolo[4,3-b]pyridin-7-amine | 42 | 5.3 | 46 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 171 | 3-[1-isopropyl-7-[(2-methoxy-3-pyridyl)methylamino]-3-methyl-pyrazolo[4,3-b]pyridin-5-yl]-1H-pyridin-2-one | 290 | 47 | 420 |
| 172 | 5-(2-ethoxy-3-pyridyl)-1-isopropyl-N-[(3-methoxy-4-pyridyl)methyl]-3-methyl-pyrazolo[4,3-b]pyridin-7-amine | 40 | 5.5 | 46 |
| 173 | 1-isopropyl-5-(2-methoxy-3-pyridyl)-3-methyl-N-[(2-methylthiazol-5-yl)methyl]pyrazolo[4,3-b]pyridin-7-amine | 49 | 6.3 | 26 |
| 174 | 5-(2-cyclopropoxypyridin-3-yl)-1-isopropyl-N-((2-methoxypyridin-3-yl)methyl)-3-methyl-1H-pyrazolo[4,3-b]pyridin-7-amine | 18 | 1.5 | 52 |
| 175 | 1-isopropyl-N-((2-methoxypyridin-3-yl)methyl)-3-methyl-5-(1-methyl-1H-pyrazol-5-yl)-1H-pyrazolo[4,3-b]pyridin-7-amine | 83 | 17 | 130 |
| 176 | 5-(2-ethoxy-3-pyridyl)-1-isopropyl-N-[(5-methoxypyrimidin-2-yl)methyl]-3-methyl-pyrazolo[4,3-b]pyridin-7-amine | 81 | 12 | 93 |
| 177 | 3-[1-isopropyl-3-methyl-7-[(1-methylpyrazol-4-yl)methylamino]pyrazolo[4,3-b]pyridin-5-yl]-1H-pyridin-2-one | 130 | 20 | 180 |
| 178 | N-[[2-(difluoromethyl)-3-pyridyl]methyl]-5-(2-ethoxy-3-pyridyl)-1-isopropyl-3-methyl-pyrazolo[4,3-b]pyridin-7-amine | 31 | 3.2 | 63 |
| 179 | 5-(2-ethoxy-3-pyridyl)-1-isopropyl-N-[(6-methoxypyrimidin-4-yl)methyl]-3-methyl-pyrazolo[4,3-b]pyridin-7-amine | 2.8 | 0.51 | 7 |
| 180 | 5-(2-(ethoxy-1,1-d$_2$)pyridin-3-yl)-1-isopropyl-N-((2-methoxypyridin-3-yl)methyl)-3-methyl-1H-pyrazolo[4,3-b]pyridin-7-amine | 27 | 0.77 | 78 |
| 181 | 5-(2-(ethoxy-d$_5$)pyridin-3-yl)-1-isopropyl-N-((2-methoxypyridin-3-yl)methyl)-3-methyl-1H-pyrazolo[4,3-b]pyridin-7-amine | 31 | 1.6 | 84 |
| 182 | 5-(2-(ethoxy-2,2,2-d$_3$)pyridin-3-yl)-1-isopropyl-N-((2-methoxypyridin-3-yl)methyl)-3-methyl-1H-pyrazolo[4,3-b]pyridin-7-amine | 24 | 1.1 | 61 |
| 183 | 1-isopropyl-N-((2-methoxypyridin-3-yl)methyl)-3-methyl-5-(2-(trifluoromethyl)pyridin-3-yl)-1H-pyrazolo[4,3-b]pyridin-7-amine | 290 | 38 | 350 |
| 184 | 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine | 13 | 2.4 | 45 |
| 185 | 1-isopropyl-3-methyl-N-((1-methyl-1H-pyrazol-4-yl)methyl)-5-(1H-1,2,4-triazol-1-yl)-1H-pyrazolo[4,3-b]pyridin-7-amine | 100 | 24 | 92 |
| 186 | 3-[1-isopropyl-3-methyl-7-[(1-methyl-1,2,4-triazol-3-yl)methylamino]pyrazolo[4,3-b]pyridin-5-yl]-1H-pyridin-2-one | 64 | 15 | 130 |
| 187 | 3-[1-isopropyl-3-methyl-7-(1H-pyrazol-3-ylmethylamino)pyrazolo[4,3-b]pyridin-5-yl]-1H-pyridin-2-one | 140 | 18 | 250 |
| 188 | 5-[2-(difluoromethoxy)-3-pyridyl]-1-isopropyl-N-[(2-methoxy-3-pyridyl)methyl]-3-methyl-pyrazolo[4,3-b]pyridin-7-amine | 61 | 7.8 | 60 |
| 189 | 5-(2-ethoxy-3-pyridyl)-1-isopropyl-N-[(4-methoxypyrimidin-2-yl)methyl]-3-methyl-pyrazolo[4,3-b]pyridin-7-amine | 3.9 | 0.49 | 19 |
| 190 | 5-(2-ethoxy-3-pyridyl)-1-isopropyl-N-[(4-methoxypyrimidin-5-yl)methyl]-3-methyl-pyrazolo[4,3-b]pyridin-7-amine | 74 | 7.9 | 94 |
| 191 | 5-(2-ethoxy-3-pyridyl)-N-[(2-ethoxy-3-pyridyl)methyl]-1-isopropyl-3-methyl-pyrazolo[4,3-b]pyridin-7-amine | 160 | 10 | 400 |
| 192 | 5-[2-(dimethylamino)-3-pyridyl]-1-isopropyl-N-[(4-methoxyphenyl)methyl]-3-methyl-pyrazolo[4,3-b]pyridin-7-amine | 630 | 71 | 490 |
| 193 | 3-[1-isopropyl-3-methyl-7-[[2-(trifluoromethyl)-3-pyridyl]methylamino]pyrazolo[4,3-b]pyridin-5-yl]-1H-pyridin-2-one | 320 | 54 | 880 |
| 194 | 1-isopropyl-3-methyl-5-(3-methylisoxazol-4-yl)-N-[(1-methylpyrazol-4-yl)methyl]pyrazolo[4,3-b]pyridin-7-amine | 95 | 23 | 21 |

TABLE 1-continued

Compounds of the invention

| Example | Compound | PDE1A, IC$_{50}$ (nM) | PDE1B, IC$_{50}$ (nM) | PDE1C, IC$_{50}$ (nM) |
|---|---|---|---|---|
| 195 | 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine | 420 | 110 | 160 |
| 196 | 1-isopropyl-3-methyl-5-(2-propoxy-3-pyridyl)-N-(1H-pyrazol-4-ylmethyl)pyrazolo[4,3-b]pyridin-7-amine | 18 | 1.7 | 27 |
| 197 | 5-(2-ethoxy-3-pyridyl)-N-[(2-methoxy-3-pyridyl)methyl]-3-methyl-1-(oxetan-3-yl)pyrazolo[4,3-b]pyridin-7-amine | 190 | 13 | 190 |
| 198 | 5-(2-(ethyl(methyl)amino)pyridin-3-yl)-1-isopropyl-N-(4-methoxybenzyl)-3-methyl-1H-pyrazolo[4,3-b]pyridin-7-amine | 1100 | 240 | 1000 |
| 199 | 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine | 7.4 | 0.75 | 26 |
| 200 | 1-isopropyl-3-methyl-N-((1-methyl-1H-pyrazol-4-yl)methyl)-5-(4-methyloxazol-5-yl)-1H-pyrazolo[4,3-b]pyridin-7-amine | 98 | 18 | 110 |
| 201 | 5-[2-(dimethylamino)-3-pyridyl]-1-isopropyl-3-methyl-N-[(1-methylpyrazol-4-yl)methyl]pyrazolo[4,3-b]pyridin-7-amine | 2100 | 230 | 2100 |
| 202 | 1-isopropyl-3-methyl-N-((1-methyl-1H-pyrazol-4-yl)methyl)-5-(4-methyloxazol-2-yl)-1H-pyrazolo[4,3-b]pyridin-7-amine | 92 | 14 | 170 |
| 203 | 1-isopropyl-3-methyl-N-[(1-methylpyrazol-4-yl)methyl]-5-(4-methyl-1,2,4-triazol-3-yl)pyrazolo[4,3-b]pyridin-7-amine | 410 | 180 | 420 |

Table 1 lists the IC$_{50}$ value for inhibition of PDE1 by the compounds of the invention. The IC$_{50}$ value refers to the concentration (nM) of the compound required to reach 50% inhibition of the PDE1 enzyme at the specified substrate concentration. PDE1 assays are described in the Experimental Section.

Experimental Section

Preparation of the Compounds of the Invention—General Methods

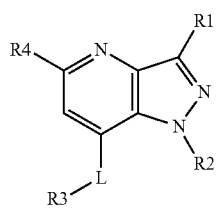
(I)

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those method described in standard reference books such as "Compendium of Organic Synthetic Methods, Vol. I-XIII" (published with Wiley-Interscience, ISSN: 1934-4783). Preferred methods include, but are not limited to, those described below.

The schemes are representative of methods useful in synthesising the compounds of the present invention. They are not to constrain the scope of the invention in any way.

Method 1:

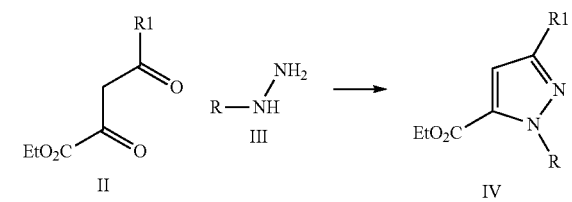

Scheme 1 where R1 is as described for formula I and R is hydrogen or R is R$_2$ as described for formula I.

Compounds of general formula IV (Scheme 1) can be prepared from compounds of general formula II and III.

Method 2:

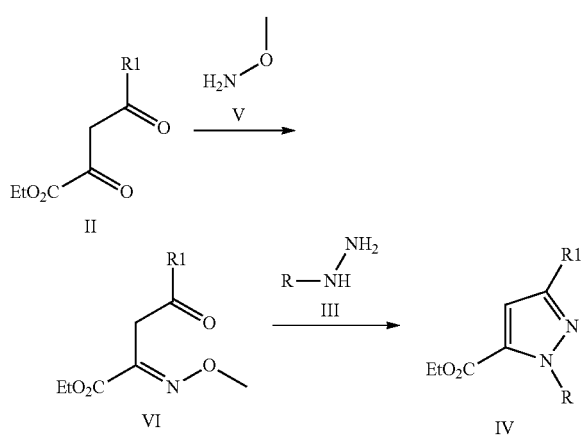

Scheme 2 where R1 is as described for formula I and R is R2 is as described for formula I or a protection group such as para-methoxy benzyl.

Compounds of general formula IV (Scheme 2) can be prepared from compounds of general formula II, III and V as described in the literature (e.g. Int. Pat. App. WO2013142307)

Method 3:

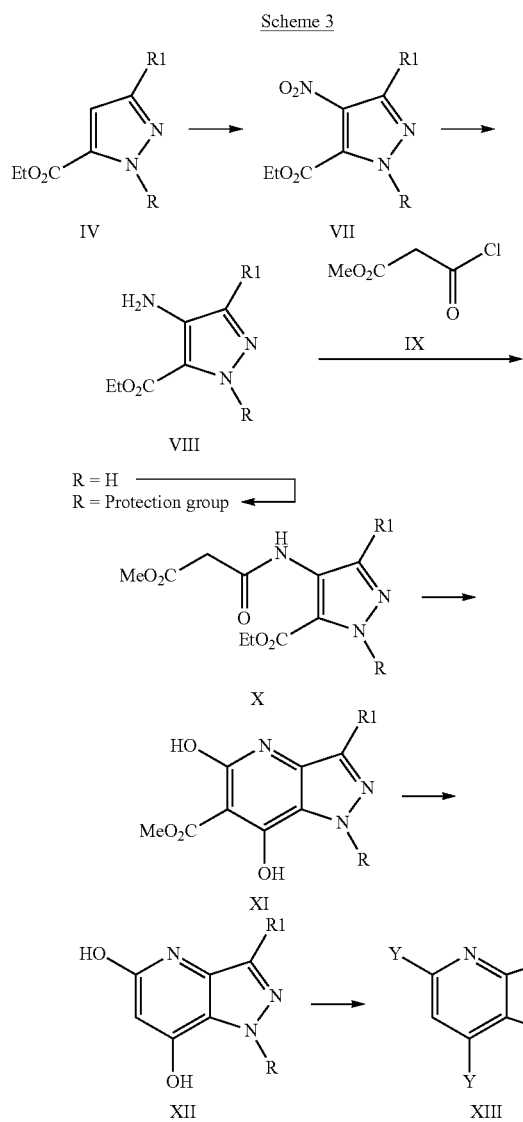

where R1 is as described for formula I, R is R2 is as described for formula I or R is a protection group such as para-methoxy benzyl and Y is a halogen such as chlorine or bromine.

Compounds of general formula VIII (Scheme 3) can be prepared by nitration of compounds of general formula IV followed by reduction. Compounds of general formula XI can be prepared by reaction of compounds of general formula VIII with methyl 3-chloro-3-oxopropanoate followed by ring-closure in the presence of a base such as sodium ethoxide or sodium methoxide. Hydrolysis and decarboxylation of compounds of general formula XI followed by treatment with phosphoryl trichloride or phosphoryl tribromide gives compounds of general formula XIII.

Method 4:

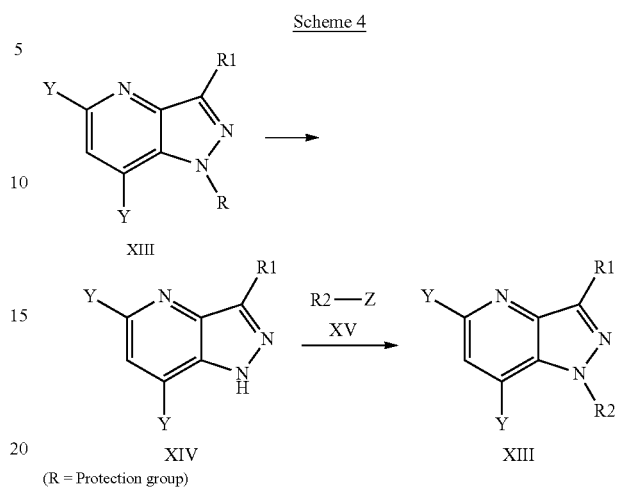

where R1 and R2 are as described for formula I, R is a protection group such as para-methoxy benzyl, Y is a halogen such as chlorine or bromine and Z is a leaving group such as chlorine, bromine, iodine or a methanesulfonate group or Z is a hydroxy group.

Compounds of general formula XIV (Scheme 4) can be prepared by the deprotection of compounds of general formula XIII where R is a protection group. If the protection group is para-methoxy benzyl, the deprotection can be performed by treatment with an acid such as trifluoroacetic acid. Compounds of general formula XIII can be prepared by reaction of compounds of general formula XIV with compounds of general formula XV in the presence of a base such as cesium carbonate or using Mitsunobu reaction conditions when Z is a hydroxy group.

Method 5:

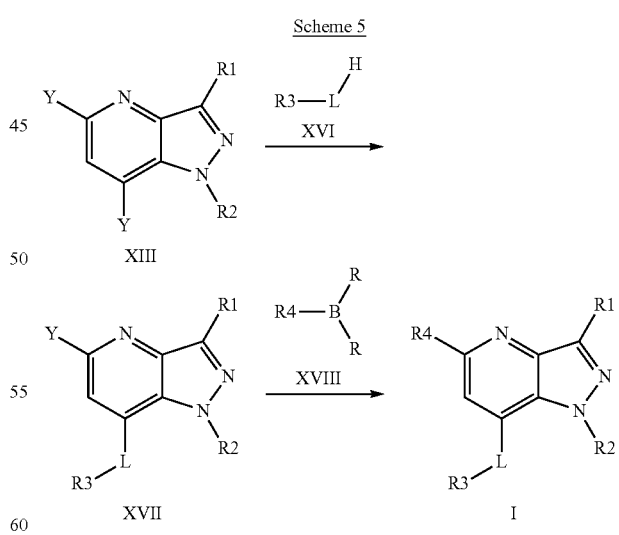

where R1, R2, R3 and R4 are as described for formula I, L is NH, O or S and R are hydroxy groups or R together with the boron atom form a 4,4,5,5-tetramethyl-1,3,2-dioxaborolane group. Y is a halogen such as chlorine or bromine.

Compounds of general formula XVII (Scheme 5) can be prepared by treatment of compounds of general formula XIII with compounds of general formula XVI in the presence of a base such as but not limited to cesium fluoride or N,N-diisopropylethylamine.

Compounds of general formula I can be prepared from compounds of general formulae XVII and XVIII in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis.

Method 6:

Scheme 6:

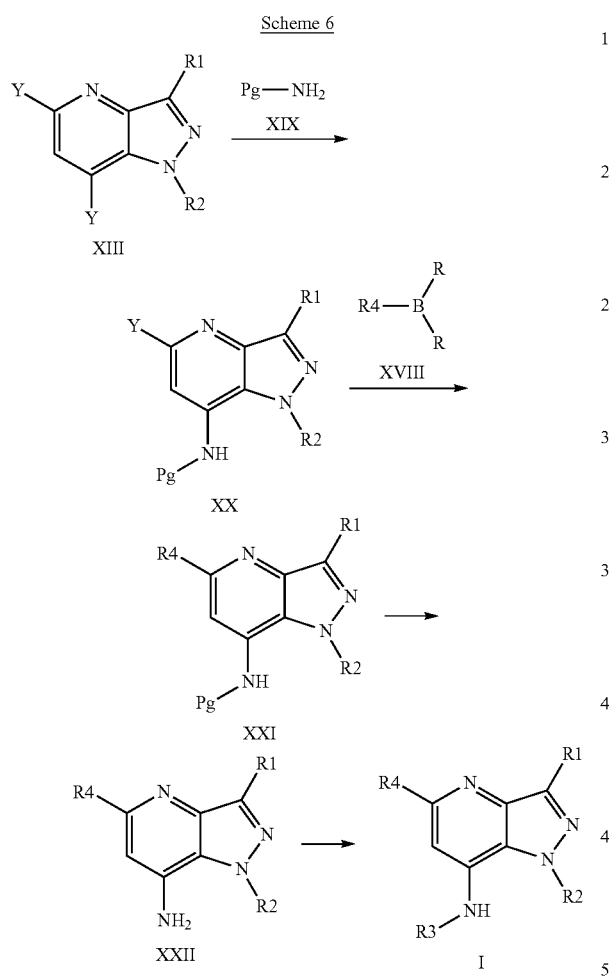

where R1, R2, R3 and R4 are as described for formula I, R are hydroxy groups or R together with the boron atom form a 4,4,5,5-tetramethyl-1,3,2-dioxaborolane group and Pg is a protection group such as para-methoxy benzyl. Y is a halogen such as chlorine or bromine.

Compounds of general formula XX (Scheme 6) can be prepared by treatment of compounds of general formula XIII with compounds of general formula XIX in the presence of a base such as but not limited to cesium fluoride or N,N-diisopropylethylamine. Compounds of general formula XXI can be prepared from compounds of general formulae XX and XVIII in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis. Compounds of general formula XXII can be prepared deprotection of compounds of general formula XXI. If the protection group is para-methoxy benzyl, the deprotection can be performed by treatment with an acid such as trifluoroacetic acid. Compounds of general formula I can be prepared by reductive amination of compounds of general formula XXII with the appropriate aldehyde or ketone.

Method 7:

Scheme 7:

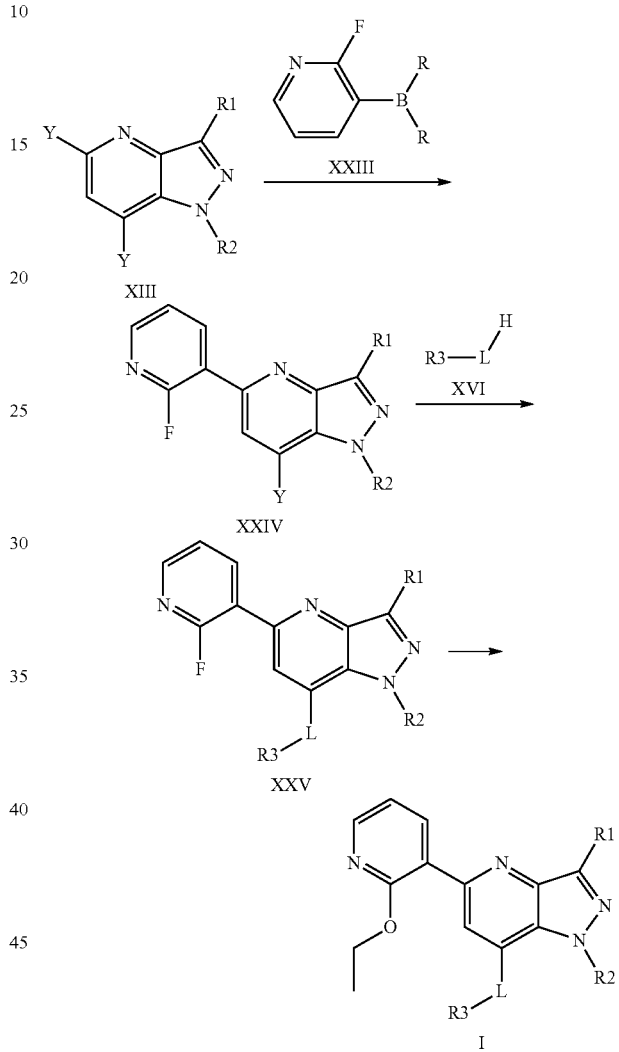

where R1, R2, and R3 are as described for formula I, L is NH, O or S, R are hydroxy groups or R together with the boron atom form a 4,4,5,5-tetramethyl-1,3,2-dioxaborolane group. Y is a halogen such as chlorine or bromine.

Compounds of general formula XXIV (Scheme 7) can be prepared from compounds of general formulae XIII and XXIII in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis. Compounds of general formula XXV can be prepared by treatment of compounds of general formula XXIV with compounds of general formula XVI in the presence of a base such as but not limited to cesium fluoride or N,N-diisopropylethylamine. Compounds of general formula I can be prepared by treatment of compounds of general formula XXV with sodium ethoxide.

Method 8:

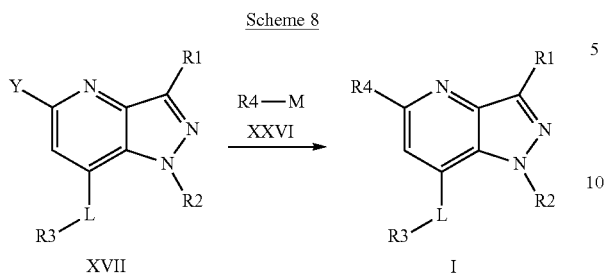

where R1, R2, R3, R4 and L are as described for formula I and M is ZnCl or SnR₃, where R are alkyl groups such as butyl or methyl. Y is a halogen such as chlorine or bromine.

Compounds of general formula I (Scheme 8) can be prepared from compounds of general formulae XVII and XXVI in the presence of a palladium catalyst such as Pd(PPh₃)₄ or other Stille or Negishi coupling reaction conditions known to chemists skilled in the art of organic synthesis.

Method 9:

Scheme 9:

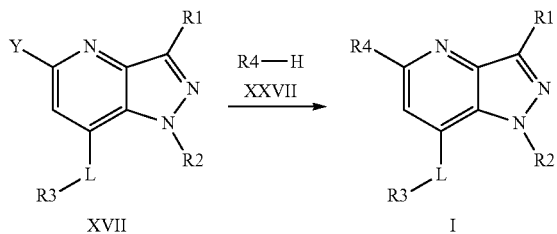

where R1, R2, R3, and L are as described for formula I and M is ZnCl or Sn(R)₃, where R are alkyl groups such as butyl or methyl. Y is a halogen such as chlorine or bromine. R4 is as described for formula I with the attachment point of R4 is a nitrogen.

Compounds of general formula I (Scheme 9) can be prepared from compounds of general formulae XVII and XXVII in the presence of a copper catalyst such as CuI in combination with a ligand or palladium catalyst such as Pd₂(dba)₃ in combination with Xantphos and a base such as Cs₂CO₃ using reaction conditions known to chemists skilled in the art of organic synthesis.

Method 10:

Scheme 10:

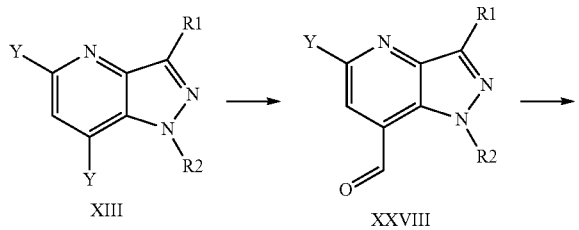

where R1, R2 and R4 are as described for formula I, L is CH₂ and

R3 is methyl substituted with phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or R3 is methyl substituted with a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy. R5 is phenyl, pyridonyl, pyridinyl, pyrimidinyl or pyrazinyl all of which can be optionally substituted one or more times with one or more substituents selected from the group consisting of halogen, cyano, $C_1$-$C_3$ alkyl, $C_1$-$C_3$ fluoroalkyl, $C_1$-$C_3$ fluoroalkoxy and $C_1$-$C_3$ alkoxy; or R5 is a 5-membered heteroaryl which is optionally substituted with one or more substituents selected from halogen, cyano, $C_1$-$C_3$ alkyl, $C_1$-$C_3$ fluoroalkyl, $C_1$-$C_3$ fluoroalkoxy and $C_1$-$C_3$ alkoxy. Y is a halogen such as chlorine or bromine. X is a halogen such as iodine or bromine.

Compounds of general formula XXVIII (Scheme 10) can be prepared by treatment of compounds of general formula XIII with a reagent such as i-PrMgCl—LiCl followed by treatment with N,N-dimethyl formamide. Compounds of general formula XXIX can be prepared by treatment of compounds of general formula XXVIII with a reagent such as 1-diazo-1-dimethoxyphosphoryl-propan-2-one and a base such as Cs₂CO₃. Compounds of general formula XXXI can be prepared from compounds of general formulae XXIX and XXX in the presence of a palladium catalyst such as [1,1'-bis(diphenylphosphino)ferrocene]palladium(II) dichloride, a base such as triethylamine and a copper catalyst such as CuI using reaction conditions known to chemists skilled in the art of organic synthesis. Compounds of general formula I can be prepared by treatment of compounds of general formula XXXI with palladium on carbon under an atmosphere of hydrogen.

Method 11:

Scheme 11:

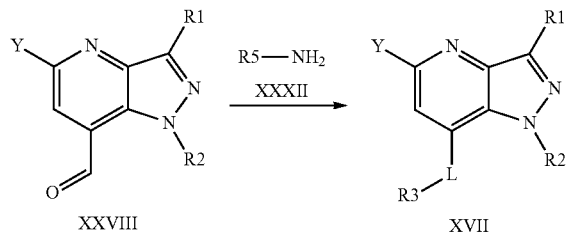

where R1, R2 and R4 are as described for formula I,

L is CH$_2$ and R3 is NH which is substituted with phenyl, pyridonyl, pyridinyl, pyrimidinyl or pyrazinyl all of which can be optionally substituted one or more times with one or more substituents selected from the group consisting of halogen, cyano, C$_1$-C$_3$ alkyl, C$_1$-C$_3$ fluoroalkyl, C$_1$-C$_3$ fluoroalkoxy and C$_1$-C$_3$ alkoxy; or L is CH$_2$ and R3 is NH which is substituted with a 5-membered heteroaryl which is optionally substituted with one or more substituents selected from halogen, cyano, C$_1$-C$_3$ alkyl, C$_1$-C$_3$ fluoroalkyl, C$_1$-C$_3$ fluoroalkoxy and C$_1$-C$_3$ alkoxy. R5 is phenyl, pyridonyl, pyridinyl, pyrimidinyl or pyrazinyl all of which can be optionally substituted one or more times with one or more substituents selected from the group consisting of halogen, cyano, C$_1$-C$_3$ alkyl, C$_1$-C$_3$ fluoroalkyl, C$_1$-C$_3$ fluoroalkoxy and C$_1$-C$_3$ alkoxy; or R5 is a 5-membered heteroaryl which is optionally substituted with one or more substituents selected from halogen, cyano, C$_1$-C$_3$ alkyl, C$_1$-C$_3$ fluoroalkyl, C$_1$-C$_3$ fluoroalkoxy and C$_1$-C$_3$ alkoxy. Y is a halogen such as chlorine or bromine.

Compounds of general formula XVII (Scheme 11) can be prepared by reductive amination of compounds of general formula XXVIII with compounds of general formula XXXII.

Method 12:

Scheme 12:

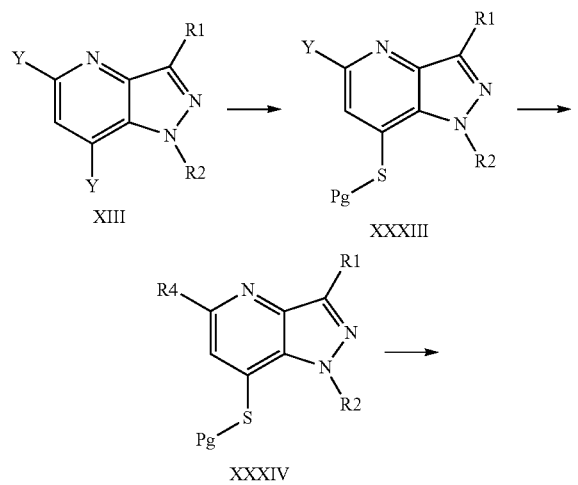

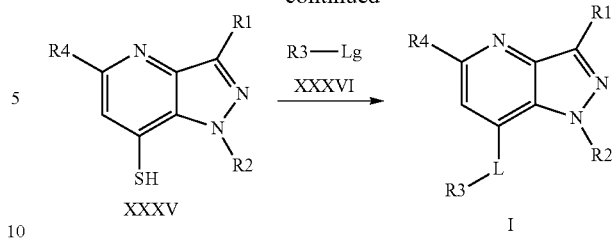

where R1, R2, R3 and R4 are as described for formula I and L is sulphur. Y is a halogen such as chlorine or bromine. Pg is a protecting group such as 6-methylheptyl propano-3-ate. Lg is a leaving group such as chlorine, bromine, iodine, 4-methylbenzenesulfonate or methanesulfonate.

Compounds of general formula XXXIII (Scheme 12) can be prepared by treatment of compounds of general formula XIII with a reagent such as 6-methylheptyl 3-mercaptopropanoate in the presence of a base such as diisopropyl ethylamine. Compounds of general formula XXXIV can be prepared by the same methods as described in methods 5, 8 and 9. Compounds of general formula I can be prepared by deprotection of compounds of general formula XXXIV by using a base such as potassium tert-butoxide followed by alkylation with compounds of general formula XXXVI.

Method 13:

Scheme 13:

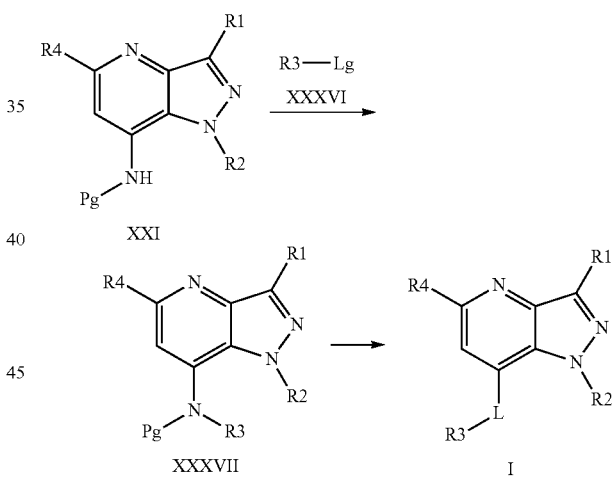

where R1, R2, R3 and R4 are as described for formula I and L is NH. Pg is a protecting group such as p-methoxybenzyl and Lg is a leaving group such as chlorine, bromine, iodine, 4-methylbenzenesulfonate or methanesulfonate.

Compounds of general formula XXXVII (Scheme 13) can be prepared by deprotonation of compounds of general formula XXI with a base such as sodium hydride followed by alkylation with compounds of general formula XXXVI. Compounds of general formula I can be prepared by removal of the protecting group (Pg) using reaction conditions known to chemists skilled in the art of organic synthesis, e.g. by treatment with trifluoroacetic acid when Pg is p-methoxybenzyl.

LC-MS Methods

Method A:

An Agilent 1200 LCMS system with ELS detector was used. Phenomenex Luna-C18, 5 µm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method B:

An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Method C:

An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method D:

A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.

Method E:

A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=90:10 to 0:100 in 1.0 minutes and with a flow rate of 1.2 mL/min.

Method F:

An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=85:15 to 0:100 in 3.4 minutes and with a flow rate of 0.8 mL/min.

Method G:

An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method H:

An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=70:30 to 0:100 in 3.4 minutes and with a flow rate of 0.8 mL/min.

Method I:

An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=75:25 to 0:100 in 3.4 minutes and with a flow rate of 0.8 mL/min.

Method J:

A Waters Autopurification was used. Column: XSelect CSH C18 3.5 micron, 4.6×50 mm; Column temperature: 25° C.; Solvent system: A=water/formic acid (99.9:0.1) and B=acetonitrile/trifluoroacetic acid (99.9:0.1); Method: Linear gradient elution with A:B=97:3 to 10:90 in 2.5 minutes and with a flow rate of 2.5 mL/min.

Method K:

A Waters Autopurification was used. Column: XSelect CSH C18 3.5 micron, 4.6×50 mm; Column temperature: 25° C.; Solvent system: A=water/formic acid (99.9:0.1) and B=acetonitrile/trifluoroacetic acid (99.9:0.1); Method: Linear gradient elution with A:B=97:3 to 10:90 in 2.5 minutes, then with A:B=10:90 for 1 minute. The flow rate was 2.5 mL/min.

Intermediates:

Preparation of ethyl 3-methyl-1H-pyrazole-5-carboxylate

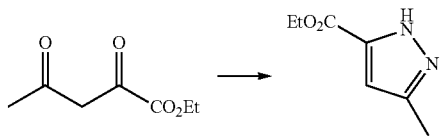

A solution of ethyl 2,4-dioxopentanoate (20 g, 126 mmol, 18 mL) and hydrazine hydrate (6.96 g, 139 mmol, 6.76 mL) in ethanol (400 mL) was stirred at 0° C. for 1 hour. The mixture was concentrated to give ethyl 3-methyl-1H-pyrazole-5-carboxylate (19 g, 123 mmol, 97% yield).

Preparation of ethyl 1,3-dimethyl-1H-pyrazole-5-carboxylate

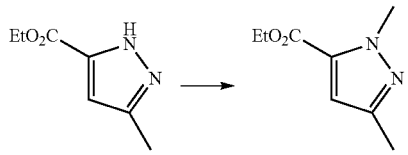

To a solution of ethyl 3-methyl-1H-pyrazole-5-carboxylate (19.5 g, 126 mmol) in DMF (200 mL) was added $Me_2SO_4$ (23.8 g, 189 mmol, 17.9 mL). The mixture was stirred at 80° C. for 18 hours. After cooling to 0° C., the mixture was diluted with ice, then aqueous ammonia (25%) was added to adjust the pH to 8. Then the mixture was extracted with ethyl acetate (300 mL×3), the combined organic layers were washed with brine (50 mL), dried, and concentrated. The crude mixture was purified by flash chromatography with petroleum ether:ethyl acetate=5:1 to give ethyl 1,3-dimethyl-1H-pyrazole-5-carboxylate (15 g, 89 mmol, 71% yield).

Preparation of ethyl 2-(methoxyimino)-4-oxopentanoate

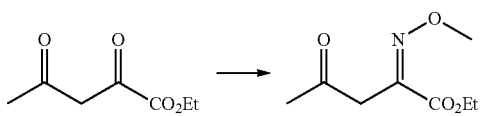

A mixture of ethyl 2,4-dioxopentanoate (27 g, 171 mmol, 24 mL) and methoxylamine (15 g, 179 mmol, 13.6 mL) in ethanol (150 mL) was stirred at 25° C. for 18 hours under a nitrogen atmosphere. The mixture was concentrated. The crude mixture was purified by flash silica gel chromatography with petroleum ether:ethyl acetate=10:1 to give ethyl 2-(methoxyimino)-4-oxopentanoate (19.9 g, 103 mmol, 60% yield). $^1$H NMR (chloroform-d 400 MHz): δ 4.34 (q, J=6.8 Hz, 2H), 4.07 (s, 3H), 3.71 (s, 2H), 2.21 (s, 3H), 1.35 (d, J=7.6 Hz, 3H).

Preparation of ethyl 1-isopropyl-3-methyl-1H-pyrazole-5-carboxylate

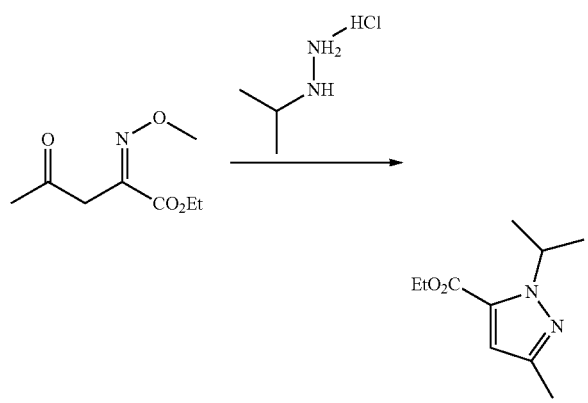

To a solution of ethyl 2-(methoxyimino)-4-oxopentanoate (14.6 g, 78.0 mmol) in ethanol (200 mL) was added isopropylhydrazine hydrochloride (17.25 g, 156 mmol). The mixture was stirred at 80° C. for 18 hours. The mixture was concentrated. Saturated aqueous NaHCO$_3$ was added into the residue to adjust the pH to 7. Then the mixture was extracted with dichloromethane (100 mL×3), the combined organic layers were washed with brine, dried over Na$_2$SO$_4$ and concentrated. The crude mixture was purified by flash silica gel chromatography with petroleum ether:ethyl acetate=10:1 to give ethyl 1-isopropyl-3-methyl-1H-pyrazole-5-carboxylate (12.3 g, 62.7 mmol, 80% yield). $^1$H NMR (chloroform-d 400 MHz): δ 6.59 (s, 1H), 5.41-5.44 (m, 1H), 4.35-4.29 (m, 2H), 2.29 (s, 3H), 1.48 (d, J=6.8 Hz, 6H), 1.39-1.35 (m, 3H).

Preparation of ethyl 1-isopropyl-3-methyl-4-nitro-1H-pyrazole-5-carboxylate

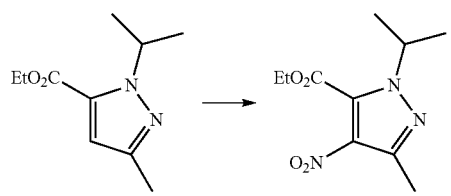 [SMILES: CCOC(=O)c1cc(C)nn1C(C)C ; CCOC(=O)c1c([N+](=O)[O-])c(C)nn1C(C)C]

To a solution of ethyl 1-isopropyl-3-methyl-1H-pyrazole-5-carboxylate (8 g, 40.8 mmol) and (2,2,2-trifluoroacetyl) 2,2,2-trifluoroacetate (59.9 g, 285.4 mmol, 39.7 mL) in TFA (80 mL) was added ammonium nitrate (6.5 g, 81.5 mmol, 3.8 mL) slowly at 0° C. The mixture was stirred at 20° C. for 18 hours. The solution was cooled to 0° C. and then neutralized with aqueous K$_2$CO$_3$ and the product was extracted with ethyl acetate:dichloromethane=40:1 (205 mL×4). The combined organic layers were washed with brine (150 mL), dried over Na$_2$SO$_4$ and concentrated to give ethyl 1-isopropyl-3-methyl-4-nitro-1H-pyrazole-5-carboxylate (9.8 g).

Ethyl 1-ethyl-3-methyl-4-nitro-1H-pyrazole-5-carboxylate was prepared in a similar way from ethylhydrazine.

Ethyl 1-cyclopropyl-3-methyl-4-nitro-1H-pyrazole-5-carboxylate was prepared in a similar way from cyclopropylhydrazine.

(±)-Ethyl 1-(sec-butyl)-3-methyl-1H-pyrazole-5-carboxylate was prepared in a similar way from (±)-sec-butylhydrazine hydrochloride.

Preparation of ethyl 3-methyl-4-nitro-1H-pyrazole-5-carboxylate

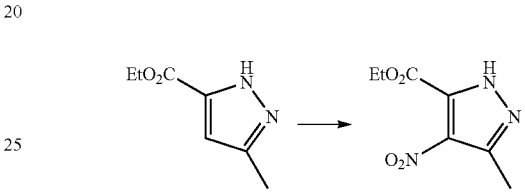

Ethyl 3-methyl-1H-pyrazole-5-carboxylate (12 g, 78 mmol) was added in portions to fuming nitric acid (140 g, 2.2 mol, 100 mL) at 0° C. The mixture was stirred at 15° C. for 16 hours. The mixture was poured into ice (200 g) and adjusted to pH 7 by saturated aqueous K$_2$CO$_3$. The mixture was extracted with ethyl acetate (500 mL×2). The organic layer was washed with H$_2$O (500 mL), brine (500 mL), dried over Na$_2$SO$_4$, filtered and concentrated to give ethyl 3-methyl-4-nitro-1H-pyrazole-5-carboxylate (13 g, 65 mmol, 84% yield). $^1$H NMR (chloroform-d 400 MHz) δ 11.41 (brs, 1H), 4.47-4.42 (m, 2H), 2.64 (s, 3H), 1.39 (t, J=7.2 Hz, 3H).

Preparation of ethyl 1-(4-methoxybenzyl)-3-methyl-4-nitro-1H-pyrazole-5-carboxylate and ethyl 1-(4-methoxybenzyl)-5-methyl-4-nitro-1H-pyrazole-3-carboxylate

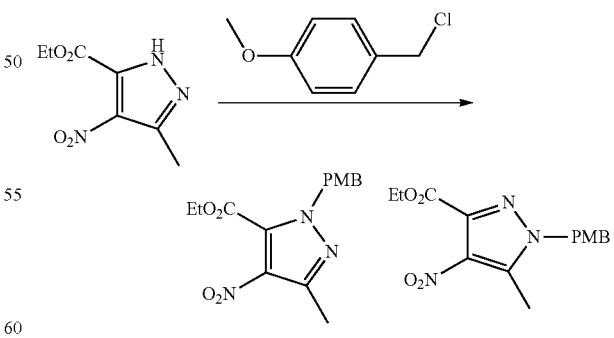

To a solution of ethyl 3-methyl-4-nitro-1H-pyrazole-5-carboxylate (4.40 g, 22.1 mmol) in dry DMF (50 mL) was added 1-(chloromethyl)-4-methoxybenzene (4.15 g, 26.5 mmol, 3.6 mL) and K$_2$CO$_3$ (6.11 g, 44.2 mmol). The mixture was stirred at 15° C. for 16 hours. The mixture was concentrated and water (20 mL) was added. The mixture was extracted with ethyl acetate (20 mL×2). The combined organic layers were washed with H₂O (20 mL×2), brine (20 mL), dried over Na₂SO₄, filtered and concentrated. The residue was purified by flash chromatography on silica gel (0% to 50% ethyl acetate in petroleum ether) to give ethyl 1-(4-methoxybenzyl)-3-methyl-4-nitro-1H-pyrazole-5-carboxylate (2.80 g, 8.77 mmol, 40% yield) and ethyl 1-(4-methoxybenzyl)-5-methyl-4-nitro-1H-pyrazole-3-carboxylate (3.50 g, 11 mmol, 50% yield).

Preparation of ethyl 4-amino-1-isopropyl-3-methyl-1H-pyrazole-5-carboxylate

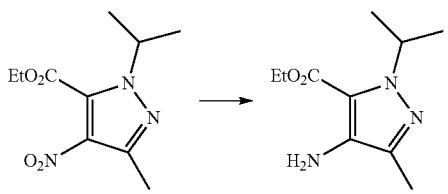 [SMILES: CCOC(=O)c1c([N+](=O)[O-])c(C)nn1C(C)C ; CCOC(=O)c1c(N)c(C)nn1C(C)C]

To a solution of ethyl 1-isopropyl-3-methyl-4-nitro-1H-pyrazole-5-carboxylate (10.23 g, 42.41 mmol) in ethyl acetate (200 mL) was added Pd—C (10%, 2.0 g, wet) under nitrogen. The suspension was degassed under vacuo and purged with hydrogen several times. The mixture was stirred under hydrogen (30 psi) at 40° C. for 18 hours. The mixture was filtered and the residue was washed with ethyl acetate (150 ml×3), the combined filtrates were concentrated to give ethyl 4-amino-1-isopropyl-3-methyl-1H-pyrazole-5-carboxylate (8.96 g).

Ethyl 4-amino-1-(4-methoxybenzyl)-3-methyl-1H-pyrazole-5-carboxylate was prepared in a similar way from ethyl 1-(4-methoxybenzyl)-3-methyl-4-nitro-1H-pyrazole-5-carboxylate.

Ethyl 4-amino-1-ethyl-3-methyl-1H-pyrazole-5-carboxylate was prepared in a similar way from ethyl 1-ethyl-3-methyl-4-nitro-1H-pyrazole-5-carboxylate.

Ethyl 4-amino-1-cyclopropyl-3-methyl-1H-pyrazole-5-carboxylate was prepared in a similar way from ethyl 1-cyclopropyl-3-methyl-4-nitro-1H-pyrazole-5-carboxylate.

Ethyl 4-amino-1,3-dimethyl-1H-pyrazole-5-carboxylate was prepared in a similar way from ethyl 1,3-dimethyl-4-nitro-1H-pyrazole-5-carboxylate.

(±)-Ethyl 4-amino-1-(sec-butyl)-3-methyl-1H-pyrazole-5-carboxylate was prepared in a similar way from (±)-ethyl 1-(sec-butyl)-3-methyl-1H-pyrazole-5-carboxylate.

Preparation of ethyl 1-isopropyl-4-(3-methoxy-3-oxopropanamido)-3-methyl-1H-pyrazole-5-carboxylate

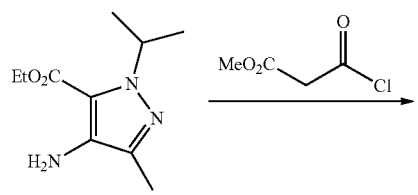

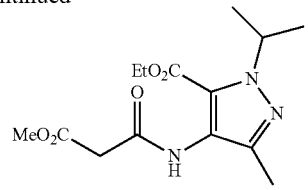

To a solution of ethyl 4-amino-1-isopropyl-3-methyl-1H-pyrazole-5-carboxylate (7.96 g, 37.7 mmol) in dichloromethane (150 mL) was added methyl 3-chloro-3-oxopropanoate (5.14 g, 37.7 mmol, 4.02 mL). The mixture was stirred at 50° C. for 45 minutes. After the reaction mixture had cooled to room temperature, the mixture was partitioned between dichloromethane (200 mL) and saturated aqueous NaHCO₃ (100 mL), the aqueous phase was extracted with dichloromethane (100 mL×2), the combined organic layers were washed with brine (50 mL), dried over MgSO₄ and concentrated to give ethyl 1-isopropyl-4-(3-methoxy-3-oxopropanamido)-3-methyl-1H-pyrazole-5-carboxylate (11.7 g, 37 mmol, >95% yield).

Ethyl 4-(3-methoxy-3-oxopropanamido)-1-(4-methoxybenzyl)-3-methyl-1H-pyrazole-5-carboxylate was prepared in a similar way from ethyl 4-amino-1-(4-methoxybenzyl)-3-methyl-1H-pyrazole-5-carboxylate.

Ethyl 1-ethyl-4-(3-methoxy-3-oxopropanamido)-3-methyl-1H-pyrazole-5-carboxylate was prepared in a similar way from ethyl 4-amino-1-ethyl-3-methyl-1H-pyrazole-5-carboxylate.

Ethyl 1-cyclopropyl-4-(3-methoxy-3-oxopropanamido)-3-methyl-1H-pyrazole-5-carboxylate was prepared in a similar way from ethyl 4-amino-1-cyclopropyl-3-methyl-1H-pyrazole-5-carboxylate.

Ethyl 4-(3-methoxy-3-oxopropanamido)-1,3-dimethyl-1H-pyrazole-5-carboxylate was prepared in a similar way from ethyl 4-amino-1,3-dimethyl-1H-pyrazole-5-carboxylate.

(±)-Ethyl 1-(sec-butyl)-4-(3-methoxy-3-oxopropanamido)-3-methyl-1H-pyrazole-5-carboxylate was prepared in a similar way from (±)-ethyl 4-amino-1-(sec-butyl)-3-methyl-1H-pyrazole-5-carboxylate.

Preparation of methyl 5,7-dihydroxy-1-isopropyl-3-methyl-1H-pyrazolo[4,3-b]pyridine-6-carboxylate

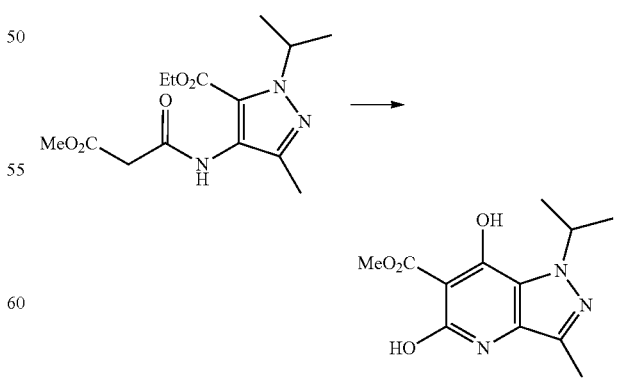

To a solution of ethyl 1-isopropyl-4-(3-methoxy-3-oxopropanamido)-3-methyl-1H-pyrazole-5-carboxylate (12.5 g, 40 mmol) in ethanol (200 mL) was added NaOEt (5.45 g, 80 mmol). The mixture was stirred at 20° C. for 1 hour. The mixture was concentrated. The crude product (10.62 g) was used into the next step without further purification.

Methyl 5,7-dihydroxy-1-(4-methoxybenzyl)-3-methyl-1H-pyrazolo[4,3-b]pyridine-6-carboxylate was prepared in a similar way from ethyl 4-(3-methoxy-3-oxopropanamido)-1-(4-methoxybenzyl)-3-methyl-1H-pyrazole-5-carboxylate.

Methyl 1-ethyl-5,7-dihydroxy-3-methyl-1H-pyrazolo[4,3-b]pyridine-6-carboxylate was prepared in a similar way from ethyl 1-ethyl-4-(3-methoxy-3-oxopropanamido)-3-methyl-1H-pyrazole-5-carboxylate.

Methyl 1-cyclopropyl-5,7-dihydroxy-3-methyl-1H-pyrazolo[4,3-b]pyridine-6-carboxylate was prepared in a similar way from ethyl 1-cyclopropyl-4-(3-methoxy-3-oxopropanamido)-3-methyl-1H-pyrazole-5-carboxylate.

Methyl 5,7-dihydroxy-1,3-dimethyl-1H-pyrazolo[4,3-b]pyridine-6-carboxylate was prepared in a similar way from ethyl 4-(3-methoxy-3-oxopropanamido)-1,3-dimethyl-1H-pyrazole-5-carboxylate.

(±)-Methyl 1-(sec-butyl)-5,7-dihydroxy-3-methyl-1H-pyrazolo[4,3-b]pyridine-6-carboxylate was prepared in a similar way from (±)-ethyl 1-(sec-butyl)-4-(3-methoxy-3-oxopropanamido)-3-methyl-1H-pyrazole-5-carboxylate.

Preparation of 1-isopropyl-3-methyl-1H-pyrazolo[4,3-b]pyridine-5,7-diol

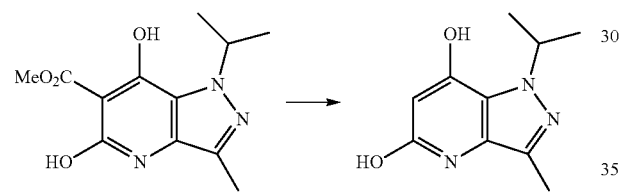

A mixture of methyl 5,7-dihydroxy-1-isopropyl-3-methyl-1H-pyrazolo[4,3-b]pyridine-6-carboxylate (10.62 g, 40.04 mmol) in aqueous NaOH (2 N, 150 mL) was stirred at 110° C. for 6 hours. The mixture was cooled to 0° C., then saturated KHSO$_4$ was added to adjust the pH to 2~3. The resulting mixture was filtered and the residue was washed with water (50 mL×3), then dried to give 1-isopropyl-3-methyl-1H-pyrazolo[4,3-b]pyridine-5,7-diol (7 g, 32.43 mmol, 81% yield). $^1$H NMR (DMSO-d$_6$ 400 MHz) δ 11.02 (brs, 1H), 5.50 (s, 1H), 5.11-5.08 (m, 1H), 2.24 (s, 3H), 1.37 (d, J=6.8 Hz, 6H).

1-(4-Methoxybenzyl)-3-methyl-1H-pyrazolo[4,3-b]pyridine-5,7-diol was prepared in a similar way from methyl 5,7-dihydroxy-1-(4-methoxybenzyl)-3-methyl-1H-pyrazolo[4,3-b]pyridine-6-carboxylate.

1-ethyl-3-methyl-1H-pyrazolo[4,3-b]pyridine-5,7-diol was prepared in a similar way from methyl 1-ethyl-5,7-dihydroxy-3-methyl-1H-pyrazolo[4,3-b]pyridine-6-carboxylate.

1-cyclopropyl-3-methyl-1H-pyrazolo[4,3-b]pyridine-5,7-diol was prepared in a similar way from methyl 1-cyclopropyl-5,7-dihydroxy-3-methyl-1H-pyrazolo[4,3-b]pyridine-6-carboxylate.

1,3-dimethyl-1H-pyrazolo[4,3-b]pyridine-5,7-diol was prepared in a similar way from 1-cyclopropyl-3-methyl-1H-pyrazolo[4,3-b]pyridine-5,7-diol.

(±)-1-(sec-Butyl)-3-methyl-1H-pyrazolo[4,3-b]pyridine-5,7-diol was prepared in a similar way from (±)-methyl 1-(sec-butyl)-5,7-dihydroxy-3-methyl-1H-pyrazolo[4,3-b]pyridine-6-carboxylate.

Preparation of 5,7-dichloro-1-isopropyl-3-methyl-1H-pyrazolo[4,3-b]pyridine

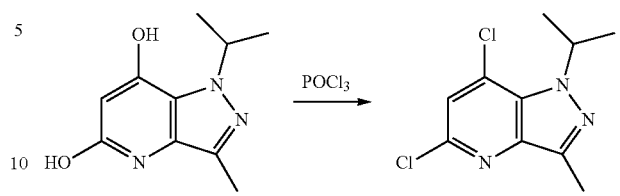

A mixture of 1-isopropyl-3-methyl-1H-pyrazolo[4,3-b]pyridine-5,7-diol (3.50 g, 16.9 mmol) in phosphoryl trichloride (30 mL) was stirred at 80° C. for 18 hours. The mixture was stirred at 85° C. for another 1 hour. The mixture was concentrated and then water (50 mL) was added slowly, followed by saturated aqueous NaHCO$_3$ to adjust pH to 7. The aqueous phase was extracted with ethyl acetate (70 mL×3), the combined organic layers were washed with brine (50 mL), dried over Na$_2$SO$_4$ and concentrated. The crude product was purified by flash chromatography with petroleum ether:ethyl acetate=20:1 to give 5,7-dichloro-1-isopropyl-3-methyl-1H-pyrazolo[4,3-b]pyridine (3.50 g, 14.3 mmol, 85% yield). $^1$H NMR (chloroform-d 400 MHz) δ 7.28 (s, 1H), 5.48-5.41 (m, 1H), 2.62 (s, 3H), 1.57 (d, J=4.8 Hz, 6H).

The following compounds were prepared in a similar manner:

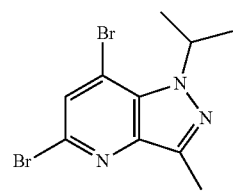

5,7-dibromo-1-isopropyl-3-methyl-1H-pyrazolo[4,3-b]pyridine from 1-isopropyl-3-methyl-1H-pyrazolo[4,3-b]pyridine-5,7-diol and phosphoryl tribromide. $^1$H NMR (chloroform-d 400 MHz) δ 7.60 (s, 1H), 5.61-5.55 (m, 1H), 2.63 (s, 3H), 1.57 (d, J=6.4 Hz, 6H).

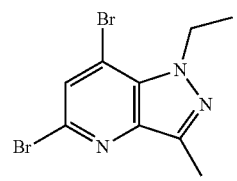

5,7-dibromo-1-ethyl-3-methyl-1H-pyrazolo[4,3-b]pyridine from 1-ethyl-3-methyl-1H-pyrazolo[4,3-b]pyridine-5,7-diol and phosphoryl tribromide.

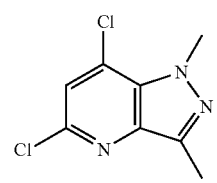

5,7-dichloro-1,3-dimethyl-1H-pyrazolo[4,3-b]pyridine from 1,3-dimethyl-1H-pyrazolo[4,3-b]pyridine-5,7-diol and phosphoryl trichloride. ¹H NMR (chloroform-d 400 MHz) δ 7.29 (s, 1H), 4.29 (s, 3H), 2.60 (s, 3H).

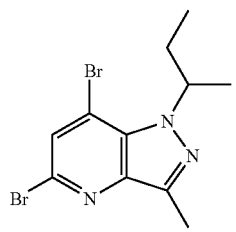 [SMILES: CCC(C)n1nc(C)c2nc(Br)cc(Br)c21]

(±)-5,7-Dibromo-1-(sec-butyl)-3-methyl-1H-pyrazolo[4,3-b]pyridine from (±)-1-(sec-butyl)-3-methyl-1H-pyrazolo[4,3-b]pyridine-5,7-diol and phosphoryl tribromide.

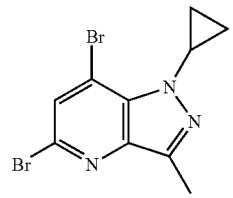

5,7-dibromo-1-cyclopropyl-3-methyl-1H-pyrazolo[4,3-b]pyridine from 1-cyclopropyl-3-methyl-1H-pyrazolo[4,3-b]pyridine-5,7-diol and phosphoryl tribromide. ¹H NMR (chloroform-d 400 MHz) δ 7.63 (s, 1H), 3.99-3.88 (m, 1H), 2.57 (s, 3H), 1.41-1.38 (m, 2H), 1.22-1.19 (m, 2H).

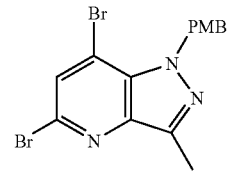

5,7-Dibromo-1-(4-methoxybenzyl)-3-methyl-1H-pyrazolo[4,3-b]pyridine from 1-(4-methoxybenzyl)-3-methyl-1H-pyrazolo[4,3-b]pyridine-5,7-diol and phosphoryl tribromide.

Preparation of 5,7-dibromo-3-methyl-1H-pyrazolo[4,3-b]pyridine

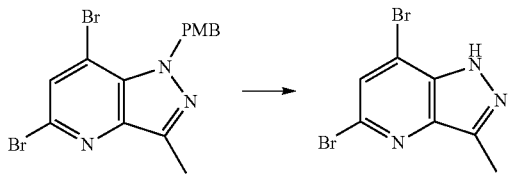

A solution of 5,7-dibromo-1-(4-methoxybenzyl)-3-methyl-1H-pyrazolo[4,3-b]pyridine (650 mg, 1.58 mmol) in TFA (5 mL) was heated at 80° C. for 2 hours. The mixture was concentrated and the residue was dissolved in H₂O (5 mL). The mixture was adjusted to pH 7 by saturated aqueous. NaHCO₃ and extracted with ethyl acetate (20 mL×2). The combined organic layers were washed with H₂O (20 mL), brine (20 mL), dried over Na₂SO₄, filtered and concentrated to give 5,7-dibromo-3-methyl-1H-pyrazolo[4,3-b]pyridine (450 mg, 1.55 mmol, 98% yield).

Preparation of 5,7-dibromo-3-methyl-1-(oxetan-3-yl)-1H-pyrazolo[4,3-b]pyridine

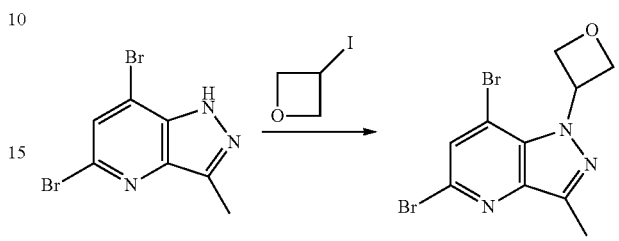

To a solution of 5,7-dibromo-3-methyl-1H-pyrazolo[4,3-b]pyridine (340 mg, 1.17 mmol) in dry DMF (10 mL) was added 3-iodooxetane (323 mg, 1.76 mmol) and Cs₂CO₃ (762 mg, 2.34 mmol). The mixture was heated under microwave at 100° C. for 1 hour. The mixture was concentrated and water (20 mL) was added. The mixture was extracted with ethyl acetate (20 mL×2). The combined organic layers were washed with H₂O (20 mL×2), brine (20 mL), dried over Na₂SO₄, filtered and concentrated. The residue was purified by flash chromatography on silica gel (0% to 50% ethyl acetate in petroleum ether) to give 5,7-dibromo-3-methyl-1-(oxetan-3-yl)-1H-pyrazolo[4,3-b]pyridine (200 mg, 49% yield).

Preparation of (−)-5,7-dibromo-1-(sec-butyl)-3-methyl-1H-pyrazolo[4,3-b]pyridine and (+)-5,7-dibromo-1-(sec-butyl)-3-methyl-1H-pyrazolo[4,3-b]pyridine

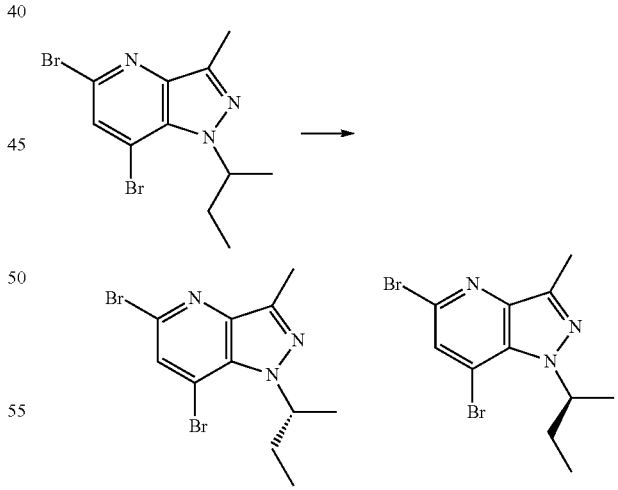

(±)-5,7-dibromo-1-(sec-butyl)-3-methyl-1H-pyrazolo[4,3-b]pyridine (2.2 g, 6.34 mmol) was purified by SFC twice to give (+)-5,7-dibromo-1-(sec-butyl)-3-methyl-1H-pyrazolo[4,3-b]pyridine (800 mg) (Rt=6.25 min) and (−)-5,7-dibromo-1-(sec-butyl)-3-methyl-1H-pyrazolo[4,3-b]pyridine (900 mg) (Rt=6.28 min).

(+)-5,7-dibromo-1-(sec-butyl)-3-methyl-1H-pyrazolo[4,3-b]pyridine 1H NMR (Chloroform-d, 400 MHz): δ 7.60 (s, 1H), 5.41-5.32 (m, 1H), 2.63 (s, 3H), 2.13-2.07 (m, 1H), 1.87-1.83 (m, 1H), 1.54 (d, J=6.4 Hz, 3H), 0.79 (t, J=7.6 Hz, 3H). SFC-MS: $t_R$=6.25 min, ee %=100%; $[\alpha]_D^{20}$=2.60 (c=1.0, dichloromethane).

(−)-5,7-dibromo-1-(sec-butyl)-3-methyl-1H-pyrazolo[4,3-b]pyridine $^1$H NMR (Chloroform-d, 400 MHz): δ 7.60 (s, 1H), 5.41-5.32 (m, 1H), 2.63 (s, 3H), 2.13-2.07 (m, 1H), 1.87-1.83 (m, 1H), 1.55 (d, J=6.8 Hz, 3H), 0.79 (t, J=7.6 Hz, 3H). SFC-MS: $t_R$=6.5 min, ee %=97.87%; $[\alpha]_D^{20}$=−2.90 (c=1.0, dichloromethane).

SFC Condition 1:
Instrument: Thar SFC 1; Column: (s, s) WHELK-O1 (250 mm×30 mm, 5 μm); Mobile phase: A: Supercritical $CO_2$, B: isopropyl alcohol (0.1% $NH_3H_2O$), A:B=85:15 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm SFC Condition 2:
Instrument: Thar SFC-13; Column: (s, s) WHELK-O1 (250 mm×30 mm, 5 μm); Mobile phase: A: Supercritical $CO_2$, B: isopropyl alcohol (0.1% $NH_3H_2O$), A:B=85:15 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm Preparation of 4,6-dibromo-2-methylpyridin-3-amine

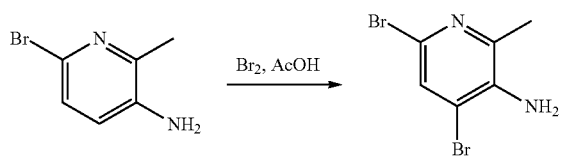

A solution of 6-bromo-2-methylpyridin-3-amine (24 g, 128 mmol) and AcOH (14.7 mL 257 mmol) in MeOH (200 mL) was cooled to 0° C., $Br_2$ (36.9 g, 230.9 mmol, 11.9 mL) was added and stirred at 0° C. for 5 hours. The mixture was quenched with saturated aqueous $Na_2SO_3$ (500 mL), extracted with ethyl acetate (300 mL×3). The organic layer was washed with brine (200 mL), dried over $Na_2SO_4$, and concentrated in vacuo. The residue was purified by silica gel chromatography (petroleum ether:ethyl acetate=2:1) to afford 4,6-dibromo-2-methylpyridin-3-amine (30 g, 87% yield).

Preparation of 5,7-dibromo-1H-pyrazolo[4,3-b]pyridine

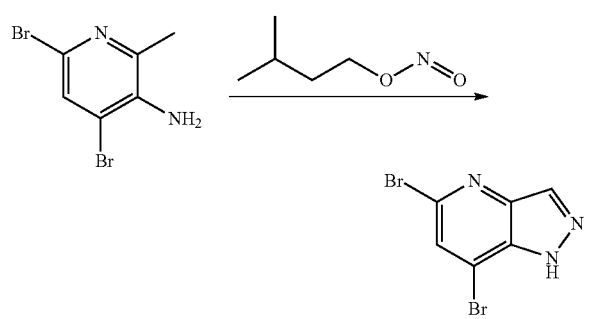

To a mixture of 4,6-dibromo-2-methylpyridin-3-amine (15.0 g, 56.4 mmol) and AcOK (13.8 g, 141 mmol) in AcOH (30 mL) and toluene (200 mL) was added isopentyl nitrite (13.2 g, 112.8 mmol). The mixture was stirred at 25° C. for 1 hour then at 60° C. for 19 hours. The mixture was concentrated in vacuo, diluted with water (300 mL) and extracted with ethyl acetate (200 mL×2). The organic layer was washed with brine (100 mL), dried over $Na_2SO_4$ and concentrated in vacuo to give 5,7-dibromo-1H-pyrazolo[4,3-b]pyridine (5.4 g, 30% yield).

Preparation of 5,7-dibromo-1-ethyl-1H-pyrazolo[4,3-b]pyridine

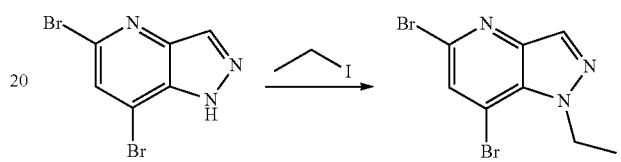

To a mixture of 5,7-dibromo-1H-pyrazolo[4,3-b]pyridine (1 g, 3.6 mmol) and $Cs_2CO_3$ (12.4 g, 7.2 mmol) in anhydrous DMF (10 mL) was added iodoethane (0.8 g, 5.4 mmol). The mixture was stirred at 0° C. for 0.5 hours. The mixture was diluted with water (20 mL), extracted with ethyl acetate (30 mL×2). The organic layer was washed with water (20 mL), brine (20 mL) and dried with $Na_2SO_4$, concentrated in vacuo. The residue was purified by silica gel chromatography (petroleum ether:ethyl acetate=10:1-5:1) to give 5,7-dibromo-1-ethyl-1H-pyrazolo[4,3-b]pyridine (0.56 g, 51% yield). $^1$H NMR (DMSO-$d_6$ 400 MHz) δ 8.37 (s, 1H), 7.98 (s, 1H), 4.72 (q, J=7.2 Hz, 2H), 1.42 (t, J=7.2 Hz, 3H).

The following compounds were prepared in a similar manner:

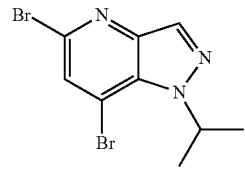

5,7-Dibromo-1-isopropyl-1H-pyrazolo[4,3-b]pyridine from 5,7-dibromo-1H-pyrazolo[4,3-b]pyridine and 2-iodopropane. $^1$H NMR (DMSO-$d_6$ 400 MHz) δ 8.36 (s, 1H), 7.94 (s, 1H), 5.62-5.55 (m, 1H), 1.49 (d, J=6.0 Hz, 6H).

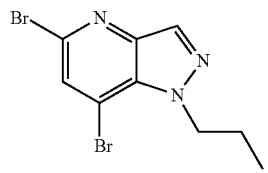

5,7-Dibromo-1-propyl-1H-pyrazolo[4,3-b]pyridine from 5,7-dibromo-1H-pyrazolo[4,3-b]pyridine and 1-iodopropane. $^1$H NMR (chloroform-d 400 MHz) δ 8.14 (s, 1H), 7.64

(s, 1H), 4.67 (t, J=7.2 Hz, 2H), 1.98-1.89 (m, 2H), 0.94 (t, J=7.6 Hz, 3H).

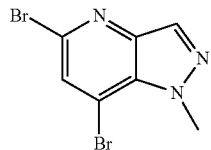

5,7-Dibromo-1-methyl-1H-pyrazolo[4,3-b]pyridine from 5,7-dibromo-1H-pyrazolo[4,3-b]pyridine and iodomethane. ¹H NMR (chloroform-d 400 MHz) δ 8.13 (s, 1H), 7.64 (s, 1H), 4.38 (s, 3H).

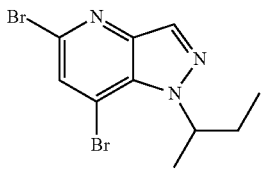

(±)-5,7-Dibromo-1-(sec-butyl)-3-methyl-1H-pyrazolo[4,3-b]pyridine from 5,7-dibromo-1H-pyrazolo[4,3-b]pyridine and (±)-2-iodobutane.

Preparation of (+)-5,7-dibromo-1-(sec-butyl)-1H-pyrazolo[4,3-b]pyridine and (−)-5,7-dibromo-1-(sec-butyl)-1H-pyrazolo[4,3-b]pyridine

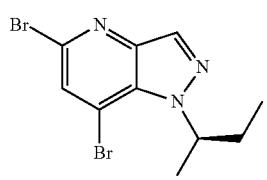

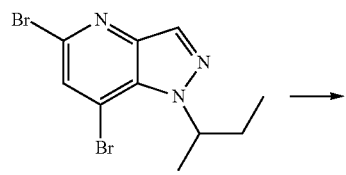

(±)-5,7-dibromo-1-sec-butyl-pyrazolo[4,3-b]pyridine (5.2 g, 15.6 mmol) was separated by SFC with column: AD (250 mm*50 mm, 10 μm); mobile phase: [0.1% NH₃H₂O in isopropyl alcohol]; B %: 20%-20%, min.

(+)-5,7-dibromo-1-(sec-butyl)-1H-pyrazolo [4,3-b]pyridine (2.5 g) (Rt=3.137 min) ([α]$_D^{20}$=1.40) (c=1.0, ethanol).

(−)-5,7-dibromo-1-(sec-butyl)-1H-pyrazolo[4,3-b]pyridine (2.5 g) (Rt=2.808 min) ([α]$_D^{20}$=−1.60) (c=1.0, ethanol).

Preparation of 5-chloro-1-isopropyl-N-(4-methoxybenzyl)-3-methyl-1H-pyrazolo[4,3-b]pyridin-7-amine

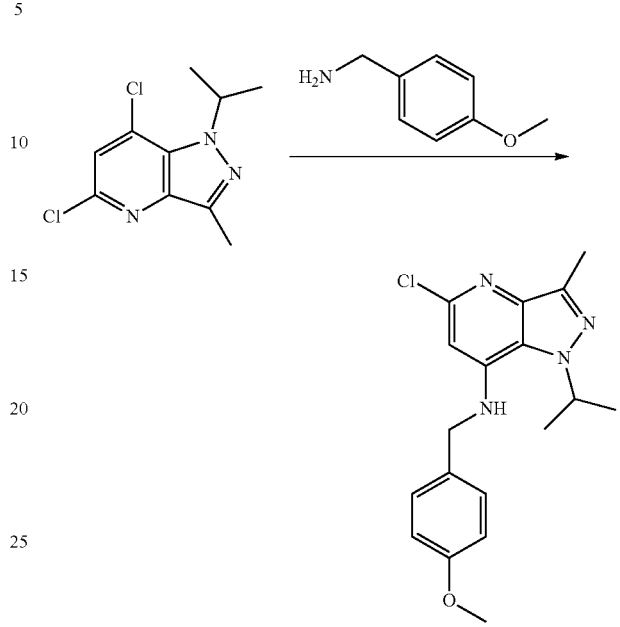

To a solution of 5,7-dichloro-1-isopropyl-3-methyl-1H-pyrazolo[4,3-b]pyridine (100 mg, 410 μmol) and (4-methoxyphenyl)methanamine (67 mg, 492 μmol, 64 μL) in NMP (5 mL) was added CsF (124 mg, 819 μmol, 30 μL). The mixture was stirred at 100° C. for 18 hours. Water (20 mL) was added and the mixture was filtered and concentrated in vacuo. The crude mixture was purified by flash chromatography with petroleum ether:ethyl acetate=3:1 to give 5-chloro-1-isopropyl-N-(4-methoxybenzyl)-3-methyl-1H-pyrazol[4,3-b]pyridin-7-amine (80 mg, 215 μmol, 53% yield). ¹H NMR (chloroform-d 400 MHz) δ 7.32 (d, J=8.4 Hz, 2H), 6.95 (d, J=8.4 Hz, 2H), 6.39 (s, 1H), 4.79 (brs, 1H), 4.70-4.63 (m, 1H), 4.39 (d, J=4.4 Hz, 2H), 3.85 (s, 3H), 2.56 (s, 3H), 1.57 (d, J=6.4 Hz, 6H).

Preparation of 5-(2-ethoxypyridin-3-yl)-1-isopropyl-N-(4-methoxybenzyl)-3-methyl-1H-pyrazolo[4,3-b]pyridin-7-amine

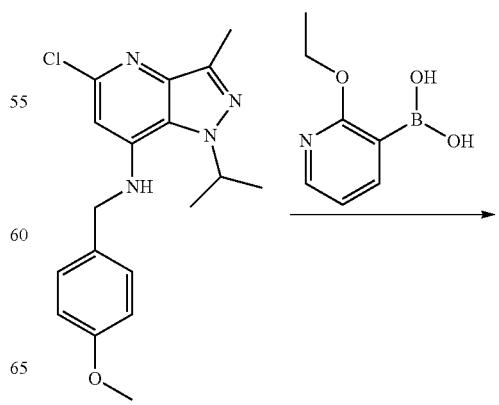

77
-continued

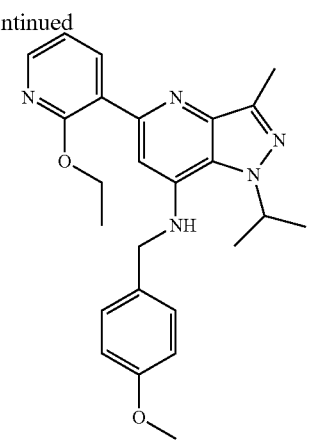

To a solution of 5-chloro-1-isopropyl-N-(4-methoxybenzyl)-3-methyl-1H-pyrazolo[4,3-b]pyridin-7-amine (60 mg, 174 μmol) in dioxane (2 mL) and H$_2$O (0.5 mL) was added Pd(1,1'-bis(diphenylphosphino)ferrocene)Cl$_2$ (25 mg, 35 μmol) and Cs$_2$CO$_3$ (141.72 mg, 435 μmol) and (2-ethoxypyridin-3-yl)boronic acid (52 mg, 313 μmol). The mixture was stirred at 100° C. for 1 hour under microwave irradiation. Water (30 mL) was added and the mixture was extracted with ethyl acetate (30 mL×3). The combined organic layers were washed with brine (20 mL), dried over Na$_2$SO$_4$ and concentrated. The crude mixture was purified by flash chromatography with petroleum ether:ethyl acetate=1:1 to 0:1 to give 5-(2-ethoxypyridin-3-yl)-1-isopropyl-N-(4-methoxybenzyl)-3-methyl-1H-pyrazolo[4,3-b]pyridin-7-amine (50 mg, 67% yield). $^1$H NMR (chloroform-d 400 MHz) δ 8.27-8.25 (m, 1H), 8.17-8.16 (m, 1H), 7.32 (d, J=8.8 Hz, 2H), 7.22 (s, 1H), 7.03-7.00 (m, 1H), 6.95 (d, J=8.4 Hz, 2H), 4.81-4.76 (m, 1H), 4.65 (brs, 1H), 4.47-4.41 (m, 4H), 3.84 (s, 3H), 2.65 (s, 3H), 1.60 (d, J=6.4 Hz, 6H), 1.36 (t, J=7.2 Hz, 3H).

The following compounds were prepared in a similar manner:

5-(2-Fluoropyridin-3-yl)-1-isopropyl-N-(4-methoxybenzyl)-3-methyl-1H-pyrazolo[4,3-b]pyridin-7-amine

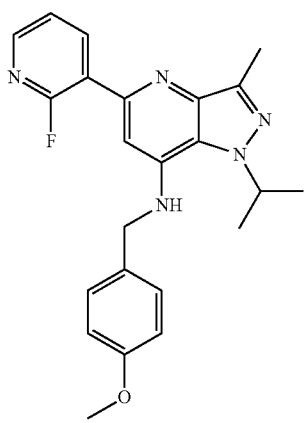 [SMILES: COc1ccc(CNc2cc(-c3cccnc3F)nc3c(C)nn(C(C)C)c23)cc1]

Prepared from 5-bromo-1-isopropyl-N-(4-methoxybenzyl)-3-methyl-1H-pyrazolo[4,3-b]pyridin-7-amine and (2-fluoropyridin-3-yl)boronic acid.

78

3-(1-Isopropyl-7-((4-methoxybenzyl)amino)-3-methyl-1H-pyrazolo[4,3-b]pyridin-5-yl)pyridin-2(1H)-one

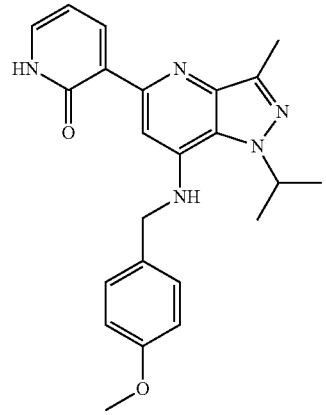 [SMILES: COc1ccc(CNc2cc(-c3ccc[nH]c3=O)nc3c(C)nn(C(C)C)c23)cc1]

Prepared from 5-chloro-1-isopropyl-N-(4-methoxybenzyl)-3-methyl-1H-pyrazolo[4,3-b]pyridin-7-amine and (2-oxo-1,2-dihydropyridin-3-yl)boronic acid.

Preparation of 5-(2-ethoxypyridin-3-yl)-1-isopropyl-3-methyl-1H-pyrazolo[4,3-b]pyridin-7-amine

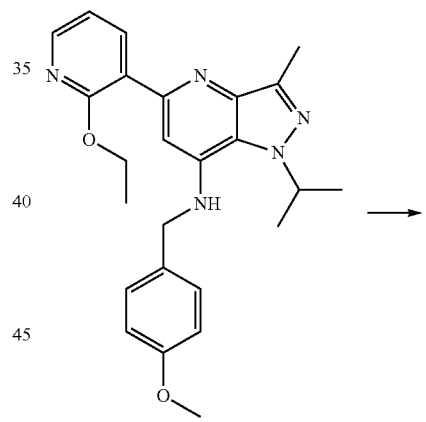

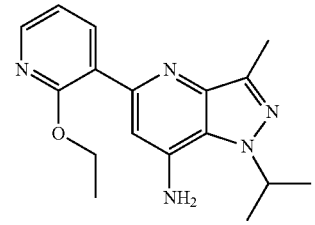 [SMILES: CCOc1ncccc1-c1cc(N)c2c(cnn2C(C)C)n1]

A solution of 5-(2-ethoxypyridin-3-yl)-1-isopropyl-N-(4-methoxybenzyl)-3-methyl-1H-pyrazolo[4,3-b]pyridin-7-amine (1.25 g, 2.90 mmol) in TFA (15 mL) was stirred at 60° C. for 18 hours. The mixture was concentrated and the residue was dissolved in ethyl acetate (200 mL). The resulting mixture was washed with saturated aqueous NaHCO$_3$ (30 mL), brine (20 mL), dried over Na$_2$SO$_4$ and concentrated. The crude mixture was purified by flash chromatography with petroleum ether:ethyl acetate=3:1 to 2:1 to give 5-(2-ethoxypyridin-3-yl)-1-isopropyl-3-methyl-1H-pyrazolo[4,3-b]pyridin-7-amine (900 mg, 96% yield).

The following compounds were prepared in a similar manner:

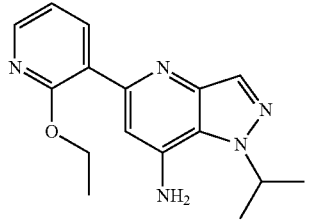

5-(2-Ethoxypyridin-3-yl)-1-isopropyl-1H-pyrazolo[4,3-b]pyridin-7-amine

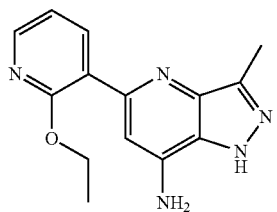 [SMILES: CCOc1ncccc1-c1cc(N)c2[nH]nc(C)c2n1]

5-(2-Ethoxypyridin-3-yl)-3-methyl-1H-pyrazolo[4,3-b]pyridin-7-amine

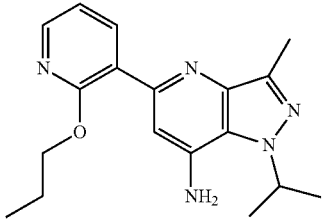 [SMILES: CCCOc1ncccc1-c1cc(N)c2c(n1)c(C)nn2C(C)C]

1-Isopropyl-3-methyl-5-(2-propoxypyridin-3-yl)-1H-pyrazolo[4,3-b]pyridin-7-amine

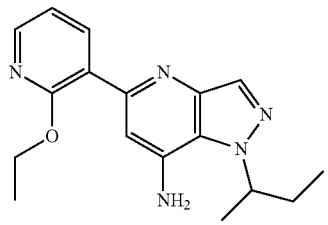 [SMILES: CCOc1ncccc1-c1cc(N)c2c(cnn2C(C)CC)n1]

1-(sec-Butyl)-5-(2-ethoxypyridin-3-yl)-1H-pyrazolo[4,3-b]pyridin-7-amine, enantiomer 1, prepared from (+)-5,7-dibromo-1-(sec-butyl)-1H-pyrazolo[4,3-b]pyridine

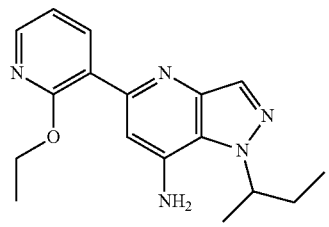 [SMILES: CCOc1ncccc1-c1cc(N)c2c(cnn2C(C)CC)n1]

1-(sec-Butyl)-5-(2-ethoxypyridin-3-yl)-1H-pyrazolo[4,3-b]pyridin-7-amine, enantiomer 2, prepared from (−)-5,7-dibromo-1-(sec-butyl)-1H-pyrazolo[4,3-b]pyridine

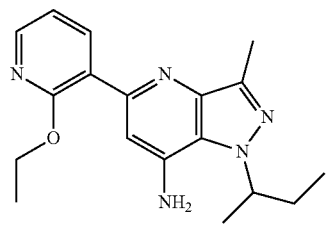 [SMILES: CCOc1ncccc1-c1cc(N)c2c(n1)c(C)nn2C(C)CC]

1-(sec-Butyl)-5-(2-ethoxypyridin-3-yl)-3-methyl-1H-pyrazolo[4,3-b]pyridin-7-amine, enantiomer 1, prepared from (+)-5,7-dibromo-1-(sec-butyl)-3-methyl-1H-pyrazolo[4,3-b]pyridine

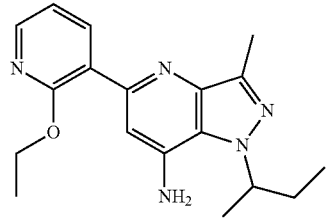 [SMILES: CCOc1ncccc1-c1cc(N)c2c(n1)c(C)nn2C(C)CC]

1-(sec-Butyl)-5-(2-ethoxypyridin-3-yl)-3-methyl-1H-pyrazolo[4,3-b]pyridin-7-amine, enantiomer 2, prepared from (−)-5,7-dibromo-1-(sec-butyl)-3-methyl-1H-pyrazolo[4,3-b]pyridine 1-Isopropyl-5-(2-methoxypyridin-3-yl)-3-methyl-1H-pyrazolo[4,3-b]pyridin-7-amine

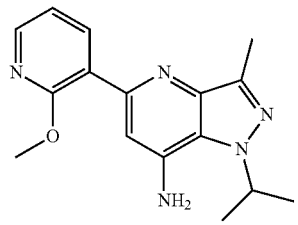 [SMILES: COc1ncccc1-c1cc(N)c2c(n1)c(C)nn2C(C)C]

Prepared from 1-isopropyl-N-(4-methoxybenzyl)-5-(2-methoxypyridin-3-yl)-3-methyl-1H-pyrazolo[4,3-b]pyridin-7-amine 5-(2-(Dimethylamino)pyridin-3-yl)-1-isopropyl-3-methyl-1H-pyrazolo[4,3-b]pyridin-7-amine

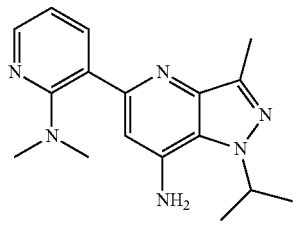 [SMILES: Cc1nn(C(C)C)c2c(N)cc(-c3cccnc3N(C)C)nc12]

Prepared from 5-(2-(dimethylamino)pyridin-3-yl)-1-isopropyl-N-(4-methoxybenzyl)-3-methyl-1H-pyrazolo[4,3-b]pyridin-7-amine 3-(7-Amino-1-isopropyl-3-methyl-1H-pyrazolo[4,3-b]pyridin-5-yl)pyridin-2(1H)-one

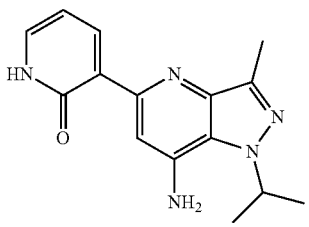 [SMILES: Cc1nn(C(C)C)c2c(N)cc(-c3ccc[nH]c3=O)nc12]

Prepared from 3-(1-isopropyl-7-((4-methoxybenzyl)amino)-3-methyl-1H-pyrazolo[4,3-b]pyridin-5-yl)pyridin-2(1H)-one Preparation of ethyl 3-methyl-1,2,4-oxadiazole-5-carboxylate

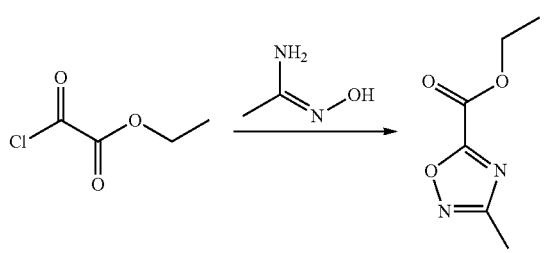

To a solution of ethyl 2-chloro-2-oxoacetate (1 g, 13.5 mmol) and pyridine (4.27 g, 54 mmol, 4.36 mL) in dichloromethane (40 mL) was added at 15-20° C. N'-hydroxyacetimidamide (2.40 g, 17.5 mmol, 1.96 mL). The solution was stirred at 50° C. for 14 hours. The reaction mixture was cooled and quenched with saturated aqueous NH$_4$Cl (30 mL). The aqueous phase was extracted with dichloromethane (2×50 mL). The organic phases were combined, washed with saturated aqueous NaHCO$_3$ (50 mL), dried over MgSO$_4$, filtered and concentrated under reduced pressure to give ethyl 3-methyl-1,2,4-oxadiazole-5-carboxylate (2.80 g, 44% yield).

Preparation of (3-methyl-1,2,4-oxadiazol-5-yl)methanol

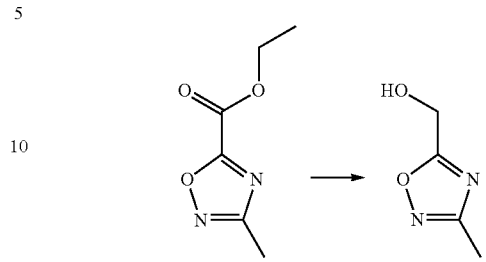

To a solution of ethyl 3-methyl-1,2,4-oxadiazole-5-carboxylate (2.10 g, 13.5 mmol) in THF (10 mL) and ethanol (10 mL) was added NaBH$_4$ (1.02 g, 26.9 mmol) at 0° C. The mixture was stirred at 0° C. for 1 hour. The mixture was quenched with saturated aqueous NH$_4$Cl, and concentrated in vacuo. The residue was dissolved in dichloromethane (50 mL) and filtered; the filtrate was dried over Na$_2$SO$_4$ and concentrated in vacuo to give (3-methyl-1,2,4-oxadiazol-5-yl)methanol (800 mg, 52% yield).

Preparation of 3-methyl-1,2,4-oxadiazole-5-carbaldehyde

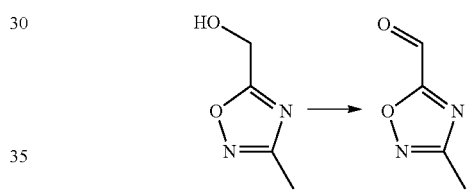

A solution of oxalyl chloride (267 mg, 2.10 mmol, 184 μL) in dry dichloromethane (5 mL) was cooled to −78° C. and then DMSO (219 mg, 2.80 mmol) was added. The mixture was stirred at −78° C. for 15 minutes. A solution of (3-methyl-1,2,4-oxadiazol-5-yl)methanol (80 mg, 0.70 mmol) in dichloromethane (0.5 mL) was added at −78° C. The mixture was stirred at −78° C. for 1 hour. Then triethylamine (0.58 mL, 4.2 mmol) was added at −78° C. The mixture was warmed to 20° C. and stirred at 20° C. for 1 hour. The mixture was poured into 1 N aqueous HCl (5 mL). The mixture was extracted with dichloromethane (20 mL×2). The combined organic layers were washed with H$_2$O (20 mL), dried over Na$_2$SO$_4$, filtered and concentrated to give 3-methyl-1,2,4-oxadiazole-5-carbaldehyde (80 mg). $^1$H NMR (chloroform-d 400 MHz) δ 9.97 (s, 1H), 2.55 (s, 3H).

Preparation of 1-methyl-1H-1,2,4-triazole-3-carbaldehyde

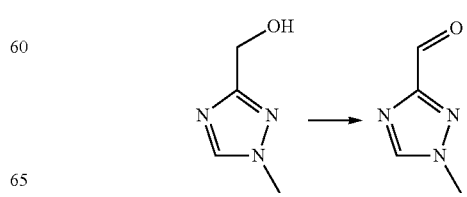

To a mixture of (1-methyl-1H-1,2,4-triazol-3-yl)methanol (400 mg, 3.54 mmol) and iodobenzene diacetate (1.25 g, 3.89 mmol) in dichloromethane (10 mL) was added TEMPO ((2,2,6,6-tetramethylpiperidin-1-yl)oxyl) (56 mg, 354 µmol). The mixture was stirred at 15-20° C. for 2 h. The mixture was concentrated in vacuo. The residue was purified by silica gel chromatography (petroleum ether:ethyl acetate=1:2) to give 1-methyl-1H-1,2,4-triazole-3-carbaldehyde (300 mg, 2.70 mmol, 76% yield). $^1$H NMR (chloroform-d 400 MHz) δ 10.01 (s, 1H), 8.19 (s, 1H), 4.06 (s, 3H).

Preparation of ethyl 2-(2-acetylhydrazinyl)-2-oxoacetate

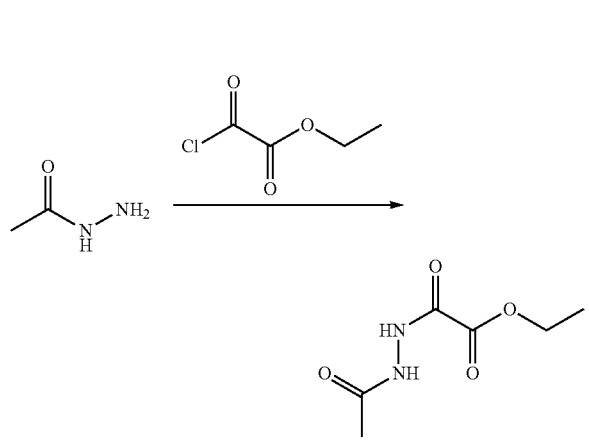

To a solution of acetohydrazide (5 g, 67 mmol) in dichloromethane (150 mL) was added N-ethoxycarbonyl-2-ethoxy-1,2-dihydroquinoline (16.7 g, 67 mmol). The mixture was stirred at 15° C. for 10 minutes. Then ethyl 2-chloro-2-oxoacetate (9.22 g, 67.5 mmol, 7.56 mL) was dropwise added to the mixture. The mixture was stirred at 15° C. for 16 hours. The mixture was washed with H$_2$O (100 mL) and extracted with dichloromethane (100 mL×3). The combined organic phases were dried over Na$_2$SO$_4$ and concentrated under vacuo. The residue was purified with column chromatography (SiO$_2$, petroleum ether:ethyl acetate=1:0 to 0:1) to give ethyl 2-(2-acetylhydrazinyl)-2-oxoacetate (9.30 g, 79% yield).

Preparation of ethyl 5-methyl-1,3,4-thiadiazole-2-carboxylate

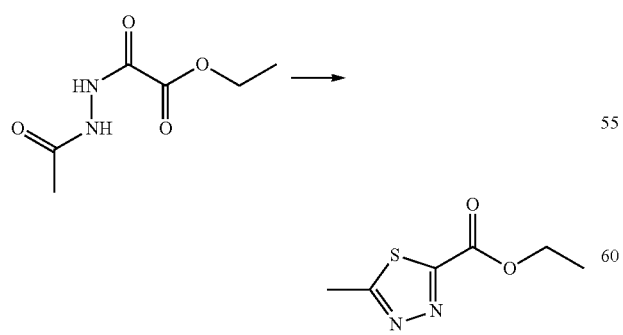

To a solution of ethyl 2-(2-acetylhydrazinyl)-2-oxoacetate (3 g, 17 mmol) in THF (100 mL) was added Lawesson's reagent (7.66 g, 19 mmol). The mixture was stirred at 75° C. for 3 hours. The mixture was diluted with ethyl acetate (500 mL) and added approximately 40 g of decolourising charcoal. The mixture was stirred at 18° C. for 16 hours. The mixture was filtered. The filtrate was concentrated under vacuo. The residue was purified with column chromatography (SiO$_2$, petroleum ether:ethyl acetate=3:7) to give ethyl 5-methyl-1,3,4-thiadiazole-2-carboxylate (921 mg, 28% yield).

Preparation of 5-methyl-1,3,4-thiadiazole-2-carbaldehyde

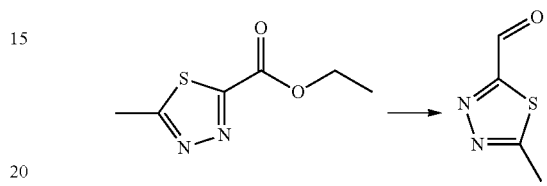

To a solution of ethyl 5-methyl-1,3,4-thiadiazole-2-carboxylate (400 mg, 2.32 mmol) in dry THF (5 mL) was dropwise added DIBAL-H (diisobutylaluminium hydride) (1 M in toluene, 6.97 mL). The mixture was stirred at −40° C. for 2 hours. The mixture was quenched with saturated aqueous NH$_4$Cl (5 mL) and filtered. The solution was extracted with dichloromethane (15 mL×3). The combined organic phases were dried over Na$_2$SO$_4$ and concentrated under vacuo. The residue was purified with preparative TLC (petroleum ether:ethyl acetate=1:1) to give 5-methyl-1,3,4-thiadiazole-2-carbaldehyde (123 mg, 41% yield). $^1$H NMR (chloroform-d 400 MHz) δ 10.19 (s, 1H), 2.92 (s, 3H).

Preparation of (5-methylthiophen-3-yl)methanol

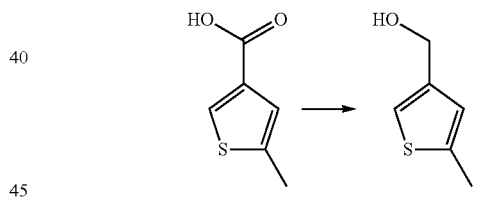

To a solution of 5-methylthiophene-3-carboxylic acid (300 mg, 2.11 mmol) in THF (10 mL) was added LiAlH$_4$ (120 mg, 3.17 mmol) slowly at 0° C. The mixture was stirred at 20° C. for 2 hours. Water (0.3 mL) was added at 0° C. to quench the reaction mixture followed by addition of 15% aqueous NaOH (0.3 mL). Ethyl acetate (50 mL) was added to the mixture, the mixture was filtered and the residue was washed with ethyl acetate (20 mL×2). The combined filtrates were dried over Na$_2$SO$_4$ and concentrated to give (5-methylthiophen-3-yl)methanol (270 mg).

Preparation of (5-methyloxazol-2-yl)methanol

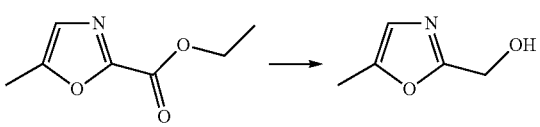

To the reaction mixture of ethyl 5-methyloxazole-2-carboxylate (500 mg, 3.22 mmol) in ethanol (10 mL) was added NaBH₄ (609 mg, 16.10 mmol) with stirring at 20° C. Then resulting solution was stirred at 20° C. for 3 hours. The reaction was quenched by water (50 mL), then concentrated under reduced pressure to remove the ethanol. The residue was extracted by ethyl acetate (50 mL×3). The combined organic layers were washed with brine (10 mL), dried over Na₂SO₄, concentrated to give (5-methyloxazol-2-yl)methanol (364 mg).

Preparation of 5-methylthiophene-3-carbaldehyde

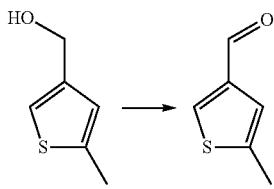

To a solution of (5-methylthiophen-3-yl)methanol (270 mg, 2.11 mmol) in dichloromethane (10 mL) was added Dess-Martin reagent (1,1,1-triacetoxy-1,1-dihydro-1,2-benziodoxol-3(1H)-one) (1.07 g, 2.53 mmol). The mixture was stirred at 20° C. for 1 hour. The mixture was filtered and the residue was washed with dichloromethane (30 mL), the combined organic layers were concentrated. The crude mixture was purified by flash chromatography with petroleum ether:ethyl acetate=5:1 to give 5-methylthiophene-3-carbaldehyde (180 mg, 1.43 mmol, 68% yield). ¹H NMR (chloroform-d 400 MHz) δ 9.81 (s, 1H), 7.89 (s, 1H), 7.20 (s, 1H), 2.51 (s, 3H).

The following compounds were prepared in a similar manner:
5-methyloxazole-2-carbaldehyde from (5-methyloxazol-2-yl)methanol
3-methylisoxazole-5-carbaldehyde from (3-methylisoxazol-5-yl)methanol
5-methyl-1,2,4-oxadiazole-3-carbaldehyde from (5-methyl-1,2,4-oxadiazol-3-yl)methanol
1,5-dimethyl-1H-pyrazole-3-carbaldehyde from (1,5-dimethyl-1H-pyrazol-3-yl)methanol Preparation of 1-((1-aminoethyl)thio)-3-chloropropan-2-one

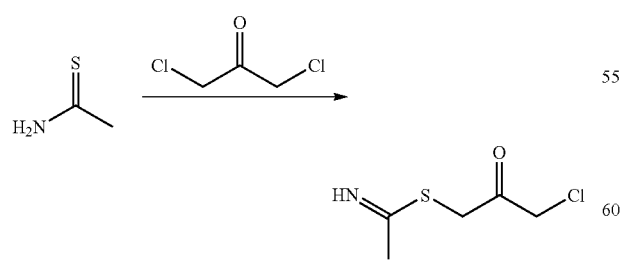

A solution of ethanethioamide (1 g, 13.3 mmol) in acetone (7 mL) was added dropwise to a solution of 1,3-dichloropropan-2-one (1.69 g, 13.3 mmol, 1.66 mL) in acetone (5 mL) at 20° C. and stirred at 20° C. for 12 hours. The mixture was filtered and the filter cake was washed with acetone (10 mL×3) to give 1-((1-aminoethyl)thio)-3-chloropropan-2-one.

Preparation of 4-(chloromethyl)-2-methylthiazole

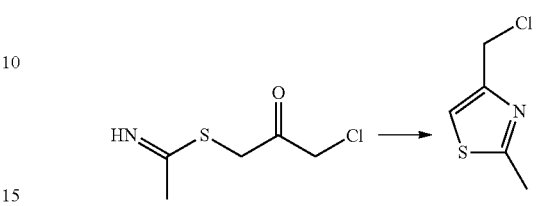

A mixture of 1-((1-aminoethyl)thio)-3-chloropropan-2-one (3 g, 17.9 mmol) in ethanol (30 mL) was stirred at 80° C. for 2 h. The mixture was concentrated in vacuo to give 4-(chloromethyl)-2-methylthiazole (2.9 g).

Preparation of 2-((2-methylthiazol-4-yl)methyl)isoindoline-1,3-dione

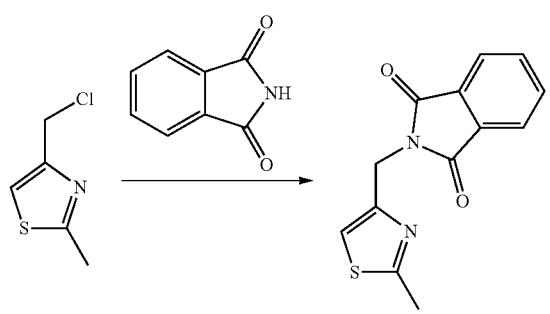

To a mixture of 4-(chloromethyl)-2-methylthiazole (2.80 g, 19.0 mmol) and isoindoline-1,3-dione in anhydrous DMF (30 mL) was added K₂CO₃ (1.31 g, 9.49 mmol). The mixture stirred at 100° C. for 0.5 hour. The mixture was diluted with water (50 mL), extracted with ethyl acetate (50 mL×2). The organic layer was washed with water (30 mL), brine (30 mL), dried with Na₂SO₄ and concentrated in vacuo. The residue was purified by silica gel chromatography (petroleum ether:ethyl acetate=10:1-2:1) to give 2-((2-methylthiazol-4-yl)methyl)isoindoline-1,3-dione (3.29 g).

Preparation of (2-methylthiazol-4-yl)methanamine

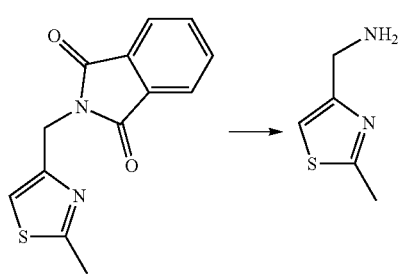

A mixture of 2-((2-methylthiazol-4-yl)methyl)isoindoline-1,3-dione (1 g, 3.87 mmol) and hydrazine hydrate (291 mg, 5.81 mmol, 282 µL) in ethanol (10 mL) was stirred at 20° C. for 0.5 hour. The mixture was concentrated in vacuo. The residue was purified by silica gel chromatography (dichloromethane:methanol=0:1 to 10:1) to give (2-methyl-thiazol-4-yl)methanamine (330 mg).

Preparation of benzyl (cyanomethyl)carbamate

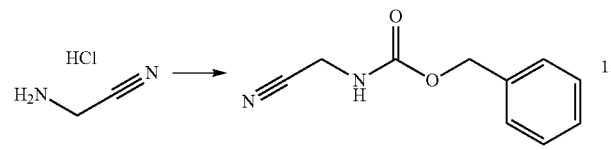

A mixture of 2-aminoacetonitrile hydrochloride (5 g, 54.0 mmol), NaHCO₃ (18.16 g, 216 mmol) and dioxane (50 mL) in H₂O (100 mL) was stirred at 0° C. Then a solution of benzyl carbonochloridate (11.06 g, 64.8 mmol, 9.22 mL) in toluene (10 mL) was added at 0° C. and stirred at 20° C. for 12 hours. The mixture was poured into water (100 mL), and the aqueous phase was extracted with ethyl acetate (100 mL×3). The combined organic phases were washed with brine (100 mL), dried with anhydrous Na₂SO₄, filtered and concentrated in vacuo. The residue was purified by silica gel chromatography to give benzyl (cyanomethyl)carbamate (1.70 g). ¹H NMR (chloroform-d 400 MHz): 7.40-7.31 (m, 5H), 5.35-5.13 (m, 3H), 4.16-4.12 (m, 2H).

Preparation of benzyl ((2H-tetrazol-5-yl)methyl)carbamate

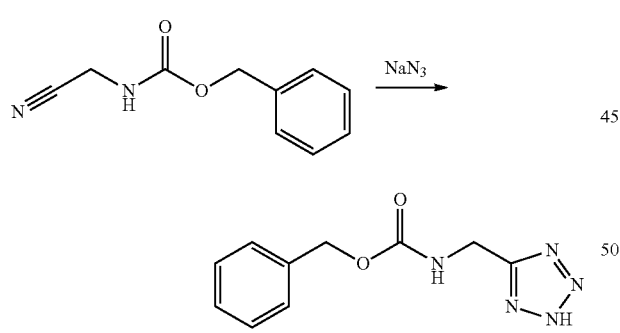

A mixture of benzyl (cyanomethyl)carbamate (200 mg, 1.05 mmol), sodium azide (250 mg, 3.85 mmol) zinc dibromide (118 mg, 525 µmol) and isopropyl alcohol (2 mL) in H₂O (4 mL) was stirred at 100° C. for 24 hours. The mixture was poured into water (50 mL), and added KHSO₄ (aq.) until pH=2. The aqueous phase was extracted with ethyl acetate (20 mL×3). The combined organic phases were washed with brine (10 mL), dried with anhydrous Na₂SO₄, filtered and concentrated in vacuo. The residue was purified by silica gel chromatography (petroleum ether/ethyl acetate=10/1 to 3/1) to give benzyl ((2H-tetrazol-5-yl)methyl)carbamate (200 mg).

Preparation of benzyl ((2-methyl-2H-tetrazol-5-yl)methyl)carbamate

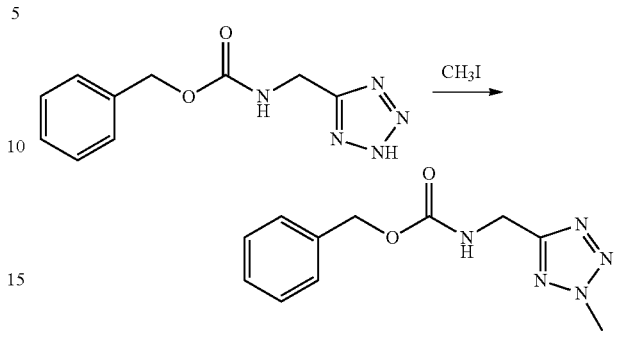

To a mixture of benzyl ((2H-tetrazol-5-yl)methyl)carbamate (1 g, 4.29 mmol) and K₂CO₃ (1.19 g, 8.58 mmol) in DMF (20 mL) was added CH₃I (0.91 g, 6.4 mmol) at 0° C., and the reaction mixture was stirred at 30° C. for 12 hours. The mixture was filtrated and the filtrate was concentrated in vacuo. The residue was purified by silica gel chromatography (petroleum ether/ethyl acetate=10/1 to 3/1) to give benzyl ((2-methyl-2H-tetrazol-5-yl)methyl)carbamate (400 mg).

Preparation of (2-methyl-2H-tetrazol-5-yl)methanamine

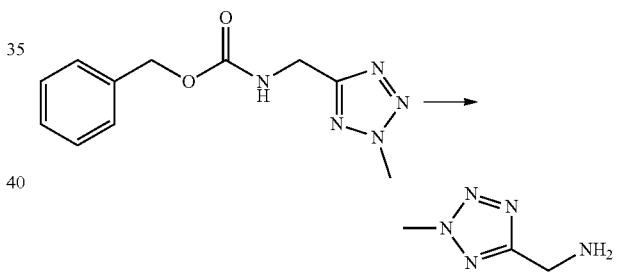

To a solution of benzyl ((2-methyl-2H-tetrazol-5-yl)methyl)carbamate (250 mg, 1.0 mmol) in MeOH (10 mL) was added Pd/C (10%, wet) (10 mg) under N₂. The suspension was degassed in vacuo and purged with H₂ several times. The mixture was stirred under H₂ (15 psi) at 25° C. for 12 hours. The mixture was filtered and the filtrate was concentrated under vacuum to give (2-methyl-2H-tetrazol-5-yl)methanamine (120 mg, crude).

Preparation of m-tolylmethanamine Hydrochloride

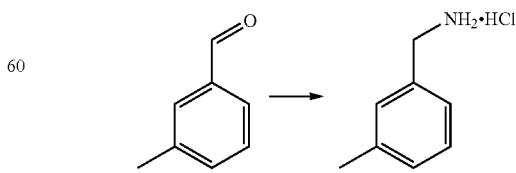

A mixture 3-methylbenzaldehyde (500 mg, 4.16 mmol, 490.20 µL) in NH₃/MeOH (7 M, 1 mL) was stirred at 80° C.

for 14 hours. Then NaBH₄ (315 mg, 8.32 mmol) was added and the reaction mixture was stirred at 20° C. for 1 hour. The mixture was diluted with water (20 mL) and extracted with ethyl acetate (20 mL×2). The organic layers were washed with water (10 mL), brine (10 mL), dried with Na₂SO₄ and concentrated in vacuo. The residue was purified by preparative HPLC to give m-tolylmethanamine (370 mg) as the HCl salt.

Preparation of p-tolylmethanol

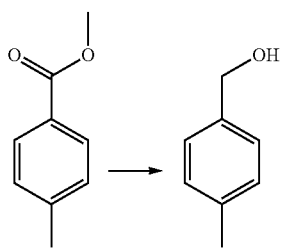

To a suspension of LiAlH₄ (5.56 g, 147 mmol) in anhydrous THF (100 mL) was added a solution of methyl 4-methylbenzoate (11 g, 73.3 mmol) in anhydrous THF (50 mL), and the resulting mixture was stirred at 0° C. for 1 hour. The reaction mixture was quenched by addition H₂O (5 mL), 15% aqueous NaOH (5 mL) and H₂O (8 mL) at 0° C., 8 g of anhydrous Na₂SO₄ was added and the reaction mixture was filtered. The filtered cake was washed with additional THF (80 mL×3). The combined organic layers were concentrated to give p-tolylmethanol (8.30 g, 93% yield). ¹H NMR (chloroform-d 400 MHz) δ 7.26 (d, J=8.0 Hz, 2H), 7.18 (d, J=7.6 Hz, 2H), 4.65 (d, J=5.2 Hz, 2H), 2.36 (s, 3H).

Preparation of 1-(bromomethyl)-4-methylbenzene

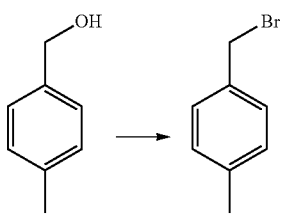

To a solution of p-tolylmethanol (8.30 g, 68 mmol) in dichloromethane (200 mL) was added tribromophosphane (20.2 g, 74.7 mmol). The mixture was stirred at 0° C. for 1 hour. The reaction mixture was poured into H₂O (10 mL) and extracted with dichloromethane (25 mL), The organic phase was separated, washed with brine (10 mL), dried over anhydrous Na₂SO₄, filtered and concentrated to give 1-(bromomethyl)-4-methylbenzene (12.5 g, 99% yield). ¹H NMR (chloroform-d 400 MHz) δ 7.29 (d, J=7.6 Hz, 2H), 7.16 (d, J=7.6 Hz, 2H), 4.50 (s, 2H), 2.36 (s, 3H).

Preparation of 2-(4-methylbenzyl)isoindoline-1,3-dione

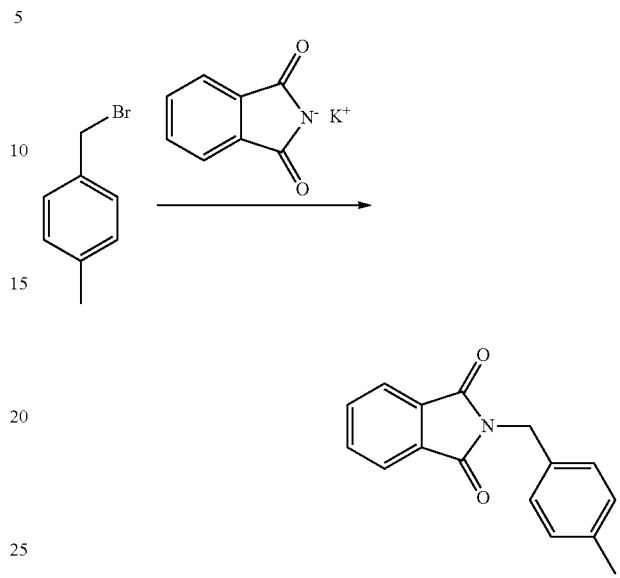

To a solution of 1-(bromomethyl)-4-methylbenzene (5 g, 27 mmol) in DMF (30 mL) was added potassium 1,3-dioxoisoindolin-2-ide (7.51 g, 40.5 mmol). The mixture was stirred at 100° C. for 14 hours. The reaction mixture was concentrated under reduced pressure to remove DMF. The residue was purified by column chromatography (SiO₂, petroleum ether:ethyl acetate=0 to 20%) to give 2-(4-methylbenzyl)isoindoline-1,3-dione (5.50 g, 81% yield). ¹H NMR (chloroform-d 400 MHz) δ 7.85 (d, J=3.2 Hz, 2H), 7.84 (d, J=3.2 Hz, 2H), 7.34 (d, J=7.6 Hz, 2H), 7.13 (d, J=8.0 Hz, 2H), 4.82 (s, 2H), 2.32 (s, 3H).

Preparation of p-tolylmethanamine

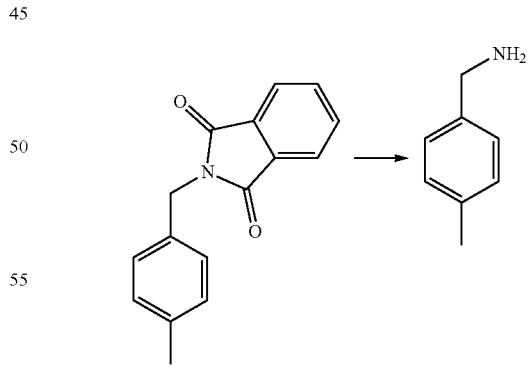

To a mixture of 2-(4-methylbenzyl)isoindoline-1,3-dione (1 g, 3.8 mmol) and hydrazine hydrate (752 mg, 15 mmol, 730 μL) in MeOH (10 mL) was stirred at 20° C. for 3 hours. The mixture was concentrated in vacuo. The residue was purified by silica gel chromatography (dichloromethane:methanol (with 5% ammonia in water)=0:1 to 5:1) to give p-tolylmethanamine (160 mg).

Preparation of ethyl
5-methyl-1,2,4-oxadiazole-3-carboxylate

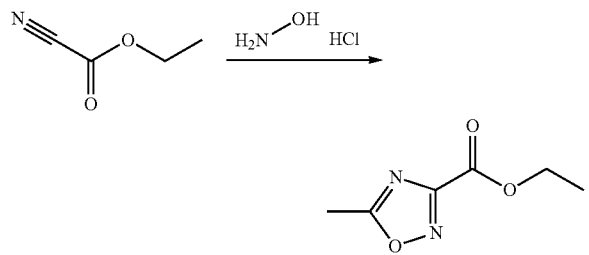

To a solution of hydroxylamine hydrochloride (1.71 g, 24.6 mmol) in acetic acid (10 mL) was added ethyl carbonocyanidate (2.00 g, 20.18 mmol, 1.98 mL, 1.00 eq) and NaOAc (2.02 g, 24.62 mmol, 1.22 eq) at room temperature and the reaction mixture was for stirred 0.5 hours. To the reaction mixture was added acetic anhydride (3.25 mL, 34.7 mmol) at room temperature and the reaction mixture was stirred for 0.5 hours. Then it was stirred at 100° C. for 12 hours. The mixture was cooled to room temperature, and acetic acid was removed under vacuo. Ethyl acetate (25 mL) and water (5 mL) were added to the reaction mixture. The solution was neutralized with $K_2CO_3$ (aq.) to pH 7. The aqueous phase was extracted with ethyl acetate (5 mL×3). The combined organic phases were washed with brine (10 mL), dried with anhydrous $Na_2SO_4$, filtered and concentrated in vacuo. The residue was purified by preparative HPLC to give ethyl 5-methyl-1,2,4-oxadiazole-3-carboxylate (1.40 g).

Preparation of
(5-methyl-1,2,4-oxadiazol-3-yl)methanol

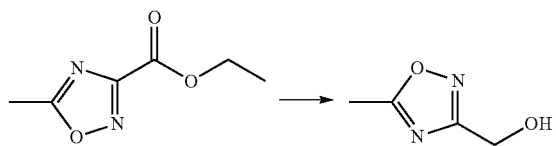

To a solution of 5-methyl-1,2,4-oxadiazole-3-carboxylate (400 mg, 2.56 mmol) in THF (4 mL) and ethanol (4 mL) was added $NaBH_4$ (290 mg, 7.68 mmol) at 0° C. The reaction mixture was stirred at 0° C. for 1 hour. The reaction was quenched with $NH_4Cl$, and the mixture was concentrated under vacuo. The residue was purified by silica gel chromatography (petroleum ether:ethyl acetate=1/0 to 1/1) to give (5-methyl-1,2,4-oxadiazol-3-yl)methanol (250 mg).

Preparation of
5-methyl-1,2,4-oxadiazole-3-carbaldehyde

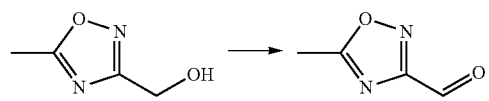

A solution of (5-methyl-1,2,4-oxadiazol-3-yl)methanol (250 mg, 2.19 mmol) and Dess-Martin periodinane (1.39 g, 3.29 mmol) in dichloromethane (5 mL) was stirred at room temperature for 12 hours. The mixture was filtered and the filtrate was concentrated under vacuo to give 5-methyl-1,2,4-oxadiazole-3-carbaldehyde (300 mg).

Preparation of methyl
(tert-butoxycarbonyl)glycinate

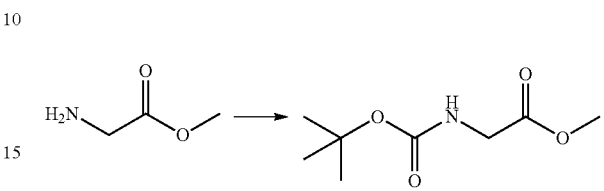

To a solution of methyl glycinate (20 g, 159.30 mmol) in dioxane (120 mL) and water (80 mL) was added $Na_2CO_3$ (33.77 g, 318.60 mmol) at 0° C., $Boc_2O$ (43.9 mL, 191 mmol) was added dropwise at room temperature. The mixture was stirred at room temperature for 18 h. The mixture was concentrated, water (200 mL) was added and the mixture was extracted with ethyl acetate (100 mL×3). The organic layer was washed with water (50 mL×2) and brine (50 mL×2), dried with anhydrous $Na_2SO_4$, filtered, concentrated to give methyl (tert-butoxycarbonyl)glycinate (30 g) which was used for next step directly.

Preparation of tert-butyl
(2-hydrazinyl-2-oxoethyl)carbamate

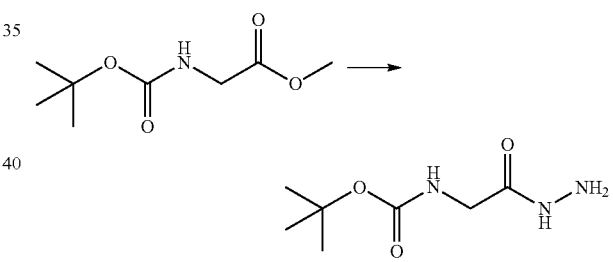

A mixture of methyl (tert-butoxycarbonyl)glycinate (10 g, 52.9 mmol) and hydrazine hydrate (4.37 mL, 89.85 mmol) in methanol (60 mL) and water (15 mL) were stirred at room temperature for 48 hours. The mixture was concentrated to give tert-butyl (2-hydrazinyl-2-oxoethyl)carbamate (10 g).

Preparation of tert-butyl
((1,3,4-oxadiazol-2-yl)methyl)carbamate

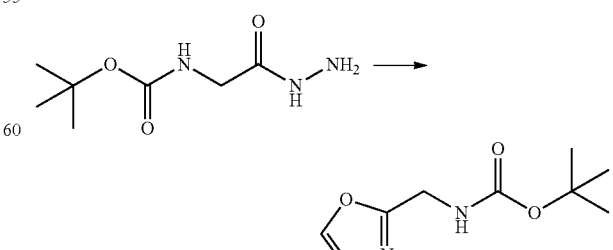

To a solution of tert-butyl (2-hydrazinyl-2-oxoethyl)carbamate (5.00 g, 26.4 mmol) in trimethoxymethane (50 mL) was added 4-methylbenzenesulfonic acid (45.5 mg, 0.26 mmol).

The mixture was stirred at 80° C. for 4 hour. The mixture was concentrated. The crude mixture was purified by flash chromatography with petroleum ether:ethyl acetate=3:1 to give tert-butyl ((1,3,4-oxadiazol-2-yl)methyl)carbamate (850 mg).

Preparation of (1,3,4-oxadiazol-2-yl)methanamine hydrobromide

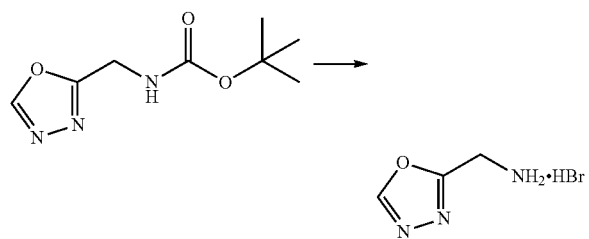

A solution of tert-butyl ((1,3,4-oxadiazol-2-yl)methyl)carbamate (450 mg, 2.26 mmol, 1.00 eq) in 35% hydrobromic acid in acetic acid (5 mL) was stirred at room temperature for 2 hours. The mixture was concentrated to give (1,3,4-oxadiazol-2-yl)methanamine hydrobromide (406 mg).

Preparation of methyl 1,2,4-oxadiazole-3-carboxylate

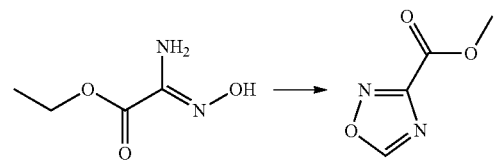

To a solution of ethyl 2-amino-2-(hydroxyimino)acetate (1.90 g, 14.4 mmol) in triethoxymethane (9.58 mL, 57.5 mmol) was added BF$_3$.Et$_2$O (0.089 mL, 0.72 mmol). The mixture was heated at 90° C. for 2 hours. The mixture was concentrated and the residue was dissolved in dichloromethane (30 mL). The organic layer was washed with 2N HCl (aq) (20 mL), Saturated aqueous NaHCO$_3$ (20 mL), water (20 mL), brine (20 mL) and dried over Na$_2$SO$_4$, filtered and concentrated to give methyl 1,2,4-oxadiazole-3-carboxylate (1.60 g).

Preparation of (1,2,4-oxadiazol-3-yl)methanol

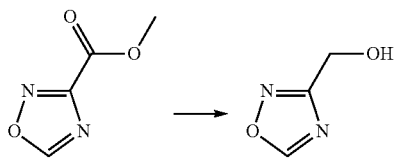

To a cooled (0° C.) solution of methyl 1,2,4-oxadiazole-3-carboxylate (300 mg, 2.11 mmol) in ethanol (2 mL) and THF (2 mL) was added NaBH$_4$ (239 mg, 6.33 mmol). The mixture was stirred at 0° C. for 1 hour. Saturated aqueous NH$_4$Cl (5 mL) was added, the mixture was concentrated and the residue was dissolved in 10% methanol in dichloromethane (20 mL). The mixture was filtered and the filtrate was concentrated. The residue was purified by flash chromatography on silica gel (10%~100% ethyl acetate in petroleum ether) to give (1,2,4-oxadiazol-3-yl)methanol (40 mg).

Preparation of 1,2,4-oxadiazole-3-carbaldehyde

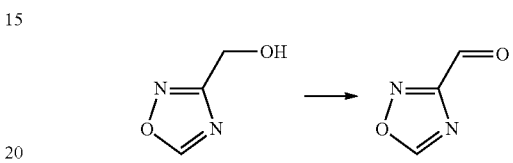

To a cooled (0° C.) solution of (1,2,4-oxadiazol-3-yl)methanol (40 mg, 0.40 mmol) in dichloromethane (5 mL) was added Dess-Martin periodinane (254 mg, 0.60 mmol). The mixture was stirred at room temperature for 1 hour. The mixture was filtered and the filtrate was concentrated to give 1,2,4-oxadiazole-3-carbaldehyde (39 mg).

Preparation of ethyl (5-methyl-1H-1,2,4-triazol-3-yl)methanol

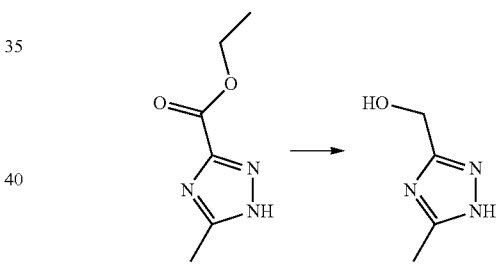

To a mixture of ethyl 5-methyl-1H-1,2,4-triazole-3-carboxylate (200 mg, 1.29 mmol) in THF (5 mL) was added LiAlH$_4$ (245 mg, 6.45 mmol) at 0° C. under N$_2$. The mixture was stirred at 30° C. for 1 hour. The mixture was filtrated and washed with methanol, concentrated in vacuo to give (5-methyl-1H-1,2,4-triazol-3-yl)methanol (350 mg).

Preparation of 5-methyl-1H-1,2,4-triazole-3-carbaldehyde

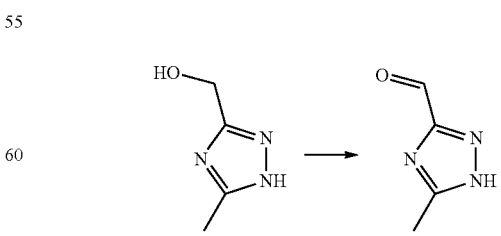

To a mixture of (5-methyl-1H-1,2,4-triazol-3-yl)methanol (350 mg, 3.09 mmol) in dichloromethane (10 mL) and acetonitrile (10 mL) was added Dess-Martin periodinane (2.62 g, 6.19 mmol). The mixture was stirred at 30° C. for 14 hours. The mixture was filtrated and washed with petroleum ether and ethyl acetate and concentrated in vacuo to give 5-methyl-1H-1,2,4-triazole-3-carbaldehyde (90 mg).

Preparation of 4-bromo-6-chloro-2-methylpyridin-3-amine

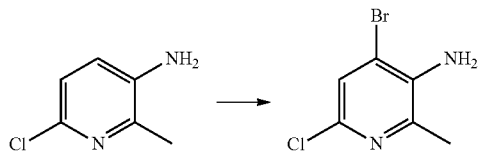

To an ice cold solution of 6-chloro-2-methylpyridin-3-amine (12 g, 84 mmol) and AcOH (5.1 g, 84 mmol) in MeOH (198 g, 250 mL) was dropwise added bromine (13.5 g, 84 mmol). The resulting solution was stirred at ice bath temperature overnight after which it was concentrated under vacuo. The obtained residue was dissolved in EtOAc and sequentially washed with saturated aqueous NaHCO₃ solution, 10% Na₂S₂O₃ aqueous solution, brine and dried (Na₂SO₄). The solvent was removed under vacuo and the obtained crude material was purified by flash chromatography to afford 4-bromo-6-chloro-2-methylpyridin-3-amine (12.6 g). $^1$H NMR (500 MHz, Chloroform-d) δ 7.30 (s, 1H), 4.04 (brs, 2H), 2.46 (s, 3H).

Preparation of 7-bromo-5-chloro-1H-pyrazolo[4,3-b]pyridine

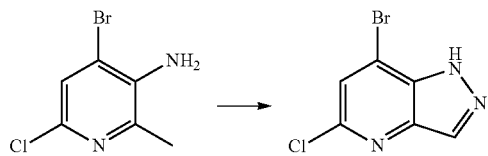

Isopentyl nitrite (3.97 g, 33.9 mmol) was dropwise added to an ice cold suspension of 4-bromo-6-chloro-2-methylpyridin-3-amine (5 g, 22.6 mmol), KOAc (4.43 g, 45.2 mmol) and AcOH (44.1 g, 734 mmol) in toluene (125 mL) under an inert atmosphere. A reflux condenser was inserted and the reaction mixture was heated at 30° C. over 4 h, after which most of the solvent was removed under vacuo. The obtained residue was dissolved in ethyl acetate and carefully washed with saturated aqueous NaHCO₃ solution ensuring that pH 8-9 was obtained. The organic layer was washed with brine, dried (Na₂SO₄) and concentrated to a crude material which was purified by flash chromatography (SiO₂) to deliver 7-bromo-5-chloro-1H-pyrazolo[4,3-b]pyridine (2.3 g, 44% yield). $^1$H NMR (500 MHz, Chloroform-d) δ 10.61 (brs, 1H), 8.35 (s, 1H), 7.60 (s, 1H)

Preparation of 7-bromo-5-chloro-1-(oxetan-3-yl)-1H-pyrazolo[4,3-b]pyridine

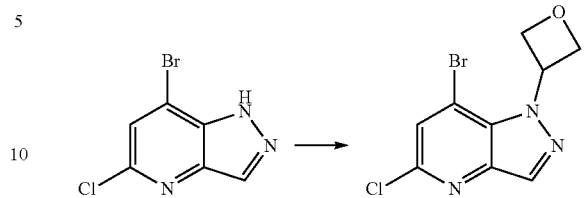

Diisopropyl azodicarboxylate (979 mg, 4.84 mmol) was dropwise added to an ice cold solution of 7-bromo-5-chloro-1H-pyrazolo[4,3-b]pyridine (250 mg, 1.08 mmol), triphenylphosphine (1.27 g, 4.84 mmol) and oxetan-3-ol (319 mg, 4.30 mmol) in THF (10 mL) under an inert atmosphere. The ice bath was allowed to warm to room temperature and stirring continued at room temperature overnight. Most of the solvent was removed under vacuo and the crude material obtained was purified by flash chromatography delivering 7-bromo-5-chloro-1-(oxetan-3-yl)-1H-pyrazolo[4,3-b]pyridine (130 mg, 38% yield). $^1$H NMR (Chloroform-d, 500 MHz) δ 8.31 (s, 1H), 7.56 (s, 1H), 6.48 (p, J=6.9 Hz, 1H), 5.35 (t, J=6.5 Hz, 2H), 5.11 (t, J=7.1 Hz, 2H).

Preparation of 3-(1,3-dioxolan-2-yl)pyridine

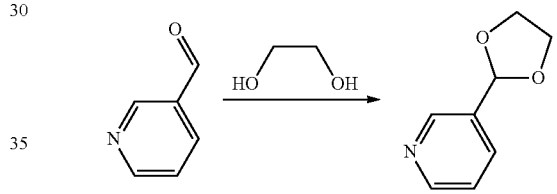

A solution of nicotinaldehyde (1 g, 9.34 mmol) in toluene (20 mL) was added toluene-4-sulfonic acid (1.93 g, 11 mmol) and stirred at 120° C. for 0.5 hour. Ethane-1,2-diol (637 mg, 10 mmol) was added and the resulting solution was stirred at 120° C. for 15 hours. The solution was quenched with saturated aqueous NaHCO₃ (60 mL) and the aqueous phase was extracted with DCM (30 mL×3). The combined organic phases were washed with brine, dried with Na₂SO₄, filtered and concentrated in vacuo. The residue was purified by silica gel chromatography (petroleum ether:ethyl acetate=10:1 to 1:1) to give 3-(1,3-dioxolan-2-yl)pyridine (1.30 g, 92% yield). $^1$H NMR (Chloroform-d, 400 MHz) δ8.70 (d, J=2.0 Hz, 1H), 8.61-8.60 (m, 1H), 7.79-7.77 (m, 1H), 7.32-7.29 (m, 1H), 5.84 (s, 1H), 4.12-4.01 (m, 4H).

Preparation of 5-(1,3-dioxolan-2-yl)-1-methylpyridin-2(1H)-one

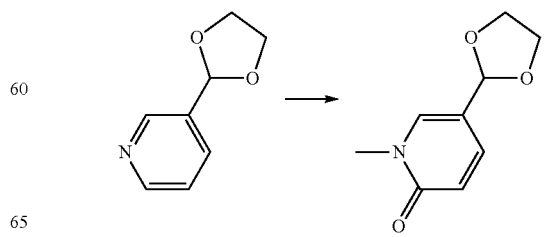

Dimethyl sulfate (1 g, 7.9 mmol) was slowly added dropwise to 3-(1,3-dioxolan-2-yl)pyridine (1.20 g, 7.94 mmol) and stirred at 100° C. for 1 hour. The resulting solution was dissolved in H₂O (4 mL) and an aqueous solution of K₃[Fe(CN)₆] (6.27 g) in H₂O (24 mL) was added under stirring and cooling. KOH (3.56 g) was added slowly, keeping the temperature at 5° C. After adding DCM (12 mL), the solution was stirred at 20° C. for 0.5 hours, before additional portions of K₃[Fe(CN)₆] (3.1 g) in H₂O (11 mL) and KOH (1.8 g) were added at 20° C. and stirred at 20° C. for 12 hours. The aqueous phase was extracted with ethyl acetate (30 mL×3). The combined organic phases were washed with brine, dried with Na₂SO₄, filtered and concentrated in vacuo. The residue was purified by preparative HPLC to give 5-(1,3-dioxolan-2-yl)-1-methylpyridin-2 (1H)-one (250 mg).

Preparation of 1-methyl-6-oxo-1,6-dihydropyridine-3-carbaldehyde

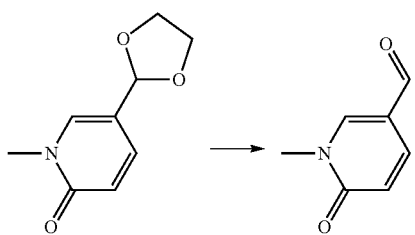

A solution of 5-(1,3-dioxolan-2-yl)-1-methylpyridin-2 (1H)-one (250 mg, 1.38 mmol) in 3% aqueous HCl (5 mL) was stirred at 100° C. for 3 hours. The solution was extracted with DCM (10 mL×3). The combined organic phases were washed with brine, dried with Na₂SO₄, filtered and concentrated in vacuo to give 1-methyl-6-oxo-1,6-dihydropyridine-3-carbaldehyde (150 mg).

Preparation of 6-(difluoromethyl)nicotinaldehyde

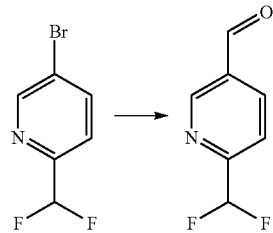 [SMILES: FC(F)c1ccc(Br)cn1 ; O=Cc1ccc(C(F)F)nc1]

To a solution of 5-bromo-2-(difluoromethyl)pyridine (400 mg, 1.92 mmol) in THF (2 mL) at 0° C. was added isopropylmagnesium chloride-lithium chloride complex (1.3 M, 2.96 mL) dropwise. The reaction was allowed to stir at room temperature for 2 hours, then DMF (703 mg, 9.62 mmol) was added at 0° C. and the reaction was stirred for an additional 12 hours at room temperature. The reaction was quenched with 2M HCl (aq) and basified with 1M NaOH (aq) until pH=7. The organic layer was separated and the aqueous layer was extracted with dichloromethane. The combined organic layers were dried over Na₂SO₄ and concentrated. The residue was purified by column chromatography (SiO₂, Petroleum ether/Ethyl acetate=1/0 to 10:1) to give 6-(difluoromethyl)nicotinaldehyde (130 mg).

Preparation of methyl 5-methoxypyrazine-2-carboxylate

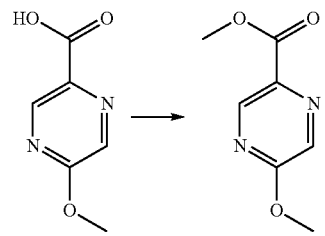

To a solution of 5-methoxypyrazine-2-carboxylic acid (1 g, 6.49 mmol) in MeOH (20 mL) was added SOCl₂ (927 mg, 7.79 mmol) at 15° C. The mixture was refluxed at 60° C. for 2 hours to give a brown solution. The reaction mixture was concentrated under reduced pressure to give a residue. The residue was diluted with dichloromethane (20 mL) and the pH was adjusted to 8 by NaHCO₃ (aq, 50 mL). The mixture was extracted with dichloromethane (100 mL×3). The combined organic layers were washed with brine (100 mL), dried over anhydrous Na₂SO₄, filtered and concentrated under reduced pressure to give methyl 5-methoxypyrazine-2-carboxylate (1.02 g).

Preparation of (5-methoxypyrazin-2-yl)methanol

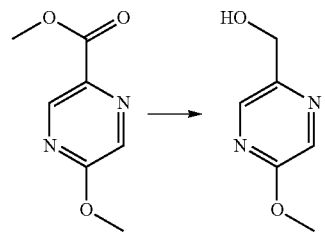

To a solution of methyl 5-methoxypyrazine-2-carboxylate (200 mg, 1.19 mmol) in THF (0.1 mL) and MeOH (4 mL) was added NaBH₄ (225 mg, 5.95 mmol). The mixture was stirred at 15° C. for 16 hours. The mixture was quenched with water (5 mL), then diluted with further water (15 mL), extracted with ethyl acetate (2×25 mL) then 20 percent 2-propanol in dichloromethane (25 mL). The combined organic extracts were dried over anhydrous Na₂SO₄, filtered and concentrated to give (5-methoxypyrazin-2-yl)methanol (122 mg).

Preparation of 5-methoxypyrazine-2-carbaldehyde

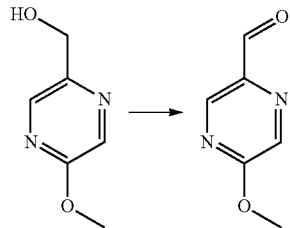

To a solution of (5-methoxypyrazin-2-yl)methanol (115 mg, 0.82 mmol) in dichloromethane (3 mL) was added MnO$_2$ (714 mg, 8.21 mmol) at 15° C. The reaction mixture was refluxed at 50° C. for 18 hours. The reaction mixture was cooled to 20° C., filtered through celite and washed with dichloromethane (100 ml). The filtrate was concentrated to afford 5-methoxypyrazine-2-carbaldehyde (45 mg).

Preparation of 4-ethyloxazolidin-2-one

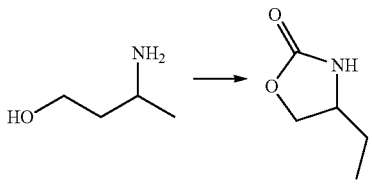

To a solution of 2-aminobutan-1-ol (1 g, 11.2 mmol), carbonyl diimidazole (2.18 g, 13.5 mmol) in THF (3 mL) was added Et$_3$N (1.14 g, 11.2 mmol) under argon atmosphere. The reaction was stirred at room temperature for 12 h. The mixture was concentrated and the residue was purified by column chromatography (SiO$_2$, Petroleum ether: Ethyl acetate=10:1 to 5:1) to give 4-ethyloxazolidin-2-one (800 mg).

Preparation of 5-bromo-1-isopropyl-3-methyl-1H-pyrazolo[4,3-b]pyridine-7-carbaldehyde

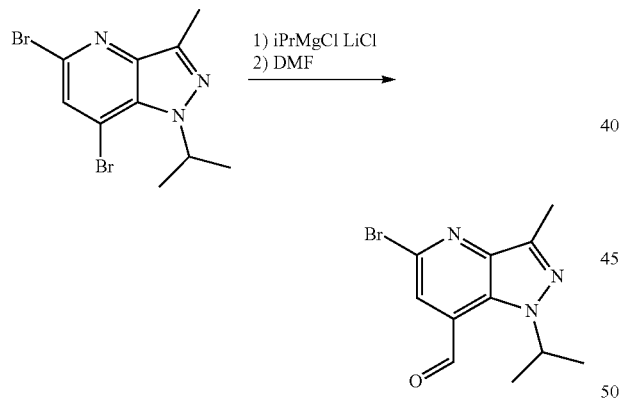

A solution of i-PrMgCl—LiCl (1.3 M, 3.6 mL) in THF was dropwise added into a mixture of 5,7-dibromo-1-isopropyl-3-methyl-pyrazolo[4,3-b]pyridine (1.3 g, 3.9 mmol) in THF (25 mL) at 0° C. The mixture was stirred at room temperature for 30 min. Then the mixture was recooled to 0° C. and DMF (1.4 g, 19.5 mmol, 1.5 mL) was added and the resulting mixture was stirred at room temperature for another 2.5 hours. NH$_4$Cl (aq. 2 mL) was added to quench the reaction, then water (20 mL) was added and the mixture was extracted with ethyl acetate (20 mL×3). The combined organic layer was washed with brine (10 mL), dried over Na$_2$SO$_4$ and concentrated. The crude mixture was purified by flash chromatography with petroleum ether:ethyl acetate=30:1-20:1 to give 5-bromo-1-isopropyl-3-methyl-1H-pyrazolo[4,3-b]pyridine-7-carbaldehyde (800 mg).

Preparation of N-((5-bromo-1-isopropyl-3-methyl-1H-pyrazolo[4,3-b]pyridin-7-yl)methyl)-5-methoxy-pyridin-3-amine

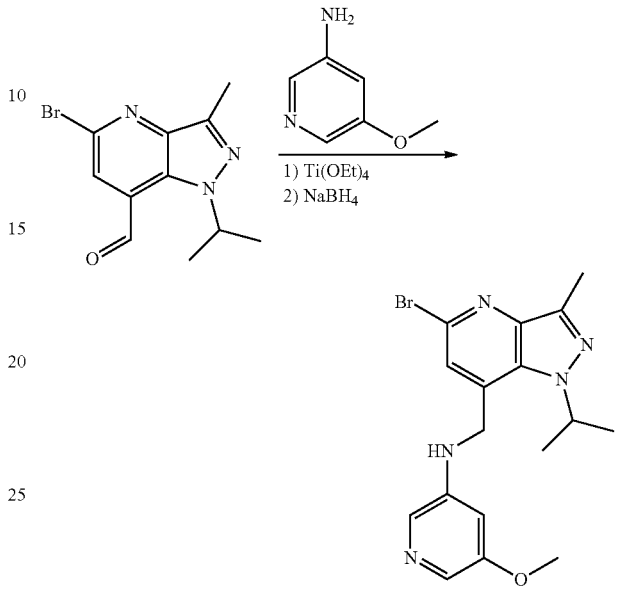

To a solution of 5-bromo-1-isopropyl-3-methyl-pyrazolo[4,3-b]pyridine-7-carbaldehyde (50 mg, 0.18 mmol) in dioxane (3 mL) was added Ti(i-PrO)$_4$ (101 mg, 0.35 mmol) and 5-methoxypyridin-3-amine (44 mg, 0.35 mmol). The mixture was stirred at 80° C. for 14 hours. After the reaction mixture had cooled to room temperature, EtOH (3 mL) was added followed by addition of NaBH$_4$ (35 mg, 0.9 mmol). The mixture was stirred at room temperature for 15 minutes. Water (0.5 mL) was added to quench the reaction at 0° C. And the resulting mixture was stirred at room temperature for 10 minutes, then filtered and the residue was washed with ethyl acetate (30 mL×3). The combined organic layers was dried and concentrated. The crude product N-[(5-bromo-1-isopropyl-3-methyl-pyrazolo[4,3-b]pyridin-7-yl)methyl]-5-methoxy-pyridin-3-amine (69 mg) was used into the next step without further purification.

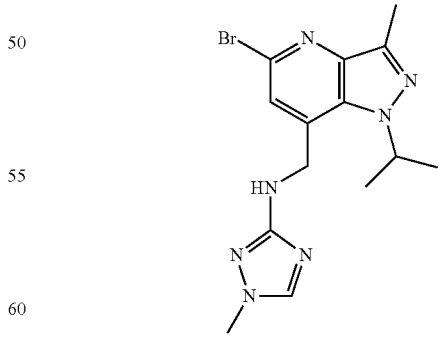

N-((5-bromo-1-isopropyl-3-methyl-1H-pyrazolo[4,3-b]pyridin-7-yl)methyl)-1-methyl-1H-1,2,4-triazol-3-amine was prepared in similar manner from 5-bromo-1-isopropyl-3-methyl-pyrazolo[4,3-b]pyridine-7-carbaldehyde and 1-methyl-1,2,4-triazol-3-amine.

101

Preparation of 5-(2-ethoxypyridin-3-yl)-1-isopropyl-3-methyl-1H-pyrazolo[4,3-b]pyridine-7-carbaldehyde

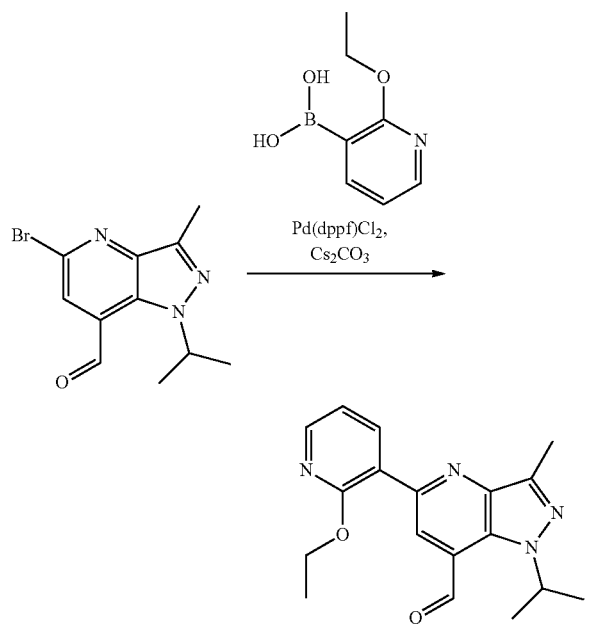

A mixture of 5-bromo-1-isopropyl-3-methyl-1H-pyrazolo[4,3-b]pyridine-7-carbaldehyde (0.56 g, 1.98 mmol), (2-ethoxy-3-pyridyl)boronic acid (497 mg, 2.98 mmol), Pd(dppf)C₂ (145 mg, 0.2 mmol), Cs₂CO₃ (1.94 g, 5.95 mmol) in dioxane (8 mL), water (2 mL) was stirred at 100° C. for 2 hours. The mixture was concentrated under reduced pressure. The residue was extracted with ethyl acetate (30 mL×2). The combined organic layers were washed with brine (20 mL), dried over Na₂SO₄, filtered and concentrated under reduced pressure to give a residue. The residue was purified by column chromatography (SiO₂, Petroleum ether/Ethyl acetate=10:1 to 3:1) to give 5-(2-ethoxypyridin-3-yl)-1-isopropyl-3-methyl-1H-pyrazolo[4,3-b]pyridine-7-carbaldehyde (0.55 g).

Preparation of 5-(2-ethoxypyridin-3-yl)-7-ethynyl-1-isopropyl-3-methyl-1H-pyrazolo[4,3-b]pyridine

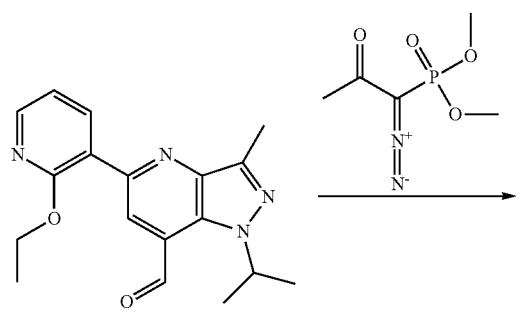

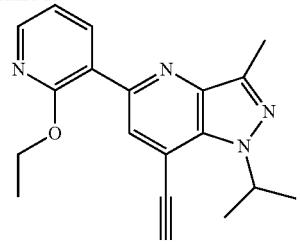

A mixture of 5-(2-ethoxypyridin-3-yl)-1-isopropyl-3-methyl-1H-pyrazolo[4,3-b]pyridine-7-carbaldehyde (0.55 g, 1.70 mmol), 1-diazo-1-dimethoxyphosphoryl-propan-2-one (423 mg, 2.20 mmol) and Cs₂CO₃ (1.66 g, 5.09 mmol) in MeOH (7 mL) was stirred at room temperature for 2 hours. The mixture was concentrated under reduced pressure and extracted with DCM (20 mL×2). The combined organic layers were washed with brine (20 mL), dried over Na₂SO₄, filtered and concentrated under reduced pressure to give crude. 5-(2-ethoxypyridin-3-yl)-7-ethynyl-1-isopropyl-3-methyl-1H-pyrazolo[4,3-b]pyridine (0.5 g).

Preparation of tert-butyl ((6-chloropyrazin-2-yl)methyl)carbamate

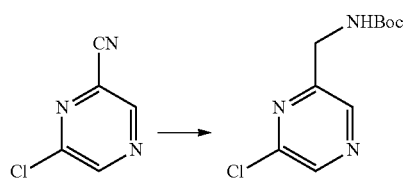 [SMILES: N#Cc1cncc(Cl)n1 ; CC(C)(C)OC(=O)NCc1cncc(Cl)n1]

To a suspension of Raney-Ni (307 mg, 3.59 mmol) in EtOH (20 mL) was added 6-chloropyrazine-2-carbonitrile (1.00 g, 7.17 mmol) and tert-butoxycarbonyl tert-butyl carbonate (1.72 g, 7.88 mmol), then the reaction mixture was stirred at room temperature under H₂ (45 psi) for 16 hours. The reaction mixture was filtered through celite and the filtrate was concentrated under reduced pressure to give a residue. The residue was purified by flash silica gel chromatography (eluention with 0~10% Ethyl acetate/Petroleum ether gradient) to give tert-butyl N-[(6-chloropyrazin-2-yl)methyl]carbamate (1.05 g).

Preparation of tert-butyl ((6-methoxypyrazin-2-yl)methyl)carbamate

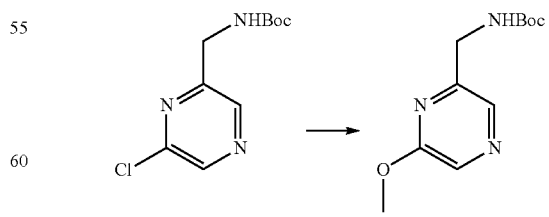

To an ice cold solution of tert-butyl N-[(6-chloropyrazin-2-yl)methyl]carbamate (500 mg, 2.05 mmol) in MeOH (10 mL) was added sodium methoxide (443 mg, 8.21 mmol), then the reaction mixture was stirred at room temperature for 16 hours. The reaction mixture was concentrated under reduced pressure. The residue was diluted with water (100 mL) and extracted with ethyl acetate (100 mL×3). The combined organic layers were washed with saturated aqueous NH$_4$Cl (100 mL×2), dried over anhydrous Na$_2$SO$_4$, filtered and concentrated under reduced pressure to give a residue. The residue was purified by flash silica gel chromatography (eluention with 0~16% Ethyl acetate/Petroleum ether) to give tert-butyl N-[(6-methoxypyrazin-2-yl)methyl]carbamate (300 mg).

Preparation of (6-methoxypyrazin-2-yl)methanamine hydrochloride

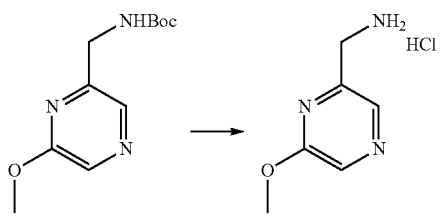

A solution of tert-butyl N-[(6-methoxypyrazin-2-yl)methyl]carbamate (350 mg, 1.46 mmol) in 4N HCl/dioxane (10 mL) was stirred at room temperature for 2 hours. The reaction mixture was concentrated under pressure to give a (6-methoxypyrazin-2-yl)methanamine hydrochloride. The crude product was used directly without further purification.

The following compound was prepared in a similar manner:

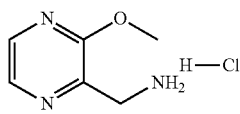

(3-methoxypyrazin-2-yl)methanamine hydrochloride

Preparation of (4-methoxy-3-pyridyl)methanamine

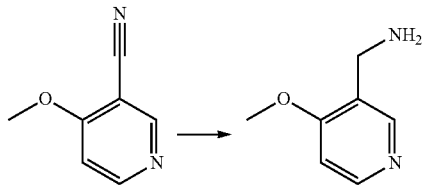

To a solution of 4-methoxypyridine-3-carbonitrile (200 mg, 1.49 mmol), 25% ammonia in water (0.23 mL) and MeOH (5 mL) was added to Raney-Ni (30 mg, 10%), the reaction mixture was stirred at room temperature for 4 hours under a H$_2$ atmosphere (45 psi). The reaction mixture was filtered to remove the catalyst and the filter cake was washed with MeOH (10 mL×3), the filtrate was concentrated under vacuo to give the crude product (4-methoxy-3-pyridyl)methanamine (150 mg).

Preparation of 6-methylheptyl 3-((5-bromo-1-isopropyl-3-methyl-1H-pyrazolo[4,3-b]pyridin-7-yl)thio)propanoate

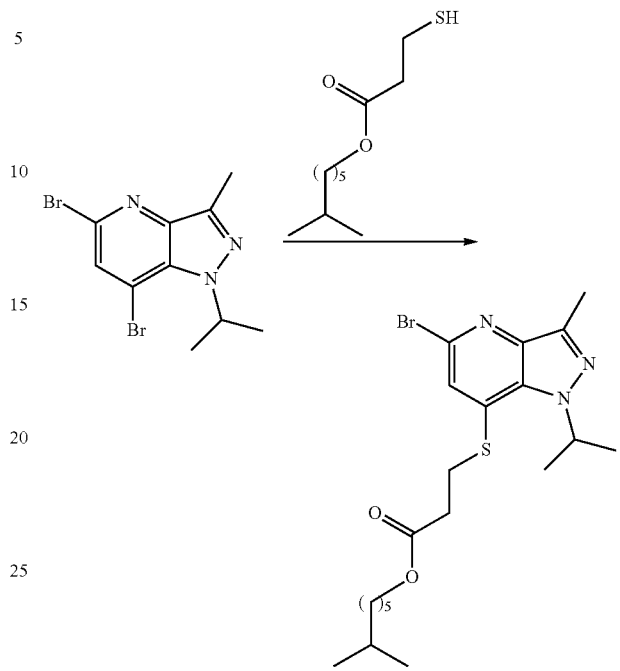

A solution of 5,7-dibromo-1-isopropyl-3-methyl-1H-pyrazolo[4,3-b]pyridine (150 mg, 0.45 mmol), 6-methylheptyl 3-mercaptopropanoate (124 mg, 0.57 mmol), DIPEA (116 mg, 157 μL, 0.90 mmol) in NMP (2 mL) was stirred at rt under inert atmosphere over 15 minutes after which it was inserted in an oil bath at 50° C. and stirred overnight. Partitioned between water (25 mL) and a solution of pentane:ethyl acetate (1:1) (50 mL). The aq. layer was extracted with fresh pentane:ethyl acetate (1:1) (20 mL). The combined org. layers were dried (Na$_2$SO$_4$) and concentrated. The crude material was purified by flash chromatography with heptane:ethyl acetate 1:0 to 0:1 to give 6-methylheptyl 3-((5-bromo-1-isopropyl-3-methyl-1H-pyrazolo[4,3-b]pyridin-7-yl)thio)propanoate (194 mg).

Preparation of 6-methylheptyl 3-((5-(2-ethoxypyridin-3-yl)-1-isopropyl-3-methyl-1H-pyrazolo[4,3-b]pyridin-7-yl)thio) propanoate

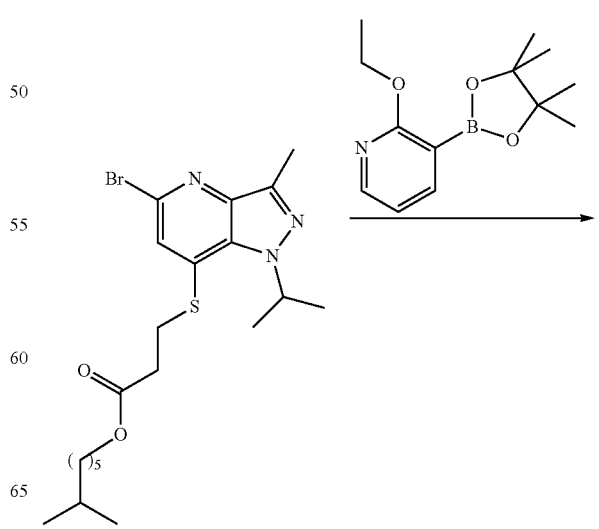

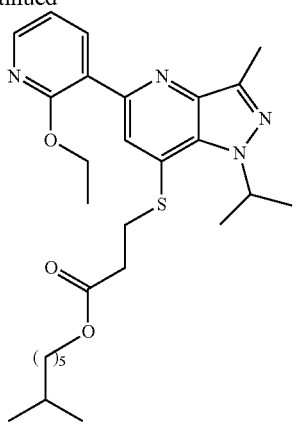

A suspension of 6-methylheptyl 3-((5-bromo-1-isopropyl-3-methyl-1H-pyrazolo[4,3-b]pyridin-7-yl)thio)propanoate (194 mg, 0.41 mmol), 2-ethoxy-3-(4,4,5,5-tetramethyl-1,3,2-dioxaborolan-2-yl)pyridine (123 mg, 0.50 mmol), PdCl$_2$(dppf)-CH$_2$Cl$_2$ (84 mg, 0.10 mmol), K$_2$CO$_3$ (85 mg, 0.62 mmol) in 1,4-dioxane (5.5 mL) and water (0.3 mL) was degassed by bubbling nitrogen over 3 minutes and then stirred at 105° C. over 4 hours. Most of the solvent was removed under vacuo. The obtained residue was taken in ethyl acetate (25 mL) and filtered through a short pad of Celite which was rinsed with ethyl acetate (10 mL×2). The combined filtrates were washed with brine (20 mL), dried (Na$_2$SO$_4$) and concentrated. The crude material was purified by flash chromatography with heptane:ethyl acetate 1:0 to 0:1 to give 6-methylheptyl 3-((5-(2-ethoxypyridin-3-yl)-1-isopropyl-3-methyl-1H-pyrazolo[4,3-b]pyridin-7-yl)thio)propanoate (128 mg).

Preparation of ethyl 5-(hydroxymethyl)isoxazole-3-carboxylate

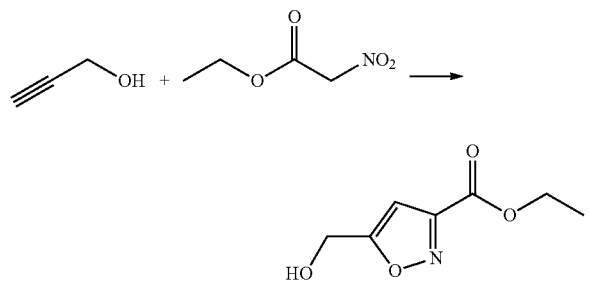

To a solution of prop-2-yn-1-ol (500 mg, 0.52 ml, 8.92 mmol) and ethyl 2-nitroacetate (2.26 g, 1.88 ml, 16.95 mmol) in EtOH (15 ml) was added DABCO (1.0 g, 8.92 mmol). The mixture was stirred at 80° C. for 72 hours under microwave irradiation. The mixture was concentrated and purified directly by flash chromatography with heptane:ethyl acetate=1:0 to 0:1 to give ethyl 5-(hydroxymethyl)isoxazole-3-carboxylate (400 mg).

Preparation of ethyl 5-(fluoromethyl)isoxazole-3-carboxylate

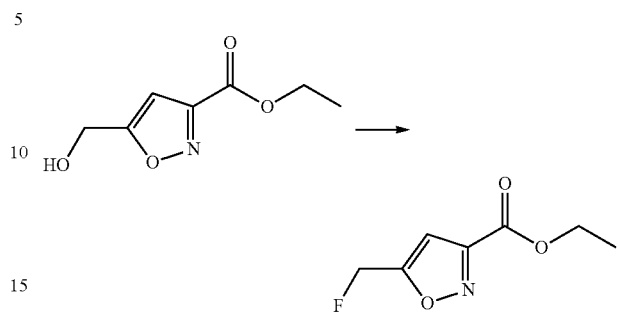

To a solution of ethyl 5-(hydroxymethyl)isoxazole-3-carboxylate (50.0 mg, 0.29 mmol) in DCM (2 mL) was added diethylaminosulfur trifluoride (70.6 mg, 0.06 ml, 0.44 mmol). The mixture was stirred at 40° C. for 1 hour. Water (3 mL) was added and the mixture was extracted with ethyl acetate (5 mL×3). The combined organic layers were washed with brine (5 mL), dried over Na$_2$SO$_4$ and concentrated. The crude mixture was purified by flash chromatography with heptane:ethyl acetate=1:0 to 0:1 to give ethyl 5-(fluoromethyl)isoxazole-3-carboxylate (41.0 mg).

Preparation of (5-(fluoromethyl)isoxazol-3-yl)methanol

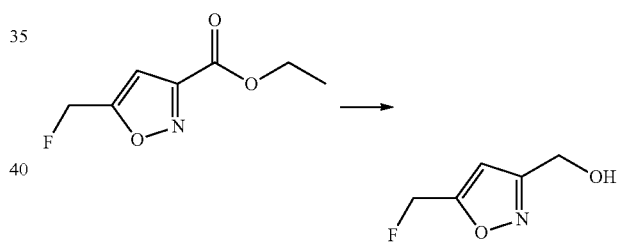

To a solution of ethyl 5-(fluoromethyl)isoxazole-3-carboxylate (50.0 mg, 0.29 mmol) in THF (4 mL) at 0° C. was added lithium aluminum hydride (0.43 mL, 0.43 mmol, 1 M in THF). The mixture was stirred at 0° C. for 1 hour. A half saturated solution of sodium potassium tartarate (5 mL) was added and the mixture was stirred vigorously for 30 minutes. The mixture was then extracted with ethyl acetate (10 mL×3). The combined organic layers were washed with brine (10 mL), dried over Na$_2$SO$_4$ and concentrated. The crude mixture was purified by flash chromatography with heptane:ethyl acetate=1:0 to 0:1 to give (5-(fluoromethyl)isoxazol-3-yl)methanol (29.0 mg).

Preparation of 3-(bromomethyl)-5-(fluoromethyl)isoxazole

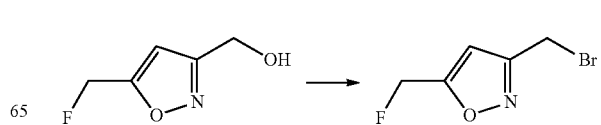

To a solution of (5-(fluoromethyl)isoxazol-3-yl)methanol (17.0 mg 0.13 mmol) in MeCN (2 mL) was added triphenylphosphine (68 mg, 0.26 mmol), 2,6-lutidine (13.9 mg, 0.015 mL, 0.13 mmol) and CBr₄ (86 mg, 0.26 mmol). The reaction mixture was stirred at room temperature for 1 hour. The mixture was concentrated purified directly by flash chromatography with heptane:ethyl acetate=1:0 to 0:1 to give 3-(bromomethyl)-5-(fluoromethyl)isoxazole (12 mg).

Preparation of ethyl 5-(bromomethyl)isoxazole-3-carboxylate

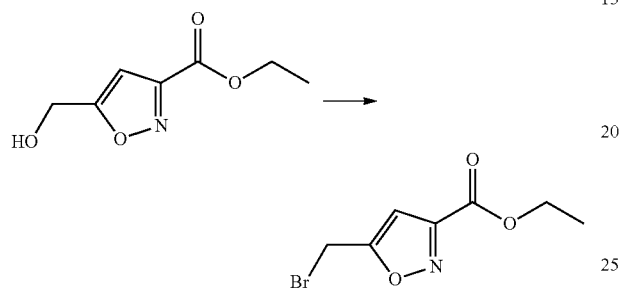

To a solution of ethyl 5-(hydroxymethyl)isoxazole-3-carboxylate (50 mg, 0.29 mmol) in MeCN (2 mL) was added triphenylphosphine (153 mg, 0.58 mmol), 2,6-lutidine (31.3 mg, 0.034 mL, 0.29 mmol) and CBr₄ (194 mg, 0.58 mmol). The reaction mixture was stirred at room temperature for 1.5 hours. The mixture is concentrated and purified directly by flash chromatography with heptane:ethyl acetate=1:0 to 0:1 to give ethyl 5-(bromomethyl)isoxazole-3-carboxylate (68 mg).

Preparation of (5-(bromomethyl)isoxazol-3-yl)methanol

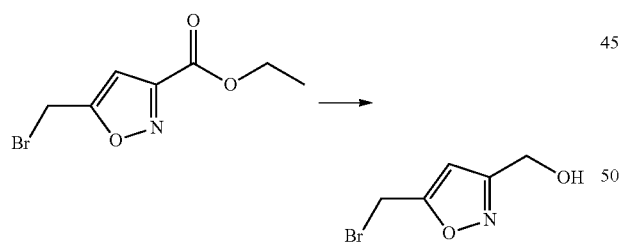

To a solution of ethyl 5-(bromomethyl)isoxazole-3-carboxylate (26 mg, 0.11 mmol) in THF (1 mL) at 0° C. was added diisopropyl aluminium hydride (0.12 ml, 0.12 mmol, 1 M in THF). The mixture was stirred at 0° C. for 2 hours. Another 0.12 mmol of diisopropyl aluminium hydride solution was added and the mixture was stirred for another hour. 3 drops of 4M HCl (aq) was added followed by a half saturated solution of sodium potassium tartarate (5 mL). The mixture was stirred vigorously for 30 minutes. The mixture was then extracted with ethyl acetate (10 mL×3). The combined organic layers were washed with brine (10 mL), dried over Na₂SO₄ and concentrated to give (5-(bromomethyl)isoxazol-3-yl)methanol (21.3 mg, 0.11 mmol).

Preparation of 5-(bromomethyl)-3-(fluoromethyl)isoxazole

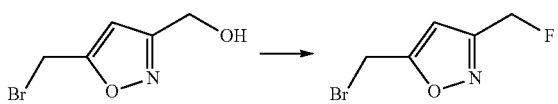 [SMILES: OCc1cc(CBr)on1 ; FCc1cc(CBr)on1]

To a solution of (5-(bromomethyl)isoxazol-3-yl)methanol in DCM (1 mL) was added diethylaminosulfur trifluoride (70.6 mg, 0.06 ml, 0.44 mmol). The mixture was stirred at 40° C. for 1 hour. Water (3 mL) was added and the mixture was extracted with ethyl acetate (5 mL×3). The combined organic layers were washed with brine (5 mL), dried over Na₂SO₄ and concentrated. The crude mixture was purified by flash chromatography with heptane:ethyl acetate=1:0 to 0:1 to give 5-(bromomethyl)-3-(fluoromethyl)isoxazole (7.0 mg, 0.04 mmol).

Preparation of methyl 1-(difluoromethyl)-1H-pyrazole-4-carboxylate

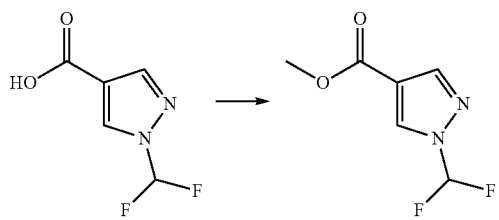

To a solution of 1-(difluoromethyl)-1H-pyrazole-4-carboxylic acid (100 mg, 0.62 mmol) in DCM (4 mL) was added (diazomethyl)trimethylsilane (0.62 mL, 1.23 mmol, 2 M in hexane). The mixture was stirred at room temperature for 2 hours. Acetic acid (0.2 mL) was added and the mixture was co-evaporated with toluene (2×20 mL) to give methyl 1-(difluoromethyl)-1H-pyrazole-4-carboxylate (99.0 mg, 0.56 mmol).

Preparation of (1-(difluoromethyl)-1H-pyrazol-4-yl)methanol

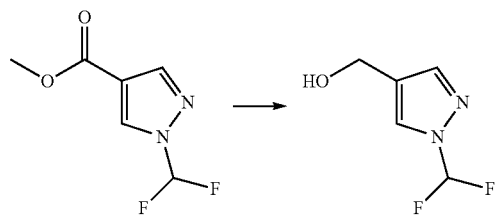

To a solution of methyl 1-(difluoromethyl)-1H-pyrazole-4-carboxylate (120 mg, 0.68 mmol) in THF (4 mL) at 0° C. was added lithium aluminum hydride (1.0 mL, 1.0 mmol, 1 M in THF). The mixture was stirred at 0° C. for 1 hour. A half saturated solution of sodium potassium tartarate (5 mL) was added and the mixture was stirred vigorously for 30 minutes. The mixture was then extracted with ethyl acetate (10 mL×3). The combined organic layers were washed with brine (10 mL), dried over Na$_2$SO$_4$ and concentrated. The crude mixture was purified by flash chromatography with heptane:ethyl acetate=1:0 to 0:1 to give (1-(difluoromethyl)-1H-pyrazol-4-yl)methanol (101 mg, 0.68 mmol).

Preparation of 4-(bromomethyl)-1-(difluoromethyl)-1H-pyrazole

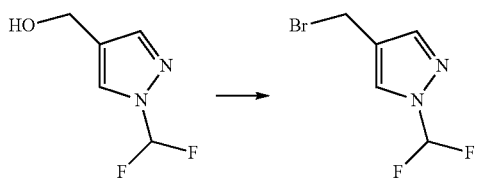 [SMILES: OCc1cnn(C(F)F)c1 ; FC(F)n1cc(CBr)cn1]

To a solution of (1-(difluoromethyl)-1H-pyrazol-4-yl)methanol (30 mg, 0.20 mmol) in MeCN (1.5 mL) was added triphenylphosphine (106 mg, 0.41 mmol), 2,6-lutidine (21.7 mg, 23.6 µl, 0.20 mmol) and CBr$_4$ (134 mg, 0.41 mmol). The reaction mixture was stirred at room temperature for 1 hour. The mixture is concentrated and purified directly by flash chromatography with heptane:ethyl acetate=1:0 to 0:1 to give 4-(bromomethyl)-1-(difluoromethyl)-1H-pyrazole (29 mg).

Preparation of N-((1-(difluoromethyl)-1H-pyrazol-4-yl)methyl)-5-(2-ethoxypyridin-3-yl)-1-isopropyl-N-(4-methoxybenzyl)-3-methyl-1H-pyrazolo[4,3-b]pyridin-7-amine

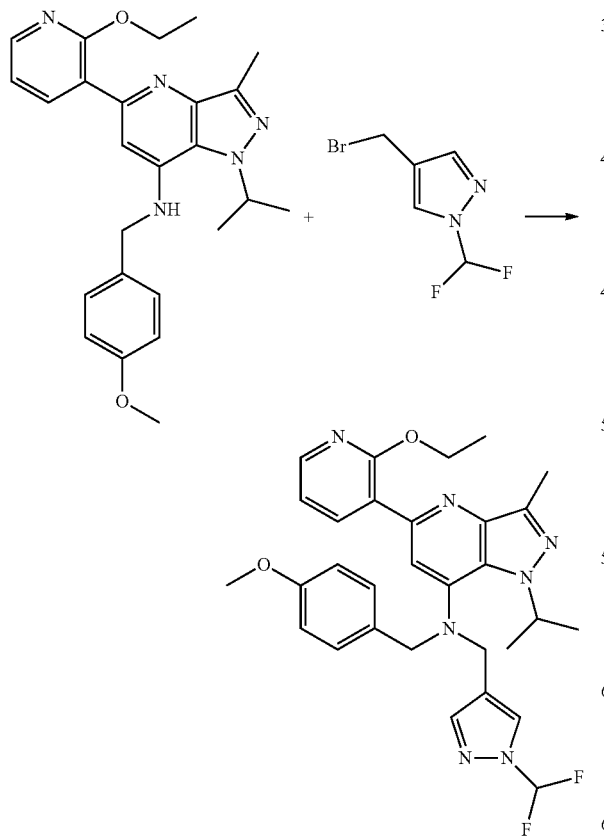

To a suspension of NaH (3.79 mg, 0.095 mmol, 60% w/w) in THF (1 mL) at 0° C. was added 5-(2-ethoxypyridin-3-yl)-1-isopropyl-N-(4-methoxybenzyl)-3-methyl-1H-pyrazolo[4,3-b]pyridin-7-amine (20.5 mg, 0.05 mmol). The mixture was stirred at 0° C. for 15 minutes before 4-(bromomethyl)-1-(difluoromethyl)-1H-pyrazole (10 mg, 0.05 mmol) in THF (1 mL) was added. The reaction mixture was slowly allowed to reach room temperature and stirred for 2 hours. Water (5 mL) was added and the mixture was extracted with ethyl acetate (5 mL×3). The combined organic layers were washed with brine (10 mL), dried over Na$_2$SO$_4$ and concentrated. The crude mixture was purified by flash chromatography with heptane:ethyl acetate=1:0 to 0:1 to give N-((1-(difluoromethyl)-1H-pyrazol-4-yl)methyl)-5-(2-ethoxypyridin-3-yl)-1-isopropyl-N-(4-methoxybenzyl)-3-methyl-1H-pyrazolo[4,3-b]pyridin-7-amine (23 mg, 0.04 mmol).

The following examples were prepared in a similar manner:

5-(2-ethoxypyridin-3-yl)-N-((5-(fluoromethyl)isoxazol-3-yl)methyl)-1-isopropyl-N-(4-methoxybenzyl)-3-methyl-1H-pyrazolo[4,3-b]pyridin-7-amine

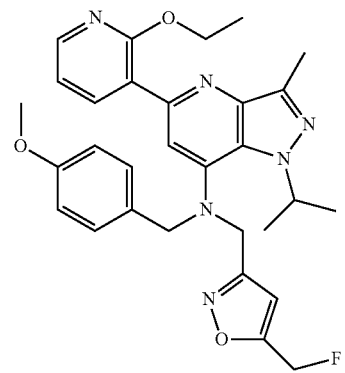 [SMILES: CCOc1ncccc1-c1cc(N(Cc2ccc(OC)cc2)Cc2cc(CF)on2)c2c(n1)c(C)nn2C(C)C]

Prepared from 5-(2-ethoxypyridin-3-yl)-1-isopropyl-N-(4-methoxybenzyl)-3-methyl-1H-pyrazolo[4,3-b]pyridin-7-amine and 3-(bromomethyl)-5-(fluoromethyl)isoxazole.

5-(2-ethoxypyridin-3-yl)-N-((3-(fluoromethyl)isoxazol-5-yl)methyl)-1-isopropyl-N-(4-methoxybenzyl)-3-methyl-1H-pyrazolo[4,3-b]pyridin-7-amine

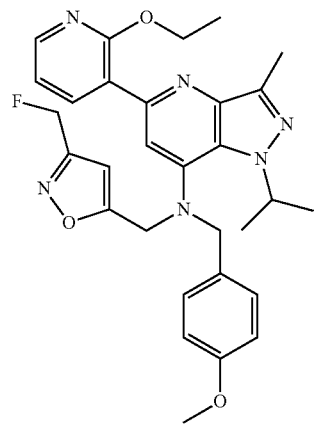 [SMILES: CCOc1ncccc1-c1cc(N(Cc2ccc(OC)cc2)Cc2cc(CF)no2)c2c(n1)c(C)nn2C(C)C]

Prepared from 5-(2-ethoxypyridin-3-yl)-1-isopropyl-N-(4-methoxybenzyl)-3-methyl-1H-pyrazolo[4,3-b]pyridin-7-amine and 5-(bromomethyl)-3-(fluoromethyl)isoxazole.

Preparation of (2-oxo-1,2-dihydropyridin-3-yl)boronic Acid

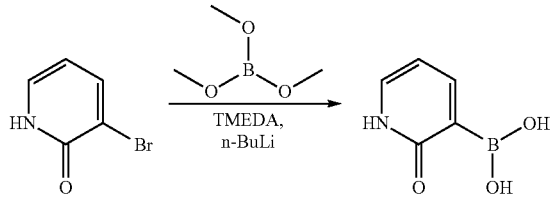

To a solution of 3-bromopyridin-2(1H)-one (3.3 g, 19 mmol) in THF (200 mL) cooled to −78° C., TMEDA (tetramethylethylenediamine) (6.6 g, 57 mmol) was added dropwise over 15 minutes followed by addition of n-BuLi (in hexane, 2.5 M, 23 mL). The resulting mixture was stirred for 15 min at −78° C. and then warmed to room temperature. The reaction mixture was cooled to 0° C., and trimethyl borate (3.9 g, 38 mmol) was added dropwise over 30 minutes. After the addition was complete, the reaction mixture was warmed to room temperature and was stirred for 15 hours. The mixture was then cooled to 0° C. and a small amount of ice was added followed by HCl (aq. 100 mL, 2M). The THF was removed under reduced pressure, and the aqueous solution was washed twice with dichloromethane (50 mL×2). Concentrated aqueous NaOH was added slowly until pH=5 was attained and a precipitate formed. The mixture was cooled to 0° C. and stirred for 10 minutes. The solid was collected by filtration, washed with cold water, and dried under vacuum to afford (2-oxo-1,2-dihydropyridin-3-yl)boronic acid.

Preparation of 2-(trifluoromethyl)pyridine-3-carbonitrile

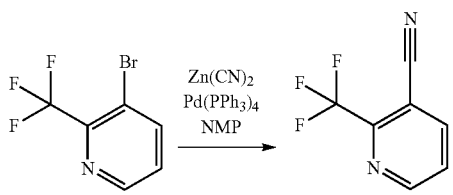 [SMILES: FC(F)(F)c1ncccc1Br ; N#Cc1cccnc1C(F)(F)F]

To 3-bromo-2-(trifluoromethyl)pyridine (1 g, 4.42 mmol) in NMP (10 mL) was added Zn(CN)$_2$ (572 mg, 4.87 mmol) and Pd(PPh$_3$)$_4$(1 g, 0.885 mmol), then the reaction mixture was stirred at 140° C. for 1 hour by microwave heating. The reaction mixture was cooled to room temperature, filtered through celite and washed with ethyl acetate (100 mL). The reaction mixture was extracted with ethyl acetate (100 mL×2) and the organic layers were washed with water (100×3 mL), brine (100 mL), dried over anhydrous Na$_2$SO$_4$, filtered and concentrated under reduced pressure to give a residue. The residue was purified by flash chromatography on silica gel (petroleum ether/ethyl acetate) to give 2-(trifluoromethyl) pyridine-3-carbonitrile.

Preparation of (2-(trifluoromethyl) pyridin-3-yl)methanamine

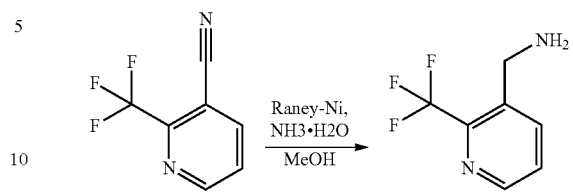

To a solution of Raney-Ni (50 mg, 0.581 mmol) in MeOH (20 mL) was added 2-(trifluoromethyl)pyridine-3-carbonitrile (500 mg, 2.91 mmol) and NH$_3$.water (6 M, 5 mL), then the reaction mixture was stirred at 30° C. for 2 hours. The reaction mixture was concentrated under reduced pressure to give a residue. To the residue was added HCl (2M, 2 mL) and water (10 mL). The resulting solution was lyophilized. The crude product was used for next step without further purification.

Preparation of tert-butyl ((5-methoxypyrimidin-2-yl)methyl)carbamate

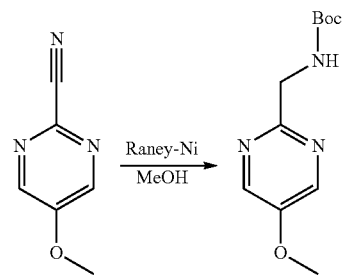

A mixture of 5-methoxypyrimidine-2-carbonitrile (100 mg, 0.74 mmol) and Boc$_2$O (194 mg, 0.89 mmol) and MeOH (5 mL) was added to Raney-Ni (30 mg, 10%), the reaction mixture was stirred at room temperature for 2 hours under a H$_2$ atmosphere (45 psi). The reaction mixture was filtered to remove the catalyst and the filter cake was washed with MeOH (10 mL×3), and the filtrate was concentrated under vacuum. The crude product was purified by flash chromatography on silica gel (0~10% ethyl acetate in petroleum ether) to give tert-butyl ((5-methoxypyrimidin-2-yl)methyl)carbamate.

Preparation of (5-methoxypyrimidin-2-yl)methanamine Hydrochloride

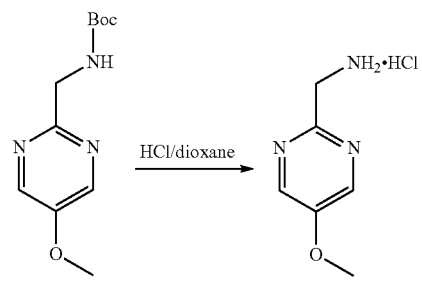

A mixture of tert-butyl ((5-methoxypyrimidin-2-yl)methyl)carbamate (100 mg, 0.42 mmol) and dichloromethane (5 mL) and HCl/dioxane (4 M, 2 mL) was stirred at room temperature for 0.5 hour. Water (10 mL) was added to the reaction mixture and the solution was concentrated under vacuum to remove the organic phase and the aqueous phase was lyophilized to give the crude product. The crude product (5-methoxypyrimidin-2-yl)methanamine was obtained.

Preparation of 4-methoxypyrimidine-2-carbonitrile

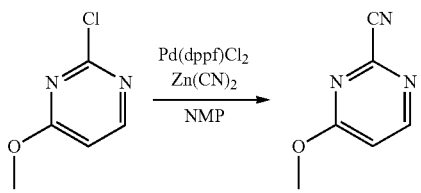

2-chloro-4-methoxy-pyrimidine (600 mg, 4.15 mmol) and Zn(CN)$_2$ (292 mg, 2.49 mmol) and Pd(dppf)C$_2$ (607 mg, 0.83 mmol) were taken up into a microwave tube in NMP (3 mL). The sealed tube was heated at 140° C. for 1 hour under microwave irradiation. The reaction mixture was cooled to room temperature, filtered through celite and washed with ethyl acetate (20 mL). The reaction mixture was extracted with ethyl acetate (20 mL×3) and the organic layers were washed with water (20×3 mL), brine (20 mL), dried over anhydrous Na$_2$SO$_4$, filtered and concentrated under reduced pressure to give a residue. The residue was purified by flash chromatography on silica gel (petroleum ether/ethyl acetate) to give 4-methoxypyrimidine-2-carbonitrile.

Preparation of tert-butyl N-[(4-methoxypyrimidin-2-yl)methyl]carbamate

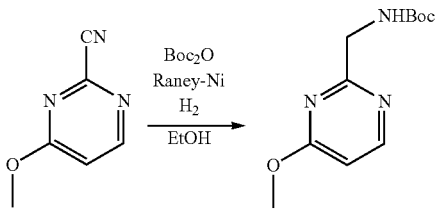

To a solution of Raney-Ni (25 mg, 0.296 mmol) in EtOH (5 mL) was added 4-methoxypyrimidine-2-carbonitrile (200 mg, 1.48 mmol) and Boc$_2$O (355 mg, 1.63 mmol, 0.374 mL) under N$_2$, then the reaction mixture was stirred at room temperature under H$_2$ (45 psi) for 2 hours. The reaction mixture was filtered through celite and concentrated under reduced pressure to give a residue. The residue was purified by flash chromatography on silica gel (petroleum ether/ethyl acetate) to give tert-butyl N-[(4-methoxypyrimidin-2-yl)methyl]carbamate.

Preparation of (4-methoxypyrimidin-2-yl)methanamine hydrobromide

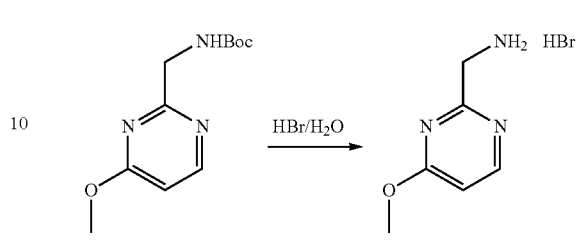

A solution of tert-butyl N-[(4-methoxypyrimidin-2-yl)methyl]carbamate (100 mg, 0.418 mmol) in HBr/water (3 mL) was stirred at room temperature for 1 hour. The reaction mixture was concentrated under reduced pressure to give a residue. The crude product was used in the next step without further purification.

Preparation of 6-methoxypyrimidine-4-carbonitrile

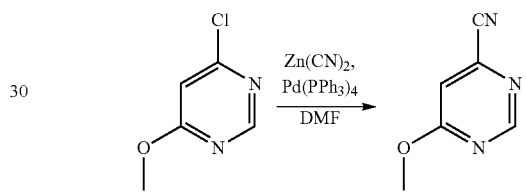

To a solution of 4-chloro-6-methoxy-pyrimidine (1 g, 6.92 mmol) in DMF (10 mL) was added Pd(PPh$_3$)$_4$(2 g, 1.38 mmol) and Zn(CN)$_2$ (487 mg, 4.15 mmol). The reaction mixture was stirred at 80° C. for 16 hours. The reaction mixture was cooled to room temperature, filtered through celite and washed with dichloromethane (100 mL). The reaction mixture was extracted with dichloromethane (100 mL×3) and the organic layers were washed with water (100×3 mL) and brine (50 mL), dried over anhydrous Na$_2$SO$_4$, filtered and concentrated under reduced pressure to give a residue. The residue was purified by flash chromatography on silica gel (petroleum ether/ethyl acetate) to give 6-methoxypyrimidine-4-carbonitrile.

Preparation of tert-butyl N-((6-methoxypyrimidin-4-yl)methyl)carbamate

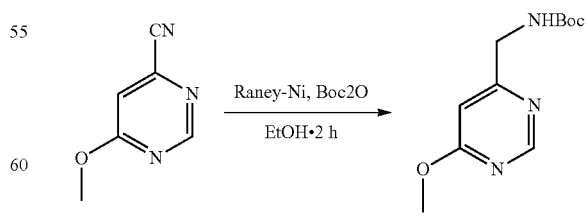

To a solution of Raney-Ni (25 mg, 0.296 mmol) in EtOH (5 mL) was added 6-methoxypyrimidine-4-carbonitrile (200 mg, 1.48 mmol) and Boc$_2$O (355 mg, 1.63 mmol, 0.374 mL), then the reaction mixture was stirred at room temperature under H₂ (45 psi) for 2 hours. The reaction mixture was filtered through celite and washed with EtOH (20 mL×2), the filtrated was concentrated under reduced pressure to give a residue. The residue was purified by flash chromatography on silica gel (petroleum ether/ethyl acetate) to give tert-butyl N-[(6-methoxypyrimidin-4-yl)methyl]carbamate.

Preparation of (6-methoxypyrimidin-4-yl)methanamine

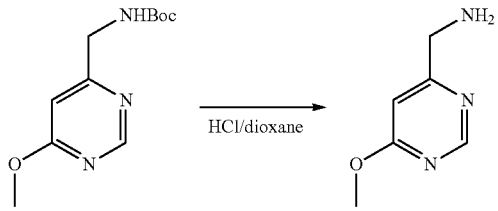

A solution of tert-butyl N-[(6-methoxypyrimidin-4-yl) methyl]carbamate (240 mg, 1.00 mmol) in HCl/dioxane (10 mL) was stirred at room temperature for 2 hours. The reaction mixture was concentrated under reduced pressure to give a residue. The residue was used in the next step without further purification.

Preparation of 3-bromopicolinaldehyde

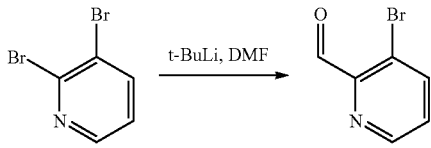 [SMILES: Brc1cccnc1Br ; O=Cc1ncccc1Br]

To a solution of 2,3-dibromopyridine (5 g, 21.11 mmol) in toluene (50 mL), t-BuLi (1.3 M, 19.50 mL) was dropwise added at −78° C. under N₂. The resulting mixture was stirred at −78° C. for 2 hours. DMF (1.9 g, 25.33 mmol) was added dropwise at −78° C. The mixture was stirred at −78° C. for another 2 hours. The solution was quenched with NH₄Cl (aq. 1 mL) at −78° C., and the mixture was concentrated under vacuum. The residue was purified by column chromatography on silica gel (Petroleum ether/ethyl acetate=10/1 to 1/1) to afford 3-bromopicolinaldehyde.

Preparation of 3-bromo-2-(difluoromethyl)pyridine

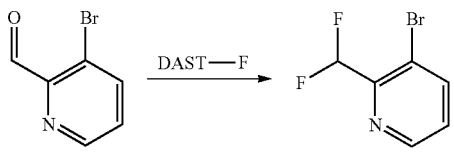

To a solution of 3-bromopicolinaldehyde (1.3 g, 6.99 mmol) in dichloromethane (30 mL) was added diethylaminosulfur trifluoride (2.25 g, 13.98 mmol) at 0° C. The reaction mixture was stirred at 0° C. for 2 hours under N₂. The solution was quenched with NaHCO₃ (aq. 15 mL) at 0° C. The aqueous phase was extracted with dichloromethane (10 mL×3). The combined organic phases were washed with brine (15 mL×1), dried with anhydrous Na₂SO₄, filtered and concentrated in vacuo. The residue was purified by silica gel chromatography (petroleum ether/ethyl acetate=1/0, 10/1) to afford 3-bromo-2-(difluoromethyl)pyridine Preparation of 2-(difluoromethyl)nicotinonitrile

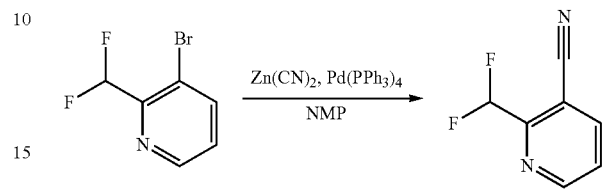

To a mixture of 3-bromo-2-(difluoromethyl)pyridine (600 mg, 2.88 mmol) and Zn(CN)₂ (373 mg, 3.17 mmol) in NMP (10 mL) was added Pd(PPh₃)₄ (333 mg, 0.29 mmol). The reaction mixture was heated by microwave irradiation at 140° C. for 1 hour. The reaction mixture was poured into ethyl acetate (50 mL). The mixture was washed with water (20 mL×3) and brine (15 mL×1), dried over Na₂SO₄ and filtered. The filtrate was concentrated under reduced pressure. The residue was purified by silica gel chromatography (petroleum ether/ethyl acetate=1/0, 2/1) to afford 2-(difluoromethyl)nicotinonitrile.

Preparation of tert-butyl ((2-(difluoromethyl)pyridin-3-yl)methyl)carbamate

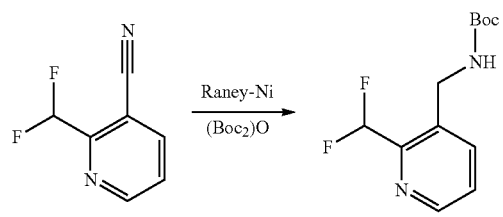

A mixture of 2-(difluoromethyl)nicotinonitrile (0.4 g, 2.60 mmol), (Boc)₂O (680 mg, 3.11 mmol) and Raney-Ni (22 mg, 0.26 mmol) in MeOH (20 mL) was stirred at 30° C. for 2 hours under H₂ (40 psi). The mixture was filtered and the filtrate was concentrated under vacuum. The residue was purified by silica gel chromatography (petroleum ether/ethyl acetate=1/0, 3/1) to afford tert-butyl ((2-(difluoromethyl) pyridin-3-yl)methyl)carbamate.

Preparation of (2-(difluoromethyl)pyridin-3-yl)methanamine Hydrochloride

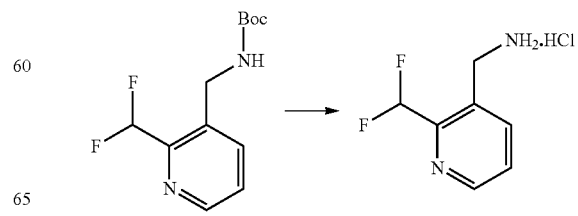

To a solution of tert-butyl ((2-(difluoromethyl)pyridin-3-yl)methyl)carbamate (0.6 g, 2.32 mmol) in dichloromethane (5 mL) was added HCl/dioxane (4M, 1 mL) at 0° C. The reaction mixture was stirred at room temperature for 12 hours. The mixture was concentrated under vacuum to afford (2-(difluoromethyl)pyridin-3-yl)methanamine hydrochloride.

Preparation of 3-bromo-2-ethoxypyridine

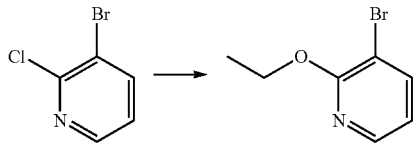

To a mixture of 3-bromo-2-chloropyridine (200 mg, 1 mmol) in EtOH (5 mL) was added t-BuOK (233 mg, 2 mmol). The mixture was stirred at 80° C. for 12 hours. The reaction mixture was filtered and the filtrate was concentrated in vacuo to give the crude product. The residue was purified by flash chromatography on silica gel (0%~40% ethyl acetate in petroleum ether) to afford 3-bromo-2-ethoxypyridine.

Preparation of 2-ethoxynicotinonitrile

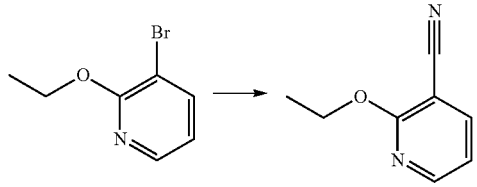

To a solution of 3-bromo-2-ethoxy-pyridine (350 mg, 1.7 mmol) in NMP (2 mL) was added Zn(CN)$_2$ (244 mg, 2.1 mmol) and Pd(dppf)Cl$_2$ (127 mg, 0.17 mmol). The mixture was degassed with N$_2$ and heated at 140° C. under microwave irradiation for 1 hour. The mixture was cooled to room temperature and filtered through celite. The filtered cake was washed with ethyl acetate (30 mL). The filtrate was washed with water (20 mL×2) and brine (20 mL), dried over Na$_2$SO$_4$, filtered and concentrated. The residue was purified by flash chromatography on silica gel (0%~20% ethyl acetate in petroleum ether) to give 2-ethoxynicotinonitrile.

Preparation of tert-butyl ((2-ethoxypyridin-3-yl)methyl)carbamate

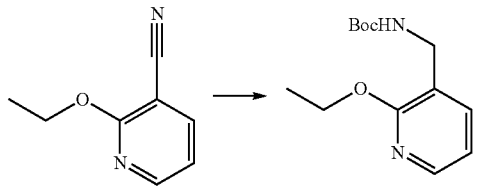 [SMILES: CCOc1ncccc1C#N ; CCOc1ncccc1CNC(=O)OC(C)(C)C]

To a solution of Raney-Ni (24 mg, 0.28 mmol) in EtOH (5 mL) was added 2-ethoxynicotinonitrile (210 mg, 1.4 mmol) and Boc$_2$O (371 mg, 1.7 mmol). The reaction mixture was stirred at room temperature under H$_2$ (45 psi) for 2 hours. The reaction mixture was filtered through celite and washed with EtOH (20 mL×2), then the filtrate was concentrated under reduced pressure to give a residue. The residue was purified by preparative HPLC to afford tert-butyl ((2-ethoxypyridin-3-yl)methyl)carbamate.

Preparation of (2-ethoxypyridin-3-yl)methanamine

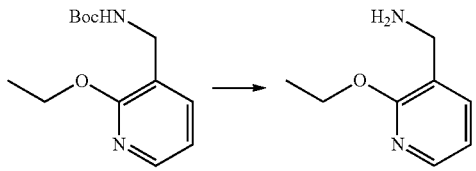 [SMILES: CCOc1ncccc1CNC(=O)OC(C)(C)C ; CCOc1ncccc1CN]

A solution of tert-butyl ((2-ethoxypyridin-3-yl)methyl)carbamate (85 mg, 0.34 mmol) in HCl/dioxane (4 M, 2 mL) was stirred at room temperature for 12 hours. The reaction mixture was concentrated under reduced pressure to afford 2-ethoxypyridin-3-yl)methanamine.

Preparation of 3-methoxypyridine-4-carbonitrile

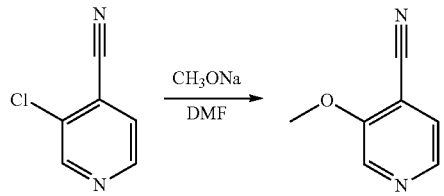

3-chloropyridine-4-carbonitrile (250 mg, 1.80 mmol) was dissolved in DMF (5 mL) and cooled to ice bath temperature. CH$_3$ONa (194.95 mg, 3.61 mmol) was added slowly and the reaction mixture was stirred at room temperature for 2 hours under a N$_2$ atmosphere. Water (20 mL) and ethyl acetate (20 mL) were added to the reaction mixture. The aqueous phase was extracted with ethyl acetate (20 mL×2). The organic phases were combined and dried over anhydrous Na$_2$SO$_4$ (5 g), filtered and concentrated under vacuum to give the product 3-methoxypyridine-4-carbonitrile.

Preparation of (3-methoxy-4-pyridyl)methanamine

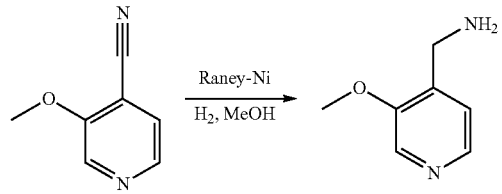

A mixture of 3-methoxypyridine-4-carbonitrile (200 mg, 1.49 mmol), NH$_3$ in water (314 mg, 2.24 mmol, 25%) and Raney-Ni (30 mg) in MeOH (5 mL) was stirred at room temperature for 3 hours under a $H_2$ atmosphere (45 psi). The reaction mixture was filtered to remove the catalyst and the filter cake was washed with MeOH (10 mL×3). The filtrate was concentrated under vacuum. The residue was dissolved in 1 M HCl (30 mL) and the solution was lyophilized to give (3-methoxy-4-pyridyl)methanamine hydrochloride (296 mg). A mixture of (3-methoxy-4-pyridyl)methanamine hydrochloride (100 mg, 0.57 mmol), Ambersep 900(OH) and iron exchange resin (150 mg) in MeCN (5 mL) was stirred at room temperature for 0.5 hour. Universal indicator paper showed that pH of the solution was 9~10. The reaction mixture was filtered to remove the resin and the filtrate was dried over anhydrous $Na_2SO_4$, filtered and concentrated under vacuum to give (3-methoxy-4-pyridyl)methanamine.

Preparation of methyl 4-methoxypyrimidine-5-carboxylate

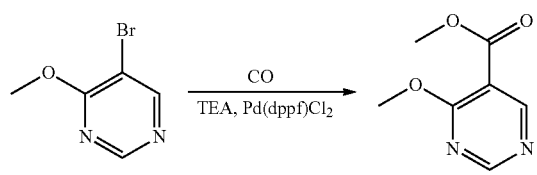

To a solution of 5-bromo-4-methoxypyrimidine (1 g, 5.29 mmol) in MeOH (20 mL) was added triethylamine (1.07 g, 10.58 mmol) and Pd(dppf)Cl$_2$ (774 mg, 1.06 mmol). The suspension was degassed and purged with CO several times. The mixture was heated at 80° C. under CO (50 psi) for 16 hours. The mixture was filtered through celite and the filtrate was concentrated. The residue was purified by flash chromatography on silica gel (petroleum ether/ethyl acetate) to give methyl 4-methoxypyrimidine-5-carboxylate.

Preparation of (4-methoxypyrimidin-5-yl)methanol

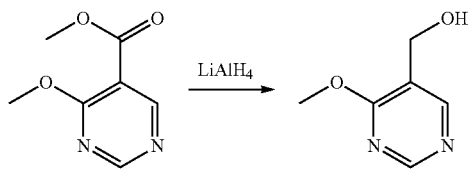

To a solution of methyl 4-methoxypyrimidine-5-carboxylate (250 mg, 1.49 mmol) in THF (5 mL) was added LiAlH$_4$ (169 mg, 4.46 mmol) at −40° C. The mixture was stirred at −40° C. for 0.5 hour. Water (0.5 mL) and 15% NaOH (0.5 mL) were added. The mixture was extracted with ethyl acetate (20 mL×2). The combined organic layer was washed with water (10 mL), dried over Na$_2$SO$_4$, filtered and concentrated. The residue was purified by flash chromatography on silica gel (petroleum ether/ethyl acetate) to give (4-methoxypyrimidin-5-yl)methanol.

Preparation of 5-(bromomethyl)-4-methoxypyrimidine

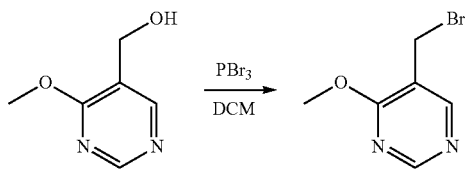

To a solution of (4-methoxypyrimidin-5-yl)methanol (50 mg, 0.36 mmol) in dry dichloromethane (2 mL) was added PBr$_3$ (144 mg, 0.53 mmol) at 0° C. The mixture was stirred at 0° C. for 0.5 hour. The mixture was concentrated and ice-water (5 g) was added. The aqueous layer was extracted with ethyl acetate (20 mL×2). The organic layer was dried over Na$_2$SO$_4$, filtered and concentrated to give 5-(bromomethyl)-4-methoxypyrimidine (70 mg, crude).

Preparation of 3-bromo-2-(ethoxy-d$_5$)pyridine

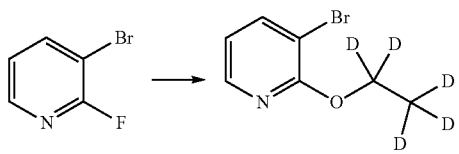 [SMILES: Fc1ncccc1Br ; [2H]C([2H])([2H])C([2H])([2H])Oc1ncccc1Br]

NaH (60% dispersion in oil) (227 mg, 5.68 mmol) was suspended in THF (13 ml) and cooled to ice bath temperature. A solution of ethanol-d$_6$ (296 mg, 5.68 mmol) in THF (1.2 ml) was added dropwise. The resulting suspension was stirred at ice bath temperature over 10 minutes after which the cooling bath was removed and stirring continued for 0.5 hour. The resulting mixture was recooled to ice bath temperature and a solution of 3-bromo-2-fluoropyridine (500 mg, 2.84 mmol) in THF (1.2 ml) was added dropwise. After stirring for 15 minutes at ice bath temperature the cooling was removed and stirring continued for 45 minutes further at room temperature after which a reflux condenser was inserted and the mixture was heated to 65° C. for 10 hours. The mixture was recooled to ice bath temperature and quenched with a few drops of water. Most of the solvent was removed under vacuo. The obtained residue was partioned between ethyl acetate (25 ml) and brine (10 ml). The organic layer was dried (Na$_2$SO$_4$) and concentrated. The residue was purified by flash chromatography on silica gel (heptane/ethyl acetate) to give 3-bromo-2-(ethoxy-d$_5$)pyridine.

The following compounds were prepared in a similar manner:

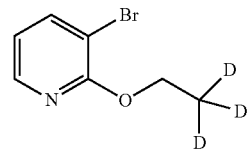 [SMILES: [2H]C([2H])([2H])COc1ncccc1Br]

3-bromo-2-(ethoxy-2,2,2-d$_3$)pyridine prepared from 3-bromo-2-fluoropyridine and ethanol-2,2,2-d$_3$.

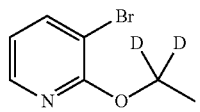

3-bromo-2-(ethoxy-1,1-d₂)pyridine prepared from 3-bromo-2-fluoropyridine and ethanol(1,1-d₂).

Preparation of 2-(ethoxy-d₅)-3-(4,4,5,5-tetramethyl-1,3,2-dioxaboran-2yl)pyridine

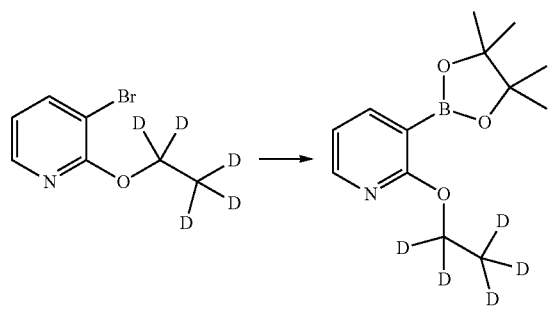 [SMILES: [2H]C([2H])([2H])C([2H])([2H])Oc1ncccc1Br ; [2H]C([2H])([2H])C([2H])([2H])Oc1ncccc1B1OC(C)(C)C(C)(C)O1]

A suspension of 3-bromo-2-(ethoxy-d₅)pyridine (152 mg, 0.73 mmol), 4,4,4',4',5,5,5',5'-octamethyl-2,2'-bi(1,3,2-dioxaborolane) (242 mg, 0.95 mmol), PdCl₂(dppf)-CH₂Cl₂ (120 mg, 0.15 mmol) and KOAc (216 mg, 2.20 mmol) in 1,4-dioxane (2.5 ml) was degassed by bubbling N₂ through the suspension for approx. 3 minutes after which it was heated to 110° C. for 4.5 hours. The resulting suspension was diluted with ethyl acetate (10 ml) and filtered through a short pad of Celite which was rinsed with ethyl acetate (2×10 ml). Most of the solvent was removed under vacuo. The obtained residue was taken into ethyl acetate (50 ml) and washed with brine (30 ml). The organic layer was dried (Na₂SO₄), filtered and concentrated. Purification by flash chromatography on silica gel (elution from heptane to ethyl acetate) delivered 2-(ethoxy-d₅)-3-(4,4,5,5-tetramethyl-1,3,2-dioxaboran-2yl)pyridine.

The following compounds were prepared in a similar manner:

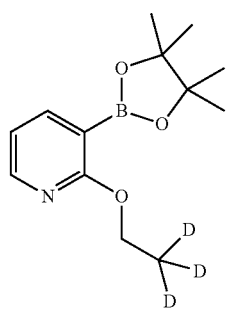 [SMILES: [2H]C([2H])([2H])COc1ncccc1B1OC(C)(C)C(C)(C)O1]

2-(Ethoxy-2,2,2-d₃)-3-(4,4,5,5-tetramethyl-1,3,2-dioxaboran-2yl)pyridine prepared from 3-bromo-2-(ethoxy-2,2,2-d₃)pyridine.

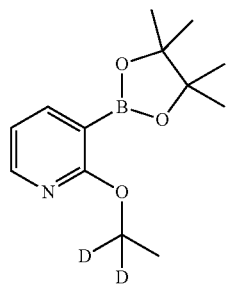 [SMILES: [2H]C([2H])(C)Oc1ncccc1B1OC(C)(C)C(C)(C)O1]

2-(Ethoxy-1,1-d₂)-3-(4,4,5,5-tetramethyl-1,3,2-dioxaboran-2yl)pyridine prepared from 3-bromo-2-(ethoxy-1,1-d₂) pyridine.

Preparation of 2'-ethoxy-6-methyl-[2,3'-bipyridin]-5-amine

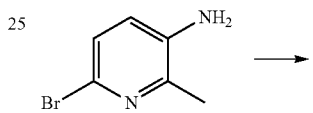

N₂ was bubbled through a mixture of 6-bromo-2-methyl-pyridin-3-amine (2.5 g, 13.4 mmol), 2-ethoxy-3-(4,4,5,5-tetramethyl-1,3,2-dioxaborolan-2-yl)pyridine (5.0 g, 20.1 mmol), PdCl₂(dppf)-CH₂Cl₂ (2.18 g, 2.67 mmol) and potassium carbonate (3.69 g, 26.7 mmol) in 1,4-dioxane (126 ml) and water (12 ml) for 10 minutes. A reflux condenser was inserted and the reaction mixture was heated at 105° C. for 2.5 hours under an inert atmosphere after which most of the solvent was removed under vacuo. The obtained residue was taken into ethyl acetate (150 ml) and filtered through a short pad of Celite which was rinsed with ethyl acetate (2×50 ml). Concentration and purification by flash chromatography on silica gel (elution with heptane to heptane/dichloromethane (1:1) to heptane/dichloromethane/ethyl acetate (1:1:1.5)) delivered 2'-ethoxy-6-methyl-[2,3'-bipyridin]-5-amine.

Preparation of 4-chloro-2'-ethoxy-6-methyl-[2,3'-bipyridin]-5-amine

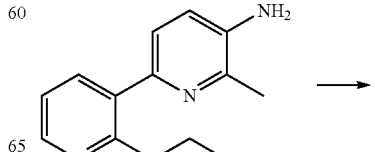

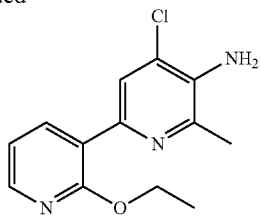

A solution of 2'-ethoxy-6-methyl-[2,3'-bipyridin]-5-amine (7.40 g, 22.6 mmol) and N-chloro succinimide (3.77 g, 28.2 mmol) in NMP (104 ml) was stirred at room temperature for 15 minutes under an inert atmosphere. A reflux condenser was inserted and the solution was heated to 80° C. for 3.5 hours after which it was allowed to reach room temperature and partitioned between ethyl acetate (300 ml) and aqueous saturated NaHCO$_3$ (3×200 ml). The combined aqueous layers were extracted with ethyl acetate (50 ml). The combined organic layers were further washed with brine (2×100 ml), dried (Na$_2$SO$_4$) and concentrated. The residue was purified by flash chromatography on silica gel (heptane/ethyl acetate) to give 4-chloro-2'-ethoxy-6-methyl-[2,3'-bipyridin]-5-amine.

Preparation of 7-chloro-5-(2-ethoxypyridin-3-yl)-1H-pyrazolo[4,3-b]pyridine

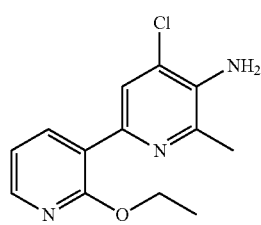

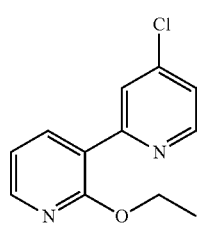

A suspension of 4-chloro-2'-ethoxy-6-methyl-[2,3'-bipyridin]-5-amine (4.01 g, 12.2 mmol) and potassium acetate (2.98 g, 30.4 mmol) in toluene (84 ml) and acetic acid (28 ml) was stirred at ice bath temperature for 5 minutes under an inert atmosphere. Isopentyl nitrite (2.71 g, 23.11 mmol) was added dropwise for 5 minutes. After stirring at ice bath temperature over 10 minutes a reflux condenser was inserted and the mixture was heated to 35° C. for 2.5 hours. Most of the solvent was removed under vacuo. The obtained residue was suspended in ethyl acetate (350 ml) and washed with aqueous saturated NaHCO$_3$ (2×250 ml), brine (200 ml), dried (Na$_2$SO$_4$) and concentrated. The residue was purified by flash chromatography on silica gel (heptane/ethyl acetate) to give 7-chloro-5-(2-ethoxypyridin-3-yl)-1H-pyrazolo[4,3-b]pyridine.

Preparation of 7-chloro-5-(2-ethoxypyridin-3-yl)-3-iodo-1H-pyrazolo[4,3-b]pyridine

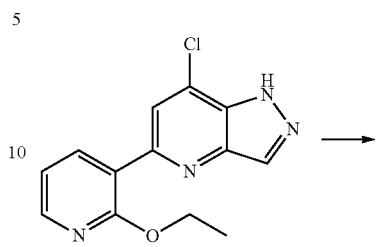

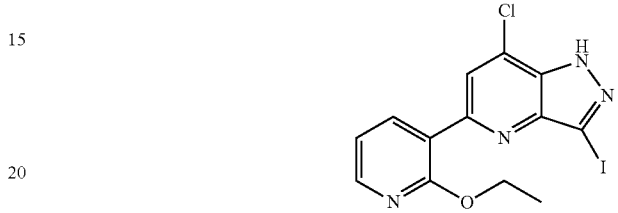

A solution of 7-chloro-5-(2-ethoxypyridin-3-yl)-1H-pyrazolo[4,3-b]pyridine (1.0 g, 3.64 mmol) and N-iodo succinimide (1.11 g, 4.91 mmol) in DMF (50.0 ml) was stirred at room temperature for 15 minutes under an inert atmosphere after which a reflux condenser was inserted and stirring continued at 35° C. for 11 hours. The solution was diluted with ethyl acetate (350 ml) and washed with aqueous 10% Na$_2$S$_2$O$_3$ (100 ml), aqueous % saturated NaHCO$_3$ (2×150 ml) and brine (50 ml). The organic layer was dried (Na$_2$SO$_4$) and concentrated to deliver 7-chloro-5-(2-ethoxypyridin-3-yl)-3-iodo-1H-pyrazolo[4,3-b]pyridine which was used without further purification.

Preparation of 7-chloro-5-(2-ethoxypyridin-3-yl)-3-iodo-1-isopropyl-1H-pyrazolo[4,3-b]pyridine

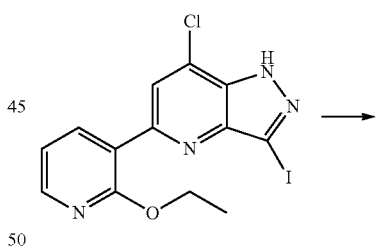

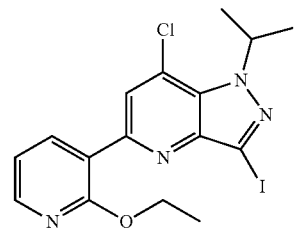

A solution of diisopropyl azodicarboxylate (1.59 g, 7.86 mmol) in THF (3.0 ml) was dropwise added to an ice cold solution of 7-chloro-5-(2-ethoxypyridin-3-yl)-3-iodo-1H-pyrazolo[4,3-b]pyridine (1.0 g, 2.25 mmol), isopropanol (0.60 ml, 7.86 mmol) and triphenylphosphine (2.06 g, 7.86 mmol) in THF (25 ml) under an inert atmosphere. After stirring at ice bath temperature for 0.5 hours. the solution was allowed to reach room temperature and stirring continued for 4.5 hours. Most of the solvent was removed under vacuo and the obtained residue was dissolved in ethyl acetate (150 ml) and washed with aqueous saturated NaHCO$_3$ (150 ml), brine (100 ml), dried (Na$_2$SO$_4$) and concentrated. Purification by flash chromatography on silica gel (elution gradient from heptane to ethyl acetate) delivered 7-chloro-5-(2-ethoxypyridin-3-yl)-3-iodo-1-isopropyl-1H-pyrazolo[4,3-b]pyridine.

Preparation of 7-chloro-5-(2-ethoxypyridin-3-yl)-1-isopropyl-3-vinyl-1H-pyrazolo[4,3-b]pyridine

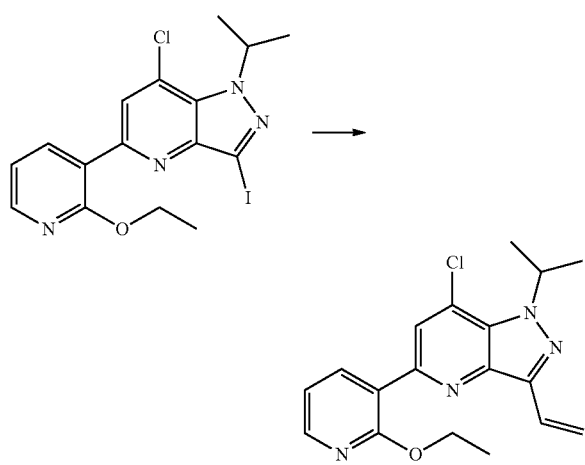

N$_2$ was bubbled through a suspension of 7-chloro-5-(2-ethoxypyridin-3-yl)-3-iodo-1-isopropyl-1H-pyrazolo[4,3-b]pyridine (10 mg, 0.023 mmol), tributyl(vinyl)stannane (9.9 µl, 0.034 mmol), bis(triphenylphosphine) palladiumI(II) dichloride (4 mg, 5.7 µmol) in 1,4-dioxane (0.30 ml) over 2 minutes. The mixture was stirred at 105° C. for 6.5 hours after which additional tributyl(vinyl)stannane (5.0 µl, 0.017 mmol), bis(triphenylphosphine) palladiumI(II) dichloride (1.6 mg, 2.3 µmol) and 1,4-dioxane (0.15 ml) were added. The mixture was degassed by bubbling N$_2$ over 2 minutes and reheated to 105° C. for 5 hours. Most of the solvent was removed under vacuo. The obtained residue was dissolved in ethyl acetate (20 ml), washed with brine (10 ml) and dried (Na$_2$SO$_4$). Concentration under vacuo delivered a residue which was purified by flash chromatography on silica gel (elution gradient from heptane to ethyl acetate) to deliver 7-chloro-5-(2-ethoxypyridin-3-yl)-1-isopropyl-3-vinyl-1H-pyrazolo[4,3-b]pyridine.

Preparation of 1-(7-chloro-5-(2-ethoxypyridin-3-yl)-1-isopropyl-1H-pyrazolo[4,3-b]pyridin-3-yl)ethane-1,2-diol

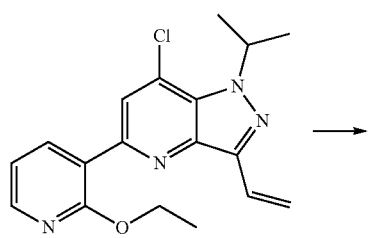

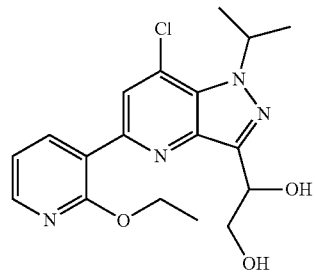

A mixture of 7-chloro-5-(2-ethoxypyridin-3-yl)-1-isopropyl-3-vinyl-1H-pyrazolo[4,3-b]pyridine (10 mg, 0.03 mmol), osmium tetraoxide (as a 2.5 wt % in 2-methyl-2-propanol) (37 µl, 2.9 µmol), N-methylmorpholine (as a 50% aqueous solution) (14 mg, 0.06 mmol) in THF (0.29 ml) and water (0.10 ml) was stirred at room temperature for 24 hours. The reaction was quenched at room temperature with aqueous 10% Na$_2$S$_2$O$_3$ (0.2 ml) and the resulting mixture was stirred for 5 minutes, diluted with brine (0.3 ml) and extracted with ethyl acetate (2×5 ml). The combined organic layers were dried (Na$_2$SO$_4$) and concentrated to deliver crude 1-(7-chloro-5-(2-ethoxypyridin-3-yl)-1-isopropyl-1H-pyrazolo[4,3-b]pyridin-3-yl)ethane-1,2-diol which was used without further purification.

Preparation of 7-chloro-5-(2-ethoxypyridin-3-yl)-1-isopropyl-1H-pyrazolo[4,3-b]pyridine-3-carbaldehyde

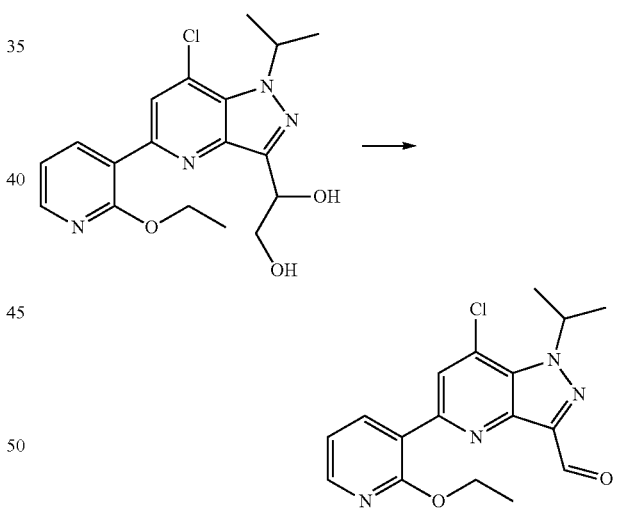

A mixture of 1-(7-chloro-5-(2-ethoxypyridin-3-yl)-1-isopropyl-1H-pyrazolo[4,3-b]pyridin-3-yl)ethane-1,2-diol (9.0 mg, 0.024 mmol) and sodium periodate (7.7 mg, 0.04 mmol) in THF (0.25 ml) and water (55 µl) was stirred at room temperature for 40 minutes after which sodium periodate (10.0 mg, 0.05 mmol) and 3 drops of water were added. After stirring for further 15 minutes, the resulting suspension was diluted with ethyl acetate (5 ml) and stirred for 3 minutes. The mixture was filtered through a short pad of Celite which was rinsed with ethyl acetate (2×5 ml). The combined filtrates were washed with brine (5 ml), dried (Na$_2$SO$_4$) and concentrated to deliver 7-chloro-5-(2-ethoxypyridin-3-yl)-1-isopropyl-1H-pyrazolo[4,3-b]pyridine-3-carbaldehyde which was used without further purification.

Preparation of (7-chloro-5-(2-ethoxypyridin-3-yl)-1-isopropyl-1H-pyrazolo[4,3-b]pyridin-3-yl)methanol

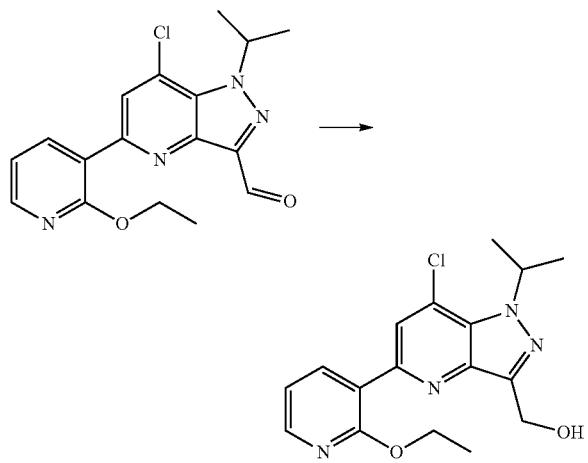

NaBH₄ (2.0 mg, 0.05 mmol) was added to an ice cold solution of 7-chloro-5-(2-ethoxypyridin-3-yl)-1-isopropyl-1H-pyrazolo[4,3-b]pyridine-3-carbaldehyde (4.0 mg, 0.01 mmol) in methanol (0.1 ml) under an inert atmosphere. After stirring for 5 minutes at ice bath temperature the resulting solution was allowed to reach room temperature and stirring continued for 1 hour Recooled to ice bath temperature and quenched with a few drops of water. Most of the solvent was removed under vacuo. The obtained residue was partitioned between ethyl acetate (15 ml) and brine (10 ml). The aqueous layer was back-extracted with ethyl acetate (5 ml). The combined organic layers were dried (Na₂SO₄) and concentrated. The residue was purified by flash chromatography on silica gel (heptane/ethyl acetate) to give (7-chloro-5-(2-ethoxypyridin-3-yl)-1-isopropyl-1H-pyrazolo[4,3-b]pyridin-3-yl)methanol.

Preparation of 7-chloro-5-(2-ethoxypyridin-3-yl)-3-(fluoromethyl)-1-isopropyl-1H-pyrazolo[4,3-b]pyridine

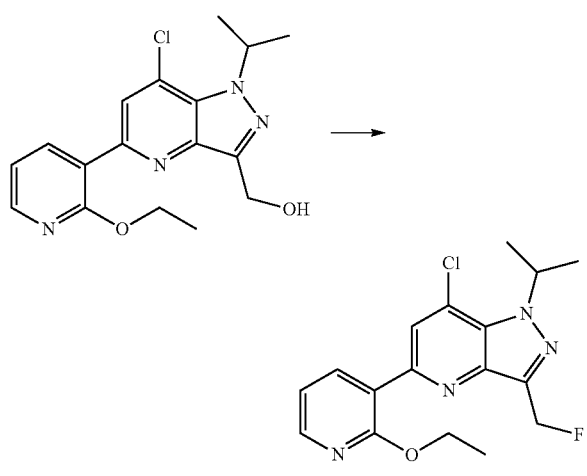

Diethylaminosulfur trifluoride (5 µl, 0.04 mmol) was added to an ice cold solution of (7-chloro-5-(2-ethoxypyridin-3-yl)-1-isopropyl-1H-pyrazolo[4,3-b]pyridin-3-yl)methanol (4.0 mg, 0.01 mmol) in CHCl₃ (0.2 ml). The reaction vial was capped and the solution was stirred at 0° C. for 5 minutes after which the cooling bath was removed and stirring continued at room temperature for 12 hours. The solution was diluted with ethyl acetate (25 ml) and washed with aqueous saturated NaHCO₃ (2×15 ml), brine (10 ml), dried (Na₂SO₄) and concentrated. The residue was purified by flash chromatography on silica gel (heptane/ethyl acetate) to give 7-chloro-5-(2-ethoxypyridin-3-yl)-3-(fluoromethyl)-1-isopropyl-1H-pyrazolo[4,3-b]pyridine.

Preparation of 7-chloro-3-(difluoromethyl)-5-(2-ethoxypyridin-3-yl)-1-isopropyl-1H-pyrazolo[4,3-b]pyridine

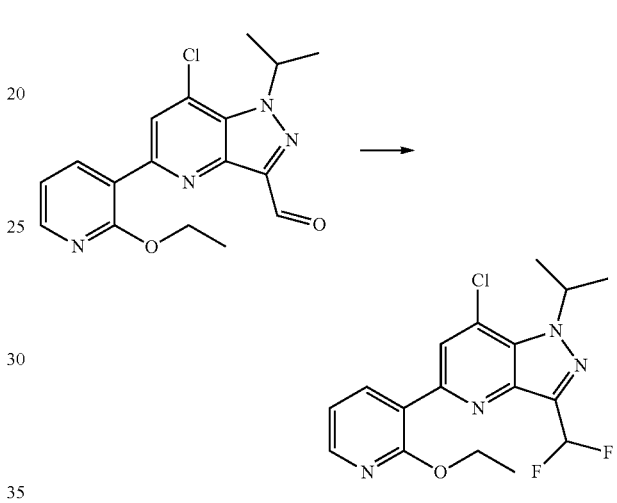

A solution of 7-chloro-5-(2-ethoxypyridin-3-yl)-1-isopropyl-1H-pyrazolo[4,3-b]pyridine-3-carbaldehyde (5.0 mg, 0.01 mmol) and diethylaminosulfur trifluoride (10 µl, 0.08 mmol) in dichloromethane (0.15 ml) was stirred at room temperature for 4.5 hours. under an inert atmosphere. The mixture was diluted with ethyl acetate (20 ml) and washed with aqueous saturated NaHCO₃ (10 ml) and brine (10 ml). The organic layer was dried (Na₂SO₄) and concentrated. The residue was purified by flash chromatography on silica gel (heptane/ethyl acetate) to give 7-chloro-3-(difluoromethyl)-5-(2-ethoxypyridin-3-yl)-1-isopropyl-1H-pyrazolo[4,3-b]pyridine.

Compounds of the Invention

Example 1: 5-(2-ethoxypyridin-3-yl)-1-isopropyl-3-methyl-N-((5-methyl-1,3,4-oxadiazol-2-yl)methyl)-1H-pyrazolo[4,3-b]pyridin-7-amine

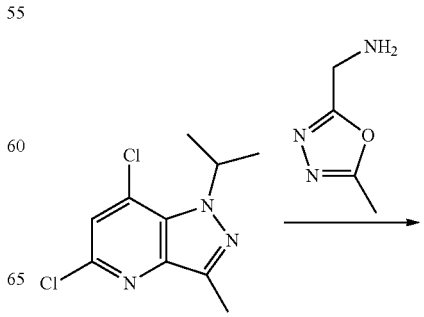

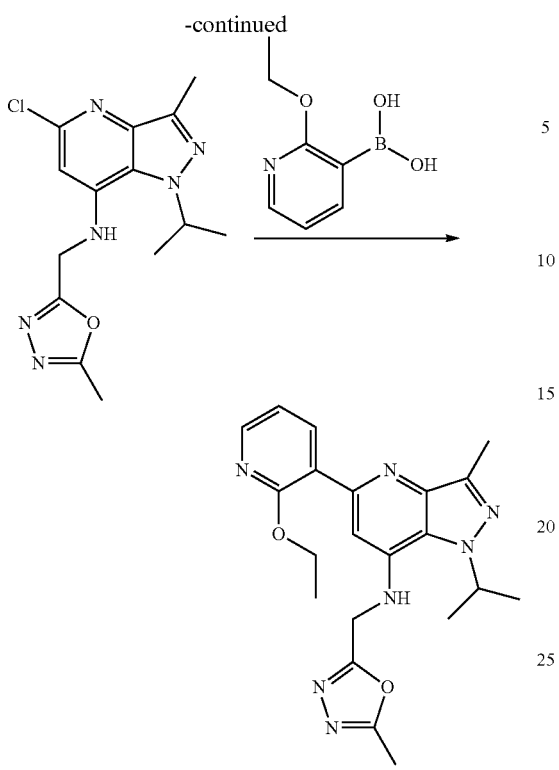

To a solution of 5,7-dichloro-1-isopropyl-3-methyl-1H-pyrazolo[4,3-b]pyridine (100 mg, 0.41 mmol) in NMP (2 mL) was added CsF (187 mg, 1.23 mmol, 45 μL) and (5-methyl-1,3,4-oxadiazol-2-yl)methanamine hydrochloride (74 mg, 0.49 mmol). The mixture was stirred at 100° C. for 18 hours. Water (30 mL) was added and the mixture was extracted with ethyl acetate (30 mL×3). The combined organic layers were washed with brine (20 mL), dried over $Na_2SO_4$ and concentrated. The crude mixture was purified by preparative HPLC to give 5-chloro-1-isopropyl-3-methyl-N-((5-methyl-1,3,4-oxadiazol-2-yl)methyl)-1H-pyrazolo[4,3-b]pyridin-7-amine (50 mg).

To a solution of 5-chloro-1-isopropyl-3-methyl-N-((5-methyl-1,3,4-oxadiazol-2-yl)methyl)-1H-pyrazolo[4,3-b]pyridin-7-amine (50 mg, 70 μmol) and (2-ethoxypyridin-3-yl)boronic acid (21 mg, 0.13 mmol) in dioxane (2 mL) and $H_2O$ (0.7 mL) was added $Cs_2CO_3$ (57 mg, 175 μmol) and Pd(1,1'-bis(diphenylphosphino)ferrocene)$Cl_2$ (10 mg, 14 μmol). The mixture was purged with nitrogen for 3 minutes then stirred at 100° C. for 30 minutes under microwave irradiation. Water (30 mL) was added and the mixture was extracted with ethyl acetate (30 mL×3). The combined organic layers were washed with brine (20 mL), dried over $Na_2SO_4$ and concentrated. The crude mixture was purified by preparative TLC with dichloromethane:methanol=20:1 twice, and then the crude product was further purified by preparative HPLC to give 5-(2-ethoxypyridin-3-yl)-1-isopropyl-3-methyl-N-((5-methyl-1,3,4-oxadiazol-2-yl)methyl)-1H-pyrazolo[4,3-b]pyridin-7-amine (6.1 mg).

$^1$H NMR (chloroform-d, 400 MHz) δ 8.28-8.26 (m, 1H), 8.19-8.18 (m, 1H), 7.23 (s, 1H), 7.05-7.02 (m, 1H), 5.27 (brs, 1H), 4.96-4.90 (m, 1H), 4.71 (d, J=1.2 Hz, 2H), 4.53-4.48 (m, 2H), 2.65 (s, 3H), 2.57 (s, 3H), 1.66 (d, J=6.4 Hz, 6H), 1.43 (t, J=6.8 Hz, 3H). LC-MS (m/z) 408.2 (MH$^+$); $t_R$=2.08 minutes (Method B).

The following examples were prepared in a similar manner:

Example 2: 5-(2-ethoxy-3-pyridyl)-1-isopropyl-3-methyl-N-[(5-methylthiazol-2-yl)methyl]pyrazolo[4,3-b]pyridin-7-amine

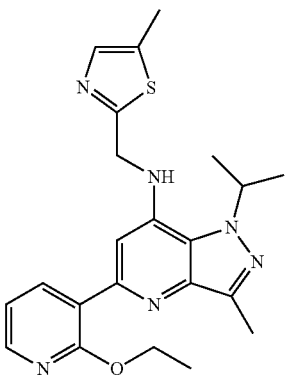 [SMILES: CCOc1ncccc1-c1cc(NCc2ncc(C)s2)c2c(n1)c(C)nn2C(C)C]

Prepared from (5-methylthiazol-2-yl)methanamine dihydrochloride and 5,7-dichloro-1-isopropyl-3-methyl-1H-pyrazolo[4,3-b]pyridine.

$^1$H NMR (DMSO-d$_6$, 500 MHz) δ 8.21-8.14 (m, 2H), 7.42 (d, J=1.4 Hz, 1H), 7.21 (t, J=5.6 Hz, 1H), 7.11-7.05 (m, 2H), 5.23 (hept, J=6.4 Hz, 1H), 4.75 (d, J=5.5 Hz, 2H), 4.31 (q, J=7.0 Hz, 2H), 2.48 (s, 3H), 2.35 (s, 3H), 1.50 (d, J=6.4 Hz, 6H), 1.24 (t, J=7.1 Hz, 3H). LC-MS (m/z) 423 (MH$^+$); $t_R$=0.61 minutes (Method D).

Example 3: 5-(2-ethoxy-3-pyridyl)-1-isopropyl-3-methyl-N-[(5-methylisoxazol-3-yl)methyl]pyrazolo[4,3-b]pyridin-7-amine

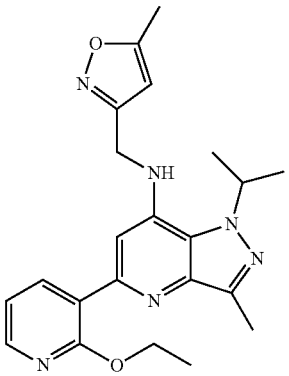 [SMILES: CCOc1ncccc1-c1cc(NCc2cc(C)on2)c2c(n1)c(C)nn2C(C)C]

Prepared from (5-methylisoxazol-3-yl)methanamine and 5,7-dichloro-1-isopropyl-3-methyl-1H-pyrazolo[4,3-b]pyridine.

$^1$H NMR (Chloroform-d, 500 MHz) δ 8.28 (d, J=7.3 Hz, 1H), 8.29-8.17 (m, 1H), 7.29 (s, 1H), 7.04 (m, 1H), 6.07 (s, 1H), 5.19 (brs, 1H), 4.90 (hept, J=6.4 Hz, 1H), 4.59 (d, J=5.2 Hz, 2H), 4.50 (q, J=7.0 Hz, 2H), 2.67 (s, 3H), 2.47 (s, 3H), 1.66 (d, J=6.1, 6H), 1.43 (q, J=7.1 Hz, 3H). LC-MS (m/z) 407.3 (MH$^+$); $t_R$=0.54 minutes (Method E).

Example 4: 5-(2-ethoxy-3-pyridyl)-1-isopropyl-3-methyl-N-[(2-methyloxazol-5-yl)methyl]pyrazolo[4,3-b]pyridin-7-amine

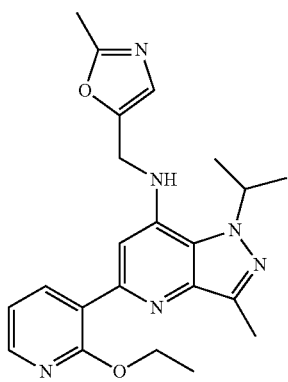 [SMILES: CCOc1ncccc1-c1cc(NCc2cnc(C)o2)c2c(n1)c(C)nn2C(C)C]

Prepared from (2-methyloxazol-5-yl)methanamine and 5,7-dichloro-1-isopropyl-3-methyl-1H-pyrazolo[4,3-b]pyridine.

$^1$H NMR (DMSO-$d_6$, 600 MHz) δ 8.21-8.15 (m, 2H), 7.14 (s, 1H), 7.09 (dd, J=7.3, 4.8 Hz, 1H), 6.90 (s, 1H), 6.82 (t, J=5.7 Hz, 1H), 5.16 (hept, J=6.4 Hz, 1H), 4.55 (d, J=5.5 Hz, 2H), 4.39 (q, J=7.0 Hz, 2H), 2.47 (s, 3H), 2.37 (s, 3H), 1.45 (d, J=6.4 Hz, 6H), 1.26 (t, J=7.0 Hz, 3H). LC-MS (m/z) 407.1 (MH$^+$); $t_R$=0.53 minutes (Method D).

Example 5: 5-(2-ethoxy-3-pyridyl)-1-isopropyl-3-methyl-N-[(2-methyltriazol-4-yl)methyl]pyrazolo[4,3-b]pyridin-7-amine

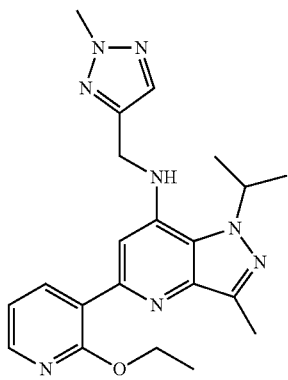 [SMILES: CCOc1ncccc1-c1cc(NCc2cnn(C)n2)c2c(n1)c(C)nn2C(C)C]

Prepared from (2-methyl-2H-1,2,3-triazol-4-yl)methanamine and 5,7-dichloro-1-isopropyl-3-methyl-1H-pyrazolo[4,3-b]pyridine.

$^1$H NMR (DMSO-$d_6$, 600 MHz) δ 8.21-8.15 (m, 2H), 7.64 (s, 1H), 7.10-7.08 (m, 2H), 6.88 (t, J=5.6 Hz, 1H), 5.19 (hept, J=6.3 Hz, 1H), 4.59 (d, J=5.1 Hz, 2H), 4.34 (q, J=7.0 Hz, 2H), 4.11 (s, 3H), 2.48 (s, 3H), 1.48 (d, J=5.7 Hz, 6H), 1.28-1.20 (t, J=7.0 Hz, 3H). LC-MS (m/z) 407.1 (MH$^+$); $t_R$=0.55 minutes (Method D).

Example 6: 5-(2-ethoxy-3-pyridyl)-1-isopropyl-3-methyl-N-[(1-methyltriazol-4-yl)methyl]pyrazolo[4,3-b]pyridin-7-amine

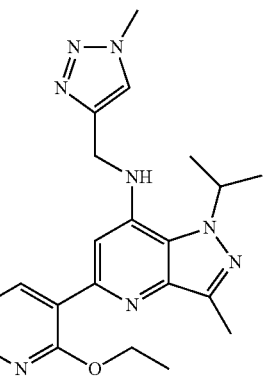

Prepared from (1-methyl-1H-1,2,3-triazol-4-yl)methanamine and 5,7-dichloro-1-isopropyl-3-methyl-1H-pyrazolo[4,3-b]pyridine.

$^1$H NMR (DMSO-$d_6$, 600 MHz) δ 8.21-8.14 (m, 2H), 7.90 (s, 1H), 7.13 (s, 1H), 7.08 (dd, J=7.3, 4.9 Hz, 1H), 6.88 (t, J=5.7 Hz, 1H), 5.18 (hept, J=6.4 Hz, 1H), 4.59 (d, J=5.6 Hz, 2H), 4.34 (q, J=7.0 Hz, 2H), 3.98 (s, 3H), 2.47 (s, 3H), 1.47 (d, J=6.3 Hz, 6H), 1.25 (t, J=7.0 Hz, 3H). LC-MS (m/z) 407.3 (MH$^+$); $t_R$=0.45 minutes (Method E).

Example 7: 5-(2-ethoxy-3-pyridyl)-1-isopropyl-3-methyl-N-(1H-pyrazol-4-ylmethyl)pyrazolo[4,3-b]pyridin-7-amine

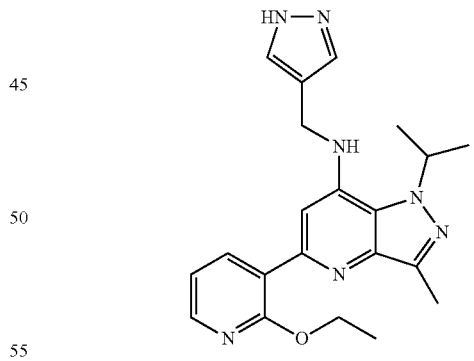

Prepared from (1H-pyrazol-4-yl)methanamine hydrochloride and 5,7-dichloro-1-isopropyl-3-methyl-1H-pyrazolo[4,3-b]pyridine.

$^1$H NMR (Chloroform-d, 600 MHz) δ 8.27 (dd, J=7.3, 2.0 Hz, 1H), 8.18 (dd, J=4.8, 1.9 Hz, 1H), 7.69 (s, 2H), 7.25 (s, 1H), 7.03 (dd, J=7.3, 4.9 Hz, 1H), 4.76 (hept, J=6.4 Hz, 1H), 4.55 (brds, 1H), 4.46 (m, 4H), 2.63 (s, 3H), 1.59 (d, J=6.5 Hz, 6H), 1.39 (t, J=7.0 Hz, 3H). LC-MS (m/z) 392.1 (MH$^+$); $t_R$=0.50 minutes (Method D).

Example 8: 5-(2-ethoxy-3-pyridyl)-1-isopropyl-3-methyl-N-[(2-methyltetrazol-5-yl)methyl]pyrazolo[4,3-b]pyridin-7-amine

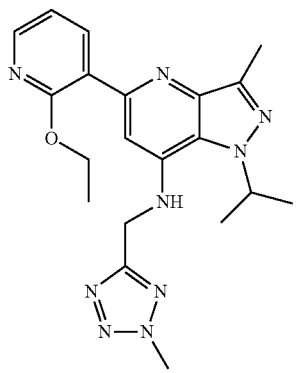 [SMILES: CCOc1ncccc1-c1cc(NCc2nnn(C)n2)c2c(n1)c(C)nn2C(C)C]

Prepared from (2-methyl-2H-tetrazol-5-yl)methanamine and 5,7-dibromo-1-isopropyl-3-methyl-1H-pyrazolo[4,3-b]pyridine.

$^1$H NMR (Chloroform-d, 400 MHz) δ 8.27 (dd, J=7.2, 2.0 Hz, 1H), 8.18 (dd, J=5.2, 2.0 Hz, 1H), 7.26 (s, 1H), 7.04-7.01 (m, 1H), 5.33-5.31 (m, 1H), 4.96-4.93 (m, 1H), 4.80 (d, J=5.2 Hz, 2H), 4.50 (q, J=6.8 Hz, 2H), 4.39 (s, 3H), 2.65 (s, 3H), 1.67 (d, J=6.4 Hz, 6H), 1.44 (t, J=6.8 Hz, 3H). LC-MS (m/z) 408.1 (MH$^+$); $t_R$=1.96 minutes (Method C).

Example 9: 5-(2-ethoxypyridin-3-yl)-1-isopropyl-3-methyl-N-((1-methyl-1H-pyrazol-4-yl)methyl)-1H-pyrazolo[4,3-b]pyridin-7-amine

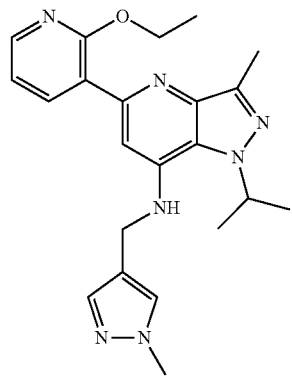 [SMILES: CCOc1ncccc1-c1cc(NCc2cnn(C)c2)c2c(n1)c(C)nn2C(C)C]

Prepared from (1-methyl-1H-pyrazol-4-yl)methanamine and 5,7-dibromo-1-isopropyl-3-methyl-1H-pyrazolo[4,3-b]pyridine.

$^1$H NMR (DMSO-d6, 400 MHz): δ 8.18-8.16 (m, 2H), 7.60 (s, 1H), 7.41 (s, 1H), 7.10-7.06 (m, 2H), 6.68-6.65 (m, 1H), 5.19-5.12 (m, 1H), 4.39-4.34 (m, 4H), 3.77 (s, 3H), 2.46 (s, 3H), 1.15 (d, J=6.4 Hz, 6H), 1.25 (t, J=7.2 Hz, 3H). LC-MS (m/z) 406.1 (MH$^+$); $t_R$=2.50 minutes (Method B).

Example 10: 5-(2-ethoxy-3-pyridyl)-1-isopropyl-3-methyl-N-[(3-methylisoxazol-5-yl)methyl]pyrazolo[4,3-b]pyridin-7-amine

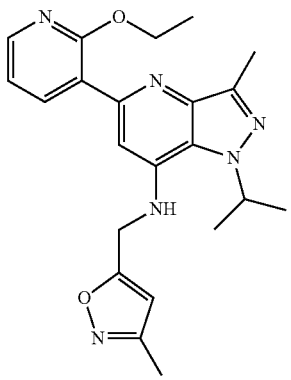 [SMILES: CCOc1ncccc1-c1cc(NCc2cc(C)no2)c2c(n1)c(C)nn2C(C)C]

Prepared from (3-methylisoxazol-5-yl)methanamine and 5,7-dichloro-1-isopropyl-3-methyl-1H-pyrazolo[4,3-b]pyridine.

$^1$H NMR (Chloroform-d, 400 MHz) δ 8.28-8.26 (m, 1H), 8.15-8.18 (m, 1H), 7.20 (s, 1H), 7.04-7.00 (m, 1H), 6.10 (s, 1H), 4.87 (brs, 2H), 4.66-4.65 (m, 2H), 4.45 (q, J=7.2 Hz, 2H), 2.64 (s, 3H), 2.29 (s, 3H), 1.63 (d, J=6.8 Hz, 6H), 1.36 (t, J=7.2 Hz, 3H). LC-MS (m/z) 407.1 (MH$^+$); $t_R$=2.05 minutes (Method C).

Example 11: 5-(2-ethoxy-3-pyridyl)-1-isopropyl-3-methyl-N-[(2-methylthiazol-4-yl)methyl]pyrazolo[4,3-b]pyridin-7-amine

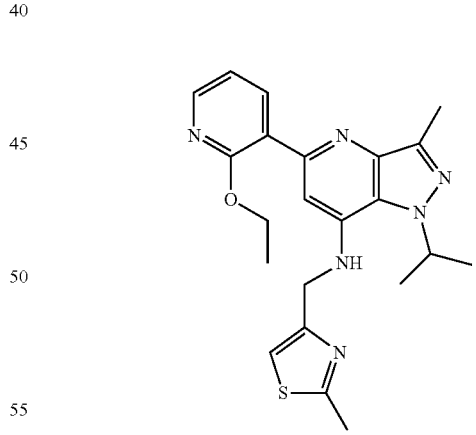

Prepared from (2-methylthiazol-4-yl)methanamine and 5,7-dibromo-1-isopropyl-3-methyl-1H-pyrazolo[4,3-b]pyridine.

$^1$H NMR (Chloroform-d, 400 MHz) δ 8.26 (dd, JJJ=7.6, 2.0 Hz, 1H), 8.17 (dd, J=4.8, 2.0 Hz, 1H), 7.18 (s, 1H), 7.05-7.01 (m, 2H), 5.40-5.27 (m, 1H), 4.96-4.90 (m, 1H), 4.59 (d, J=5.2 Hz, 2H), 4.46 (q, J=7.2 Hz, 2H), 2.75 (s, 3H), 2.65 (s, 3H), 1.65 (d, J=6.4 Hz, 6H), 1.38 (t, J=7.2 Hz, 3H). LC-MS (m/z) 423 (MH$^+$); $t_R$=1.90 minutes (Method A).

Example 12: 1-cyclopropyl-5-(2-ethoxy-3-pyridyl)-3-methyl-N-[(1-methylpyrazol-4-yl)methyl]pyrazolo[4,3-b]pyridin-7-amine

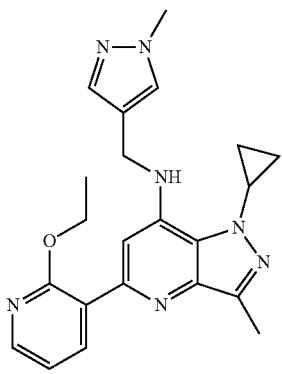 [SMILES: CCOc1ncccc1-c1cc(NCc2cnn(C)c2)c2c(n1)c(C)nn2C1CC1]

Prepared from (1-methyl-1H-pyrazol-4-yl)methanamine and 5,7-dibromo-1-cyclopropyl-3-methyl-1H-pyrazolo[4,3-b]pyridine.

$^1$H NMR (Chloroform-d, 400 MHz): δ 8.26-8.23 (m, 1H), 8.19-8.17 (m, 1H), 7.57 (s, 1H), 7.44 (s, 1H), 7.16 (s, 1H), 7.04-7.01 (m, 1H), 5.64 (brs, 1H), 4.50-4.45 (m, 2H), 4.39 (d, J=4.4 Hz, 2H), 3.93 (s, 3H), 3.72-3.70 (m, 1H), 2.61 (s, 3H), 1.46-1.38 (m, 5H), 1.16-1.11 (m, 2H). LC-MS (m/z) 404.1 (MH$^+$); t$_R$=1.88 minutes (Method C).

Example 13: 5-(2-ethoxy-3-pyridyl)-N-[(1-methyl-pyrazol-4-yl)methyl]-1-propyl-pyrazolo[4,3-b]pyridin-7-amine

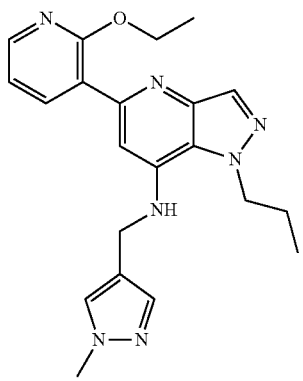 [SMILES: CCCn1ncc2nc(-c3cccnc3OCC)cc(NCc3cnn(C)c3)c21]

Prepared from (1-methyl-1H-pyrazol-4-yl)methanamine dihydrochloride and 5,7-dibromo-1-propyl-1H-pyrazolo[4,3-b]pyridine.

$^1$H NMR (Chloroform-d, 400 MHz) δ 8.16-8.11 (m, 2H), 8.04 (s, 1H), 7.49 (s, 1H), 7.37 (s, 1H), 7.17 (s, 1H), 6.97-6.94 (m, 1H), 4.42-4.32 (m, 7H), 3.86 (s, 3H), 1.85 (q, J=7.2 Hz, 2H), 1.33 (t, J=7.2 Hz, 3H), 0.86 (t, J=7.2 Hz, 3H). LC-MS (m/z) 392.2 (MH$^+$); t$_R$=1.87 minutes (Method C).

Example 14: 5-(2-ethoxypyridin-3-yl)-N-((1-methyl-1H-pyrazol-4-yl)methyl)-1-(oxetan-3-yl)-1H-pyrazolo[4,3-b]pyridin-7-amine

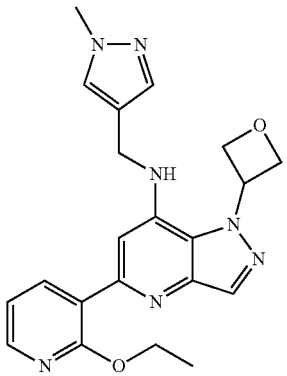 [SMILES: CCOc1ncccc1-c1cc(NCc2cnn(C)c2)c2c(cnn2C2COC2)n1]

Prepared from (1-methyl-1H-pyrazol-4-yl)methanamine and 7-bromo-5-chloro-1-(oxetan-3-yl)-1H-pyrazolo[4,3-b]pyridine.

$^1$H NMR (Methanol-d$_4$, 600 MHz) δ 8.18-8.14 (m, 2H), 7.95 (dd, J=7.3, 2.0 Hz, 1H), 7.62 (s, 1H), 7.51 (s, 1H), 7.08-7.04 (m, 2H), 6.24-6.17 (m, 1H), 5.24-5.18 (m, 2H), 5.15-5.08 (m, 2H), 4.45 (s, 2H), 4.38 (q, J=7.0 Hz, 2H), 3.85 (s, 3H), 1.26 (t, J=7.0 Hz, 3H). LC-MS (m/z) 406.2 (MH$^+$); t$_R$=0.41 minutes (Method D).

Example 15: 5-(2-ethoxypyridin-3-yl)-1-methyl-N-(1-(1-methyl-1H-pyrazol-4-yl)ethyl)-1H-pyrazolo[4,3-b]pyridin-7-amine (Racemic)

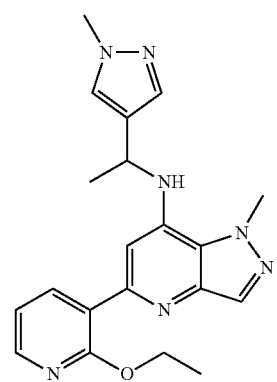 [SMILES: CCOc1ncccc1-c1cc(NC(C)c2cnn(C)c2)c2c(cnn2C)n1]

Prepared from 1-(1-methyl-1H-pyrazol-4-yl)ethan-1-amine and 7-bromo-5-chloro-1-methyl-1H-pyrazolo[4,3-b]pyridine.

$^1$H NMR (Chloroform-d, 500 MHz) δ 8.24-8.17 (m, 2H), 8.09 (s, 1H), 7.54 (s, 1H), 7.39 (s, 1H), 7.17 (s, 1H), 7.03 (dd, J=7.3, 5.1 Hz, 1H), 4.84 (m, 1H), 4.73 (d, J=5.9 Hz, 1H), 4.54-4.37 (m, 2H), 4.35 (s, 3H), 3.91 (s, 3H), 1.72 (d, J=7.0 Hz 3H), 1.36 (t, J=6.5 Hz, 3H). LC-MS (m/z) 378.2 (MH$^+$); t$_R$=0.44 minutes (Method D).

Example 16: 5-(2-ethoxypyridin-3-yl)-1-methyl-N-((1-methyl-1H-pyrazol-4-yl)methyl)-1H-pyrazolo[4,3-b]pyridin-7-amine

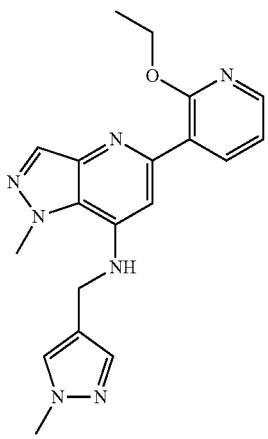 [SMILES: CCOc1ncccc1-c1cc(NCc2cnn(C)c2)c2c(cnn2C)n1]

Prepared from (1-methyl-1H-pyrazol-4-yl)methanamine and 5,7-dibromo-1-methyl-1H-pyrazolo[4,3-b]pyridine $^1$H NMR (Methanol-d$_4$, 400 MHz) δ8.15-8.14 (m, 1H), 7.93-7.92 (m, 2H), 7.60 (s, 1H), 7.50 (s, 1H), 7.038 (dd, J=4.8 Hz, J=6.8 Hz, 1H), 6.94 (s, 1H), 4.46 (s, 2H), 4.40-4.34 (m, 6H), 3.83 (s, 3H), 1.25 (t, J=6.8 Hz, 3H). LC-MS (m/z) 364.1 (MH$^+$); t$_R$=1.71 minutes (Method C).

Example 17: 5-(2-ethoxy-3-pyridyl)-1-isopropyl-N-[(1-methylimidazol-2-yl)methyl]pyrazolo[4,3-b]pyridin-7-amine

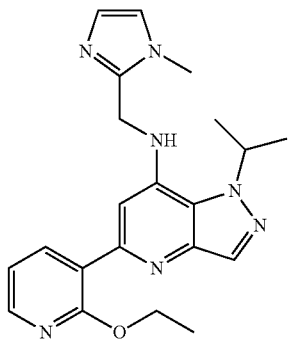 [SMILES: CCOc1ncccc1-c1cc(NCc2nccn2C)c2c(cnn2C(C)C)n1]

Prepared from (1-methyl-1H-imidazol-2-yl)methanamine and 5,7-dibromo-1-isopropyl-1H-pyrazolo[4,3-b]pyridine.

$^1$H NMR (DMSO-d$_6$, 600 MHz) δ 8.19 (dd, J=4.9, 2.0 Hz, 1H), 8.09-8.12 (m, 2H), 7.35 (s, 1H), 7.13-7.05 (m, 2H), 6.83-6.76 (m, 2H), 5.25 (hept, J=6.5 Hz, 1H), 4.56 (d, J=4.9 Hz, 2H), 4.42 (q, J=7.0 Hz, 2H), 3.71 (s, 3H), 1.51 (d, J=6.4 Hz, 6H), 1.38 (t, J=7.0 Hz, 3H). LC-MS (m/z) 392.1 (MH$^+$); t$_R$=0.35 minutes (Method D).

Example 18: 5-(2-ethoxypyridin-3-yl)-1-isopropyl-N-((1-methyl-1H-pyrazol-5-yl)methyl)-1H-pyrazolo[4,3-b]pyridin-7-amine Prepared from (1-methyl-1H-pyrazol-5-yl)methanamine dihydrochloride and 5,7-dibromo-1-isopropyl-1H-pyrazolo[4,3-b]pyridine.

$^1$H NMR (DMSO-d$_6$, 600 MHz) δ 8.20-8.12 (m, 3H), 7.33 (d, J=1.8 Hz, 1H), 7.14 (s, 1H), 7.08 (dd, J=7.4, 4.8 Hz, 1H), 6.89 (t, J=5.4 Hz, 1H), 6.19 (d, J=1.8 Hz, 1H), 5.29 (hept, J=6.5 Hz, 1H), 4.59 (d, J=5.3 Hz, 2H), 4.36 (q, J=7.0 Hz, 2H), 3.88 (s, 3H), 1.50 (d, J=6.3 Hz, 6H), 1.24 (t, J=7.0 Hz, 3H). LC-MS (m/z) 392.1 (MH$^+$); t$_R$=0.49 minutes (Method D).

Example 19: 5-(2-ethoxypyridin-3-yl)-1-isopropyl-N-((1-methyl-1H-pyrazol-3-yl)methyl)-1H-pyrazolo[4,3-b]pyridin-7-amine Prepared from (1-methyl-1H-pyrazol-3-yl)methanamine and 5,7-dibromo-1-isopropyl-1H-pyrazolo[4,3-b]pyridine.

$^1$H NMR (DMSO-d$_6$, 600 MHz) δ 8.19-8.13 (m, 2H), 8.09 (s, 1H), 7.59 (d, J=2.2 Hz, 1H), 7.14 (s, 1H), 7.07 (dd, J=7.4, 4.8 Hz, 1H), 6.85 (t, J=5.7 Hz, 1H), 6.17 (d, J=2.1 Hz, 1H), 5.27 (hept, J=6.4 Hz, 1H), 4.46 (d, J=5.6 Hz, 2H), 4.36 (q, J=7.0 Hz, 2H), 3.78 (s, 3H), 1.50 (d, J=6.3 Hz, 6H), 1.29 (t, J=7.0 Hz, 3H). LC-MS (m/z) 392.1 (MH$^+$); t$_R$=0.54 minutes (Method D).

Example 20: 5-(2-ethoxy-3-pyridyl)-1-isopropyl-N-(thiazol-2-ylmethyl)pyrazolo[4,3-b]pyridin-7-amine Example 22: 5-(2-ethoxy-3-pyridyl)-1-isopropyl-N-(4-pyridylmethyl)pyrazolo[4,3-b]pyridin-7-amine

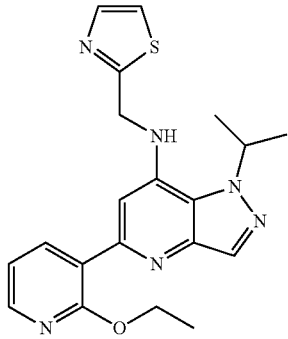 [SMILES: CCOc1ncccc1-c1cc(NCc2nccs2)c2c(cnn2C(C)C)n1]

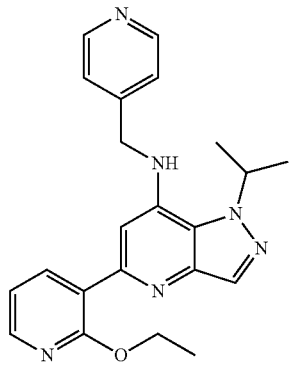

Prepared from thiazol-2-ylmethanamine hydrochloride and 5,7-dibromo-1-isopropyl-1H-pyrazolo[4,3-b]pyridine $^1$H NMR (DMSO-$d_6$, 600 MHz). δ 8.18-8.13 (m, 3H), 7.78 (d, J=3.3 Hz, 1H), 7.62 (d, J=3.3 Hz, 1H), 7.32 (t, J=5.7 Hz, 1H), 7.12 (s, 1H), 7.06 (dd, J=6.9, 5.4 Hz, 1H), 5.32 (hept, J=6.5 Hz, 1H), 4.86 (d, J=5.6 Hz, 2H), 4.29 (q, J=7.0 Hz, 2H), 1.54 (d, J=6.4 Hz, 6H), 1.21 (t, J=7.0 Hz, 3H). LC-MS (m/z) 395 (MH$^+$); $t_R$=0.54 minutes (Method D).

Example 21: 5-(2-ethoxy-3-pyridyl)-1-isopropyl-N-[(1-methylimidazol-4-yl)methyl]pyrazolo[4,3-b]pyridin-7-amine Prepared from pyridin-4-ylmethanamine and 5,7-dibromo-1-isopropyl-1H-pyrazolo[4,3-b]pyridine.

$^1$H NMR (Methanol-$d_4$, 600 MHz) δ 8.52-8.48 (m, 2H), 8.11 (dd, J=5.0, 1.9 Hz, 1H), 8.06 (s, 1H), 7.90 (dd, J=7.4, 2.0 Hz, 1H), 7.51-7.47 (m, 2H), 7.01 (dd, J=7.4, 4.9 Hz, 1H), 6.74 (s, 1H), 5.28 (hept, J=6.5 Hz, 1H), 4.72 (s, 2H), 4.19 (q, J=7.1 Hz, 2H), 1.64 (d, J=6.4 Hz, 6H), 1.07 (t, J=7.0 Hz, 3H). LC-MS (m/z) 389.1 (MH$^+$); $t_R$=0.38 minutes (Method D).

Example 23: 5-(2-ethoxy-3-pyridyl)-1-isopropyl-N-(m-tolylmethyl)pyrazolo[4,3-b]pyridin-7-amine

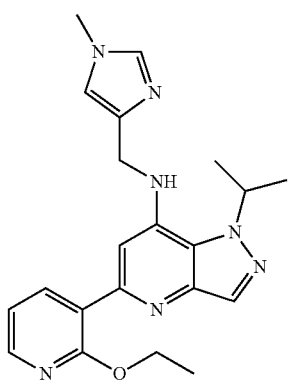 [SMILES: CCOc1ncccc1-c1cc(NCc2cn(C)cn2)c2c(cnn2C(C)C)n1]

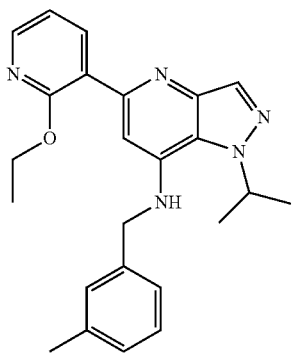 [SMILES: CCOc1ncccc1-c1cc(NCc2cccc(C)c2)c2c(cnn2C(C)C)n1]

Prepared from (1-methyl-1H-imidazol-4-yl)methanamine and 5,7-dibromo-1-isopropyl-1H-pyrazolo[4,3-b]pyridine.

$^1$H NMR (DMSO-$d_6$, 600 MHz) δ 8.19-8.13 (m, 2H), 8.09 (s, 1H), 7.52 (s, 1H), 7.15 (s, 1H), 7.07 (dd, J=7.3, 4.9 Hz, 1H), 6.96 (s, 1H), 6.76 (t, J=5.5 Hz, 1H), 5.25 (hept, J=6.5 Hz, 1H), 4.40 (d, J=5.4 Hz, 2H), 4.35 (q, J=7.0 Hz, 2H), 3.57 (s, 3H), 1.50 (d, J=6.3 Hz, 6H), 1.27 (t, J=7.0 Hz, 3H). LC-MS (m/z) 392.1 (MH$^+$); $t_R$=0.39 minutes (Method D).

Prepared from m-tolylmethanamine hydrochloride and 5,7-dibromo-1-isopropyl-1H-pyrazolo[4,3-b]pyridine.

$^1$H NMR (Chloroform-d, 400 MHz) δ 8.22-8.17 (m, 3H), 7.33-7.19 (m, 5H), 7.03-7.00 (m, 1H), 4.89-4.86 (m, 2H), 4.53 (d, J=5.2 Hz, 2H), 4.42 (q, J=7.2 Hz, 2H), 2.39 (s, 3H), 1.65 (d, J=6.4 Hz, 6H), 1.33 (t, J=7.2 Hz, 3H). LC-MS (m/z) 402.1 (MH$^+$); $t_R$=2.57 minutes (Method F).

Example 24: 5-(2-ethoxy-3-pyridyl)-1-isopropyl-N-(p-tolylmethyl)pyrazolo[4,3-b]pyridin-7-amine

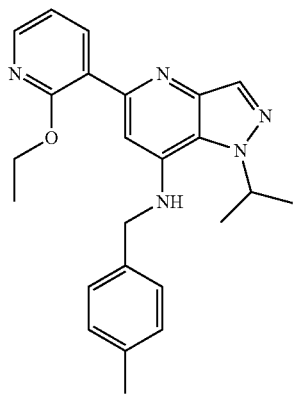 [SMILES: CCOc1ncccc1-c1cc(NCc2ccc(C)cc2)c2c(cnn2C(C)C)n1]

Prepared from p-tolylmethanamine and 5,7-dibromo-1-isopropyl-1H-pyrazolo[4,3-b]pyridine.

$^1$H NMR (Chloroform-d, 400 MHz) δ 8.23-8.17 (m, 3H), 7.34-7.32 (m, 2H), 7.24-7.22 (m, 3H), 7.03-7.00 (m, 1H), 4.89-4.74 (m, 2H), 4.52 (d, J=4.8 Hz, 2H), 4.42 (q, J=6.8 Hz, 2H), 2.39 (s, 3H), 1.65 (d, J=6.8 Hz, 6H), 1.35 (t, J=6.8 Hz, 3H). LC-MS (m/z) 402.1 (MH$^+$); t$_R$=2.17 minutes (Method A).

Example 25: 5-(2-ethoxy-3-pyridyl)-1-isopropyl-N-[(1-methylpyrazol-4-yl)methyl]pyrazolo[4,3-b]pyridin-7-amine

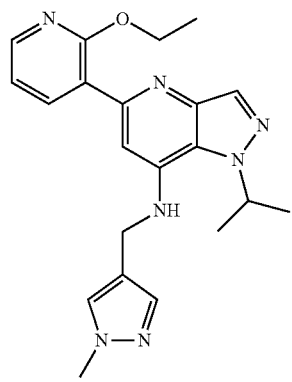 [SMILES: CCOc1ncccc1-c1cc(NCc2cnn(C)c2)c2c(cnn2C(C)C)n1]

Prepared from (1-methyl-1H-pyrazol-4-yl)methanamine dihydrochloride and 5,7-dibromo-1-isopropyl-1H-pyrazolo[4,3-b]pyridine.

$^1$H NMR (Chloroform-d, 400 MHz) δ 8.22-8.16 (m, 3H), 7.57 (s, 1H), 7.44 (s, 1H), 7.24 (s, 1H), 7.03-7.00 (m, 1H), 4.82-4.77 (m, 1H), 4.60 (brs, 1H), 4.46 (q, J=7.2 Hz, 2H), 4.39 (d, J=4.8 Hz, 2H), 3.93 (s, 3H), 1.62 (d, J=6.4 Hz, 6H), 1.39 (t, J=7.2 Hz, 3H). LC-MS (m/z) 392.2 (MH$^+$); t$_R$=1.86 minutes (Method C).

Example 26: 5-(2-ethoxy-3-pyridyl)-1-ethyl-N-[(1-methylpyrazol-4-yl)methyl]pyrazolo[4,3-b]pyridin-7-amine

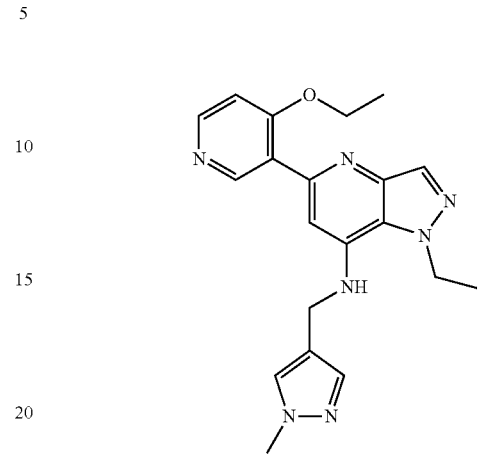

Prepared from (1-methyl-1H-pyrazol-4-yl)methanamine and 5,7-dibromo-1-ethyl-1H-pyrazolo[4,3-b]pyridine.

$^1$H NMR (Chloroform-d, 400 MHz) δ 8.22-8.11 (m, 3H), 7.56 (s, 1H), 7.43 (s, 1H), 7.23 (s, 1H), 7.03-7.00 (m, 1H), 4.56-4.39 (m, 7H), 3.92 (s, 3H), 1.51 (t, J=7.2 Hz, 3H), 1.38 (t, J=7.2 Hz, 3H). LC-MS (m/z) 378.2 (MH$^+$); t$_R$=1.79 minutes (Method G).

Example 27: 5-(2-ethoxy-3-pyridyl)-3-methyl-N-[(1-methylpyrazol-4-yl)methyl]-1-(oxetan-3-yl)pyrazolo[4,3-b]pyridin-7-amine

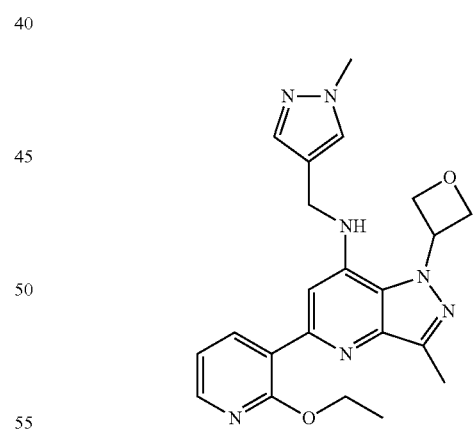

Prepared from (1-methyl-1H-pyrazol-4-yl)methanamine and 5,7-dibromo-3-methyl-1-(oxetan-3-yl)-1H-pyrazolo[4,3-b]pyridine.

$^1$H NMR (Chloroform-d, 400 MHz) δ 8.30-8.28 (m, 1H), 8.20-8.18 (m, 1H), 7.54 (s, 1H), 7.43 (s, 1H), 7.32 (s, 1H), 7.05-7.02 (m, 1H), 5.85-5.75 (m, 1H), 5.55 (brs, 1H), 5.18-5.11 (m, 4H), 4.51-4.45 (m, 2H), 4.41 (d, J=4.8 Hz, 2H), 3.92 (s, 3H), 2.64 (s, 3H), 1.40 (t, J=7.2 Hz, 3H). LC-MS (m/z) 420.1 (MH$^+$); t$_R$=1.99 minutes (Method B).

Example 28: 5-(2-ethoxy-3-pyridyl)-1,3-dimethyl-N-[(1-methylpyrazol-4-yl)methyl]pyrazolo[4,3-b]pyridin-7-amine

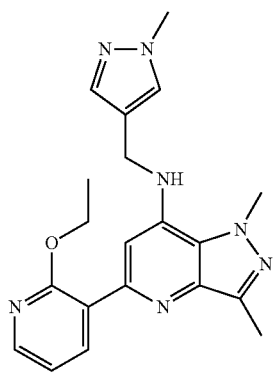 [SMILES: CCOc1ncccc1-c1cc(NCc2cnn(C)c2)c2c(n1)c(C)nn2C]

Prepared from (1-methyl-1H-pyrazol-4-yl)methanamine and 5,7-dichloro-1,3-dimethyl-1H-pyrazolo[4,3-b]pyridine.

$^1$H NMR (Chloroform-d, 400 MHz) δ 8.28-8.26 (m, 1H), 8.19-8.18 (m, 1H), 7.56 (s, 1H), 7.44 (s, 1H), 7.21 (s, 1H), 7.04-7.01 (m, 1H), 4.63 (brs, 1H), 4.47 (q, J=6.8 Hz, 2H), 4.38 (d, J=4.8 Hz, 2H), 4.23 (s, 3H), 3.92 (s, 3H), 2.62 (s, 3H), 1.39 (t, J=7.2 Hz, 3H). LC-MS (m/z) 378.2 (MH$^+$); $t_R$=1.93 minutes (Method B).

Example 29: 5-(2-ethoxypyridin-3-yl)-1-isopropyl-3-methyl-N-((4-methylthiazol-2-yl)methyl)-1H-pyrazolo[4,3-b]pyridin-7-amine

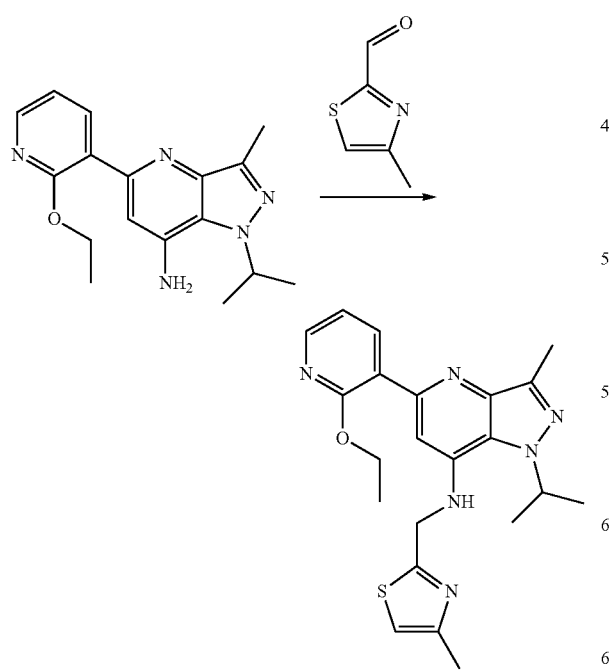

To a solution of 5-(2-ethoxypyridin-3-yl)-1-isopropyl-3-methyl-1H-pyrazolo[4,3-b]pyridin-7-amine (50 mg, 0.16 mmol) in THF (3 mL) was added Ti(i-PrO)$_4$ (91 mg, 0.32 mmol, 95 μL) and 4-methylthiazole-2-carbaldehyde (41 mg, 0.32 mmol, 35 μL). The mixture was stirred at 50° C. for 18 hours. The reaction mixture was cooled to 0° C., then NaBH$_4$ (30 mg, 0.80 mmol) was added into the mixture slowly and the reaction was stirred at 0° C. for 10 min. Water (2 mL) was added to quench the reaction, the resulting mixture was filtered and the residue was washed with ethyl acetate (20 mL×2). The combined filtrates were washed with brine (10 mL), dried over Na$_2$SO$_4$, and concentrated. The residue was purified by column chromatography (SiO$_2$, petroleum ether:ethyl acetate=2:1 to 1:1) followed by purification by preparative HPLC to give 5-(2-ethoxypyridin-3-yl)-1-isopropyl-3-methyl-N-((4-methylthiazol-2-yl)methyl)-1H-pyrazolo[4,3-b]pyridin-7-amine (14 mg).

$^1$H NMR (Chloroform-d, 400 MHz) δ 8.26-8.24 (m, 1H), 8.18-8.17 (m, 1H), 7.19 (s, 1H), 7.03-7.00 (m, 1H), 6.87 (s, 1H), 5.01-4.95 (m, 1H), 4.82 (d, J=4.8 Hz, 2H), 4.47-4.42 (q, J=7.2 Hz, 2H), 2.66 (s, 3H), 2.48 (s, 3H), 1.68 (d, J=6.4 Hz, 6H), 1.37 (t, J=7.2 Hz, 3H). LC-MS (m/z) 423.0 (MH$^+$); $t_R$=1.92 minutes (Method C).

The following examples were prepared in a similar manner:

Example 30: 5-(2-ethoxy-3-pyridyl)-1-isopropyl-3-methyl-N-[(3-methyl-1,2,4-oxadiazol-5-yl)methyl]pyrazolo[4,3-b]pyridin-7-amine

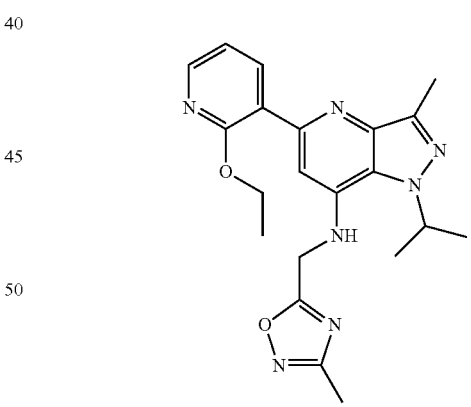

Prepared from 3-methyl-1,2,4-oxadiazole-5-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.27 (dd, J=7.2, 2.0 Hz, 1H), 8.19-8.18 (m, 1H), 7.17 (s, 1H), 7.05-7.02 (m, 1H), 4.95 (brs, 1H), 4.76 (d, J=4.8 Hz, 2H), 4.49 (q, J=6.8 Hz, 2H), 2.65 (s, 3H), 2.44 (s, 3H), 1.67 (d, J=6.4 Hz, 6H), 1.42 (t, J=6.8 Hz, 3H). LC-MS (m/z) 408.2 (MH$^+$); $t_R$=2.31 minutes (Method B).

Example 31: 5-(2-ethoxy-3-pyridyl)-1-isopropyl-3-methyl-N-[(1-methyl-1,2,4-triazol-3-yl)methyl]pyrazolo[4,3-b]pyridin-7-amine

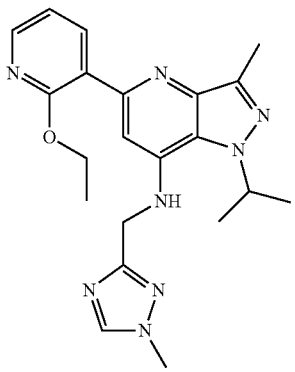 [SMILES: CCOc1ncccc1-c1cc(NCc2ncn(C)n2)c2c(n1)c(C)nn2C(C)C]

Prepared from 1-methyl-1H-1,2,4-triazole-3-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.27 (dd, J=1.6, 7.2 Hz, 1H), 8.18 (dd, J=1.6, 4.8 Hz, 1H), 8.05 (s, 1H), 7.22 (s, 1H), 7.04-7.01 (m, 1H), 5.50 (brs, 1H), 5.01-4.96 (m, 1H), 4.58 (d, J=4.8 Hz, 2H), 4.50 (q, J=7.2 Hz, 2H), 3.95 (s, 3H), 2.66 (s, 3H), 1.66 (d, J=6.0 Hz, 6H), 1.45 (t, J=7.2 Hz, 3H). LC-MS (m/z) 407.1 (MH$^+$); $t_R$=1.87 minutes (Method C).

Example 32: 5-(2-ethoxy-3-pyridyl)-1-isopropyl-3-methyl-N-[(2-methylthiazol-5-yl)methyl]pyrazolo[4,3-b]pyridin-7-amine

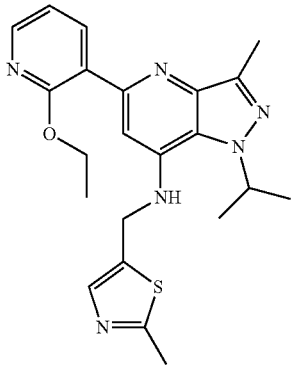 [SMILES: CCOc1ncccc1-c1cc(NCc2cnc(C)s2)c2c(n1)c(C)nn2C(C)C]

Prepared from 2-methylthiazole-5-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.17-8.25 (m, 1H), 8.19-8.18 (m, 1H), 7.62 (s, 1H), 7.26 (s, 1H), 7.05-7.02 (m, 1H), 4.83-4.80 (m, 1H), 4.70 (s, 2H), 4.48 (q, J=7.2 Hz, 2H), 2.71 (s, 3H), 2.65 (s, 3H), 1.62 (d, J=6.4 Hz, 6H), 1.40 (t, J=7.2 Hz, 3H). LC-MS (m/z) 423 (MH$^+$); $t_R$=1.80 minutes (Method A).

Example 33: 5-(2-ethoxy-3-pyridyl)-1-isopropyl-3-methyl-N-[(5-methyl-1,3,4-thiadiazol-2-yl)methyl]pyrazolo[4,3-b]pyridin-7-amine

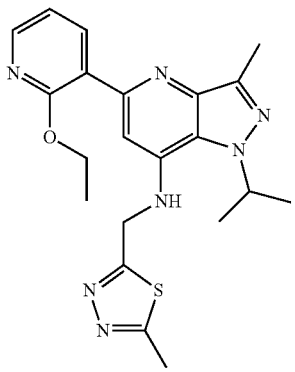 [SMILES: CCOc1ncccc1-c1cc(NCc2nnc(C)s2)c2c(n1)c(C)nn2C(C)C]

Prepared from 5-methyl-1,3,4-thiadiazole-2-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.32-8.29 (m, 1H), 8.22-8.20 (m, 1H), 7.30 (s, 1H), 7.07-7.04 (m, 1H), 5.51 (brs, 1H), 4.97 (d, J=5.2 Hz, 2H), 4.57-4.48 (m, 2H), 2.82 (s, 3H), 2.69 (s, 3H), 1.69 (d, J=6.4 Hz, 6H), 1.42 (t, J=7.2 Hz, 3H). LC-MS (m/z) 424 (MH$^+$); $t_R$=2.14 minutes (Method B).

Example 34: 5-(2-ethoxy-3-pyridyl)-1-isopropyl-3-methyl-N-[(5-methyl-3-thienyl)methyl]pyrazolo[4,3-b]pyridin-7-amine

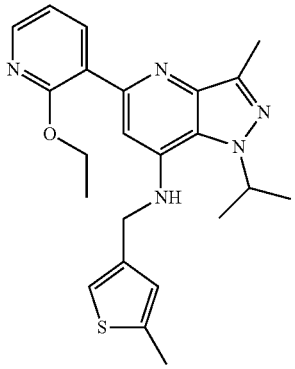 [SMILES: CCOc1ncccc1-c1cc(NCc2csc(C)c2)c2c(n1)c(C)nn2C(C)C]

Prepared from 5-methylthiophene-3-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.28-8.26 (m, 1H), 8.18-8.17 (m, 1H), 7.22 (s, 1H), 7.04-7.01 (m, 2H), 6.80 (s, 1H), 4.84-4.77 (m, 1H), 4.66 (brs, 1H), 4.48-4.43 (m, 4H), 2.65 (s, 3H), 2.51 (s, 3H), 1.62 (d, J=6.8 Hz, 6H), 1.38 (t, J=7.2 Hz, 3H). LC-MS (m/z) 422 (MH$^+$); $t_R$=2.21 minutes (Method H).

Example 35: 5-(2-ethoxy-3-pyridyl)-1-isopropyl-3-methyl-N-[(4-methyl-2-thienyl)methyl]pyrazolo[4,3-b]pyridin-7-amine

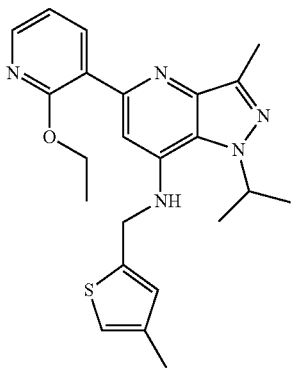 [SMILES: CCOc1ncccc1-c1cc(NCc2cc(C)cs2)c2c(n1)c(C)nn2C(C)C]

Prepared from 4-methylthiophene-2-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.27 (dd, J=7.6, 1.6 Hz, 1H), 8.18 (dd, J=4.8, 2.0 Hz, 1H), 7.26 (s, 1H), 7.04-7.01 (m, 1H), 6.92 (s, 1H), 6.87 (s, 1H), 4.86-4.81 (m, 1H), 4.72 (brs, 1H), 4.66-4.65 (m, 2H), 4.47 (q, J=7.2 Hz, 2H), 2.65 (s, 3H), 2.27 (s, 3H), 1.62 (d, J=6.4 Hz, 6H), 1.39 (t, J=7.2 Hz, 3H). LC-MS (m/z) 422.1 (MH$^+$); $t_R$=1.78 minutes (Method I).

Example 36: 5-(2-ethoxy-3-pyridyl)-1-isopropyl-3-methyl-N-[(5-methyl-2-thienyl)methyl]pyrazolo[4,3-b]pyridin-7-amine

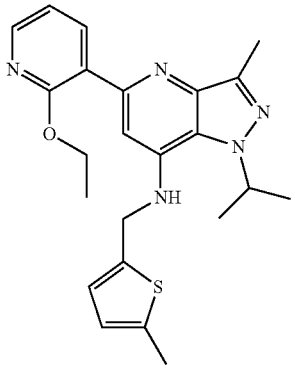 [SMILES: CCOc1ncccc1-c1cc(NCc2ccc(C)s2)c2c(n1)c(C)nn2C(C)C]

Prepared from 5-methylthiophene-2-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.28-8.25 (m, 1H), 8.18-8.17 (m, 1H), 7.25 (s, 1H), 7.04-7.01 (m, 1H), 6.90-6.89 (m, 1H), 6.67-6.66 (s, 1H), 4.86-4.81 (m, 1H), 4.72 (brs, 1H), 4.63-4.62 (m, 2H), 4.48 (q, J=6.8 Hz, 2H), 2.65 (s, 3H), 2.49 (s, 3H), 1.62 (d, J=6.4 Hz, 6H), 1.39 (t, J=7.2 Hz, 3H). LC-MS (m/z) 422 (MH$^+$); $t_R$=1.78 minutes (Method I).

Example 37: 5-(2-ethoxy-3-pyridyl)-1-isopropyl-3-methyl-N-[(2-methyloxazol-4-yl)methyl]pyrazolo[4,3-b]pyridin-7-amine

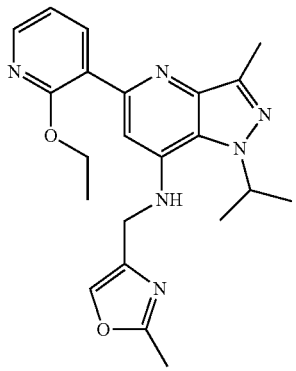

Prepared from 2-methyloxazole-4-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.26-8.24 (m, 1H), 8.17-8.16 (m, 1H), 7.53 (s, 1H), 7.17 (s, 1H), 7.03-7.00 (m, 1H), 5.01 (brs, 1H), 4.88-4.83 (m, 1H), 4.49-4.44 (m, 2H), 4.39 (d, J=5.2 Hz, 2H), 2.64 (s, 3H), 2.48 (s, 3H), 1.62 (d, J=6.8 Hz, 6H), 1.38 (t, J=7.2 Hz, 3H). LC-MS (m/z) 407.1 (MH$^+$); $t_R$=2.03 minutes (Method C).

Example 38: 5-(2-ethoxy-3-pyridyl)-1-isopropyl-3-methyl-N-[(5-methyloxazol-2-yl)methyl]pyrazolo[4,3-b]pyridin-7-amine

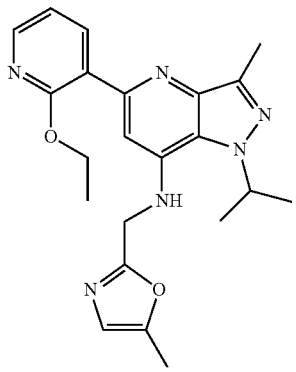 [SMILES: CCOc1ncccc1-c1cc(NCc2ncc(C)o2)c2c(n1)c(C)nn2C(C)C]

Prepared from 5-methyloxazole-2-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.27-8.25 (m, 1H), 8.19-8.17 (m, 1H), 7.17 (s, 1H), 7.04-7.01 (m, 1H), 6.75 (s, 1H), 5.41 (brs, 1H), 4.99-4.95 (m, 1H), 4.55 (d, J=4.8 Hz, 2H), 4.49 (q, J=7.2 Hz, 2H), 2.65 (s, 3H), 2.35 (s, 3H), 1.67 (d, J=6.4 Hz, 6H), 1.44 (t, J=7.2 Hz, 3H). LC-MS (m/z) 407.1 (MH$^+$); $t_R$=2.06 minutes (Method C).

Example 39: 5-(2-ethoxy-3-pyridyl)-1-isopropyl-3-methyl-N-(1H-pyrazol-3-ylmethyl)pyrazolo[4,3-b]pyridin-7-amine

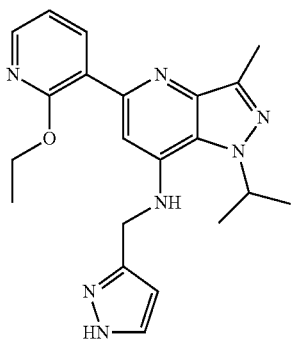

Prepared from 1H-pyrazole-3-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.25-8.23 (m, 1H), 8.18-8.16 (m, 1H), 7.58 (d, J=2.4 Hz, 1H), 7.19 (s, 1H), 7.03-7.00 (m, 1H), 6.35 (d, J=2.4 Hz, 1H), 5.31 (brs, 1H), 4.93-4.87 (m, 1H), 4.57 (d, J=4.8 Hz, 2H), 4.50-4.45 (m, 2H), 2.65 (s, 3H), 1.63 (d, J=6.4 Hz, 6H), 1.41 (t, J=7.2 Hz, 3H). LC-MS (m/z) 392.1 (MH$^+$); $t_R$=1.92 minutes (Method C).

Example 40: 5-(2-ethoxy-3-pyridyl)-N-(1H-imidazol-4-ylmethyl)-1-isopropyl-3-methyl-pyrazolo[4,3-b]pyridin-7-amine

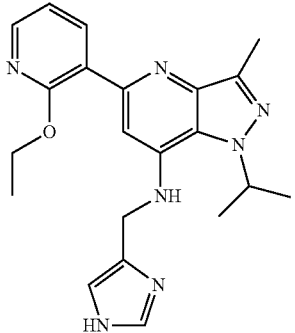 [SMILES: CCOc1ncccc1-c1cc(NCc2c[nH]cn2)c2c(n1)c(C)nn2C(C)C]

Prepared from 1H-imidazole-4-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) δ 8.24-8.22 (m, 1H), 8.17-8.15 (m, 1H), 7.65 (m, 1H), 7.19 (m, 1H), 7.03-7.00 (m, 2H), 5.27 (brs, 1H), 4.92-4.86 (m, 1H), 4.49-4.44 (m, 4H), 2.64 (s, 3H), 1.61 (d, J=6.4 Hz, 6H), 1.40 (t, J=7.2 Hz, 3H). LC-MS (m/z) 392.1 (MH$^+$); $t_R$=1.52 minutes (Method C).

Example 41: N-benzyl-5-(2-ethoxy-3-pyridyl)-1-isopropyl-pyrazolo[4,3-b]pyridin-7-amine

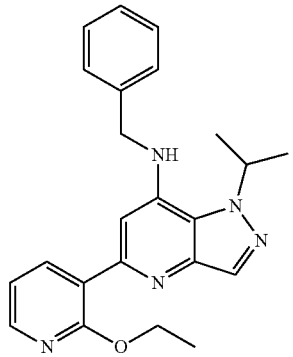 [SMILES: CCOc1ncccc1-c1cc(NCc2ccccc2)c2c(cnn2C(C)C)n1]

Prepared from benzaldehyde and 5-(2-ethoxypyridin-3-yl)-1-isopropyl-1H-pyrazolo[4,3-b]pyridin-7-amine.

$^1$H NMR (DMSO-d$_6$, 600 MHz) δ 8.16-8.07 (m, 3H), 7.43-7.38 (m, 2H), 7.35 (dd, J=8.4, 7.0 Hz, 2H), 7.27-7.21 (m, 1H), 7.04 (dd, J=7.4, 4.9 Hz, 2H), 6.96 (s, 1H), 5.34 (hept, J=6.4 Hz, 1H), 4.58 (d, J=5.6 Hz, 2H), 4.23 (q, J=7.0 Hz, 2H), 1.56-1.45 (d, J=6.4 Hz, 6H), 1.13 (t, J=7.0 Hz, 3H). LC-MS (m/z) 388 (MH$^+$); $t_R$=0.66 minutes (Method D).

Example 42: 5-(2-ethoxy-3-pyridyl)-1-isopropyl-N-[(3-methylisoxazol-5-yl)methyl]pyrazolo[4,3-b]pyridin-7-amine

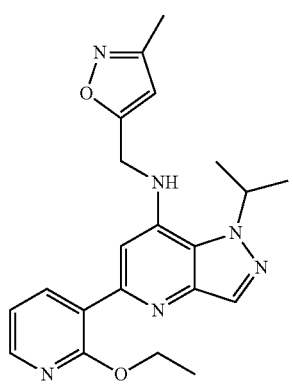 [SMILES: CCOc1ncccc1-c1cc(NCc2cc(C)no2)c2c(cnn2C(C)C)n1]

Prepared from 3-methylisoxazole-5-carbaldehyde and 5-(2-ethoxypyridin-3-yl)-1-isopropyl-1H-pyrazolo[4,3-b]pyridin-7-amine.

$^1$H NMR (DMSO-d$_6$, 600 MHz) δ 8.25-8.17 (m, 3H), 7.16-7.11 (m, 2H), 7.08 (t, J=5.8 Hz, 1H), 6.31 (s, 1H), 5.31 (hept, J=6.5 Hz, 1H), 4.71 (d, J=5.7 Hz, 2H), 4.40 (q, J=7.0 Hz, 2H), 2.23 (s, 3H), 1.56 (d, J=6.5 Hz, 6H), 1.29 (t, J=7.0 Hz, 3H). LC-MS (m/z) 393.1 (MH$^+$); $t_R$=0.55 minutes (Method D).

Example 43: 5-(2-ethoxy-3-pyridyl)-1-isopropyl-N-[(5-methyl-1,2,4-oxadiazol-3-yl)methyl]pyrazolo[4,3-b]pyridin-7-amine

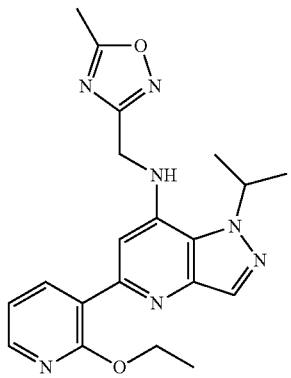 [SMILES: CCOc1ncccc1-c1cc(NCc2noc(C)n2)c2c(cnn2C(C)C)n1]

Prepared from 5-methyl-1,2,4-oxadiazole-3-carbaldehyde and 5-(2-ethoxypyridin-3-yl)-1-isopropyl-1H-pyrazolo[4,3-b]pyridin-7-amine.

$^1$H NMR (DMSO-$d_6$, 600 MHz) δ 8.20-8.10 (m, 3H), 7.13 (s, 1H), 7.08 (dd, J=7.4, 4.9 Hz, 1H), 7.00 (t, J=5.9 Hz, 1H), 5.26 (hept, J=6.4 Hz, 1H), 4.66 (d, J=5.8 Hz, 2H), 4.36 (q, J=7.0 Hz, 2H), 2.56 (s, 3H), 1.50 (d, J=6.4 Hz, 6H), 1.28 (t, J=7.0 Hz, 3H). LC-MS (m/z) 394 (MH$^+$); $t_R$=0.54 minutes (Method D).

Example 44: N-[(1,5-dimethylpyrazol-3-yl)methyl]-5-(2-ethoxy-3-pyridyl)-1-isopropyl-pyrazolo[4,3-b]pyridin-7-amine

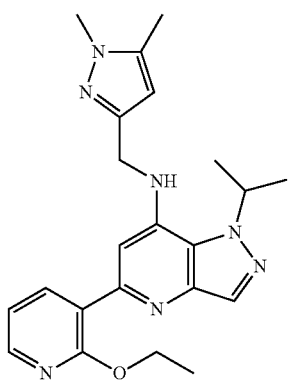 [SMILES: CCOc1ncccc1-c1cc(NCc2cc(C)n(C)n2)c2c(cnn2C(C)C)n1]

Prepared from 1,5-dimethyl-1H-pyrazole-3-carbaldehyde and 5-(2-ethoxypyridin-3-yl)-1-isopropyl-1H-pyrazolo[4,3-b]pyridin-7-amine.

$^1$H NMR (Methanol-$d_4$, 600 MHz) δ 8.17 (dd, J=5.0, 2.0 Hz, 1H), 8.04 (s, 1H), 7.94 (dd, J=7.3, 1.9 Hz, 1H), 7.07 (dd, J=7.3, 4.9 Hz, 1H), 6.98 (s, 1H), 6.07 (s, 1H), 5.22 (hept, J=6.4 Hz, 1H), 4.53 (d, J=1.5 Hz, 2H), 4.39 (q, J=7.0 Hz, 2H), 3.75 (s, 3H), 2.26 (s, 3H), 1.63 (d, J=6.5 Hz, 6H), 1.30 (t, J=7.1 Hz, 3H). LC-MS (m/z) 406.1 (MH$^+$); $t_R$=0.60 minutes (Method D).

Example 45: 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one

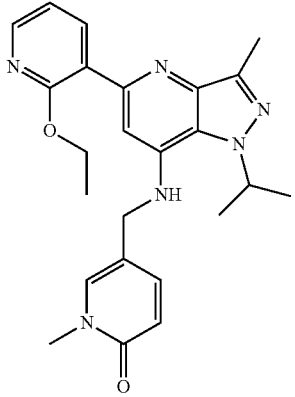 [SMILES: CCOc1ncccc1-c1cc(NCc2ccc(=O)n(C)c2)c2c(n1)c(C)nn2C(C)C]

Prepared from 1-methyl-6-oxo-1,6-dihydropyridine-3-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) 8.28-8.26 (m, 1H), 8.19-8.18 (m, 1H), 7.44-7.42 (m, 1H), 7.35 (d, J=2.0 Hz, 1H), 7.19 (s, 1H), 7.05-7.02 (m, 1H), 6.66 (d, J=9.6 Hz, 1H), 4.82-4.76 (m, 1H), 4.56 (brs, 1H), 4.47-4.42 (m, 2H), 4.29 (d, J=5.2 Hz, 2H), 3.56 (s, 3H), 2.65 (s, 3H), 1.62 (d, J=6.4 Hz, 6H), 1.35 (t, J=7.2 Hz, 3H). LC-MS (m/z) 433.1 (MH$^+$); $t_R$=1.86 min (Method C).

Example 46: 5-(2-ethoxypyridin-3-yl)-1-isopropyl-3-methyl-N-((2-methyl-1H-imidazol-4-yl)methyl)-1H-pyrazolo[4,3-b]pyridin-7-amine

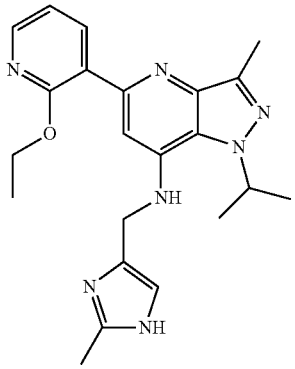 [SMILES: CCOc1ncccc1-c1cc(NCc2c[nH]c(C)n2)c2c(n1)c(C)nn2C(C)C]

Prepared from 2-methyl-1H-imidazole-4-carbaldehyde and 5-(2-ethoxypyridin-3-yl)-1-isopropyl-3-methyl-1H-pyrazolo[4,3-b]pyridin-7-amine.

$^1$H NMR (Chloroform-d, 400 MHz) 8.25-8.23 (m, 1H), 8.17-8.15 (m, 1H), 7.19 (s, 1H), 7.02-6.99 (m, 1H), 6.89 (s, 1H), 5.19 (brs, 1H), 4.90-4.85 (m, 1H), 4.49-4.41 (m, 4H), 2.63 (s, 3H), 2.43 (s, 3H), 1.61 (d, J=6.8 Hz, 6H), 1.40 (t, J=7.2 Hz, 3H). LC-MS (m/z) 406.1 (MH$^+$); $t_R$=1.60 min (Method C).

Example 47: 5-(2-ethoxypyridin-3-yl)-1-isopropyl-3-methyl-N-((5-methyl-1H-pyrazol-3-yl)methyl)-1H-pyrazolo[4,3-b]pyridin-7-amine

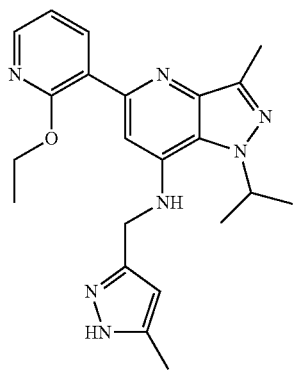 [SMILES: CCOc1ncccc1-c1cc(NCc2cc(C)[nH]n2)c2c(n1)c(C)nn2C(C)C]

Prepared from 5-methyl-1H-pyrazole-3-carbaldehyde and 5-(2-ethoxypyridin-3-yl)-1-isopropyl-3-methyl-1H-pyrazolo[4,3-b]pyridin-7-amine.

¹H NMR (Chloroform-d, 400 MHz) δ 8.27-8.25 (m, 1H), 8.19-8.17 (m, 1H), 7.20 (s, 1H), 7.04-7.01 (m, 1H), 6.08 (s, 1H), 5.29 (brs, 1H), 4.94-4.87 (m, 1H), 4.51-4.46 (m, 4H), 2.65 (s, 3H), 2.35 (s, 3H), 1.63 (d, J=6.8 Hz, 6H), 1.42 (t, J=7.2 Hz, 3H). LC-MS (m/z) 406.1 (MH⁺); $t_R$=1.90 min (Method B).

Example 48: 5-(2-ethoxypyridin-3-yl)-1-ethyl-3-methyl-N-((1-methyl-1H-pyrazol-4-yl)methyl)-1H-pyrazolo[4,3-b]pyridin-7-amine

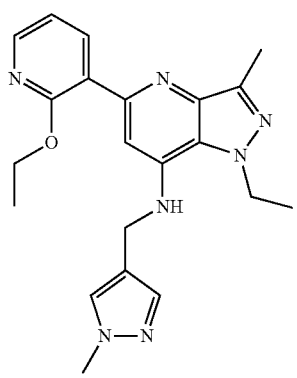 [SMILES: CCOc1ncccc1-c1cc(NCc2cnn(C)c2)c2c(n1)c(C)nn2CC]

Prepared using the same procedure as described for example 1, from (1-methyl-1H-pyrazol-4-yl)methanamine and 5,7-dibromo-1-ethyl-3-methyl-1H-pyrazolo[4,3-b]pyridine.

¹H NMR (Chloroform-d, 400 MHz) δ 8.28-8.26 (m, 1H), 8.19-8.17 (m, 1H), 7.56 (s, 1H), 7.43 (s, 1H), 7.23 (s, 1H), 7.04-7.01 (m, 1H), 4.53 (brs, 1H), 4.50-4.45 (m, 4H), 4.40 (d, J=4.8 Hz, 2H), 3.92 (s, 3H), 2.63 (s, 3H), 1.47 (t, J=7.2 Hz, 3H), 1.39 (t, J=7.2 Hz, 3H). LC-MS: LC-MS (m/z) 392.1 (MH⁺); $t_R$=1.72 min (Method F).

Example 49: 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one

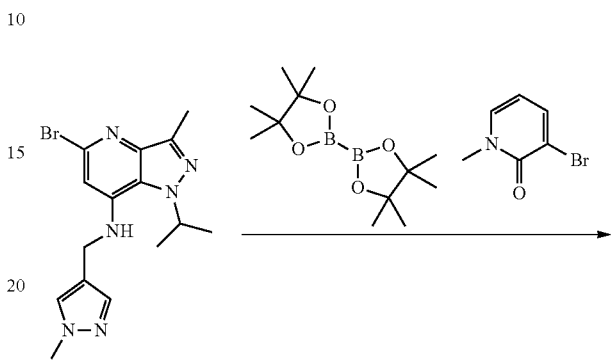

A mixture of 5-bromo-1-isopropyl-3-methyl-N-((1-methyl-1H-pyrazol-4-yl)methyl)-1H-pyrazolo[4,3-b]pyridin-7-amine (60 mg, 0.17 mmol), 3-bromo-1-methylpyridin-2(1H)-one (62 mg, 0.33 mmol), [1,1'-bis(diphenylphosphino)ferrocene]palladium(II) dichloride (24 mg, 33 mmol), Cs₂CO₃ (108 mg, 0.33 mmol) and 4,4,4',4',5,5,5',5'-octamethyl-2,2'-bi(1,3,2-dioxaborolane) (84 mg, 0.33 mmol) in dioxane (3 mL) was degassed and purged with N₂ 3 times, and then the mixture was stirred at 100° C. for 1 hour under microwave irradiation. Then water (30 mL) was added and the mixture was extracted with ethyl acetate (30 mL×3). The combined organic layers were washed with brine (20 mL), dried over Na₂SO₄ and concentrated. The crude product was purified by preparative HPLC to give 3-(1-isopropyl-3-methyl-7-(((1-methyl-1H-pyrazol-4-yl)methyl)amino)-1H-pyrazolo[4,3-b]pyridin-5-yl)-1-methylpyridin-2(1H)-one.

¹H NMR (Chloroform-d, 400 MHz) δ 8.45-8.42 (m, 1H), 7.82-7.80 (m, 1H), 7.56-7.54 (m, 2H), 7.44-7.43 (m, 1H), 6.43-6.41 (m, 1H), 4.84-4.82 (m, 1H), 4.48 (s, 2H), 3.92 (s, 3H), 3.68 (s, 3H), 2.63 (s, 3H) 1.57 (d, J=6.8 Hz, 6H). LC-MS (m/z) 392.1 (MH⁺); $t_R$=1.76 min (Method B).

Example 50: 5-(2-ethoxypyridin-3-yl)-1-isopropyl-3-methyl-N-((4-methyloxazol-2-yl)methyl)-1H-pyrazolo[4,3-b]pyridin-7-amine 2,2,2-trifluoroacetate

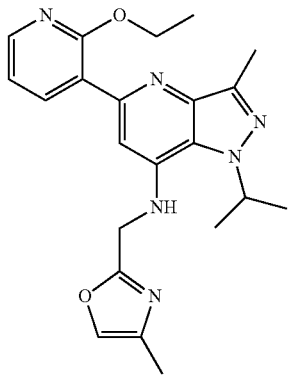 [SMILES: CCOc1ncccc1-c1cc(NCc2nc(C)co2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 4-methyloxazole-2-carbaldehyde.

$^1$H NMR (DMSO-d$_6$, 600 MHz) δ 8.37 (dd, J=4.9, 1.9 Hz, 1H), 8.03 (dd, J=7.5, 1.9 Hz, 1H), 7.81 (s, 1H), 7.22 (dd, J=7.5, 4.9 Hz, 1H), 7.11 (s, 1H), 6.64 (bds, 1H), 5.29 (p, J=6.3 Hz, 1H), 4.91 (d, J=5.6 Hz, 2H), 4.37 (q, J=7.0 Hz, 2H), 2.54 (s, 3H), 2.03 (s, 3H), 1.50 (d, J=6.3 Hz, 6H), 1.26 (t, J=7.0 Hz, 3H). LC-MS (m/z) 407.4 (MH$^+$); t$_R$=0.52 minutes (Method E).

Example 51: N-((1,2-dimethyl-1H-imidazol-4-yl)methyl)-5-(2-ethoxypyridin-3-yl)-1-isopropyl-3-methyl-1H-pyrazolo[4,3-b]pyridin-7-amine 2,2,2-trifluoroacetate

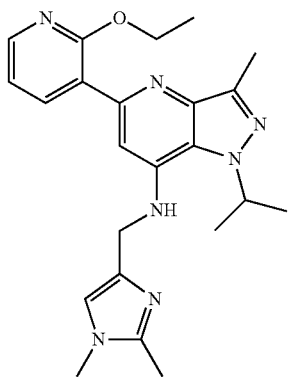 [SMILES: CCOc1ncccc1-c1cc(NCc2cn(C)c(C)n2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 1,2-dimethylimidazole-4-carbaldehyde.

$^1$H NMR (DMSO-d$_6$, 600 MHz) δ 8.35 (s, 1H), 8.05 (s, 1H), 7.61 (s, 1H), 7.23-7.17 (m, 1H), 7.09 (s, 1H), 6.66 (bds, 1H), 5.30 (m, 1H), 4.85 (m, 2H), 4.36 (q, J=7.0 Hz, 2H), 3.77 (s, 3H), 2.58 (s, 3H), 2.53 (s, 3H), 1.50 (d, J=6.3 Hz, 6H), 1.19 (t, J=7.0 Hz, 3H). LC-MS (m/z) 420.4 (MH$^+$); t$_R$=0.33 minutes (Method E).

Example 52: 5-(2-ethoxy-3-pyridyl)-1-isopropyl-3-methyl-N-[(5-methyl-1,2,4-oxadiazol-3-yl)methyl]pyrazolo[4,3-b]pyridin-7-amine

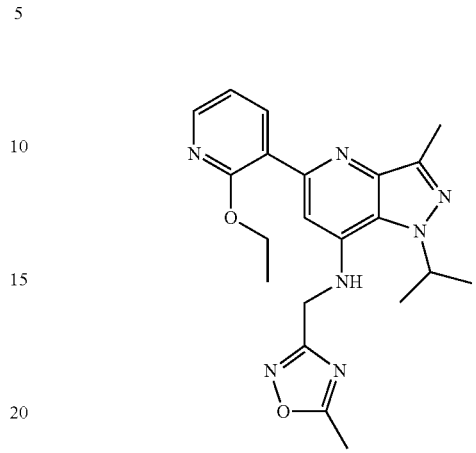

Prepared using the same procedure as described for example 29, from 5-(2-ethoxypyridin-3-yl)-1-isopropyl-3-methyl-1H-pyrazolo[4,3-b]pyridin-7-amine and 5-methyl-1,2,4-oxadiazole-3-carbaldehyde.

$^1$H NMR (Chloroform-d, 400 MHz) δ 8.27-8.25 (m, 1H), 8.19-8.18 (m, 1H), 7.23 (s, 1H), 7.04-7.01 (m, 1H), 5.23 (brs, 1H), 4.94-4.91 (m, 1H), 4.63 (d, J=5.2 Hz, 2H), 4.52-4.47 (m, 2H), 2.65 (s, 3H), 2.64 (s, 3H), 1.66 (d, J=6.4 Hz, 6H), 1.44 (t, J=6.8 Hz, 3H). LC-MS (m/z) 408.4 (MH$^+$); t$_R$=0.49 minutes (Method E).

Example 53: 5-(2-ethoxy-3-pyridyl)-1-isopropyl-3-methyl-N-(1,2,4-oxadiazol-3-ylmethyl)pyrazolo[4,3-b]pyridin-7-amine

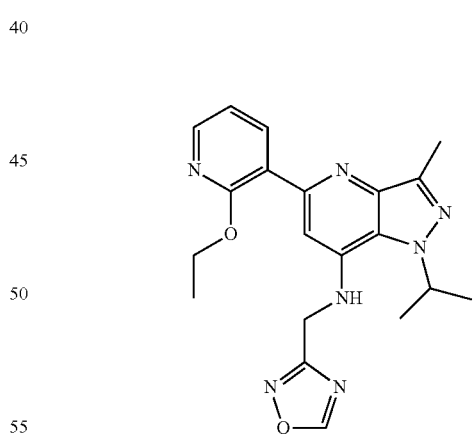

Prepared using the same procedure as described for example 29, from 5-(2-ethoxypyridin-3-yl)-1-isopropyl-3-methyl-1H-pyrazolo[4,3-b]pyridin-7-amine and 1,2,4-oxadiazole-3-carbaldehyde.

$^1$H NMR (Chloroform-d, 400 MHz) δ 8.78 (s, 1H), 8.27-8.25 (m, 1H), 8.19-8.17 (m, 1H), 7.25 (s, 1H), 7.04-7.01 (m, 1H), 5.25 (brs, 1H), 4.96-4.90 (m, 1H), 4.74 (d, J=4.4 Hz, 2H), 4.52-4.47 (m, 2H), 2.65 (s, 3H), 1.66 (d, J=6.4 Hz, 6H), 1.43 (t, J=7.2 Hz, 3H). LC-MS (m/z) 394.4 (MH$^+$); t$_R$=0.47 minutes (Method E).

Example 54: N-[(1,5-dimethylpyrazol-3-yl)methyl]-5-(2-ethoxy-3-pyridyl)-1-isopropyl-3-methyl-pyrazolo[4,3-b]pyridin-7-amine

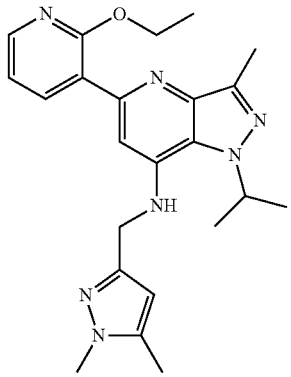 [SMILES: CCOc1ncccc1-c1cc(NCc2cc(C)n(C)n2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 1,5-dimethylpyrazole-3-carbaldehyde.

$^1$H NMR (Chloroform-d, 400 MHz) δ 8.26 (dd, J=2.0, 7.6 Hz, 1H), 8.18 (dd, J=2.0, 8.4 Hz, 1H), 7.18 (s, 1H), 7.03 (dd, J=5.2, 7.6 Hz, 1H), 6.03 (s, 1H), 5.29 (brs, 1H), 4.95-4.88 (m, 1H), 4.51-4.44 (m, 4H), 3.79 (s, 3H), 2.65 (s, 3H), 2.29 (s, 3H), 1.64 (d, J=6.8 Hz, 6H), 1.42 (t, J=7.6 Hz, 3H). LC-MS (m/z) 420.4 (MH$^+$); t$_R$=0.53 minutes (Method E).

Example 55: 5-(2-ethoxy-3-pyridyl)-1-isopropyl-3-methyl-N-[(5-methyl-1H-1,2,4-triazol-3-yl)methyl]pyrazolo[4,3-b]pyridin-7-amine

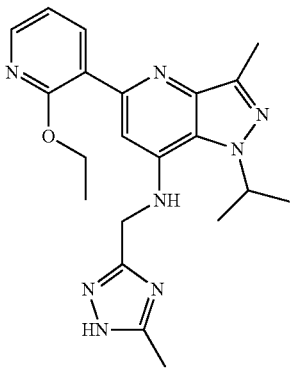 [SMILES: CCOc1ncccc1-c1cc(NCc2n[nH]c(C)n2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 5-methyl-1H-1,2,4-triazole-3-carbaldehyde.

$^1$H NMR (Chloroform-d, 400 MHz) δ 8.23 (dd, J=2.0, 7.6 Hz, 1H), 8.17 (dd, J=2.0, 5.2 Hz, 1H), 7.19 (s, 1H), 7.01 (dd, J=5.2, 7.6 Hz, 1H), 5.70 (brs, 1H), 5.00 (brs, 1H), 4.61 (br s, 2H), 4.48 (q, J=7.2 Hz, 2H), 2.64 (s, 3H), 2.48 (s, 3H), 1.65 (d, J=6.4 Hz, 6H), 1.43 (t, J=7.2 Hz, 3H). LC-MS (m/z) 407.1 (MH$^+$); t$_R$=1.86 minutes (Method C).

Example 56: 5-(2-ethoxy-3-pyridyl)-1-isopropyl-N-[(1-methyl-1,2,4-triazol-3-yl)methyl]pyrazolo[4,3-b]pyridin-7-amine

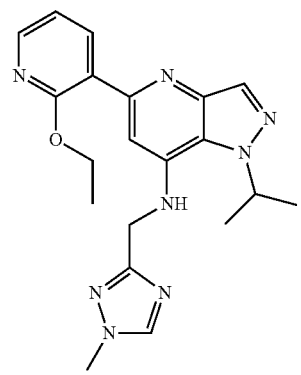 [SMILES: CCOc1ncccc1-c1cc(NCc2ncn(C)n2)c2c(cnn2C(C)C)n1]

Prepared using the same procedure as described for example 29, from 5-(2-ethoxypyridin-3-yl)-1-isopropyl-1H-pyrazolo[4,3-b]pyridin-7-amine and 1-methyl-1,2,4-triazole-3-carbaldehyde.

$^1$H NMR (Chloroform-d, 400 MHz) δ 8.24-8.17 (m, 3H), 8.06 (s, 1H), 7.23 (s, 1H), 7.04-7.01 (m, 1H), 5.61 (brs, 1H), 5.08-5.01 (m, 1H), 4.60 (d, J=4.4 Hz, 2H), 4.50 (q, J=7.2 Hz, 2H), 3.95 (s, 3H), 1.70 (d, J=6.4 Hz, 6H), 1.46 (t, J=7.2 Hz, 3H). LC-MS (m/z) 393.4 (MH$^+$); t$_R$=0.41 minutes (Method E).

Example 57: 5-(2-ethoxy-3-pyridyl)-1-isopropyl-N-(1H-pyrazol-3-ylmethyl)pyrazolo[4,3-b]pyridin-7-amine

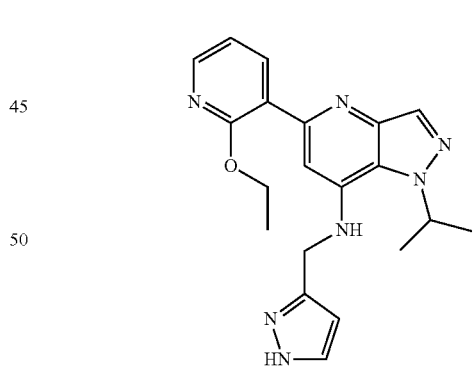

Prepared using the same procedure as described for example 29, from 5-(2-ethoxypyridin-3-yl)-1-isopropyl-1H-pyrazolo[4,3-b]pyridin-7-amine and 1H-pyrazole-3-carbaldehyde.

$^1$H NMR (Chloroform-d, 400 MHz) δ 8.23-8.17 (m, 3H), 7.61 (d, J=2.4 Hz, 1H), 7.22 (s, 1H), 7.04-7.01 (m, 1H), 6.38 (d, J=2.4 Hz, 1H), 5.46 (brs, 1H), 5.02-4.95 (m, 1H), 4.59 (d, J=4.4 Hz, 2H), 4.49 (q, J=7.2 Hz, 2H), 1.67 (d, J=6.8 Hz, 6H), 1.43 (t, J=7.2 Hz, 3H). LC-MS (m/z) 378.3 (MH$^+$); t$_R$=0.43 minutes (Method E).

Example 58: 5-(2-ethoxypyridin-3-yl)-1-isopropyl-3-methyl-N-((1-methyl-1H-imidazol-4-yl)methyl)-1H-pyrazolo[4,3-b]pyridin-7-amine 2,2,2-trifluoroacetate

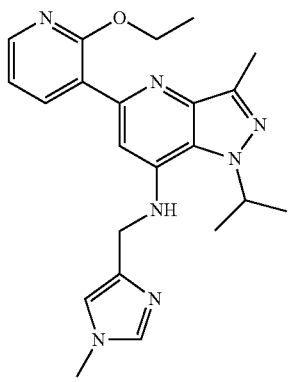 [SMILES: CCOc1ncccc1-c1cc(NCc2cn(C)cn2)c2c(n1)c(C)nn2C(C)C]

Prepared using the same procedure as described for example 1, from 5,7-dichloro-1-isopropyl-3-methyl-1H-pyrazolo[4,3-b]pyridine and (1-methyl-1H-imidazol-4-yl)methanamine.

$^1$H NMR (DMSO-d$_6$, 600 MHz) δ 8.99 (s, 1H), 8.55 (bds, 1H), 8.39 (dd, J=5.0, 1.9 Hz, 1H), 8.02 (dd, J=7.4, 1.9 Hz, 1H), 7.67 (s, 1H), 7.23 (dd, J=7.4, 5.0 Hz, 1H), 7.04 (s, 1H), 5.29 (p, J=6.4 Hz, 1H), 4.91 (d, J=5.8 Hz, 2H), 4.36 (t, J=7.0 Hz, 2H), 3.82 (s, 3H), 2.55 (s, 3H), 1.51 (d, J=6.4 Hz, 6H), 1.21 (t, J=7.0 Hz, 3H). LC-MS (m/z) 406.4 (MH$^+$); t$_R$=0.34 minutes (Method E).

Example 59: 5-(2-ethoxy-3-pyridyl)-1-isopropyl-3-methyl-N-(1,3,4-oxadiazol-2-ylmethyl)pyrazolo[4,3-b]pyridin-7-amine

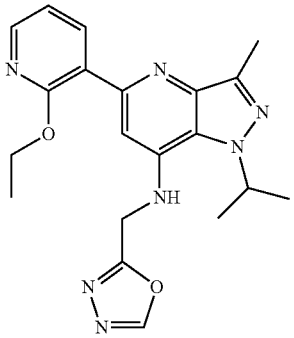 [SMILES: CCOc1ncccc1-c1cc(NCc2nnco2)c2c(n1)c(C)nn2C(C)C]

Prepared using the same procedure as described for example 1, from 5,7-dichloro-1-isopropyl-3-methyl-1H-pyrazolo[4,3-b]pyridine and (1,3,4-oxadiazol-2-yl)methanamine hydrobromide.

$^1$H NMR (Chloroform-d, 400 MHz) δ 8.42-8.37 (m, 2H), 8.24-8.22 (m, 1H), 7.88 (s, 1H), 7.10-7.08 (m, 2H), 4.86-4.79 (m, 1H), 4.52 (d, J=7.2 Hz, 2H), 4.33 (s, 2H), 2.71 (s, 3H), 1.55 (d, J=6.8 Hz, 6H), 1.45 (t, J=7.2 Hz, 3H). LC-MS (m/z) 394.3 (MH$^+$); t$_R$=0.61 minutes (Method E).

Example 60: 5-(2-ethoxy-3-pyridyl)-1-isopropyl-3-methyl-N-[(1-methylpyrazol-3-yl)methyl]pyrazolo[4,3-b]pyridin-7-amine

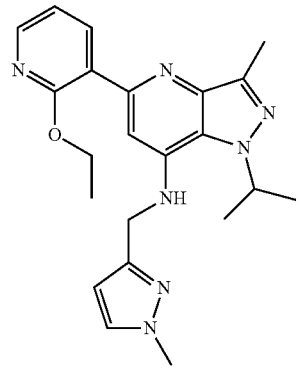 [SMILES: CCOc1ncccc1-c1cc(NCc2ccn(C)n2)c2c(n1)c(C)nn2C(C)C]

Prepared using the same procedure as described for example 1, from 5,7-dichloro-1-isopropyl-3-methyl-1H-pyrazolo[4,3-b]pyridine and (1-methyl-1H-pyrazol-3-yl)methanamine.

$^1$H NMR (Chloroform-d, 400 MHz) δ 8.27-8.25 (m, 1H), 8.18-8.17 (m, 1H), 7.37 (d, J=2.0 Hz, 1H), 7.20 (s, 1H), 7.04-7.01 (m, 1H), 6.26 (d, J=2.0 Hz, 1H), 5.25 (brs, 1H), 4.95-4.88 (m, 1H), 4.51-4.46 (m, 4H), 3.93 (s, 3H), 2.65 (s, 3H), 1.64 (d, J=6.4 Hz, 6H), 1.42 (t, J=6.8 Hz, 3H). LC-MS (m/z) 406.4 (MH$^+$); t$_R$=0.50 minutes (Method E).

Example 61: 5-(1,3-dimethylpyrazol-4-yl)-1-isopropyl-3-methyl-N-[(1-methylpyrazol-4-yl)methyl]pyrazolo[4,3-b]pyridin-7-amine

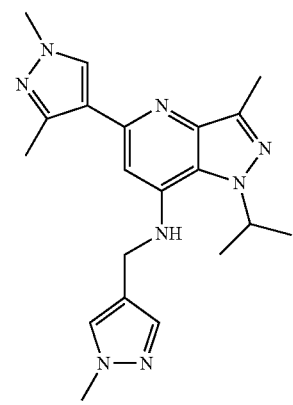 [SMILES: Cc1nn(C)cc1-c1cc(NCc2cnn(C)c2)c2c(n1)c(C)nn2C(C)C]

Prepared using the same procedure as described for example 1, from 5-chloro-1-isopropyl-3-methyl-N-[(1-methylpyrazol-4-yl)methyl]pyrazolo[4,3-b]pyridin-7-amine and 1,3-dimethyl-4-(4,4,5,5-tetramethyl-1,3,2-dioxaborolan-2-yl)pyrazole.

$^1$H NMR (Chloroform-d, 400 MHz): δ 7.75 (s, 1H), 7.55 (s, 1H), 7.40 (s, 1H), 6.56 (s, 1H), 4.74-4.67 (m, 1H), 4.54 (brs, 1H), 4.37 (d, J=4.8 Hz, 2H), 3.92 (s, 3H), 3.87 (s, 3H), 2.60 (s, 3H), 2.50 (s, 3H), 1.56 (d, J=6.4 Hz, 6H). LC-MS (m/z) 379.4 (MH$^+$); t$_R$=0.38 minutes (Method E).

Example 62: 1-isopropyl-5-(2-methoxy-3-pyridyl)-3-methyl-N-[(1-methylpyrazol-4-yl)methyl]pyrazolo[4,3-b]pyridin-7-amine

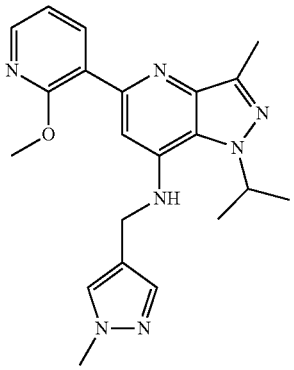 [SMILES: COc1ncccc1-c1cc(NCc2cnn(C)c2)c2c(n1)c(C)nn2C(C)C]

Prepared using the same procedure as described for example 1, from 5-chloro-1-isopropyl-3-methyl-N-[(1-methylpyrazol-4-yl)methyl]pyrazolo[4,3-b]pyridin-7-amine and (2-methoxy-3-pyridyl)boronic acid.

$^1$H NMR (Chloroform-d, 400 MHz) δ 8.21-8.17 (m, 2H), 7.57 (s, 1H), 7.45 (s, 1H), 7.08-7.04 (m, 2H), 4.79-4.73 (m, 1H), 4.57 (brs, 1H), 4.39 (d, J=4.8 Hz, 2H), 3.99 (s, 3H), 3.93 (s, 3H), 2.64 (s, 3H), 1.59 (d, J=6.4 Hz, 6H). LC-MS (m/z) 392.4 (MH$^+$); $t_R$=0.43 minutes (Method E).

Example 63: 1-isopropyl-5-(2-methoxyphenyl)-3-methyl-N-[(1-methylpyrazol-4-yl)methyl]pyrazolo[4,3-b]pyridin-7-amine

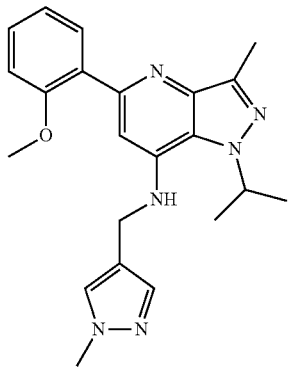 [SMILES: COc1ccccc1-c1cc(NCc2cnn(C)c2)c2c(n1)c(C)nn2C(C)C]

Prepared using the same procedure as described for example 1, from 5-chloro-1-isopropyl-3-methyl-N-[(1-methylpyrazol-4-yl)methyl]pyrazolo[4,3-b]pyridin-7-amine and (2-methoxyphenyl)boronic acid.

$^1$H NMR (Chloroform-d, 400 MHz) δ 7.74 (dd, J=1.8, 7.4 Hz, 1H), 7.56 (s, 1H), 7.43 (s, 1H), 7.40-7.31 (m, 1H), 7.13-7.05 (m, 1H), 7.00 (d, J=8.0 Hz, 1H), 6.94 (s, 1H), 4.82-4.72 (m, 1H), 4.53 (brs, 1H), 4.36 (d, J=4.8 Hz, 2H), 3.92 (s, 3H), 3.82 (s, 3H), 2.65 (s, 3H), 1.59 (d, J=6.8 Hz, 6H). LC-MS (m/z) 391.1 (MH$^+$); $t_R$=0.47 minutes (Method E).

Example 64: 1-isopropyl-3-methyl-N-[(1-methylpyrazol-4-yl)methyl]-5-phenyl-pyrazolo[4,3-b]pyridin-7-amine

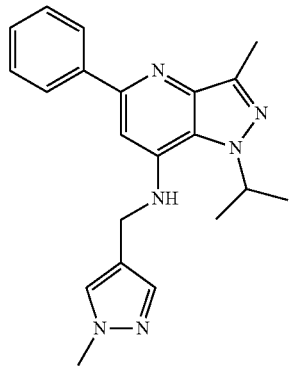 [SMILES: Cc1nn(C(C)C)c2c(NCc3cnn(C)c3)cc(-c3ccccc3)nc12]

Prepared using the same procedure as described for example 1, from 5-chloro-1-isopropyl-3-methyl-N-[(1-methylpyrazol-4-yl)methyl]pyrazolo[4,3-b]pyridin-7-amine and phenylboronic acid.

$^1$H NMR (Chloroform-d, 400 MHz) δ 8.00-7.99 (m, 2H), 7.58 (s, 1H), 7.49-7.43 (m, 3H), 7.41-7.37 (m, 1H), 6.88 (s, 1H), 4.79-4.69 (m, 1H), 4.56 (brs, 1H), 4.43 (d, J=4.8 Hz, 2H), 3.93 (s, 3H), 2.67 (s, 3H), 1.59 (d, J=6.4 Hz, 6H). LC-MS (m/z) 361.3 (MH$^+$); $t_R$=0.45 minutes (Method E).

Example 65: 1-isopropyl-3-methyl-N-[(1-methylpyrazol-4-yl)methyl]-5-(2-methyl-3-thienyl)pyrazolo[4,3-b]pyridin-7-amine

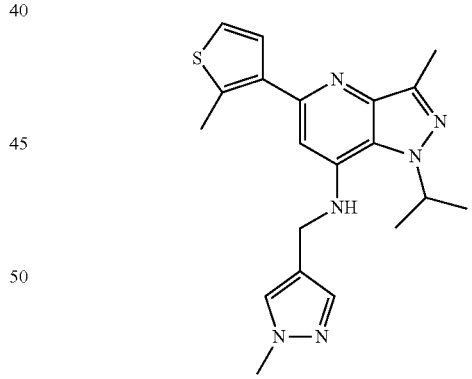

Prepared using the same procedure as described for example 1, from 5-chloro-1-isopropyl-3-methyl-N-[(1-methylpyrazol-4-yl)methyl]pyrazolo[4,3-b]pyridin-7-amine and 4,4,5,5-tetramethyl-2-(2-methyl-3-thienyl)-1,3,2-dioxaborolane.

$^1$H NMR (Chloroform-d, 400 MHz) δ 7.55 (s, 1H), 7.40 (s, 1H), 7.26 (d, JJJ=4.8 Hz 1H), 7.08 (d, JJJ=5.2 Hz 1H), 6.60 (brs, 1H), 4.77-4.72 (m, 1H), 4.57 (brs, 1H), 4.36 (d, J=4.4 Hz, 2H), 3.92 (s, 3H), 2.66 (s, 3H), 2.62 (s, 3H), 1.58 (d, J=6.4 Hz, 6H)). LC-MS (m/z) 381.0 (MH$^+$); $t_R$=2.06 minutes (Method F).

Example 66: 5-(1,5-dimethylpyrazol-4-yl)-1-isopropyl-3-methyl-N-[(1-methylpyrazol-4-yl)methyl]pyrazolo[4,3-b]pyridin-7-amine

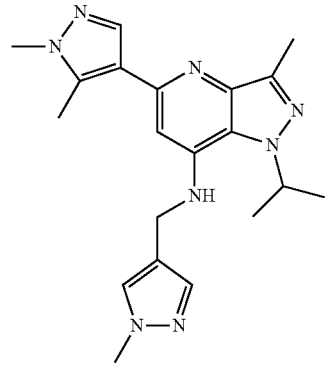 [SMILES: Cc1nn(C(C)C)c2c(NCc3cnn(C)c3)cc(-c3cnn(C)c3C)nc12]

Prepared using the same procedure as described for example 1, from 5-chloro-1-isopropyl-3-methyl-N-[(1-methylpyrazol-4-yl)methyl]pyrazolo[4,3-b]pyridin-7-amine and 1,5-dimethyl-4-(4,4,5,5-tetramethyl-1,3,2-dioxaborolan-2-yl)pyrazole.

$^1$H NMR (DMSO-$d_6$, 400 MHz) δ 7.74 (s, 1H), 7.64 (s, 1H), 7.44 (s, 1H), 6.57 (brs, 1H), 6.57 (s, 1H), 5.13-5.07 (m, 1H), 4.38 (d, J=5.2 Hz, 2H), 3.76 (s, 3H), 3.75 (s, 3H), 2.56 (s, 3H), 2.41 (s, 3H), 1.42 (d, J=6.4 Hz, 6H). LC-MS (m/z) 379.4 (MH$^+$); $t_R$=0.38 minutes (Method E).

Example 67: 5-(2-ethoxy-3-pyridyl)-3-methyl-1-[1-methylpropyl]-N-[(1-methylpyrazol-3-yl)methyl]pyrazolo[4,3-b]pyridin-7-amine, Enantiomer 2

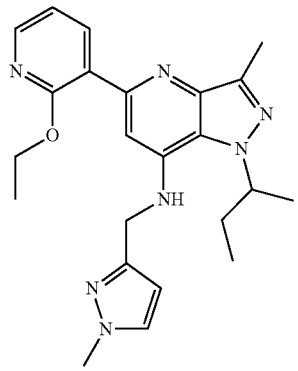

Prepared using the same procedure as described for example 1, from 1-(sec-butyl)-5-(2-ethoxypyridin-3-yl)-3-methyl-1H-pyrazolo[4,3-b]pyridin-7-amine, enantiomer 2, (2-ethoxy-3-pyridyl)boronic acid and (1-methyl-1H-pyrazol-3-yl)methanamine.

$^1$H NMR (Chloroform-d, 400 MHz) δ 8.27 (dd, J=1.6, 7.2 Hz, 1H), 8.17 (dd, J=1.6, 4.8 Hz, 1H), 7.37 (d, J=2.0 Hz, 1H), 7.21 (s, 1H), 7.02 (dd, J=4.8, 7.6 Hz, 1H), 6.25 (d, J=2.0 Hz, 1H), 5.24 (brs, 1H), 4.65-4.60 (m, 1H), 4.51-4.46 (m, 4H), 3.92 (s, 3H), 2.65 (s, 3H), 2.22-2.15 (m, 1H), 1.92-1.85 (m, 1H), 1.62 (d, J=6.4 Hz, 3H), 1.43 (t, J=6.8 Hz, 3H), 0.92 (t, J=7.6 Hz, 3H). LC-MS (m/z) 420.1 (MH$^+$); $t_R$=1.87 (Method A).

Example 68: 3-methyl-1-[1-methylpropyl]-N-[(2-methyltetrazol-5-yl)methyl]-5-(2-propoxy-3-pyridyl)pyrazolo[4,3-b]pyridin-7-amine, Enantiomer 2

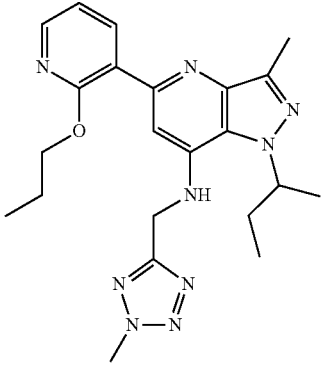

Prepared using the same procedure as described for example 1, from 1-(sec-butyl)-5-(2-ethoxypyridin-3-yl)-3-methyl-1H-pyrazolo[4,3-b]pyridin-7-amine, enantiomer 2 and (2-methyl-2H-tetrazol-5-yl)methanamine.

$^1$H NMR (Chloroform-d, 400 MHz) δ 8.27 (dd, J=7.50, 1.98 Hz, 1H) 8.19 (dd, J=5.07, 1.98 Hz, 1H) 7.25 (s, 1H) 7.03 (dd, J=7.39, 4.96 Hz, 1H) 5.29 (s, 1H) 4.78 (d, J=5.07 Hz, 2H) 4.61-4.68 (m, 1H) 4.37-4.41 (m, 5H) 2.66 (s, 3H) 2.18 (s, 1H) 1.80-1.96 (m, 3H) 1.65 (d, J=6.62 Hz, 3H) 1.06 (t, J=7.39 Hz, 3H) 0.92 (t, J=7.39 Hz, 3H). LC-MS (m/z) 436.1 (MH$^+$); $t_R$=1.97 (Method A).

Example 69: 5-(2-ethoxy-3-pyridyl)-1-[1-methylpropyl]-N-[(1-methylpyrazol-4-yl)methyl]pyrazolo[4,3-b]pyridin-7-amine, enantiomer 1

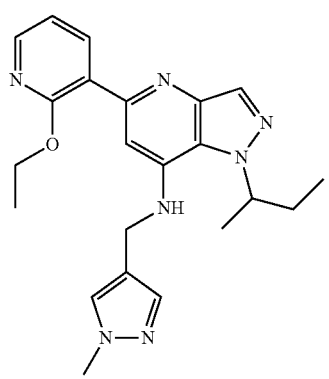 [SMILES: CCOc1ncccc1-c1cc(NCc2cnn(C)c2)c2c(cnn2C(C)CC)n1]

Prepared using the same procedure as described for example 1, from 1-(sec-butyl)-5-(2-ethoxypyridin-3-yl)-1H-pyrazolo[4,3-b]pyridin-7-amine, enantiomer 1, (2-ethoxy-3-pyridyl)boronic acid and (1-methyl-1H-pyrazol-4-yl)methanamine.

$^1$H NMR (Chloroform-d, 400 MHz) δ 8.18-8.14 (m, 2H), 8.11 (s, 1H), 7.59 (s, 1H), 7.40 (s, 1H), 7.11-7.07 (m, 2H), 6.73-6.72 (m, 1H), 5.01-4.96 (m, 1H), 4.39-4.33 (m, 4H), 3.77 (s, 3H), 2.00-1.97 (m, 1H), 1.81-1.79 (m, 1H), 1.49 (d, J=6.8 Hz, 3H), 1.25 (t, J=6.8 Hz, 3H), 0.73 (t, J=7.2 Hz, 3H). SFC-MS: $t_R$=4.72 min, ee %=97.51. LC-MS (m/z) 406.1 (MH$^+$); $t_R$=2.09 (Method A).

Example 70: 5-(2-ethoxy-3-pyridyl)-1-[1-methyl-propyl]-N-[(1-methylpyrazol-4-yl)methyl]pyrazolo[4,3-b]pyridin-7-amine, Enantiomer 2

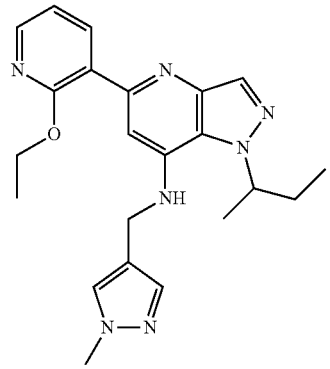 [SMILES: CCOc1ncccc1-c1cc(NCc2cnn(C)c2)c2c(cnn2C(C)CC)n1]

Prepared using the same procedure as described for example 1, from 1-(sec-butyl)-5-(2-ethoxypyridin-3-yl)-1H-pyrazolo[4,3-b]pyridin-7-amine, enantiomer 2, (2-ethoxy-3-pyridyl)boronic acid and (1-methyl-1H-pyrazol-4-yl)methanamine.

$^1$H NMR (Chloroform-d, 400 MHz) δ 8.17-8.14 (m, 2H), 8.11 (s, 1H), 7.59 (s, 1H), 7.40 (s, 1H), 7.11-7.06 (m, 2H), 6.74-6.71 (m, 1H), 5.01-4.97 (m, 1H), 4.39-4.33 (m, 4H), 3.77 (s, 3H), 2.00-1.95 (m, 1H), 1.82-1.77 (m, 1H), 1.49 (d, J=6.4 Hz, 3H), 1.25 (t, J=6.8 Hz, 3H), 0.73 (t, J=7.2 Hz, 3H). SFC-MS: $t_R$=4.48 min, ee %=95.47. LC-MS (m/z) 406.1 (MH$^+$); $t_R$=2.01 (Method A).

Example 71: 5-(2-ethoxy-3-pyridyl)-1-isopropyl-N-[(4-methylthiazol-5-yl)methyl]pyrazolo[4,3-b]pyridin-7-amine

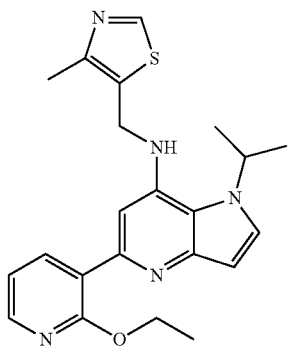 [SMILES: CCOc1ncccc1-c1cc(NCc2scnc2C)c2c(ccn2C(C)C)n1]

Prepared using the same procedure as described for example 1, from 5,7-dibromo-1-isopropyl-1H-pyrazolo[4,3-b]pyridine, 2-ethoxy-3-(4,4,5,5-tetramethyl-1,3,2-dioxaborolan-2-yl)pyridine and (4-methylthiazol-5-yl)methanamine di hydrochloride.

$^1$H NMR (DMSO-d$_6$, 600 MHz) δ 8.84 (s, 1H), 8.17 (dd, J=4.9, 1.9 Hz, 1H), 8.14-8.08 (m, 2H), 7.07 (dd, J=7.3, 4.7 Hz, 2H), 7.02 (s, 1H), 5.26 (hept, J=6.4 Hz, 1H), 4.67 (d, J=5.3 Hz, 2H), 4.34 (q, J=7.0 Hz, 2H), 2.44 (s, 3H), 1.50 (d, J=6.3 Hz, 6H), 1.21 (t, J=7.0 Hz, 3H). LC-MS (m/z) 409.5 (MH$^+$); $t_R$=0.51 (Method D).

Example 72: 5-[[5-(2-ethoxy-3-pyridyl)-1-isopropyl-3-methyl-pyrazolo[4,3-b]pyridin-7-yl]oxymethyl]-2-methyl-oxazole

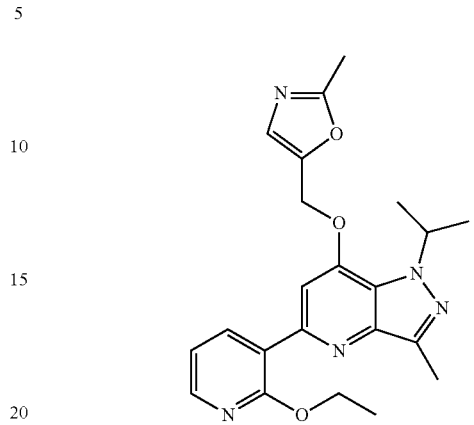

Prepared using the same procedure as described for example 1, from 5,7-dibromo-1-isopropyl-1H-pyrazolo[4,3-b]pyridine, 2-ethoxy-3-(4,4,5,5-tetramethyl-1,3,2-dioxaborolan-2-yl)pyridine and (2-methyloxazol-5-yl)methanol.

$^1$H NMR (DMSO-d$_6$, 600 MHz) δ 8.24 (dd, J=4.9, 2.0 Hz, 1H), 8.18 (dd, J=7.3, 2.0 Hz, 1H), 7.65 (s, 1H), 7.28 (s, 1H), 7.14 (dd, J=7.4, 4.9 Hz, 1H), 5.45 (s, 2H), 5.11 (hept, J=6.7 Hz, 1H), 4.45 (q, J=7.0 Hz, 2H), 2.51 (s, 3H), 2.43 (s, 3H), 1.44 (d, J=6.6 Hz, 6H), 1.36 (t, J=7.0 Hz, 3H). LC-MS (m/z) 408.6 (MH$^+$); $t_R$=0.64 (Method D).

Example 73: 5-(2-ethoxy-3-pyridyl)-1-isopropyl-3-methyl-N-(pyrimidin-4-ylmethyl)pyrazolo[4,3-b]pyridin-7-amine

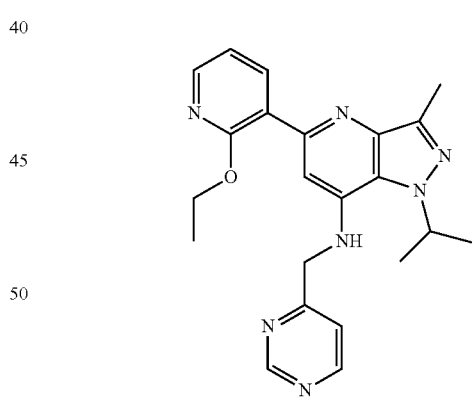

Prepared using the same procedure as described for example 1, from 5,7-dichloro-1-isopropyl-3-methyl-pyrazolo[4,3-b]pyridine, (2-ethoxy-3-pyridyl)boronic acid and pyrimidin-4-ylmethanamine.

$^1$H NMR (400 MHz, Chloroform-d) δ 9.28 (s, 1H), 8.76 (d, J=5.3 Hz, 1H), 8.27 (brd, J=7.5 Hz, 1H), 8.19 (brd, J=3.3 Hz, 1H), 7.45 (brs, 1H), 7.11 (s, 1H), 7.04 (dd, J=5.0, 6.9 Hz, 1H), 6.30 (weak br s, 1H), 5.11 (m, 1H), 4.68 (m, 2H), 4.46 (q, J=7.1 Hz, 2H), 2.68 (s, 3H), 1.72 (d, J=6.6 Hz, 6H), 1.39 (t, J=7.1 Hz, 3H). LC-MS (m/z) 404.1 (MH$^+$); $t_R$=1.89 (Method C).

Example 74: 5-(2-ethoxy-3-pyridyl)-1-isopropyl-3-methyl-N-(pyrimidin-2-ylmethyl)pyrazolo[4,3-b]pyridin-7-amine

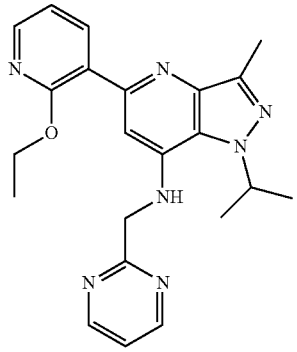

Prepared using the same procedure as described for example 1, from 5,7-dichloro-1-isopropyl-3-methyl-pyrazolo[4,3-b]pyridine, (2-ethoxy-3-pyridyl)boronic acid and pyrimidin-2-ylmethanamine.

$^1$H NMR (Chloroform-d, 400 MHz) δ 8.83 (d, J=4.8 Hz, 2H), 8.28 (dd, J=2.0, 7.2 Hz, 1H), 8.19 (dd, J=2.0, 4.8 Hz, 1H), 7.34-7.31 (m, 1H), 7.19 (s, 1H), 7.03 (dd, J=5.2, 7.6 Hz, 1H), 6.45 (brs, 1H), 5.17-5.10 (m, 1H), 4.74 (d, J=4.0 Hz, 2H), 4.50 (q, J=6.8 Hz, 2H), 2.67 (s, 3H), 1.72 (d, J=6.4 Hz, 6H), 1.46 (t, J=6.8 Hz, 3H). LC-MS (m/z) 404 (MH$^+$); $t_R$=2.20 (Method B).

Example 75: 5-(2-ethoxy-3-pyridyl)-1-isopropyl-3-methyl-N-[(4-methylpyrimidin-2-yl)methyl]pyrazolo[4,3-b]pyridin-7-amine

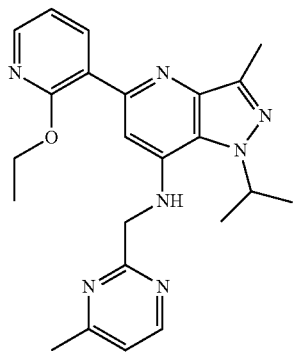

Prepared using the same procedure as described for example 1, from 5,7-dichloro-1-isopropyl-3-methyl-pyrazolo[4,3-b]pyridine, (2-ethoxy-3-pyridyl)boronic acid and (4-methylpyrimidin-2-yl)methanamine.

$^1$H NMR (Chloroform-d, 400 MHz) δ 8.65 (d, J=5.2 Hz, 1H), 8.25 (dd, J=2.0, 7.2 Hz, 1H), 8.18 (dd, J=2.0, 5.2 Hz, 1H), 7.18-7.15 (m, 2H), 7.03 (dd, J=5.2, 7.2 Hz, 1H), 6.57 (brs, 1H), 5.21-5.15 (m, 1H), 4.68 (d, J=4.0 Hz, 2H), 4.50 (q, J=7.2 Hz, 2H), 2.67 (s, 3H), 2.61 (s, 3H), 1.73 (d, J=6.4 Hz, 6H), 1.46 (t, J=7.2 Hz, 3H). LC-MS (m/z) 418.1 (MH$^+$); $t_R$=2.2 (Method C).

Example 76: 5-(2-ethoxy-3-pyridyl)-1-isopropyl-3-methyl-N-(pyrazin-2-ylmethyl)pyrazolo[4,3-b]pyridin-7-amine

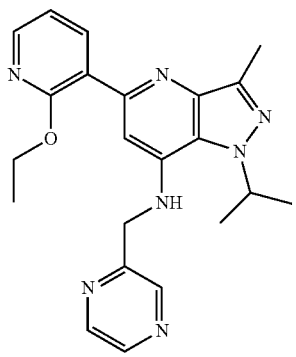

Prepared using the same procedure as described for example 1, from 5,7-dichloro-1-isopropyl-3-methyl-pyrazolo[4,3-b]pyridine, (2-ethoxy-3-pyridyl)boronic acid and pyrazin-2-ylmethanamine.

$^1$H NMR (Chloroform-d, 400 MHz) δ 8.73 (d, J=1.6 Hz, 1H), 8.63 (dd, J=2.4, 1.6 Hz, 1H), 8.59 (d, J=2.4 Hz, 1H), 8.26 (dd, J=2, 7.6 Hz, 1H), 8.18 (dd, J=2, 4.8 Hz, 1H), 7.18 (s, 1H), 7.05-7.02 (m, 1H), 6.10 (brs, 1H), 5.06-5.03 (m, 1H), 4.7 (d, J=4.0 Hz, 2H), 4.48 (q, J=7.2 Hz, 2H), 2.67 (s, 3H), 1.69 (d, J=6.4 Hz, 6H), 1.42 (t, J=7.2 Hz, 3H). LC-MS (m/z) 404.1 (MH$^+$); $t_R$=2.19 (Method B).

Example 77: 5-(2-ethoxy-3-pyridyl)-1-isopropyl-3-methyl-N-[[2-(trifluoromethyl)-3-pyridyl]methyl]pyrazolo[4,3-b]pyridin-7-amine

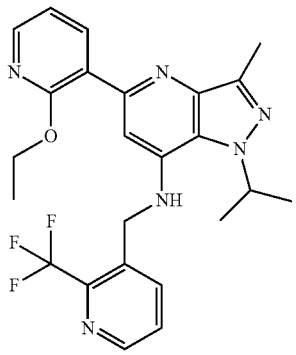

Prepared using the same procedure as described for example 1, from 5,7-dichloro-1-isopropyl-3-methyl-pyrazolo[4,3-b]pyridine, (2-ethoxy-3-pyridyl)boronic acid and (2-(trifluoromethyl)pyridin-3-yl)methanamine.

$^1$H NMR (Chloroform-d, 400 MHz) δ 8.67-8.66 (m, 1H), 8.26-8.23 (m, 1H), 8.16-8.13 (m, 1H), 7.99-7.98 (m, 1H), 7.52-7.49 (m, 1H), 7.06 (s, 1H), 7.02-6.99 (m, 1H), 4.94-4.87 (m, 4H), 4.34-4.29 (m, 2H), 2.66 (s, 3H), 1.66 (d, J=6.4 Hz, 6H), 1.17 (t, J=7.2 Hz, 3H). LC-MS (m/z) 471 (MH$^+$); $t_R$=2.1 (Method A).

Example 78: 4-[[[5-(2-ethoxy-3-pyridyl)-1-isopropyl-3-methyl-pyrazolo[4,3-b]pyridin-7-yl]amino]methyl]-1-methyl-pyridin-2-one

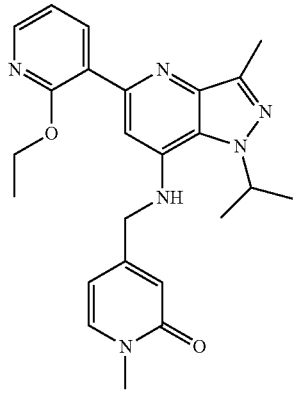 [SMILES: CCOc1ncccc1-c1cc(NCc2ccn(C)c(=O)c2)c2c(n1)c(C)nn2C(C)C]

Prepared using the same procedure as described for example 1, from 5,7-dichloro-1-isopropyl-3-methyl-pyrazolo[4,3-b]pyridine, (2-ethoxy-3-pyridyl)boronic acid and 4-(aminomethyl)-1-methylpyridin-2(1H)-one.

$^1$H NMR (Chloroform-d, 400 MHz) δ 8.23 (dd, J=1.6, 5.6 Hz, 1H), 8.16 (dd, J=2.0, 5.2 Hz, 1H), 7.29 (d, J=6.8 Hz, 1H), 7.04-7.01 (m, 2H), 6.61 (s, 1H), 6.21 (d, J=6.8 Hz, 1H), 4.89 (m, 1H), 4.44-4.39 (m, 4H), 3.54 (s, 3H), 2.65 (s, 3H), 1.66 (d, J=6.4 Hz, 6H), 1.33 (t, J=7.2 Hz, 3H). LC-MS (m/z) 433.1 (MH$^+$); $t_R$=1.88 (Method B).

Example 79: 5-(2-(ethylamino)pyridin-3-yl)-1-isopropyl-3-methyl-N-((1-methyl-1H-pyrazol-4-yl)methyl)-1H-pyrazolo[4,3-b]pyridin-7-amine

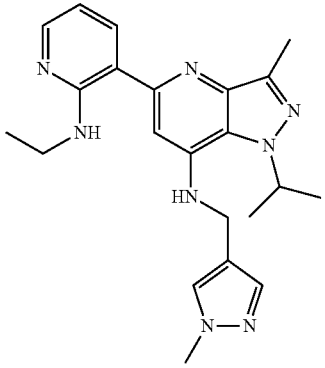 [SMILES: CCNc1ncccc1-c1cc(NCc2cnn(C)c2)c2c(n1)c(C)nn2C(C)C]

Prepared using the same procedure as described for example 1 from 5-bromo-1-isopropyl-3-methyl-N-((1-methyl-1H-pyrazol-4-yl)methyl)-1H-pyrazolo[4,3-b]pyridin-7-amine and N-ethyl-3-(4,4,5,5-tetramethyl-1,3,2-dioxaborolan-2-yl)pyridin-2-amine.

$^1$H NMR (Chloroform-d, 600 MHz) δ 9.34-9.27 (m, 1H), 8.16 (dd, J=4.9, 1.8 Hz, 1H), 7.77 (dd, J=7.6, 1.8 Hz, 1H), 7.57 (s, 1H), 7.42 (s, 1H), 6.80 (s, 1H), 6.58 (dd, J=7.5, 4.9 Hz, 1H), 4.72 (hept, J=6.6 Hz, 1H), 4.57 (t, J=5.0 Hz, 1H), 4.41 (d, J=4.7 Hz, 2H), 3.93 (s, 3H), 3.57 (qd, J=7.2, 4.6 Hz, 2H), 2.61 (s, 3H), 1.59 (d, J=6.5 Hz, 6H), 1.37 (t, J=7.2 Hz, 3H). LC-MS (m/z) 405.6 (MH$^+$); $t_R$=0.45 minutes (Method D)

Example 81: 5-(2-ethoxy-3-pyridyl)-1-isopropyl-N-[(4-methoxy-2-pyridyl)methyl]-3-methyl-pyrazolo[4,3-b]pyridin-7-amine

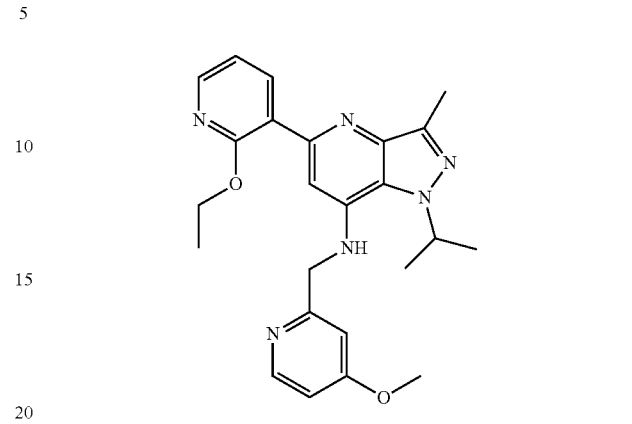

Prepared using the same procedure as described for example 1, from 5,7-dichloro-1-isopropyl-3-methyl-pyrazolo[4,3-b]pyridine, (2-ethoxy-3-pyridyl)boronic acid and (4-methoxypyridin-2-yl)methanamine.

$^1$H NMR (Chloroform-d, 400 MHz) δ 8.45 (d, J=2.4 Hz, 1H), 8.26 (d, J=7.2 Hz, 1H), 8.18 (d, J=4.4 Hz, 1H), 7.12 (s, 1H), 7.03 (dd, J=5.2, 6.8 Hz, 1H), 6.87-6.81 (m, 2H), 6.54-6.49 (m, 1H), 5.13-5.06 (m, 1H), 4.57-4.55 (m, 2H), 4.50-4.45 (m, 2H), 3.89 (s, 3H), 2.67 (s, 3H), 1.69 (d, J=6.4 Hz, 6H), 1.42 (t, J=1.6 Hz, 3H). LC-MS (m/z) 433.1 (MH$^+$); $t_R$=2.32 (Method B).

Example 82: 5-(2-ethoxy-3-pyridyl)-1-isopropyl-N-[(6-methoxypyrazin-2-yl)methyl]-3-methyl-pyrazolo[4,3-b]pyridin-7-amine

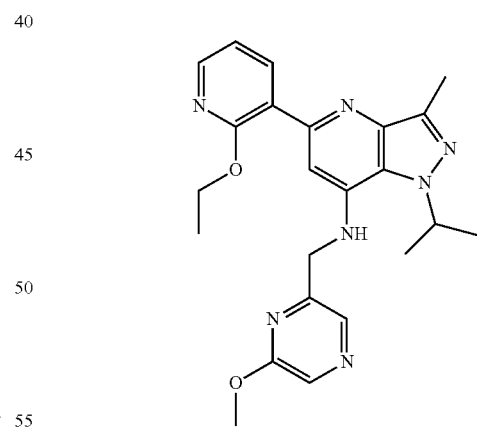

Prepared using the same procedure as described for example 1, from 5,7-dichloro-1-isopropyl-3-methyl-pyrazolo[4,3-b]pyridine, (2-ethoxy-3-pyridyl)boronic acid and (6-methoxypyrazin-2-yl)methanamine hydrochloride.

$^1$H NMR (Chloroform-d, 400 MHz) δ 8.25-8.27 (m, 2H), 8.23 (s, 1H), 8.18-8.19 (m, 1H), 7.21 (s, 1H), 7.03 (dd, J=5.2, 7.6 Hz 1H), 5.72-5.74 (m, 1H), 4.99-5.06 (s, 1H), 4.60 (d, J=4.4 Hz 2H), 4.45-4.51 (m, 2H), 4.03 (s, 3H), 2.66 (s, 3H), 1.67 (d, J=6.4 Hz, 6H), 1.42 (t, J=7.0 Hz, 3H). LC-MS (m/z) 434.1 (MH$^+$); $t_R$=1.86 (Method A).

Example 83: 5-(2-ethoxy-3-pyridyl)-N-[(5-fluoropyrimidin-2-yl)methyl]-1-isopropyl-3-methyl-pyrazolo[4,3-b]pyridin-7-amine

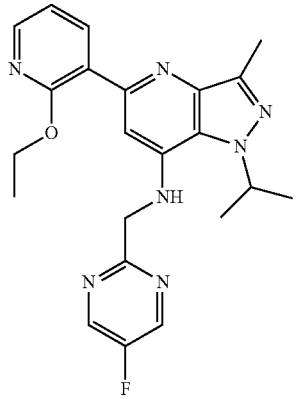 [SMILES: CCOc1ncccc1-c1cc(NCc2ncc(F)cn2)c2c(n1)c(C)nn2C(C)C]

Prepared using the same procedure as described for example 1, from 5,7-dichloro-1-isopropyl-3-methyl-pyrazolo[4,3-b]pyridine, (2-ethoxy-3-pyridyl)boronic acid and (5-fluoropyrimidin-2-yl)methanamine.

$^1$H NMR (Chloroform-d, 400 MHz) δ 8.70 (s, 2H), 8.27 (dd, J=2.0, 6.0 Hz, 1H), 8.20 (d, J=2.8 Hz, 1H), 7.18 (s, 1H), 7.04 (dd, J=4.8, 7.2 Hz, 1H), 6.25 (brs, 1H), 5.13-5.06 (m, 1H), 4.75 (d, J=4.4 Hz, 2H), 4.50 (q J=7.2 Hz, 2H), 3.69 (s, 3H), 1.71 (d, J=6.8 Hz, 6H), 1.46 (t, J=7.2 Hz, 3H) LC-MS (m/z) 422.1 (MH$^+$); $t_R$=2.2 (Method C).

Example 84: 5-(2-ethoxy-3-pyridyl)-1-isopropyl-3-methyl-N-[(2-methyl-3-pyridyl)methyl]pyrazolo[4,3-b]pyridin-7-amine

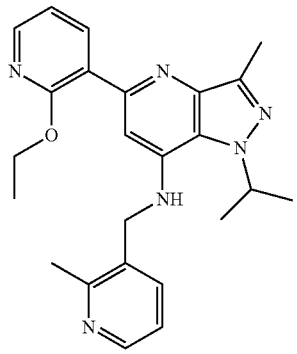 [SMILES: CCOc1ncccc1-c1cc(NCc2cccnc2C)c2c(n1)c(C)nn2C(C)C]

Prepared using the same procedure as described for example 1, from 5,7-dichloro-1-isopropyl-3-methyl-pyrazolo[4,3-b]pyridine, (2-ethoxy-3-pyridyl)boronic acid and (2-methylpyridin-3-yl)methanamine.

$^1$H NMR (Chloroform-d, 400 MHz): δ=8.50 (d, J=5.2 Hz, 1H), 8.26 (d, J=7.2 Hz, 1H), 8.16 (d, J=5.2 Hz, 1H), 7.66 (d, J=8.0 Hz, 1H), 7.19-7.16 (m, 1H), 7.14 (s, 1H), 7.03-7.00 (m, 1H), 4.83-4.78 (m, 1H), 4.68 (brs, 1H), 4.54 (d, J=5.2 Hz, 2H), 4.36 (q, J=7.2 Hz, 2H), 2.66 (s, 6H), 1.62 (d, J=6.4 Hz, 6H), 1.25 (t, J=6.8 Hz, 3H) LC-MS (m/z) 417.1 (MH$^+$); $t_R$=1.33 (Method A).

Example 85: 5-(2-ethoxy-3-pyridyl)-N-[(2-fluoro-3-pyridyl)methyl]-1-isopropyl-3-methyl-pyrazolo[4,3-b]pyridin-7-amine

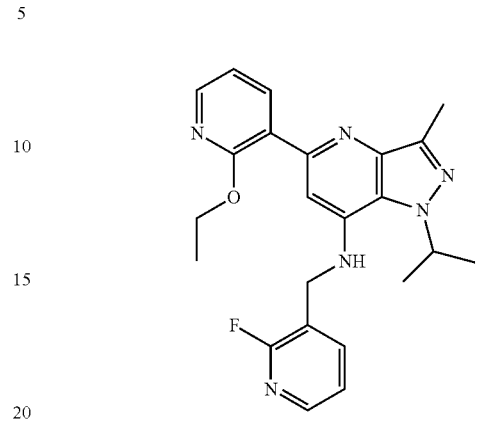

Prepared using the same procedure as described for example 1, from 5,7-dichloro-1-isopropyl-3-methyl-pyrazolo[4,3-b]pyridine, (2-ethoxy-3-pyridyl)boronic acid and (2-fluoropyridin-3-yl)methanamine.

$^1$H NMR (Chloroform-d, 400 MHz): δ 8.26-8.14 (m, 1H), 8.19-8.15 (m, 2H), 7.90-7.80 (m, 1H), 7.22-7.19 (m, 1H), 7.13 (s, 1H), 7.03-7.00 (m, 1H), 5.00-4.80 (m, 2H), 4.67-4.66 (m, 2H), 4.37 (q, J=7.2 Hz, 2H), 2.65 (s, 3H), 1.65 (d, J=6.8 Hz, 6H), 1.33 (t, J=7.2 Hz, 3H) LC-MS (m/z) 421.1 (MH$^+$); $t_R$=1.8 (Method A).

Example 86: 5-(2-ethoxy-3-pyridyl)-1-isopropyl-N-[(2-methoxy-3-pyridyl)methyl]-3-methyl-pyrazolo[4,3-b]pyridin-7-amine

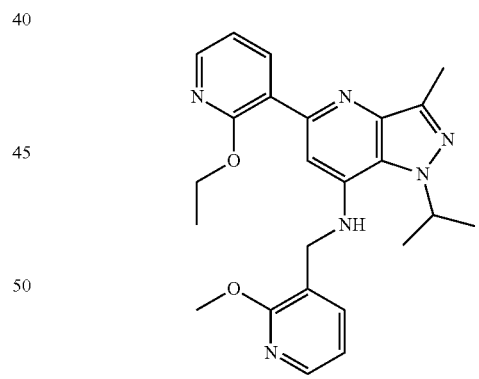

Prepared using the same procedure as described for example 1, from 5,7-dichloro-1-isopropyl-3-methyl-pyrazolo[4,3-b]pyridine, (2-ethoxy-3-pyridyl)boronic acid and (2-methoxypyridin-3-yl)methanamine.

$^1$H NMR (Chloroform-d, 400 MHz): δ 8.26-8.23 (m, 1H), 8.16-8.13 (m, 2H), 7.62-7.61 (m, 1H), 7.15 (s, 1H), 7.03-7.00 (m, 1H), 6.92-6.89 (m, 1H), 5.13-5.11 (m, 1H), 4.93-4.90 (m, 1H), 4.53-4.52 (m, 2H), 4.41 (q, J=7.2 Hz, 2H), 4.04 (s, 3H), 2.65 (s, 3H), 1.65 (d, J=6.8 Hz, 6H), 1.33 (t, J=7.2 Hz, 3H Chloroform-d, 400 MHz). LC-MS (m/z) 433 (MH$^+$); $t_R$=2.04 (Method A).

Example 87: 5-(2-ethoxy-3-pyridyl)-1-isopropyl-3-methyl-N-[(6-methyl-3-pyridyl)methyl]pyrazolo[4,3-b]pyridin-7-amine

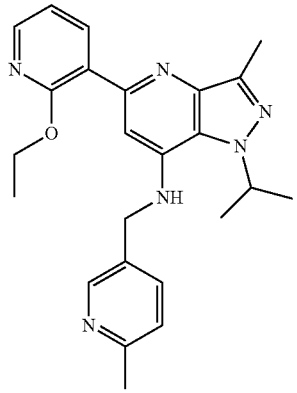 [SMILES: CCOc1ncccc1-c1cc(NCc2ccc(C)nc2)c2c(n1)c(C)nn2C(C)C]

Prepared using the same procedure as described for example 1, from 5,7-dichloro-1-isopropyl-3-methyl-pyrazolo[4,3-b]pyridine, (2-ethoxy-3-pyridyl)boronic acid and (6-methylpyridin-3-yl)methanamine $^1$H NMR (Chloroform-d, 400 MHz): δ=8.60 (s, 1H), 8.25 (brd, J=7.7 Hz, 1H), 8.17 (brd, J=4.6 Hz, 1H), 7.66 (brd, J=8.4 Hz, 1H), 7.20-7.17 (m, 1H), 7.20 (brd, J=11.5 Hz, 1H), 7.06-6.99 (m, 1H), 4.82 (s, 1H), 4.71 (s, 1H), 4.55 (br s, 2H), 4.42 (q, J=7.1 Hz, 2H), 2.65 (s, 3H), 2.59 (s, 3H), 1.62 (d, J=6.4 Hz, 6H), 1.33 (t, J=7.1 Hz, 3H). LC-MS (m/z) 417.1 (MH$^+$); t$_R$=1.36 (Method A).

Example 88: 5-(2-ethoxy-3-pyridyl)-1-isopropyl-N-[(2-methoxyphenyl)methyl]-3-methyl-pyrazolo[4,3-b]pyridin-7-amine

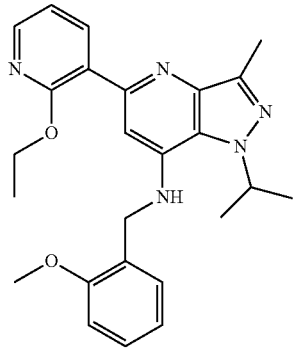 [SMILES: CCOc1ncccc1-c1cc(NCc2ccccc2OC)c2c(n1)c(C)nn2C(C)C]

Prepared using the same procedure as described for example 1, from 5,7-dichloro-1-isopropyl-3-methyl-pyrazolo[4,3-b]pyridine, (2-ethoxy-3-pyridyl)boronic acid and (2-methoxyphenyl)methanamine.

$^1$H NMR (400 MHz, Chloroform-d) δ=8.24 (d, J=7.3 Hz, 1H), 8.18-8.13 (m, 1H), 7.37-7.30 (m, 2H), 7.23 (s, 1H), 7.03-6.94 (m, 3H), 5.08 (brs, 1H), 4.89-4.81 (m, 1H), 4.53 (d, J=5.3 Hz, 2H), 4.45 (q, J=6.9 Hz, 2H), 3.90 (s, 3H), 2.64 (s, 3H), 1.62 (d, J=6.6 Hz, 6H), 1.38 (t, J=7.1 Hz, 3H). LC-MS (m/z) 432.1 (MH$^+$); t$_R$=2.19 (Method A).

Example 89: 5-(2-ethoxy-3-pyridyl)-N-[(2-fluorophenyl)methyl]-1-isopropyl-3-methyl-pyrazolo[4,3-b]pyridin-7-amine

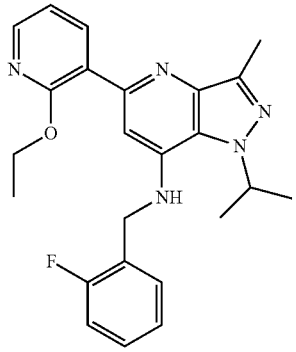

Prepared using the same procedure as described for example 1, from 5,7-dichloro-1-isopropyl-3-methyl-pyrazolo[4,3-b]pyridine, (2-ethoxy-3-pyridyl)boronic acid and (2-fluorophenyl)methanamine.

$^1$H NMR (Chloroform-d, 400 MHz): δ=8.26-8.24 (m, 1H), 8.18-8.17 (m, 1H), 7.44 (br s, J=7.7 Hz, 1H), 7.34-7.32 (m, 1H), 7.20 (s, 1H), 7.18-7.14 (m, 2H), 7.03-7.02 (m, 1H), 4.89-4.85 (m, 2H), 4.65-4.64 (m, 2H), 4.42 (q, J=7.2 Hz, 2H), 2.65 (s, 3H), 1.64 (d, J=6.4 Hz, 6H), 1.33 (t, J=6.8 Hz, 3H). LC-MS (m/z) 420 (MH$^+$); t$_R$=2.14 (Method A)

Example 90: 5-(2-ethoxy-3-pyridyl)-1-isopropyl-3-methyl-N-[[2-(trifluoromethyl)phenyl]methyl]pyrazolo[4,3-b]pyridin-7-amine

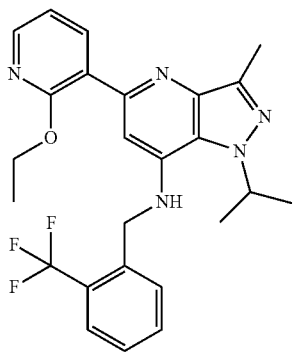 [SMILES: CCOc1ncccc1-c1cc(NCc2ccccc2C(F)(F)F)c2c(n1)c(C)nn2C(C)C]

Prepared using the same procedure as described for example 1, from 5,7-dichloro-1-isopropyl-3-methyl-pyrazolo[4,3-b]pyridine, (2-ethoxy-3-pyridyl)boronic acid and (2-(trifluoromethyl)phenyl)methanamine.

$^1$H NMR (Chloroform-d, 400 MHz): δ 8.34-8.22 (m, 1H), 8.17-8.15 (m, 1H), 7.75 (d, J=7.6 Hz, 1H), 7.63 (d, J=8.0 Hz, 1H), 7.55 (t, J=6.4 Hz, 1H), 7.45 (t, J=7.6 Hz, 1H), 7.11 (s, 1H), 7.03-6.99 (m, 1H), 4.91-4.86 (m, 1H), 4.82 (br s, 2H), 4.35 (q, J=7.2 Hz, 2H), 2.66 (s, 3H), 1.62 (d, J=6.4 Hz, 6H), 1.23 (t, J=6.8 Hz, 3H). LC-MS (m/z) 470 (MH$^+$); t$_R$=1.87 (Method I)

Example 91: 5-(2-ethoxy-3-pyridyl)-1-isopropyl-N-[(3-methoxypyrazin-2-yl)methyl]-3-methyl-pyrazolo[4,3-b]pyridin-7-amine

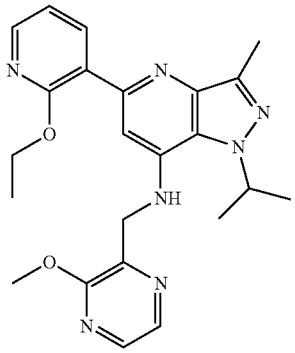

Prepared using the same procedure as described for example 1, from 5,7-dichloro-1-isopropyl-3-methyl-pyrazolo[4,3-b]pyridine, (2-ethoxy-3-pyridyl)boronic acid and (3-methoxypyrazin-2-yl)methanamine hydrochloride.

$^1$H NMR (Chloroform-d, 400 MHz): δ 8.34-8.32 (m, 1H), 8.20-8.12 (m, 3H), 7.30 (s, 1H), 7.04 (dd, J=7.6, 4.8 Hz, 1H), 6.53 (brs, 1H), 5.14-5.08 (m, 1H), 4.58 (d, J=4.0 Hz 2H), 4.52 (q, J=7.2 Hz, 2H), 4.08 (s, 3H), 2.67 (s, 3H), 1.71 (d, J=6.8 Hz, 6H), 1.51 (t, J=7.2 Hz, 3H). LC-MS (m/z) 434.1 (MH$^+$); t$_R$=2.01 (Method A).

Example 92: 5-(2-ethoxy-3-pyridyl)-1-isopropyl-N-[(4-methoxy-3-pyridyl)methyl]-3-methyl-pyrazolo[4,3-b]pyridin-7-amine

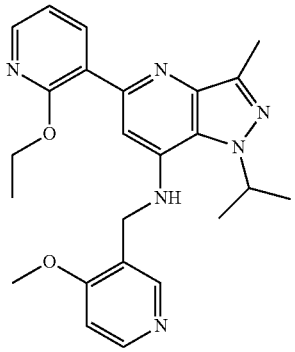 [SMILES: CCOc1ncccc1-c1cc(NCc2cnccc2OC)c2c(n1)c(C)nn2C(C)C]

Prepared using the same procedure as described for example 1, from 5,7-dichloro-1-isopropyl-3-methyl-pyrazolo[4,3-b]pyridine, (2-ethoxy-3-pyridyl)boronic acid and (4-methoxy-3-pyridyl)methanamine.

$^1$H NMR (Chloroform-d, 400 MHz) δ=8.53-8.50 (m, 2H), 8.24 (dd, J=1.6, 7.2 Hz, 1H), 8.17 (dd, J=2.8, 4.8 Hz, 1H), 7.23 (s, 1H), 7.05-7.00 (m, 1H), 6.89 (d, J=6.0 Hz, 1H), 4.95 (brs, 1H), 4.87-4.81 (m, 1H), 4.54 (d, J=6.4 Hz, 2H), 4.47 (q, J=7.8 Hz, 2H), 3.95 (s, 3H), 2.65 (s, 3H), 1.62 (d, J=6.4 Hz, 6H), 1.39 (t, J=7.8 Hz, 3H). LC-MS (m/z) 433.1 (MH$^+$); t$_R$=1.39 (Method A).

Example 93: 1-isopropyl-3-methyl-N-[(2-methyltetrazol-5-yl)methyl]-5-(2-propoxy-3-pyridyl)pyrazolo[4,3-b]pyridin-7-amine

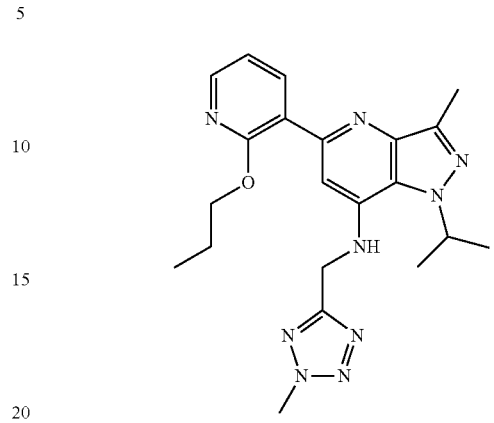

Prepared using the same procedure as described for example 1, from 5,7-dichloro-1-isopropyl-3-methyl-pyrazolo[4,3-b]pyridine, (2-propoxy-3-pyridyl)boronic acid and (2-methyl-2H-tetrazol-5-yl)methanamine.

$^1$H NMR (Chloroform-d, 400 MHz): δ=8.26-8.19 (m, 2H), 7.22 (s, 1H), 7.06-7.03 (m, 1H), 5.48 (br. s, 1H), 4.99-4.91 (m, 1H), 4.81 (d, J=3.2 Hz, 2H), 4.41-4.38 (m, 5H), 2.65 (s, 3H), 1.88-1.82 (m, 2H), 1.67 (d, J=6.4 Hz, 6H) 1.06 (t, J=7.2 Hz, 3H). LC-MS (m/z) 422.1 (MH$^+$); t$_R$=2.04 (Method C).

Example 94: 1-isopropyl-3-methyl-N-[(1-methylpyrazol-4-yl)methyl]-5-(2-propoxy-3-pyridyl)pyrazolo[4,3-b]pyridin-7-amine

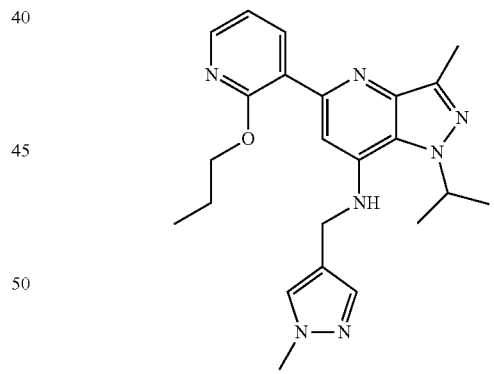

Prepared using the same procedure as described for example 1, from 5,7-dichloro-1-isopropyl-3-methyl-pyrazolo[4,3-b]pyridine, 2-propoxy-3-(4,4,5,5-tetramethyl-1,3,2-dioxaborolan-2-yl)pyridine and (1-methyl-1H-pyrazol-4-yl)methanamine.

$^1$H NMR (Chloroform-d, 400 MHz): δ 8.26 (dd, J=2.0, 7.6 Hz, 1H), 8.18 (dd, J=0.0, 5.2 Hz, 1H), 7.57 (s, 1H), 7.44 (s, 1H), 7.22 (s, 1H), 7.03 (dd, J=4.8, 7.2 Hz, 1H), 4.84-4.67 (m, 1H), 4.48 (brs, 1H), 4.40-4.33 (m, 4H), 3.94 (s, 3H), 2.65 (s, 3H), 1.89-1.74 (m, 2H), 1.59 (d, J=6.8 Hz, 6H), 1.03 (t, J=7.6 Hz, 3H). LC-MS (m/z) 420.4 (MH$^+$); t$_R$=0.59 (Method D).

Example 95: 1-isopropyl-5-(2-methoxy-3-pyridyl)-N-[(2-methoxy-3-pyridyl)methyl]-3-methyl-pyrazolo[4,3-b]pyridin-7-amine

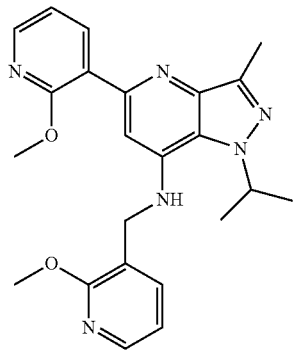 [SMILES: COc1ncccc1CNc1cc(-c2cccnc2OC)nc2c(C)nn(C(C)C)c12]

Prepared using the same procedure as described for example 1, from 5,7-dibromo-1-isopropyl-3-methyl-1H-pyrazolo[4,3-b]pyridine, (2-methoxypyridin-3-yl)boronic acid and (2-methoxypyridin-3-yl)methanamine.

¹H NMR (Chloroform-d, 400 MHz): δ 8.20-8.18 (m, 1H), 8.16-8.14 (m, 2H), 7.64-7.62 (m, 1H), 7.04-7.03 (m, 1H), 6.97 (s, 1H), 6.93-6.92 (m, 1H), 5.24-5.21 (m, 1H), 4.93-4.87 (m, 1H), 4.51 (d, J=5.6 Hz, 2H), 4.04 (s, 3H), 3.89 (s, 3H), 2.64 (s, 3H), 1.65 (d, J=6.4 Hz, 6H). LC-MS (m/z) 419.1 (MH⁺); $t_R$=1.82 (Method A).

Example 96: 1-isopropyl-5-(2-methoxy-3-pyridyl)-N-[(6-methoxy-3-pyridyl)methyl]-3-methyl-pyrazolo[4,3-b]pyridin-7-amine

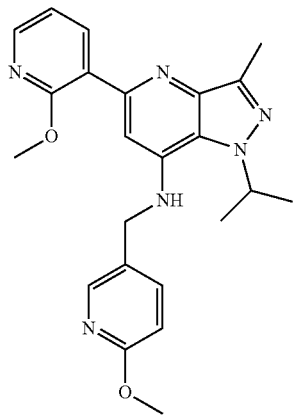 [SMILES: COc1ccc(CNc2cc(-c3cccnc3OC)nc3c(C)nn(C(C)C)c23)cn1]

Prepared using the same procedure as described for example 1, from 5,7-dibromo-1-isopropyl-3-methyl-1H-pyrazolo[4,3-b]pyridine, (2-methoxypyridin-3-yl)boronic acid and (6-methoxy-3-pyridyl) methanamine.

¹H NMR (Chloroform-d, 400 MHz): δ 8.26 (d, J=1.6 Hz, 1H), 8.16-8.21 (m, 2H), 7.67 (dd, J=2.4, 8.4 Hz, 1H), 7.02-7.07 (m, 2H), 6.80 (d, J=8.8 Hz, 1H), 4.76-4.82 (m, 1H), 4.69 (brs, 1H), 4.47 (d, J=5.2 Hz, 2H), 3.96 (s, 3H), 3.94 (s, 3H), 2.65 (s, 3H), 1.61 (d, J=6.4 Hz, 6H). LC-MS (m/z) 419 (MH⁺); $t_R$=1.83 (Method A).

Example 97: 5-(2-isopropoxy-3-pyridyl)-1-isopropyl-3-methyl-N-[(1-methylpyrazol-4-yl)methyl]pyrazolo[4,3-b]pyridin-7-amine

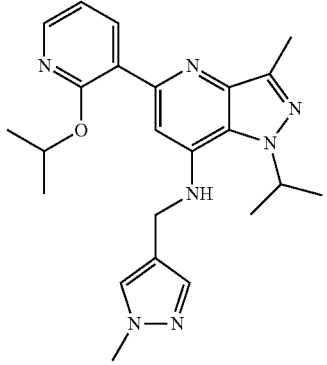 [SMILES: Cc1nn(C(C)C)c2c(NCc3cnn(C)c3)cc(-c3cccnc3OC(C)C)nc12]

Prepared using the same procedure as described for example 29, from 5-(2-isopropoxypyridin-3-yl)-1-isopropyl-3-methyl-1H-pyrazolo[4,3-b]pyridin-7-amine and 1-methyl-1H-pyrazole-4-carbaldehyde.

¹H NMR (600 MHz, DMSO) δ 8.21-8.09 (m, 2H), 7.58 (d, J=9.7 Hz, 1H), 7.38 (s, 1H), 7.08 (s, 1H), 7.06 (dd, J=7.3, 4.9 Hz, 1H), 6.67 (t, J=5.5 Hz, 1H), 5.44-5.33 (m, 1H), 5.16 (dt, J=12.7, 6.4 Hz, 1H), 4.36 (d, J=5.5 Hz, 2H), 3.76 (s, 3H), 2.46 (s, 3H), 1.45 (d, J=6.4 Hz, 6H), 1.23 (d, J=6.2 Hz, 6H). LC-MS (m/z) 420.4 (MH⁺); $t_R$=0.52 (Method E).

Example 98: 5-(2-ethoxy-3-pyridyl)-1-isopropyl-3-methyl-N-(1H-1,2,4-triazol-3-ylmethyl)pyrazolo[4,3-b]pyridin-7-amine

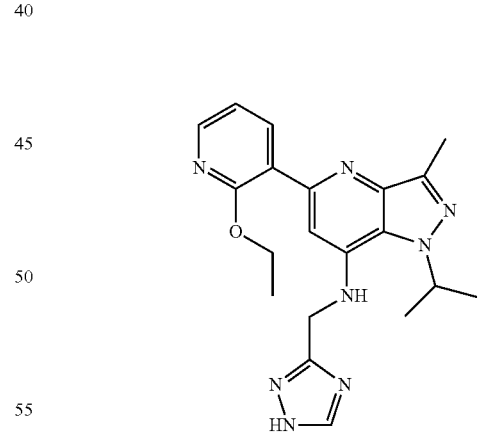

Prepared using the same procedure as described for example 29, from 5-(2-ethoxypyridin-3-yl)-1-isopropyl-3-methyl-1H-pyrazolo[4,3-b]pyridin-7-amine and 1H-1,2,4-triazole-3-carbaldehyde.

¹H NMR (Chloroform-d, 400 MHz): δ 8.21-8.17 (m, 2H), 8.12 (s, 1H), 7.15 (s, 1H), 7.02-6.99 (m, 1H), 5.60 (brs, 1H), 4.99-4.93 (m, 1H), 4.65 (s, 2H), 4.46 (q, J=7.2 Hz, 2H), 2.65 (s, 3H), 1.65 (d, J=6.4 Hz, 6H), 1.39 (t, J=7.2 Hz, 3H). LC-MS (m/z) 393.1 (MH⁺); $t_R$=2.3 (Method C).

Example 99: 5-(2-ethoxy-3-pyridyl)-1-isopropyl-3-methyl-N-(2H-tetrazol-5-ylmethyl)pyrazolo[4,3-b]pyridin-7-amine

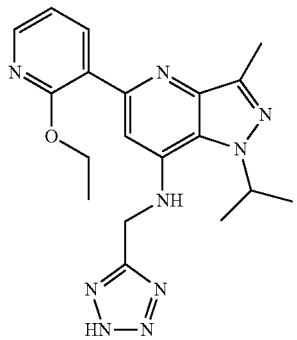 [SMILES: CCOc1ncccc1-c1cc(NCc2nn[nH]n2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 2H-tetrazole-5-carbaldehyde.

$^1$H NMR (DMSO-$d_6$ 400 MHz): δ 8.17-8.13 (m, 2H), 7.09-7.05 (m, 1H), 6.99 (s, 1H), 6.91 (br. s, 1H), 5.20-5.14 (m, 1H), 4.79 (d, J=5.2 Hz, 2H), 4.30 (q, J=6.8 Hz, 2H), 2.47 (s, 3H), 1.49 (d, J=6.4 Hz, 6H), 1.22 (t, J=6.8 Hz, 3H). LC-MS (m/z) 394 (MH$^+$); $t_R$=1.77 (Method C).

Example 100: 5-(2-ethoxy-3-pyridyl)-1-isopropyl-3-methyl-N-(2-pyridylmethyl)pyrazolo[4,3-b]pyridin-7-amine

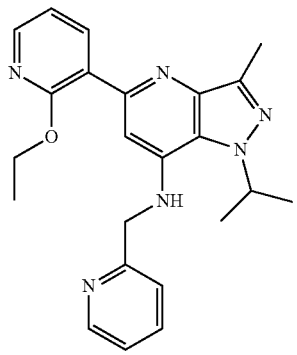 [SMILES: CCOc1ncccc1-c1cc(NCc2ccccn2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and picolinaldehyde.

$^1$H NMR (Chloroform-d, 400 MHz): δ 8.66-8.64 (m, 1H), 8.26 (dd, J=2.0, 7.2 Hz, 1H), 8.18 (dd, J=2.0, 4.8 Hz, 1H), 7.77-7.72 (m, 1H), 7.38-7.36 (m, 1H), 7.30-7.28 (m, 1H), 7.14 (s, 1H), 7.03 (dd, J=4.8, 7.2 Hz, 1H), 6.53 (brs, 1H), 5.15-5.08 (m, 1H), 4.62 (d, J=4.0 Hz, 2H), 4.48 (q, J=6.8 Hz, 2H), 2.67 (s, 3H), 1.70 (d, J=6.8 Hz, 6H), 1.42 (t, J=7.2 Hz, 3H). LC-MS (m/z) 403.1 (MH$^+$); $t_R$=2.15 (Method A).

Example 101: 5-(2-ethoxy-3-pyridyl)-1-isopropyl-3-methyl-N-[(6-methyl-2-pyridyl)methyl]pyrazolo[4,3-b]pyridin-7-amine

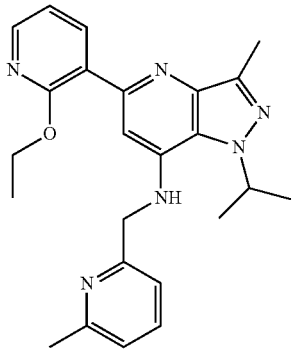 [SMILES: CCOc1ncccc1-c1cc(NCc2cccc(C)n2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 6-methylpicolinaldehyde.

$^1$H NMR (Chloroform-d, 400 MHz): δ 8.27-8.26 (m, 1H), 8.19-8.18 (m, 1H), 7.66-7.62 (m, 1H), 7.18-7.14 (m, 2H), 7.11 (s, 1H), 7.04 (dd, J=4.8, 7.2 Hz, 1H), 6.84 (brs, 1H), 5.22-5.19 (m, 1H), 4.57 (d, J=3.6 Hz, 2H), 4.49 (q, J=6.8 Hz, 2H), 2.68 (s, 3H), 2.61 (s, 3H), 1.73 (d, J=6.4 Hz, 6H), 1.43 (t, J=7.2 Hz, 3H). LC-MS (m/z) 417.1 (MH$^+$); $t_R$=2.04 (Method A).

Example 102: 5-(2-ethoxy-3-pyridyl)-1-isopropyl-N-[(6-methoxy-2-pyridyl)methyl]-3-methyl-pyrazolo[4,3-b]pyridin-7-amine

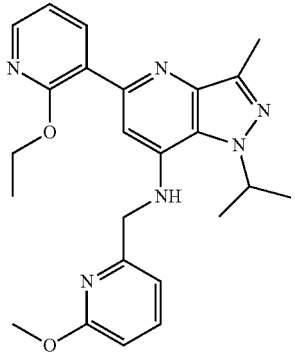

Prepared using the same procedure as described for example 29, from 5-(2-ethoxypyridin-3-yl)-1-isopropyl-3-methyl-1H-pyrazolo[4,3-b]pyridin-7-amine and 6-methoxypicolinaldehyde.

$^1$H NMR (Chloroform-d, 400 MHz): δ 8.28-8.26 (m, 1H), 8.19-8.18 (m, 1H), 7.65-7.61 (m, 1H), 7.17 (s, 1H), 7.05-7.02 (m, 1H), 6.96-6.94 (m, 1H), 6.75-6.72 (m, 1H), 6.17 (brs, 1H), 5.11-5.08 (m, 1H), 4.55-4.46 (m, 4H), 4.01 (s, 3H), 2.67 (s, 3H), 1.66 (d, J=6.0 Hz, 6H), 1.43 (t, J=7.2 Hz, 3H). LC-MS (m/z) 433.1 (MH$^+$); $t_R$=2.47 (Method A).

Example 103: 5-(2-ethoxy-3-pyridyl)-1-isopropyl-3-methyl-N-[(2-methyl-4-pyridyl)methyl]pyrazolo[4,3-b]pyridin-7-amine

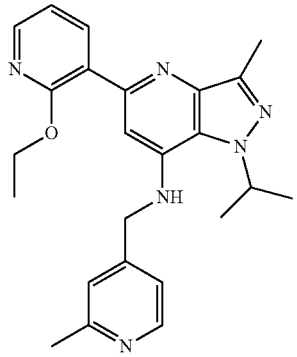 [SMILES: CCOc1ncccc1-c1cc(NCc2ccnc(C)c2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 2-methyl-isonicotinaldehyde.

$^1$H NMR (Chloroform-d, 400 MHz): δ 8.50 (d, J=5.2 Hz, 1H), 8.22 (dd, J=2.0, 7.2 Hz, 1H), 8.15 (dd, J=2.0, 4.2 Hz, 1H), 7.20 (s, 1H), 7.15 (d, J=5.2 Hz, 1H), 7.03 (s, 1H), 7.00 (dd, J=5.2, 7.6 Hz, 1H), 4.91-4.86 (m, 2H), 4.57 (d, J=5.2 Hz, 2H), 4.32 (q, J=7.2 Hz, 2H), 2.66 (s, 3H), 2.57 (s, 3H), 1.67 (d, J=6.4 Hz, 6H), 1.21 (t, J=7.2 Hz, 3H). LC-MS (m/z) 417.1 (MH$^+$); $t_R$=1.53 (Method A).

Example 104: 5-(2-ethoxy-3-pyridyl)-1-isopropyl-N-[(2-methoxy-4-pyridyl)methyl]-3-methyl-pyrazolo[4,3-b]pyridin-7-amine

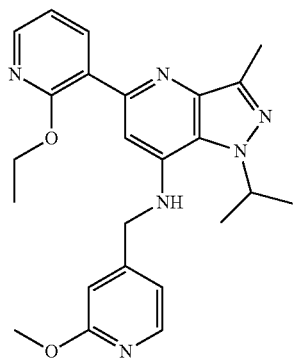 [SMILES: CCOc1ncccc1-c1cc(NCc2ccnc(OC)c2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 2-methoxy-isonicotinaldehyde.

$^1$H NMR (Chloroform-d, 400 MHz): δ 8.22 (d, J=7.6 Hz, 1H), 8.18-8.14 (m, 2H), 7.04 (s, 1H), 7 (dd, J=5.2, 7.6 Hz 1H), 6.92 (d, J=5.2 Hz 1H), 6.79 (s, 1H), 4.89-4.86 (m, 2H), 4.56 (d, J=5.2 Hz, 2H), 4.34 (q, J=7.2 Hz, 2H), 3.94 (s, 3H), 2.66 (s, 3H), 1.66 (d, J=6.8 Hz, 6H), 1.24 (t, J=7.2 Hz, 3H). LC-MS (m/z) 433.1 (MH$^+$); $t_R$=1.94 (Method A).

Example 105: 5-(2-ethoxy-3-pyridyl)-1-isopropyl-3-methyl-N-[(2-methylpyrimidin-4-yl)methyl]pyrazolo[4,3-b]pyridin-7-amine

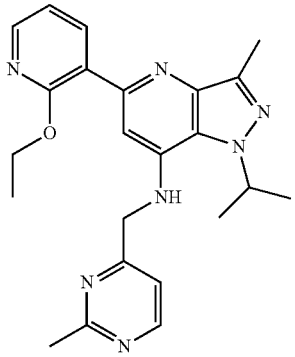 [SMILES: CCOc1ncccc1-c1cc(NCc2ccnc(C)n2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 2-methyl-pyrimidine-4-carbaldehyde.

$^1$H NMR (Chloroform-d, 400 MHz): δ 8.65 (d, J=5.2 Hz, 1H), 8.26 (dd, J=2.0, 7.6 Hz, 1H), 8.18 (dd, J=2.0, 7.6 Hz, 1H), 7.20 (d, J=5.2 Hz, 1H), 7.09 (s, 1H), 7.05-7.02 (m, 1H), 6.45 (brs, 1H), 5.16-5.13 (m, 1H), 4.59 (d, J=4.0 Hz, 2H), 4.46 (q, J=7.2 Hz, 2H), 2.81 (s, 3H), 2.67 (s, 3H), 1.73 (d, J=6.4 Hz, 6H), 1.40 (t, J=7.2 Hz, 3H). LC-MS (m/z) 418.1 (MH$^+$); $t_R$=1.96 (Method C)

Example 106: 5-(2-ethoxy-3-pyridyl)-1-isopropyl-N-[(5-methoxy-3-pyridyl)methyl]-3-methyl-pyrazolo[4,3-b]pyridin-7-amine

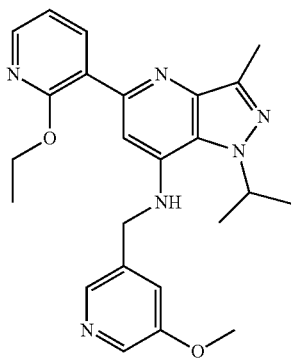 [SMILES: CCOc1ncccc1-c1cc(NCc2cncc(OC)c2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 5-methoxynicotinaldehyde.

$^1$H NMR (Chloroform-d, 400 MHz): δ 8.24 (s, 1H), 8.19-8.18 (m, 1H), 8.14-8.12 (m, 2H), 7.38 (s, 1H), 7.10-7.03 (m, 1H), 7.02-6.97 (m, 1H), 6.94 (s, 1H), 5.27-5.21 (m, 1H), 4.58 (d, J=4.8 Hz, 2H), 4.24 (q, J=7.2 Hz, 2H), 3.78 (s, 3H), 2.46 (s, 3H), 1.48 (d, J=6.0 Hz, 6H), 1.10 (t, J=6.8 Hz, 3H). LC-MS (m/z) 433.1 (MH$^+$); $t_R$=1.63 (Method A).

Example 107: 5-(2-ethoxy-3-pyridyl)-1-isopropyl-3-methyl-N-[[6-(trifluoromethyl)-2-pyridyl]methyl]pyrazolo[4,3-b]pyridin-7-amine

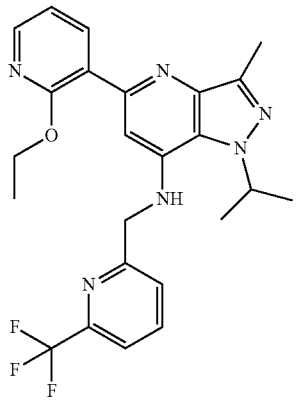 [SMILES: CCOc1ncccc1-c1cc(NCc2cccc(C(F)(F)F)n2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 6-(trifluoromethyl)picolinaldehyde.

$^1$H NMR (Chloroform-d, 400 MHz): δ 8.27 (dd, J=2.0, 7.2 Hz, 1H), 8.18 (dd, J=4.8, 2.0 Hz 1H), 8.00-7.95 (m, 1H), 7.71 (d, J=7.6 Hz, 1H), 7.59 (d, J=7.6 Hz, 1H), 7.13 (s, 1H), 7.04 (dd, J=7.2, 4.8 Hz, 1H), 6.68 (brs, 1H), 5.19-5.16 (m, 1H), 4.70 (d, J=3.6 Hz, 2H), 4.49 (q, J=7.2 Hz, 2H), 2.67 (s, 3H), 1.71 (d, J=6.4 Hz, 6H), 1.44 (t, J=7.2 Hz, 3H). LC-MS (m/z) 471 (MH$^+$); $t_R$=2.34 (Method A).

Example 108: 3-[[[5-(2-ethoxy-3-pyridyl)-1-isopropyl-3-methyl-pyrazolo[4,3-b]pyridin-7-yl]amino]methyl]-1-methyl-pyridin-2-one

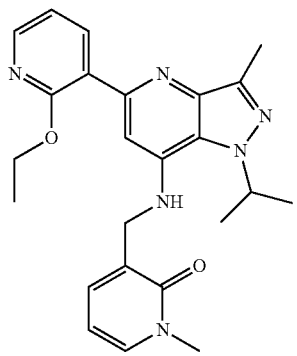 [SMILES: CCOc1ncccc1-c1cc(NCc2cccn(C)c2=O)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 1-methyl-2-oxo-1,2-dihydropyridine-3-carbaldehyde.

$^1$H NMR (Chloroform-d, 400 MHz): δ 8.31-8.24 (m, 1H), 8.19-8.17 (m, 1H), 7.50-7.42 (m, 1H), 7.30-7.28 (m, 1H), 7.15 (s, 1H), 7.05-7.02 (m, 1H), 6.21-6.17 (m, 1H), 5.06-4.95 (m, 1H), 4.51-4.45 (m, 4H), 3.59 (s, 3H), 2.65 (s, 3H), 1.64 (d, J=6.8 Hz, 6H), 1.40 (t, J=7.2 Hz, 3H). LC-MS (m/z) 433 (MH$^+$); $t_R$=1.93 (Method C).

Example 109: 5-(2-ethoxy-3-pyridyl)-N-[(1-ethylpyrazol-4-yl)methyl]-1-isopropyl-3-methyl-pyrazolo[4,3-b]pyridin-7-amine

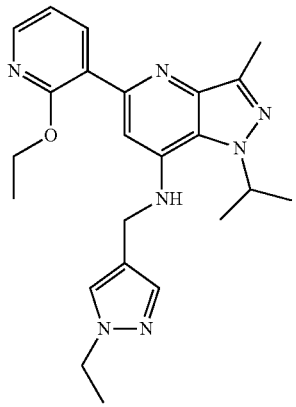 [SMILES: CCOc1ncccc1-c1cc(NCc2cnn(CC)c2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 1-ethyl-1H-pyrazole-4-carbaldehyde.

$^1$H NMR (Chloroform-d, 400 MHz): δ 8.28 (dd, J=7.6, 2.0 Hz, 1H), 8.18 (dd, J=4.8, 1.6 Hz, 1H), 7.59 (s, 1H), 7.48 (s, 1H), 7.25 (s, 1H), 7.03 (dd, J=7.6, 5.2 Hz, 1H), 4.77-4.50 (m, 1H), 4.52-4.45 (m, 3H), 4.39 (d, J=4.8 Hz, 2H), 4.2 (q, J=7.2 Hz, 2H), 2.65 (s, 3H), 1.59 (d, J=6.8 Hz, 6H), 1.52 (t, J=7.2 Hz, 3H), 1.40 (t, J=6.8 Hz, 3H). LC-MS (m/z) 420.1 (MH$^+$); $t_R$=2.13 (Method F).

Example 110: 5-(2-ethoxy-3-pyridyl)-1-isopropyl-3-methyl-N-[(1-propylpyrazol-4-yl)methyl]pyrazolo[4,3-b]pyridin-7-amine

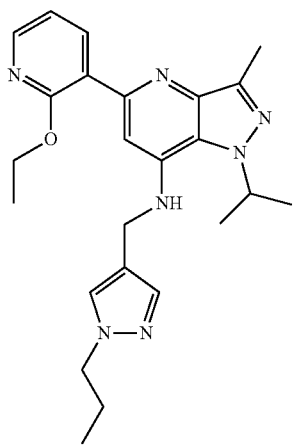 [SMILES: CCCn1cc(CNc2cc(-c3cccnc3OCC)nc3c(C)nn(C(C)C)c23)cn1]

Prepared using the same procedure as described for example 29, from 5-(2-ethoxypyridin-3-yl)-1-isopropyl-3-methyl-1H-pyrazolo[4,3-b]pyridin-7-amine and 1-propyl-1H-pyrazole-4-carbaldehyde.

$^1$H NMR (Chloroform-d, 400 MHz): δ 8.27 (dd, J=2.0, 7.2 Hz, 1H), 8.18 (dd, J=2.0, 5.2 Hz, 1H), 7.59 (s, 1H), 7.45 (s, 1H), 7.24 (s, 1H), 7.03 (dd, J=4.8, 7.2 Hz, 1H), 4.77-4.74 (m, 1H), 4.48 (q, J=7.2 Hz, 3H), 4.39 (d, J=4.4 Hz, 2H), 4.09

(t, J=7.2 Hz, 2H), 2.65 (s, 3H), 1.94-1.88 (m, 2H), 1.59 (d, J=6.4 Hz, 6H), 1.4 (t, J=6.8 Hz, 3H), 0.93 (t, J=7.2 Hz, 3H). LC-MS (m/z) 434.1 (MH+); $t_R$=1.89 (Method A).

Example 111: 5-(2-ethoxy-3-pyridyl)-1-isopropyl-N-[(6-methoxy-3-pyridyl)methyl]-3-methyl-pyrazolo[4,3-b]pyridin-7-amine

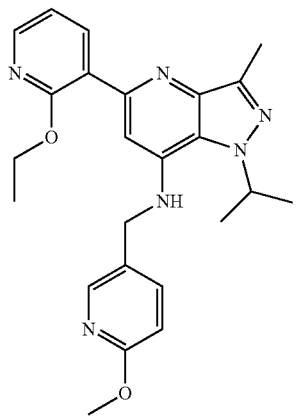 [SMILES: CCOc1ncccc1-c1cc(NCc2ccc(OC)nc2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 6-methoxynicotinaldehyde.

$^1$H NMR (Chloroform-d, 400 MHz): δ 8.30-8.24 (m, 2H), 8.20-8.15 (m, 1H), 7.67 (d, J=8.0 Hz, 1H), 7.21 (s, 1H), 7.04-7.01 (m, 1H), 6.80 (d, J=8.0 Hz, 1H), 4.80 (dd, J=4.8, 6.4 Hz, 1H), 4.65 (brs, 1H), 4.49-4.42 (m, 4H), 3.96 (s, 3H), 2.66 (s, 3H), 1.59 (d, J=4.8 Hz, 6H), 1.40-1.34 (m, 3H). LC-MS (m/z) 433.1 (MH+); $t_R$=2.33 (Method F).

Example 112: 5-(2-ethoxy-3-pyridyl)-1-isopropyl-N-[(5-methoxy-2-pyridyl)methyl]-3-methyl-pyrazolo[4,3-b]pyridin-7-amine

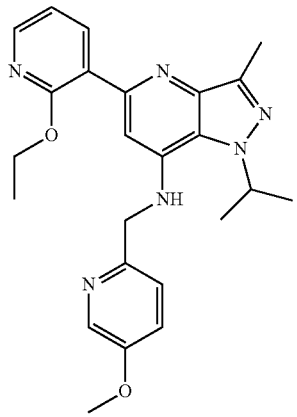 [SMILES: CCOc1ncccc1-c1cc(NCc2ccc(OC)cn2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 5-methoxypicolinaldehyde.

$^1$H NMR (Chloroform-d, 400 MHz): δ 8.33 (d, J=1.6 Hz, 1H), 8.26 (dd, J=2.0, 7.6 Hz, 1H), 8.18 (dd, J=2.0, 4.8 Hz, 1H), 7.31-7.28 (m, 2H), 7.13 (s, 1H), 7.03 (dd, J=7.2, 7.6 Hz, 1H), 6.36 (s, 1H), 5.11-5.05 (m, 1H), 4.56 (d, J=4.4 Hz, 2H), 4.48 (q, J=7.2 Hz, 2H), 3.91 (s, 3H), 2.66 (s, 3H), 1.69 (d, J=7.2 Hz, 6H), 1.42 (t, J=7.2 Hz, 3H). LC-MS (m/z) 433.1 (MH+); $t_R$=2.14 (Method A).

Example 113: 5-(2-ethoxy-3-pyridyl)-3-methyl-N-[(2-methylthiazol-4-yl)methyl]-1-(oxetan-3-yl)pyrazolo[4,3-b]pyridin-7-amine

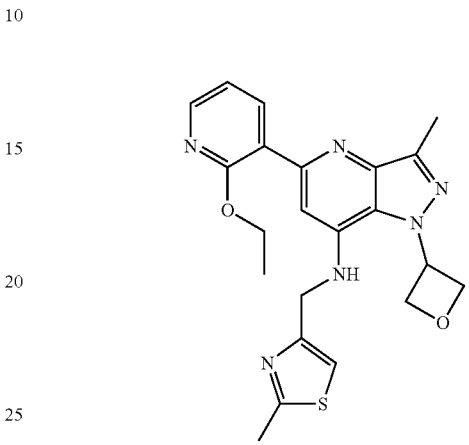

Prepared using the same procedure as described for example 1, from 5,7-dibromo-3-methyl-1-(oxetan-3-yl)pyrazolo[4,3-b]pyridine, (2-ethoxy-3-pyridyl)boronic acid and (2-methylthiazol-4-yl)methanamine.

$^1$H NMR (Chloroform-d, 400 MHz) δ 8.26 (dd, J=1.6, 7.2 Hz 1H), 8.18 (dd, J=2.0, 4.8 Hz 1H), 7.24 (s, 1H), 7.05-7.02 (m, 2H), 5.94-5.85 (m, 2H), 5.28-5.25 (m, 2H), 5.20-5.16 (m, 2H), 4.57 (d, J=5.2 Hz, 2H), 4.46 (q, J=7.2 Hz, 2H), 2.76 (s, 3H), 2.66 (s, 3H), 1.39 (t, J=7.2 Hz, 3H). LC-MS (m/z) 437.4 (MH+); $t_R$=0.46 minutes (Method E).

Example 114: 5-(2-ethoxy-3-pyridyl)-1-isopropyl-N-[(5-methoxypyrazin-2-yl)methyl]-3-methyl-pyrazolo[4,3-b]pyridin-7-amine

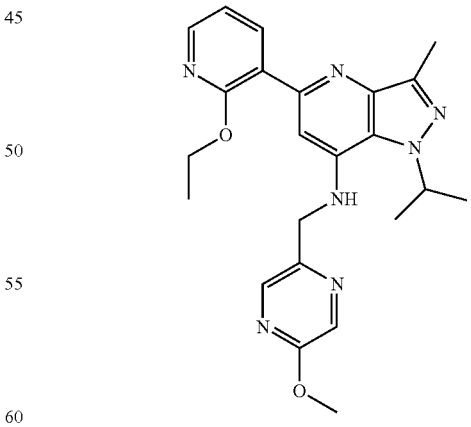

Prepared using the same procedure as described for example 29, from 5-(2-ethoxypyridin-3-yl)-1-isopropyl-3-methyl-1H-pyrazolo[4,3-b]pyridin-7-amine and 5-methoxypyrazine-2-carbaldehyde.

$^1$H NMR (400 MHz, Chloroform-d): δ 8.24-8.28 (m, 2H), 8.16-8.23 (m, 2H), 7.18 (s, 1H), 7.04 (brt, J=5.84 Hz, 1H), 5.80 (brs, 1H), 4.93-5.06 (m, 1H), 4.60 (brd, J=3.75 Hz, 2H), 4.48 (q, J=6.69 Hz, 2H), 4.00 (s, 3H), 2.66 (s, 3H), 1.66 (brd, J=6.39 Hz, 6H), 1.41 (t, J=6.95 Hz, 3H). LC-MS (m/z) 434.1 (MH⁺); $t_R$=1.99 (Method A).

Example 115: 5-(2-ethoxy-3-pyridyl)-1-isopropyl-3-methyl-N-(3-pyridylmethyl)pyrazolo[4,3-b]pyridin-7-amine

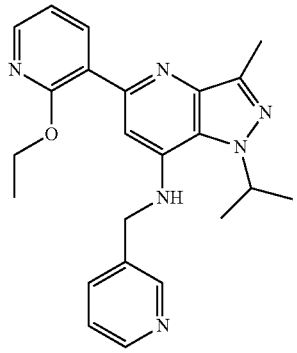 [SMILES: CCOc1ncccc1-c1cc(NCc2cccnc2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and nicotinaldehyde.

¹H NMR (Chloroform-d, 400 MHz): δ=8.73 (s, 1H), 8.61 (d, J=3.6 Hz, 1H), 8.24 (d, J=6.0 Hz, 1H), 8.16 (dd, J=1.6, 4.4 Hz, 1H), 7.76 (d, J=8.4 Hz, 1H), 7.36-7.33 (m, 1H), 7.18 (s, 1H), 7.01 (dd, J=4.8, 7.6 Hz, 1H), 4.82 (s, 1H), 4.75 (s, 1H), 4.60 (d, J=5.2 Hz, 2H), 4.40 (q, J=6.8 Hz, 2H), 2.65 (s, 3H), 1.62 (d, J=6.4 Hz, 6H), 1.30 (t, J=7.2 Hz, 3H). LC-MS (m/z) 403.1 (MH⁺); $t_R$=1.41 (Method A).

Example 116: 5-(2-ethoxy-3-pyridyl)-N-[(6-fluoro-3-pyridyl)methyl]-1-isopropyl-3-methyl-pyrazolo[4,3-b]pyridin-7-amine

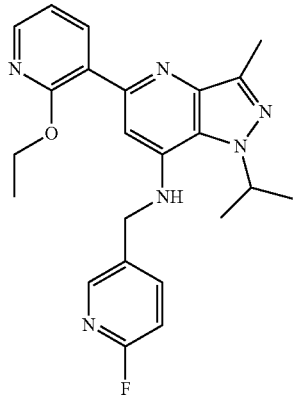 [SMILES: CCOc1ncccc1-c1cc(NCc2ccc(F)nc2)c2c(n1)c(C)nn2C(C)C]

Prepared using the same procedure as described for example 29, from 5-(2-ethoxypyridin-3-yl)-1-isopropyl-3-methyl-1H-pyrazolo[4,3-b]pyridin-7-amine and 6-fluoronicotinaldehyde.

¹H NMR (Chloroform-d, 400 MHz): δ 8.33 (s, 1H), 8.26-8.24 (m, 1H), 8.18-8.17 (m, 1H), 7.88-7.86 (m, 1H), 7.17 (s, 1H), 7.04-6.98 (m, 2H), 4.83-4.82 (m, 1H), 4.74-4.72 (m, 1H), 4.59-4.58 (m, 2H), 4.41 (q, J=6.8 Hz, 2H), 2.66 (s, 3H), 1.63 (d, J=6.8 Hz, 6H), 1.31 (t, J=6.8 Hz, 3H). LC-MS (m/z) 421 (MH⁺); $t_R$=1.89 (Method A).

Example 117: N-[[6-(difluoromethyl)-3-pyridyl]methyl]-5-(2-ethoxy-3-pyridyl)-1-isopropyl-3-methyl-pyrazolo[4,3-b]pyridin-7-amine

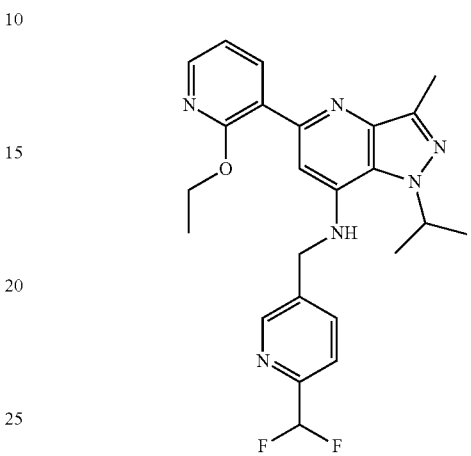

Prepared using the same procedure as described for example 29, from 5-(2-ethoxypyridin-3-yl)-1-isopropyl-3-methyl-1H-pyrazolo[4,3-b]pyridin-7-amine and 6-(difluoromethyl)nicotinaldehyde.

¹H NMR (Chloroform-d, 400 MHz): δ 8.76 (s, 1H), 8.24 (dd, J=7.2, 2.0 Hz, 1H), 8.16 (dd, J=5.2, 2.0 Hz, 1H), 7.92 (d, J=8.0, 1H), 7.68 (d, J=8.2 Hz, 1H), 7.13 (s, 1H), 7.01 (dd, J=7.2, 4.8 Hz, 1H), 6.67 (t, J=55.2 Hz, 1H), 4.87-4.83 (m, 2H), 4.68 (d, J=5.2 Hz, 2H), 4.35 (q, J=6.8 Hz, 2H), 2.66 (s, 3H), 1.65 (d, J=6.8 Hz, 6H), 1.24 (t, J=7.2 Hz, 3H). LC-MS (m/z) 453.1 (MH⁺); $t_R$=1.92 (Method A).

Example 118: 5-(2-ethoxy-3-pyridyl)-1-isopropyl-N-[(3-methoxy-2-pyridyl)methyl]-3-methyl-pyrazolo[4,3-b]pyridin-7-amine

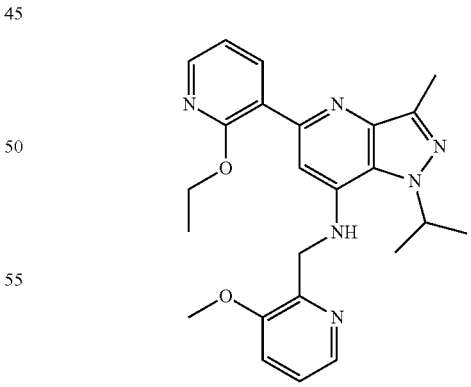

Prepared using the same procedure as described for example 29, from 5-(2-ethoxypyridin-3-yl)-1-isopropyl-3-methyl-1H-pyrazolo[4,3-b]pyridin-7-amine and 3-methoxypicolinaldehyde.

¹H NMR (Chloroform-d, 400 MHz): δ 8.33 (dd, J=2.0, 7.2 Hz, 1H), 8.23 (dd, J=1.2, 4.8 Hz, 1H), 8.19 (dd, J=2.0, 5.2 Hz, 1H), 7.28-7.30 (m, 2H), 7.22-7.24 (m, 1H), 7.04 (dd, J=4.8, 7.2 Hz, 1H), 6.96 (brs, 1H), 5.12-5.21 (m, 1H), 4.57 (d, J=4.0 Hz, 2H), 4.52 (q, J=6.8 Hz, 2H), 3.94 (s, 3H), 2.68 (s, 3H), 1.72 (d, J=6.4 Hz, 6H), 1.51 (t, J=7.0 Hz, 3H). LC-MS (m/z) 433.1 (MH⁺); $t_R$=2.08 (Method A).

Example 119: 5-(2-ethoxy-3-pyridyl)-3-methyl-1-[1-methylpropyl]-N-(1H-pyrazol-3-ylmethyl)pyrazolo[4,3-b]pyridin-7-amine, Enantiomer 1

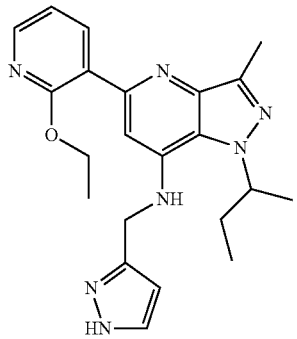 [SMILES: CCOc1ncccc1-c1cc(NCc2cc[nH]n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 1 and 1H-pyrazole-3-carbaldehyde.

¹H NMR (Chloroform-d, 400 MHz): δ 8.26 (dd, J=2.0, 7.6 Hz, 1H), 8.18 (dd, J=2.0, 4.2 Hz, 1H), 7.60 (d, J=2.4 Hz, 1H), 7.22 (s, 1H), 7.03 (dd, J=4.8, 7.2 Hz, 1H), 6.36 (d, J=2.4 Hz, 1H), 5.29 (br. s, 1H), 4.64-4.60 (m, 1H), 4.57 (d, J=4.8 Hz, 2H), 4.48 (q, J=6.8 Hz, 2H), 2.66 (s, 3H), 2.22-2.14 (m, 1H), 1.90-1.85 (m, 1H), 1.61 (d, J=6.4 Hz, 3H), 1.43 (t, J=6.8 Hz, 3H), 0.89 (t, J=7.6 Hz, 3H). LC-MS (m/z) 406.1 (MH⁺); $t_R$=2.25 (Method A).

Example 120: 5-(2-ethoxy-3-pyridyl)-3-methyl-1-[1-methylpropyl]-N-(1H-pyrazol-3-ylmethyl)pyrazolo[4,3-b]pyridin-7-amine, Enantiomer 2

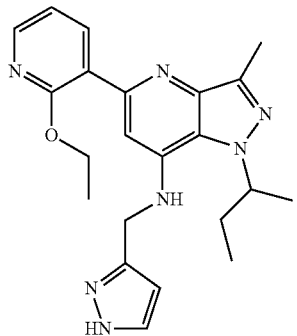 [SMILES: CCOc1ncccc1-c1cc(NCc2cc[nH]n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 1H-pyrazole-3-carbaldehyde.

¹H NMR (Chloroform-d, 400 MHz): δ 8.26 (dd, J=2.0, 7.2 Hz, 1H), 8.18 (dd, J=2.0, 4.2 Hz, 1H), 7.60 (d, J=2.4 Hz, 1H), 7.22 (s, 1H), 7.03 (dd, J=4.8, 7.2 Hz, 1H), 6.36 (d, J=2.4 Hz, 1H), 5.28 (br. s, 1H), 4.64-4.60 (m, 1H), 4.57 (d, J=4.8 Hz, 2H), 4.48 (q, J=6.8 Hz, 2H), 2.66 (s, 3H), 2.22-2.14 (m, 1H), 1.92-1.86 (m, 1H), 1.62 (d, J=6.8 Hz, 3H), 1.43 (t, J=6.8 Hz, 3H), 0.89 (t, J=7.2 Hz, 3H). LC-MS (m/z) 406.1 (MH⁺); $t_R$=2.22 (Method A).

Example 121: 5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine, Enantiomer 1

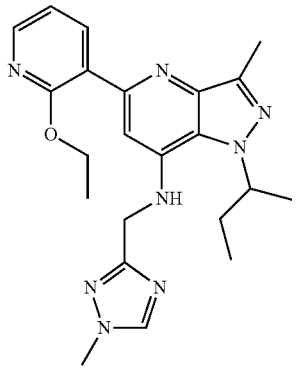 [SMILES: CCOc1ncccc1-c1cc(NCc2ncn(C)n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 1 and 1-methyl-1H-1,2,4-triazole-3-carbaldehyde ¹H NMR (Chloroform-d, 400 MHz): δ 8.27 (dd, J=2.0, 7.2 Hz, 1H), 8.18 (dd, J=2.0, 5.2 Hz, 1H), 8.05 (s, 1H), 7.20 (s, 1H), 7.03 (dd, J=4.8, 7.2 Hz, 1H), 5.49 (br. s, 1H), 4.69-4.65 (m, 1H), 4.57 (d, J=4.8 Hz, 2H), 4.49 (q, J=6.8 Hz, 2H), 3.95 (s, 3H), 2.66 (s, 3H), 2.21-2.16 (m, 1H), 1.94-1.91 (m, 1H), 1.64 (d, J=6.4 Hz, 3H), 1.45 (t, J=7.2 Hz, 3H), 0.93 (t, J=7.2 Hz, 3H). LC-MS (m/z) 421.1 (MH⁺); $t_R$=2.26 (Method C).

Example 122: 5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine, Enantiomer 2

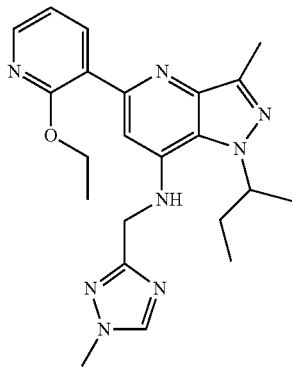 [SMILES: CCOc1ncccc1-c1cc(NCc2ncn(C)n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 1-methyl-1H-1,2,4-triazole-3-carbaldehyde.

¹H NMR (Chloroform-d, 400 MHz): δ 8.26 (dd, J=2.0, 7.2 Hz, 1H), 8.18 (dd, J=2.0, 5.2 Hz, 1H), 8.05 (s, 1H), 7.21

(s, 1H), 7.03 (dd, J=4.8, 7.2 Hz, 1H), 5.49 (br. s, 1H), 4.68-4.65 (m, 1H), 4.57 (d, J=4.8 Hz, 2H), 4.49 (q, J=6.8 Hz, 2H), 3.95 (s, 3H), 2.65 (s, 3H), 2.21-2.16 (m, 1H), 1.94-1.89 (m, 1H), 1.64 (d, J=6.8 Hz, 3H), 1.45 (t, J=6.8 Hz, 3H), 0.93 (t, J=7.6 Hz, 3H). LC-MS (m/z) 421.1 (MH$^+$); t$_R$=2.29 (Method C).

Example 123: 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, Enantiomer 1

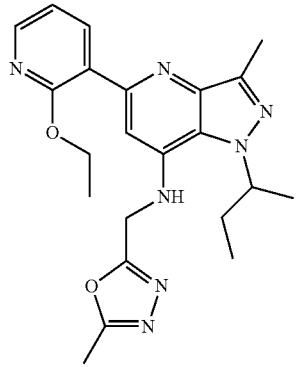 [SMILES: CCOc1ncccc1-c1cc(NCc2nnc(C)o2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 1 and 5-methyl-1,3,4-oxadiazole-2-carbaldehyde.

$^1$H NMR (Chloroform-d, 400 MHz): δ 8.30-8.28 (m, 1H), 8.21-8.20 (m, 1H), 7.25 (s, 1H), 7.06-7.01 (m, 1H), 5.28-5.20 (m, 1H), 4.76-4.64 (m, 3H), 4.51 (q, J=7.2 Hz, 2H), 2.66 (s, 3H), 2.58 (s, 3H), 2.23-2.18 (m, 1H), 1.94-1.91 (m, 1H), 1.65 (d, J=6.4 Hz, 3H), 1.45 (t, J=6.8 Hz, 3H), 0.91 (t, J=7.2 Hz, 3H). LC-MS (m/z) 422.1 (MH$^+$); t$_R$=2.22 (Method C).

Example 124: 5-(2-ethoxy-3-pyridyl)-3-methyl-N-[(5-methyl-1,3,4-oxadiazol-2-yl)methyl]-1-[1-methylpropyl]pyrazolo[4,3-b]pyridin-7-amine, Enantiomer 2

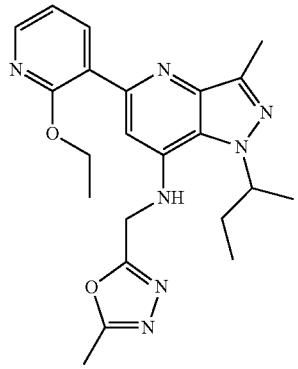 [SMILES: CCOc1ncccc1-c1cc(NCc2nnc(C)o2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 5-methyl-1,3,4-oxadiazole-2-carbaldehyde.

$^1$H NMR (Chloroform-d, 400 MHz): δ 8.30-8.28 (m, 1H), 8.20-8.19 (m, 1H), 7.25 (s, 1H), 7.06-7.02 (m, 1H), 5.20-5.18 (m, 1H), 4.73-4.71 (m, 2H), 4.63-4.61 (m, 1H), 4.51 (q, J=7.2 Hz, 2H), 2.66 (s, 3H), 2.58 (s, 3H), 2.23-2.16 (m, 1H), 1.94-1.90 (m, 1H), 1.65 (d, J=6.4 Hz, 3H), 1.44 (t, J=6.8 Hz, 3H), 0.91 (t, J=7.2 Hz, 3H). LC-MS (m/z) 422.1 (MH$^+$); t$_R$=2.17 (Method C).

Example 125: 5-(2-ethoxy-3-pyridyl)-N-[(5-methoxy-3-pyridyl)methyl]-3-methyl-1-[1-methylpropyl]pyrazolo[4,3-b]pyridin-7-amine, Enantiomer 2

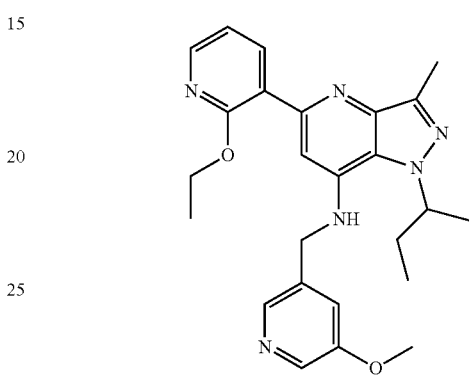

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 5-methoxynicotinaldehyde.

$^1$H NMR (DMSO-d$_6$ 400 MHz): δ=8.21 (s, 1H), 8.16 (d, J=2.8 Hz, 1H), 8.13 (s, 1H), 8.12-8.09 (m, 1H), 7.33-7.32 (m, 1H), 7.05-7.02 (m, 1H), 6.93 (s, 1H), 6.91 (s, 1H), 4.96-4.93 (m, 1H), 4.57-4.56 (m, 2H), 4.25-4.20 (m, 2H), 3.75 (s, 3H), 2.44 (s, 3H), 1.98-1.74 (m, 2H), 1.48 (d, J=6.4 Hz, 3H), 1.08 (t, J=7.0 Hz, 3H), 0.73 (t, J=7.6 Hz, 3H). LC-MS (m/z) 447.1 (MH$^+$); t$_R$=1.62 (Method A).

Example 126: 5-(2-ethoxy-3-pyridyl)-N-[(2-methoxy-4-pyridyl)methyl]-3-methyl-1-[1-methylpropyl]pyrazolo[4,3-b]pyridin-7-amine, Enantiomer 2

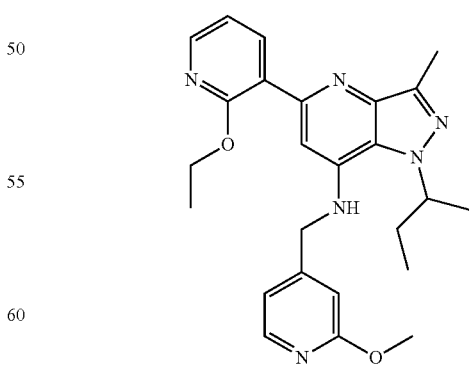

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 2-methoxyisonicotinaldehyde.

¹H NMR (Chloroform-d, 400 MHz): δ=8.24 (dd, J=2.0, 7.6 Hz, 1H), 8.17 (d, J=5.6 Hz, 1H), 8.15 (dd, J=1.6, 4.8 Hz, 1H), 7.07 (s, 1H), 7.00 (dd, J=5.2, 7.6 Hz, 1H), 6.91 (d, J=4.0 Hz, 1H), 6.78 (s, 1H), 4.80 (brs, 1H), 4.55 (d, J=5.6 Hz, 3H), 4.35 (q, J=6.8 Hz, 2H), 3.94 (s, 3H), 2.66 (s, 3H), 2.26-2.15 (m, 1H), 1.95-1.85 (m, 1H), 1.64 (d, J=6.4 Hz, 3H), 1.25 (t, J=6.8 Hz, 3H), 0.90 (t, J=7.6 Hz, 3H). LC-MS (m/z) 447.1 (MH⁺); t_R=1.96 (Method A).

Example 127: 5-(2-ethoxy-3-pyridyl)-3-methyl-1-[1-methylpropyl]-N-[(2-methyltetrazol-5-yl)methyl]pyrazolo[4,3-b]pyridin-7-amine, Enantiomer 2

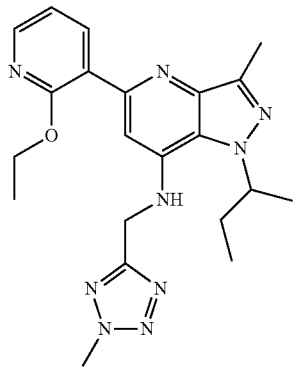

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 2-methyl-2H-tetrazole-5-carbaldehyde.
¹H NMR (Chloroform-d, 400 MHz): δ 8.28 (dd, J=7.6, 2.0 Hz, 1H), 8.18 (dd, J=5.2, 2.0 Hz, 1H), 7.27 (s, 1H), 7.05-7.02 (m, 1H), 5.31-5.28 (m, 1H), 4.79 (d, J=5.2 Hz, 2H), 4.67-4.62 (m, 1H), 4.50 (q, J=6.8 Hz, 2H), 4.39 (s, 3H), 2.67 (s, 3H), 2.24-2.17 (m, 1H), 1.95-1.88 (m, 1H), 1.65 (d, J=6.8 Hz, 3H), 1.45 (t, J=7.2 Hz, 3H), 0.92 (t, J=7.2 Hz, 3H). LC-MS (m/z) 422.1 (MH⁺); t_R=2.03 (Method C).

Example 128: 5-(2-ethoxy-3-pyridyl)-3-methyl-N-[(5-methyl-1,2,4-oxadiazol-3-yl)methyl]-1-[1-methylpropyl]pyrazolo[4,3-b]pyridin-7-amine, Enantiomer 2

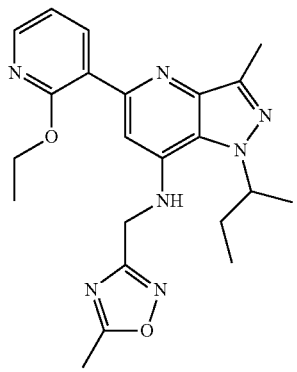 [SMILES: CCOc1ncccc1-c1cc(NCc2noc(C)n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 5-methyl-1,2,4-oxadiazole-3-carbaldehyde.
¹H NMR (Chloroform-d, 400 MHz): δ 8.26 (dd, J=2.0, 7.2 Hz, 1H), 8.18 (dd, J=2.0, 4.2 Hz, 1H), 7.24 (s, 1H), 7.03 (dd, J=4.4, 7.2 Hz, 1H), 5.17 (br. s, 1H), 4.65-4.60 (m, 3H), 4.50 (q, J=7.2 Hz, 2H), 2.65 (s, 3H), 2.64 (s, 3H), 2.23-2.16 (m, 1H), 1.93-1.90 (m, 1H), 1.64 (d, J=6.4 Hz, 3H), 1.44 (t, J=6.8 Hz, 3H), 0.92 (t, J=7.6 Hz, 3H). LC-MS (m/z) 422.1 (MH⁺); t_R=2.05 (Method C).

Example 129: 5-(2-ethoxy-3-pyridyl)-3-methyl-N-[(2-methyloxazol-4-yl)methyl]-1-[1-methylpropyl]pyrazolo[4,3-b]pyridin-7-amine, Enantiomer 2

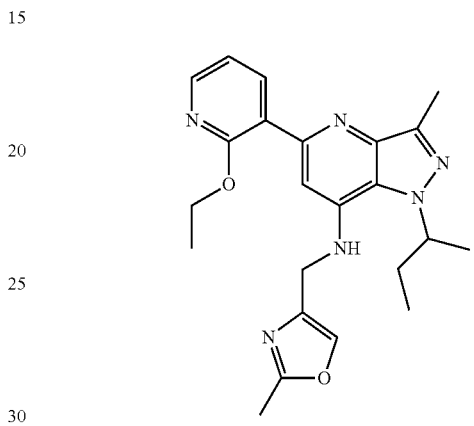

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 2-methyloxazole-4-carbaldehyde.
¹H NMR (Chloroform-d, 400 MHz): δ=8.27 (dd, J=2.0, 7.2 Hz, 1H), 8.18 (dd, J=2.0, 5.2 Hz, 1H), 7.54 (s, 1H), 7.18 (s, 1H), 7.03 (dd, J=4.8, 7.2 Hz, 1H), 5.11-4.91 (m, 1H), 4.61-4.55 (m, 1H), 4.48 (q, J=7.2 Hz, 2H), 4.40 (d, J=4.8 Hz, 2H), 2.65 (s, 3H), 2.49 (s, 3H), 2.21-2.14 (m, 1H), 1.92-1.85 (m, 1H), 1.63 (s, 3H), 1.40 (t, J=7.2 Hz, 3H), 0.89 (t, J=7.2 Hz, 3H). LC-MS (m/z) 421.1 (MH⁺); t_R=1.9 (Method A).

Example 130: 5-(2-ethoxy-3-pyridyl)-N-(1H-imidazol-4-ylmethyl)-3-methyl-1-[1-methylpropyl]pyrazolo[4,3-b]pyridin-7-amine, Enantiomer 2

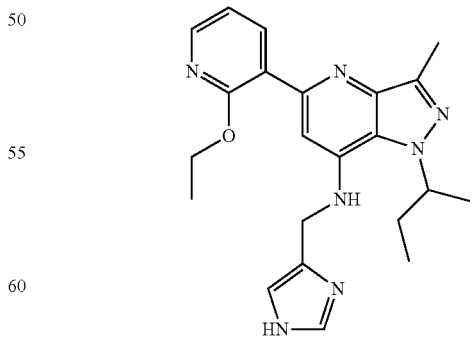

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 1H-imidazole-4-carbaldehyde.

¹H NMR (Chloroform-d, 400 MHz): δ=8.25 (dd, J=2.0, 7.2 Hz, 1H), 8.17 (dd, J=2.0, 4.8 Hz, 1H), 7.67 (d, J=1.2 Hz, 1H), 7.21 (s, 1H), 7.03 (s, 1H), 7.02-7.00 (m, 1H), 5.57-5.08 (m, 1H), 4.63-4.60 (m, 1H), 4.50-4.51 (m, 4H), 2.64 (s, 3H), 2.18-2.12 (m, 1H), 1.90-1.85 (m, 1H), 1.61 (d, J=6.4 Hz, 3H), 1.41 (t, J=7.2 Hz, 3H), 0.87 (t, J=7.2 Hz, 3H). LC-MS (m/z) 406.1 (MH⁺); $t_R$=1.35 (Method A).

Example 131: 5-(2-ethoxy-3-pyridyl)-3-methyl-1-[1-methylpropyl]-N-[(5-methyl-1H-pyrazol-3-yl)methyl]pyrazolo[4,3-b]pyridin-7-amine, Enantiomer 2

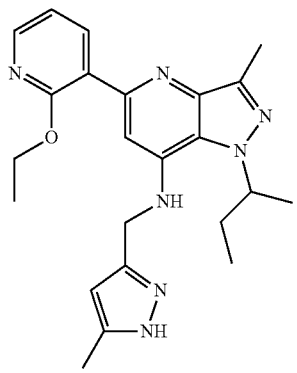 [SMILES: CCOc1ncccc1-c1cc(NCc2cc(C)[nH]n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 5-methyl-1H-pyrazole-3-carbaldehyde.

¹H NMR (Chloroform-d, 400 MHz): δ=8.27 (dd, J=2.0, 7.2 Hz, 1H), 8.18 (dd, J=2.0, 4.8 Hz, 1H), 7.20 (s, 1H), 7.04-7.01 (m, 1H), 6.08 (s, 1H), 5.28 (brs, 1H), 4.61-4.58 (m, 1H), 4.51-4.46 (m, 4H), 2.65 (s, 3H), 2.35 (s, 3H), 2.21-2.14 (m, 1H), 1.91-1.85 (m, 1H), 1.62 (d, J=6.8 Hz, 3H), 1.43 (t, J=6.8 Hz, 3H), 0.89 (t, J=7.6 Hz, 3H). LC-MS (m/z) 420.1 (MH⁺); $t_R$=1.85 (Method A).

Example 132: 5-(2-ethoxy-3-pyridyl)-3-methyl-N-[(1-methylimidazol-4-yl)methyl]-1-[1-methylpropyl]pyrazolo[4,3-b]pyridin-7-amine, Enantiomer 2

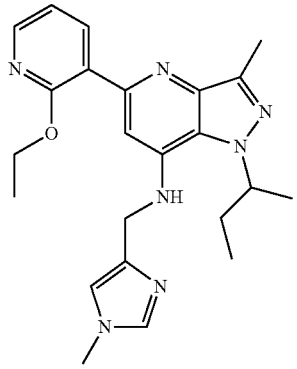 [SMILES: CCOc1ncccc1-c1cc(NCc2cn(C)cn2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 1-methyl-1H-imidazole-4-carbaldehyde.

¹H NMR (Chloroform-d, 400 MHz): δ=8.28 (dd, J=2.0, 7.6 Hz, 1H), 8.17 (dd, J=2.0, 4.8 Hz, 1H), 7.45 (s, 1H), 7.20 (s, 1H), 7.04-7.01 (m, 1H), 6.88 (s, 1H), 5.25 (brs, 1H), 4.61-4.58 (m, 1H), 4.48 (q, J=6.8 Hz, 2H), 4.42 (d, J=4.8 Hz, 2H), 3.70 (s, 3H), 2.65 (s, 3H), 2.18-2.13 (m, 1H), 1.89-1.85 (m, 1H), 1.60 (d, J=6.8 Hz, 3H), 1.42 (t, J=6.8 Hz, 3H), 0.88 (t, J=7.2 Hz, 3H). LC-MS (m/z) 420.1 (MH⁺); $t_R$=1.38 (Method A).

Example 133: 5-(2-ethoxy-3-pyridyl)-3-methyl-N-[(2-methyloxazol-5-yl)methyl]-1-[1-methylpropyl]pyrazolo[4,3-b]pyridin-7-amine, Enantiomer 2

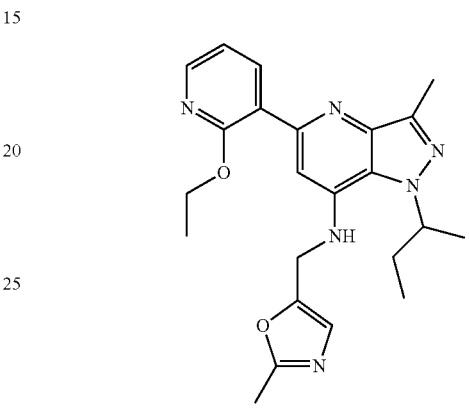

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 2-methyloxazole-5-carbaldehyde.

¹H NMR (Chloroform-d, 400 MHz): δ=8.27 (dd, J=2.0, 7.6 Hz, 1H), 8.18 (dd, J=2.0, 4.8 Hz, 1H), 7.25 (s, 1H), 7.03 (dd, J=4.8, 7.6 Hz, 1H), 6.94 (s, 1H), 4.62 (brd, J=4.8 Hz, 1H), 4.55-4.46 (m, 5H), 2.65 (s, 3H), 2.47 (s, 3H), 2.21-2.13 (m, 1H), 1.91-1.84 (m, 1H), 1.62 (d, J=6.8 Hz, 3H), 1.41 (t, J=6.8 Hz, 3H), 0.87 (t, J=7.6 Hz, 3H). LC-MS (m/z) 421.1 (MH⁺); $t_R$=1.81 (Method A).

Example 134: 3-methyl-1-[1-methylpropyl]-N-[(1-methyl-1,2,4-triazol-3-yl)methyl]-5-(2-propoxy-3-pyridyl)pyrazolo[4,3-b]pyridin-7-amine, Enantiomer 2

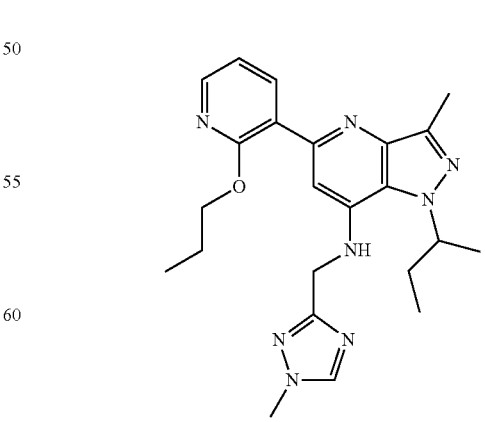

Prepared using the same procedure as described for example 29, from 1-(sec-butyl)-5-(2-ethoxypyridin-3-yl)-3- methyl-1H-pyrazolo[4,3-b]pyridin-7-amine, enantiomer 2 and 1-methyl-1H-1,2,4-triazole-3-carbaldehyde.

¹H NMR (Chloroform-d, 400 MHz): δ 8.27-8.25 (m, 1H), 8.19-8.17 (m, 1H), 8.06 (s, 1H), 7.19 (s, 1H), 7.04-7.01 (m, 1H), 5.50-5.48 (m, 1H), 4.71-4.66 (m, 1H), 4.56 (d, J=2.2 Hz, 2H), 4.39 (t, J=6.8 Hz, 2H), 3.96 (s, 3H), 2.66 (s, 3H), 2.24-2.18 (m, 1H), 1.91-1.83 (m, 3H), 1.65 (d, J=3.2 Hz, 3H), 1.06 (t, J=7.2 Hz, 3H), 0.94 (t, J=7.2 Hz, 3H). LC-MS (m/z) 435.1 (MH⁺); t$_R$=2.05 (Method C).

Example 135: 3-methyl-1-[1-methylpropyl]-5-(2-propoxy-3-pyridyl)-N-(1H-pyrazol-3-ylmethyl)pyrazolo[4,3-b]pyridin-7-amine, Enantiomer 2

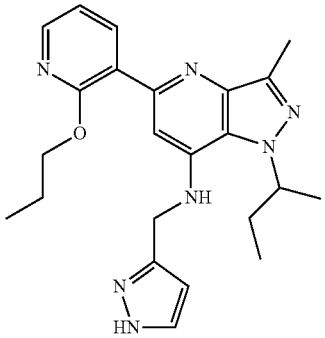 [SMILES: CCCOc1ncccc1-c1cc(NCc2cc[nH]n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 1H-pyrazole-3-carbaldehyde.

¹H NMR (Chloroform-d, 400 MHz): δ 12.66 (s, 1H), 8.16-8.11 (m, 2H), 7.57 (s, 1H), 7.10-7.06 (m, 2H), 6.71 (t, J=6.0 Hz, 1H), 6.15-6.14 (m, 1H), 4.93-4.91 (m, 1H), 4.50 (d, J=5.6 Hz, 2H), 4.26 (t, J=6.8 Hz, 2H), 2.45 (s, 3H), 2.00-1.92 (m, 1H), 1.76-1.67 (m, 3H), 1.47 (d, J=6.4 Hz, 3H), 0.94 (t, J=7.2 Hz, 3H), 0.73 (t, J=7.2 Hz, 3H). LC-MS (m/z) 420.1 (MH⁺); t$_R$=2.1 (Method C).

Example 136: 5-(2-ethoxy-3-pyridyl)-1-[1-methylpropyl]-N-(1H-pyrazol-3-ylmethyl)pyrazolo[4,3-b]pyridin-7-amine, Enantiomer 1

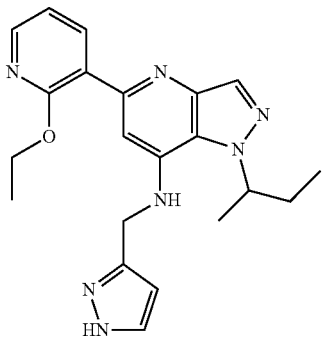 [SMILES: CCOc1ncccc1-c1cc(NCc2cc[nH]n2)c2c(cnn2C(C)CC)n1]

Prepared using the same procedure as described for example 29, from 1-(sec-butyl)-5-(2-ethoxypyridin-3-yl)-1H-pyrazolo[4,3-b]pyridin-7-amine, enantiomer 1 and 1H-pyrazole-3-carbaldehyde.

¹H NMR (Chloroform-d, 400 MHz): δ 8.24-8.19 (m, 3H), 7.62 (d, J=2.0 Hz, 1H), 7.23 (s, 1H), 7.04-7.01 (m, 1H), 6.37 (d, J=2.4 Hz, 1H), 5.45 (s, 1H), 4.71-4.67 (m, 1H), 4.59 (d, J=4.8 Hz, 2H), 4.49 (q, J=6.8 Hz, 2H), 2.25-2.18 (m, 1H), 1.94-1.90 (m, 1H), 1.66 (d, J=6.4 Hz, 3H), 1.44 (t, J=7.2 Hz, 3H), 0.9 (t, J=7.2 Hz, 3H). SFC: t$_R$=4.729 min, ee %=97.49%. LC-MS (m/z) 392 (MH⁺); t$_R$=2.23 (Method A).

Example 137: 5-(2-ethoxy-3-pyridyl)-1-[1-methylpropyl]-N-(1H-pyrazol-3-ylmethyl)pyrazolo[4,3-b]pyridin-7-amine, Enantiomer 2

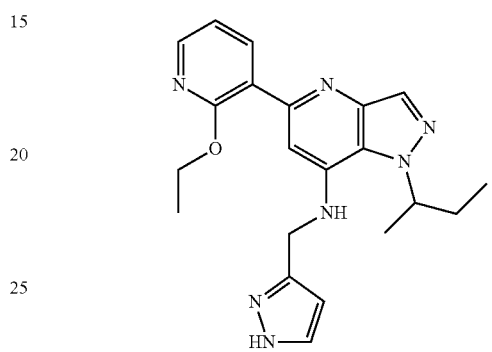

Prepared using the same procedure as described for example 29, from 1-(sec-butyl)-5-(2-ethoxypyridin-3-yl)-1H-pyrazolo[4,3-b]pyridin-7-amine, enantiomer 2 and 1H-pyrazole-3-carbaldehyde.

¹H NMR (Chloroform-d, 400 MHz): δ 8.24-8.18 (m, 3H), 7.61 (d, J=2.4 Hz, 1H), 7.23 (s, 1H), 7.04-7.01 (m, 1H), 6.37 (d, J=2.4 Hz, 1H), 5.44 (s, 1H), 4.71-4.67 (m, 1H), 4.59 (d, J=4.8 Hz, 2H), 4.49 (q, J=6.8 Hz, 2H), 2.25-2.18 (m, 1H), 1.96-1.90 (m, 1H), 1.66 (d, J=6.8 Hz, 3H), 1.43 (t, J=7.2 Hz, 3H), 0.9 (t, J=7.2 Hz, 3H). SFC: t$_R$=4.453 min, ee %=94.84%. LC-MS (m/z) 392.1 (MH⁺); t$_R$=2.23 (Method A).

Example 138: 5-(2-ethoxy-3-pyridyl)-N-[(5-methyl-1,3,4-oxadiazol-2-yl)methyl]-1-[1-methylpropyl]pyrazolo[4,3-b]pyridin-7-amine, Enantiomer 1

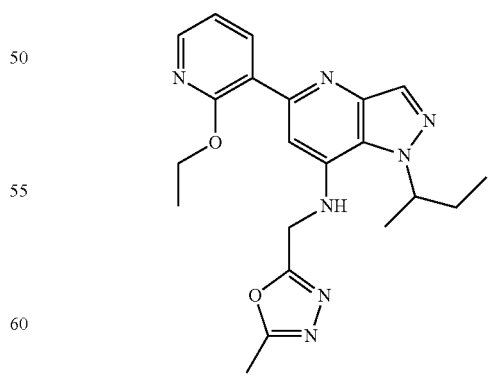

Prepared using the same procedure as described for example 29, from 1-(sec-butyl)-5-(2-ethoxypyridin-3-yl)-1H-pyrazolo[4,3-b]pyridin-7-amine, enantiomer 1 and 5-methyl-1,3,4-oxadiazole-2-carbaldehyde.

¹H NMR (Chloroform-d, 400 MHz): δ 8.24-8.20 (m, 3H), 7.25 (s, 1H), 7.03 (dd, J=4.8, 7.2 Hz, 1H), 5.37 (brs, 1H), 4.73-4.69 (m, 3H), 4.51 (q, J=7.2 Hz, 2H), 2.58 (s, 3H), 2.27-2.19 (m, 1H), 1.97-1.93 (m, 1H), 1.68 (d, J=6.4 Hz, 3H), 1.44 (t, J=7.2 Hz, 3H), 0.92 (t, J=7.2 Hz, 3H). SFC-MS: $t_R$=4.24 min, ee %=98.70%. LC-MS (m/z) 408 (MH$^+$); $t_R$=2.4 (Method C).

Example 139: 5-(2-ethoxy-3-pyridyl)-N-[(5-methyl-1,3,4-oxadiazol-2-yl)methyl]-1-[1-methylpropyl]pyrazolo[4,3-b]pyridin-7-amine, Enantiomer 2

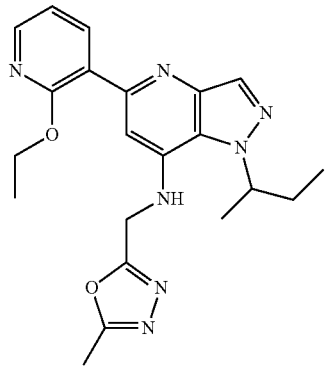 [SMILES: CCOc1ncccc1-c1cc(NCc2nnc(C)o2)c2c(cnn2C(C)CC)n1]

Prepared using the same procedure as described for example 29, from 1-(sec-butyl)-5-(2-ethoxypyridin-3-yl)-1H-pyrazolo[4,3-b]pyridin-7-amine, enantiomer 2 and 5-methyl-1,3,4-oxadiazole-2-carbaldehyde.

¹H NMR (Chloroform-d, 400 MHz): δ 8.25-8.20 (m, 3H), 7.25 (s, 1H), 7.03 (dd, J=4.8, 7.2 Hz, 1H), 5.31 (brs, 1H), 4.73-4.68 (m, 3H), 4.51 (q, J=7.2 Hz, 2H), 2.59 (s, 3H), 2.27-2.20 (m, 1H), 1.97-1.94 (m, 1H), 1.68 (d, J=6.4 Hz, 3H), 1.45 (t, J=7.2 Hz, 3H), 0.92 (t, J=7.2 Hz, 3H). SFC-MS: $t_R$=3.997 min, ee %=97.68%. LC-MS (m/z) 408.1 (MH$^+$); $t_R$=2.4 (Method C).

Example 140: 5-(2-ethoxy-3-pyridyl)-1-[1-methylpropyl]-N-[(1-methyl-1,2,4-triazol-3-yl)methyl]pyrazolo[4,3-b]pyridin-7-amine, Enantiomer 1

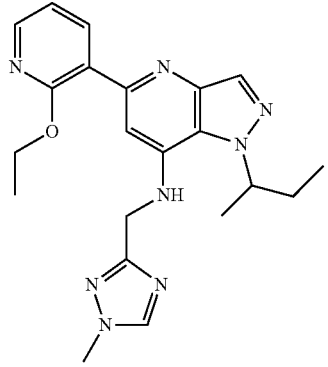 [SMILES: CCOc1ncccc1-c1cc(NCc2ncn(C)n2)c2c(cnn2C(C)CC)n1]

Prepared using the same procedure as described for example 29, from 1-(sec-butyl)-5-(2-ethoxypyridin-3-yl)-1H-pyrazolo[4,3-b]pyridin-7-amine, enantiomer 1 and 1-methyl-1H-1,2,4-triazole-3-carbaldehyde.

¹H NMR (Chloroform-d, 400 MHz): δ 8.25-8.19 (m, 3H), 8.07 (s, 1H), 7.23 (s, 1H), 7.03 (dd, J=4.8, 7.2 Hz, 1H), 5.61 (brs, 1H), 4.79-4.74 (m, 1H), 4.59 (d, J=4.8 Hz, 2H), 4.50 (q, J=7.2 Hz, 2H), 3.96 (s, 3H), 2.27-2.22 (m, 1H), 1.98-1.93 (m, 1H), 1.68 (d, J=6.8 Hz, 3H), 1.46 (t, J=7.2 Hz, 3H), 0.95 (t, J=7.2 Hz, 3H). SFC-MS: $t_R$=4.97 min, ee %=98.60%. LC-MS (m/z) 407 (MH$^+$); $t_R$=2.44 (Method C).

Example 141: 5-(2-ethoxy-3-pyridyl)-1-[1-methylpropyl]-N-[(1-methyl-1,2,4-triazol-3-yl)methyl]pyrazolo[4,3-b]pyridin-7-amine, Enantiomer 2

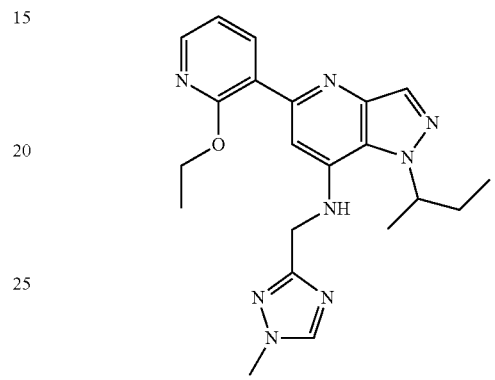

Prepared using the same procedure as described for example 29, from 1-(sec-butyl)-5-(2-ethoxypyridin-3-yl)-1H-pyrazolo[4,3-b]pyridin-7-amine, enantiomer 2 and 1-methyl-1H-1,2,4-triazole-3-carbaldehyde.

¹H NMR (Chloroform-d, 400 MHz): δ 8.24-8.19 (m, 3H), 8.07 (s, 1H), 7.23 (s, 1H), 7.03 (dd, J=4.8, 7.2 Hz, 1H), 5.60 (brs, 1H), 4.78-4.73 (m, 1H), 4.59 (d, J=4.8 Hz, 2H), 4.50 (q, J=7.2 Hz, 2H), 3.96 (s, 3H), 2.27-2.22 (m, 1H), 1.98-1.93 (m, 1H), 1.68 (d, J=6.8 Hz, 3H), 1.46 (t, J=7.2 Hz, 3H), 0.95 (t, J=7.2 Hz, 3H). SFC-MS: $t_R$=4.66 min, ee %=96.90%. LC-MS (m/z) 407.1 (MH$^+$); $t_R$=2.44 (Method C).

Example 142: 1-isopropyl-3-methyl-N-[(1-methylimidazol-4-yl)methyl]-5-(2-propoxy-3-pyridyl)pyrazolo[4,3-b]pyridin-7-amine

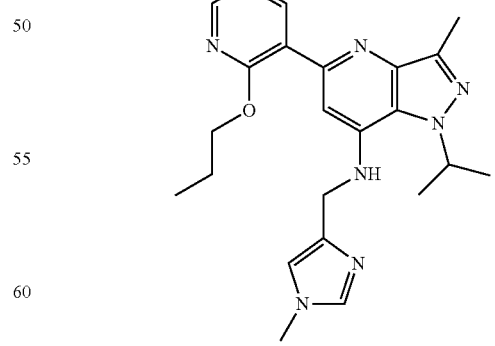

Prepared using the same procedure as described for example 29, from 1-isopropyl-3-methyl-5-(2-propoxypyridin-3-yl)-1H-pyrazolo[4,3-b]pyridin-7-amine and 1-methyl-1H-imidazole-4-carbaldehyde.

¹H NMR (Chloroform-d, 400 MHz): δ 8.28-8.26 (m, 1H), 8.20-8.18 (m, 1H), 7.46 (s, 1H), 7.18 (s, 1H), 7.05-7.02 (m, 1H), 6.91 (s, 1H), 5.43 (brs, 1H), 4.94-4.90 (m, 1H), 4.45-4.44 (m, 2H), 4.38 (t, J=6.8 Hz, 2H), 3.70 (s, 3H), 2.65 (s, 3H), 1.87-1.78 (m, 2H), 1.62 (d, J=6.8 Hz, 6H), 1.05 (t, J=7.6 Hz, 3H). LC-MS (m/z) 420.1 (MH⁺); $t_R$=1.75 (Method C).

Example 143: 1-isopropyl-3-methyl-5-(2-propoxy-3-pyridyl)-N-(1H-pyrazol-3-ylmethyl)pyrazolo[4,3-b]pyridin-7-amine

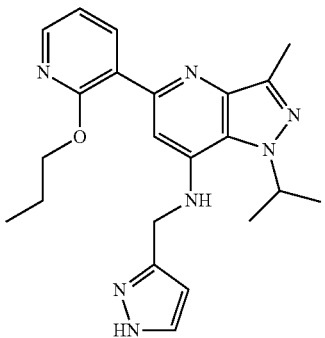 [SMILES: CCCOc1ncccc1-c1cc(NCc2cc[nH]n2)c2c(n1)c(C)nn2C(C)C]

Prepared using the same procedure as described for example 29, from 1-isopropyl-3-methyl-5-(2-propoxypyridin-3-yl)-1H-pyrazolo[4,3-b]pyridin-7-amine and 1H-pyrazole-3-carbaldehyde.

¹H NMR (Chloroform-d, 400 MHz): δ 8.25-8.23 (m, 1H), 8.19-8.17 (m, 1H), 7.61 (d, J=1.2 Hz, 1H), 7.18 (s, 1H), 7.05-7.01 (m, 1H), 6.36 (d, J=1.2 Hz, 1H), 5.40 (brs, 1H), 4.96-4.90 (m, 1H), 4.58 (d, J=2.4 Hz, 2H), 4.38 (t, J=7.2 Hz, 2H), 2.65 (s, 3H), 1.86-1.82 (m, 2H), 1.64 (d, J=3.2 Hz, 6H), 1.05 (t, J=7.6 Hz, 3H). LC-MS (m/z) 406.1 (MH⁺); $t_R$=1.83 (Method A).

Example 144: 5-(2-ethoxy-3-pyridyl)-3-methyl-1-[1-methylpropyl]-N-(1H-1,2,4-triazol-3-ylmethyl)pyrazolo[4,3-b]pyridin-7-amine, Enantiomer 2

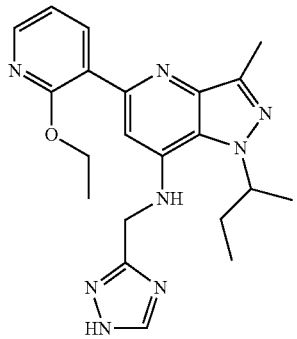 [SMILES: CCOc1ncccc1-c1cc(NCc2nc[nH]n2)c2c(n1)c(C)nn2C(C)CC]

Prepared using the same procedure as described for example 29, from 1-(sec-butyl)-5-(2-ethoxypyridin-3-yl)-3-methyl-1H-pyrazolo[4,3-b]pyridin-7-amine, enantiomer 2 and 1-((2-(trimethylsilyl)ethoxy)methyl)-1H-1,2,4-triazole-3-carbaldehyde followed by deprotection with TFA.

¹H NMR (Chloroform-d, 400 MHz): δ 11.58 (brs, 1H), 8.25 (d, J=2.0 Hz, 1H), 8.23-8.17 (m, 2H), 7.19 (s, 1H), 7.01 (dd, J=4.8, 7.2 Hz, 1H), 5.51 (brs, 1H), 4.69-4.66 (m, 3H), 4.48 (q, J=7.2 Hz, 2H), 2.66 (s, 3H), 2.22-2.16 (m, 1H), 1.93-1.89 (m, 1H), 1.64 (d, J=6.8 Hz, 3H), 1.42 (t, J=6.8 Hz, 3H), 0.91 (t, J=7.2 Hz, 3H). LC-MS (m/z) 407.1 (MH⁺); $t_R$=1.91 (Method C) $[α]_D^{20}$ −3.40 (c=1.0, DCM).

Example 145: 1-isopropyl-3-methyl-N-[(1-methyl-1,2,4-triazol-3-yl)methyl]-5-(2-propoxy-3-pyridyl)pyrazolo[4,3-b]pyridin-7-amine

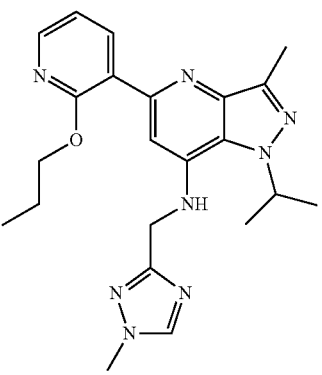 [SMILES: CCCOc1ncccc1-c1cc(NCc2ncn(C)n2)c2c(n1)c(C)nn2C(C)C]

Prepared using the same procedure as described for example 29, from 1-isopropyl-3-methyl-5-(2-propoxypyridin-3-yl)-1H-pyrazolo[4,3-b]pyridin-7-amine and 1H-1,2,4-triazole-3-carbaldehyde.

¹H NMR (Chloroform-d, 400 MHz): δ=8.26-8.23 (m, 1H), 8.19-8.17 (m, 1H), 8.06 (s, 1H), 7.18 (s, 1H), 7.04-7.01 (m, 1H), 5.52-5.51 (m, 1H), 5.01-4.95 (m, 1H), 4.57 (d, J=4.8 Hz, 2H), 4.38 (t, J=6.8 Hz, 2H), 3.95 (s, 3H), 2.65 (s, 3H), 1.90-1.81 (m, 2H), 1.66 (d, J=6.4 Hz, 6H), 1.05 (t, J=7.6 Hz, 3H). LC-MS (m/z) 421.1 (MH⁺); $t_R$=2.1 (Method B).

Example 146: 1-isopropyl-3-methyl-5-(2-propoxy-3-pyridyl)-N-(1H-1,2,4-triazol-3-ylmethyl)pyrazolo[4,3-b]pyridin-7-amine

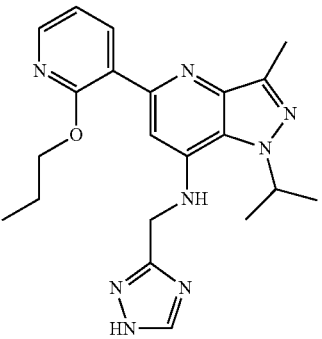 [SMILES: CCCOc1ncccc1-c1cc(NCc2nc[nH]n2)c2c(n1)c(C)nn2C(C)C]

Prepared using the same procedure as described for example 29, from 1-isopropyl-3-methyl-5-(2-propoxypyridin-3-yl)-1H-pyrazolo[4,3-b]pyridin-7-amine and 1-((2-(trimethylsilyl)ethoxy)methyl)-1H-1,2,4-triazole-3-carbaldehyde followed by deprotection with TFA.

$^1$H NMR (Chloroform-d, 400 MHz): δ 8.20-8.17 (m, 2H), 8.14 (s, 1H), 7.14 (s, 1H), 7.03 (dd, J=4.2, 7.6 Hz, 1H), 5.59 (brs, 1H), 5.00-4.94 (m, 1H), 4.64 (s, 2H), 4.36 (t, J=6.8 Hz, 2H), 2.65 (s, 3H), 1.85-1.76 (m, 2H), 1.65 (d, J=6.8 Hz, 6H), 1.01 (t, J=7.2 Hz, 3H). LC-MS (m/z) 407.1 (MH$^+$); $t_R$=1.91 (Method C).

Example 147: 1-isopropyl-3-methyl-N-[(1-methyl-pyrazol-4-yl)methyl]-5-thiazol-2-yl-pyrazolo[4,3-b]pyridin-7-amine

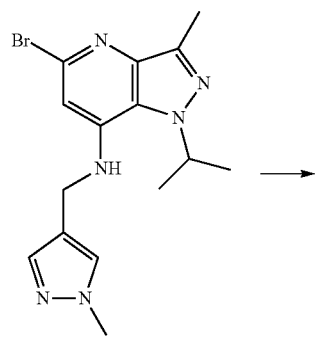

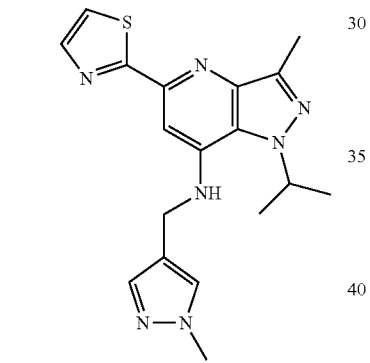

To a solution of 5-bromo-1-isopropyl-3-methyl-N-((1-methyl-1H-pyrazol-4-yl)methyl)-1H-pyrazolo[4,3-b]pyridin-7-amine (50 mg, 0.14 mmol) in DMF (2 mL) was added 2-(tributylstannyl)thiazole (103 mg, 0.28 mmol) and Pd(PPh$_3$)$_4$ (16 mg, 0.013 mmol). The mixture was bubbled with N$_2$ and heated at 80° C. for 2 hours. The mixture was cooled to room temperature. ethyl acetate (20 mL) and water (10 mL) were added. The organic layer was washed with water (10 mL×2), brine (10 mL), dried over Na$_2$SO$_4$, filtered and concentrated. The crude was purified by preparative TLC (SiO$_2$, ethyl acetate) to give 1-isopropyl-3-methyl-N-((1-methyl-1H-pyrazol-4-yl)methyl)-5-(thiazol-2-yl)-1H-pyrazolo[4,3-b]pyridin-7-amine (10 mg).

$^1$H NMR (Chloroform-d, 400 MHz): δ 7.88 (d, J=3.2 Hz, 1H), 7.58 (s, 1H), 7.46 (s, 2H), 7.40 (d, J=3.2 Hz, 1H), 4.75-4.68 (m, 1H), 4.54 (brs, 1H), 4.46 (d, J=4.8 Hz, 2H), 3.94 (s, 3H), 2.65 (s, 3H), 1.58 (d, J=6.8 Hz, 6H). LC-MS (m/z) 368 (MH$^+$); $t_R$=1.91 (Method C).

Example 148: 1-isopropyl-3-methyl-N-[(1-methyl-pyrazol-4-yl)methyl]-5-(5-methylthiazol-2-yl)pyrazolo[4,3-b]pyridin-7-amine

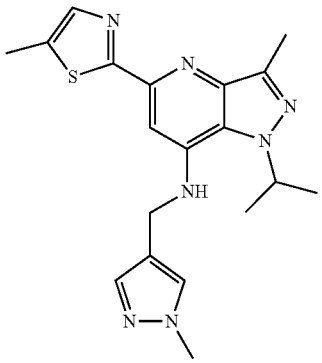 [SMILES: Cc1cnc(-c2cc(NCc3cnn(C)c3)c3c(n2)c(C)nn3C(C)C)s1]

Prepared using the same procedure as described for example 147, from 5-bromo-1-isopropyl-3-methyl-N-((1-methyl-1H-pyrazol-4-yl)methyl)-1H-pyrazolo[4,3-b]pyridin-7-amine and 5-methyl-2-(tributylstannyl)thiazole.

$^1$H NMR (600 MHz, DMSO-d$_6$) δ 7.62 (s, 1H), 7.56 (s, 1H), 7.43 (s, 1H), 7.20 (s, 1H), 6.86 (t, J=5.6 Hz, 1H), 5.16 (m, 1H), 4.41 (d, J=5.5 Hz, 2H), 3.77 (s, 3H), 2.47 (s, 3H), 2.45 (s, 3H), 1.44 (d, J=6.3 Hz, 6H). LC-MS (m/z) 382.3 (MH$^+$); $t_R$=0.51 (Method D).

Example 149: 1-isopropyl-3-methyl-N-[(1-methyl-pyrazol-4-yl)methyl]-5-(4-methylthiazol-2-yl)pyrazolo[4,3-b]pyridin-7-amine

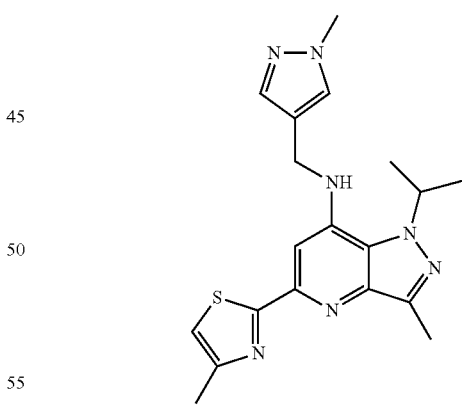

Prepared using the same procedure as described for example 147, from 5-bromo-1-isopropyl-3-methyl-N-((1-methyl-1H-pyrazol-4-yl)methyl)-1H-pyrazolo[4,3-b]pyridin-7-amine and 4-methyl-2-(tributylstannyl)thiazole.

$^1$H NMR (500 MHz, Chloroform-d) δ 7.60 (s, 1H), 7.47 (s, 1H), 7.45 (s, 1H), 6.96 (s, 1H), 4.73 (m, 1H), 4.53 (s, 1H), 4.49 (s, 2H), 3.96 (s, 3H), 2.65 (s, 3H), 2.55 (s, 3H), 1.59 (d, J=6.4 Hz, 6H). LC-MS (m/z) 382.4 (MH$^+$); $t_R$=0.51 (Method D).

Example 150: 3-[1-isopropyl-3-methyl-7-[(1-methylpyrazol-4-yl)methylamino]pyrazolo[4,3-b]pyridin-5-yl]-5-methyl-oxazolidin-2-one

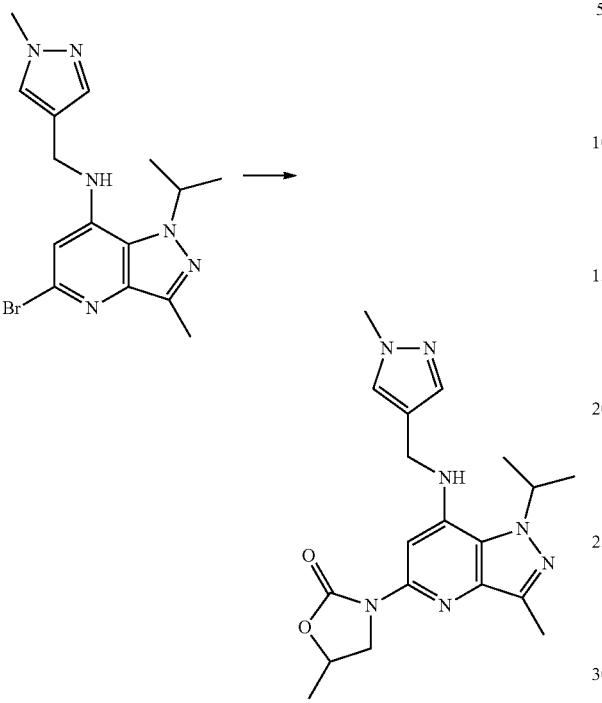

A mixture of 5-bromo-1-isopropyl-3-methyl-N-[(1-methylpyrazol-4-yl)methyl]pyrazolo[4,3-b]pyridin-7-amine (20 mg, 0.06 mmol), 5-methyloxazolidin-2-one (7 mg, 0.07 mmol), Pd$_2$(dba)$_3$ (5 mg, 0.006 mmol), Xantphos (10 mg, 0.02 mmol), Cs$_2$CO$_3$ (25 mg, 0.08 mmol) in dioxane (2 mL) was stirred at 85° C. for 12 hours. The mixture was concentrated to give a residue. The residue was purified by preparative HPLC to give 3-[1-isopropyl-3-methyl-7-[(1-methylpyrazol-4-yl)methylamino]pyrazolo[4,3-b]pyridin-5-yl]-5-methyl-oxazolidin-2-one (15 mg).
$^1$H NMR (Chloroform-d, 400 MHz): δ=7.59 (s, 1H), 7.55 (s, 2H), 4.80 (brd, J=6.8 Hz, 1H), 4.74-4.64 (m, 1H), 4.63-4.56 (m, 1H), 4.47 (dd, J=8.4, 10.4 Hz, 1H), 4.39 (d, J=5.0 Hz, 2H), 3.98-3.93 (m, 1H), 3.92 (s, 3H), 2.51 (s, 3H), 1.58 (s, 3H), 1.55 (d, J=6.3 Hz, 6H). LC-MS (m/z) 384.1 (MH$^+$); t$_R$=1.9 (Method C).

Example 151: 3-[1-isopropyl-3-methyl-7-[(1-methylpyrazol-4-yl)methylamino]pyrazolo[4,3-b]pyridin-5-yl]oxazolidin-2-one

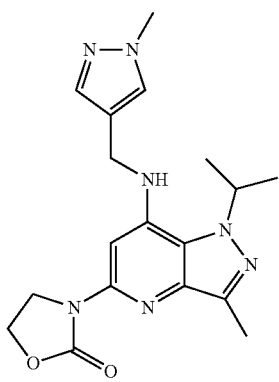 [SMILES: Cc1nn(C(C)C)c2c(NCc3cnn(C)c3)cc(N3CCOC3=O)nc12]

Prepared using the same procedure as described for example 150, from 5-bromo-1-isopropyl-3-methyl-N-((1-methyl-1H-pyrazol-4-yl)methyl)-1H-pyrazolo[4,3-b]pyridin-7-amine and oxazolidin-2-one.
$^1$H NMR (600 MHz, DMSO-d$_6$) δ 7.65 (s, 1H), 7.45 (s, 1H), 7.41 (s, 1H), 6.78 (t, J=5.7 Hz, 1H), 5.09 (m, 1H), 4.41 (m, 2H), 4.28 (d, J=5.6 Hz, 2H), 4.19 (m, 2H), 3.77 (s, 3H), 2.36 (s, 3H), 1.40 (d, J=6.3 Hz, 6H). LC-MS (m/z) 370.2 (MH$^+$); t$_R$=1.51 (Method J).

Example 152: 1-[1-isopropyl-3-methyl-7-[(1-methylpyrazol-4-yl)methylamino]pyrazolo[4,3-b]pyridin-5-yl]azetidin-2-one

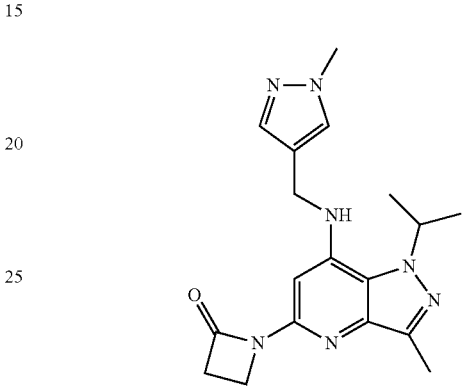

Prepared using the same procedure as described for example 150, from 5-bromo-1-isopropyl-3-methyl-N-((1-methyl-1H-pyrazol-4-yl)methyl)-1H-pyrazolo[4,3-b]pyridin-7-amine and azetidin-2-one.
$^1$H NMR (600 MHz, DMSO-d$_6$) δ 7.64 (s, 1H), 7.45 (s, 1H), 6.94 (s, 1H), 6.81 (t, J=5.6 Hz, 1H), 5.07 (m, 1H), 4.27 (d, J=5.5 Hz, 2H), 3.77 (s, 3H), 3.66 (s, 2H), 3.04 (t, J=4.5 Hz, 2H), 2.35 (s, 3H), 1.40 (d, J=6.3 Hz, 6H). LC-MS (m/z) 354.2 (MH$^+$); t$_R$=1.46 (Method K).

Example 153: 1-tert-butyl-3-[1-isopropyl-3-methyl-7-[(1-methylpyrazol-4-yl)methylamino]pyrazolo[4,3-b]pyridin-5-yl]imidazolidin-2-one

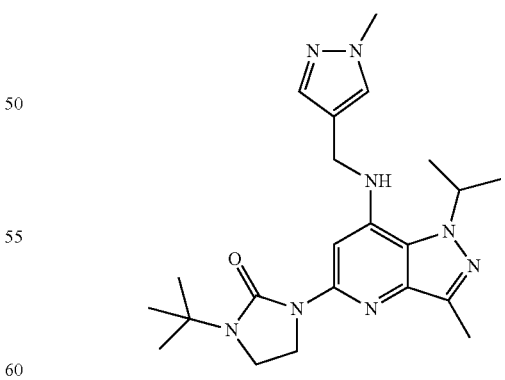

Prepared using the same procedure as described for example 150, from 5-bromo-1-isopropyl-3-methyl-N-((1-methyl-1H-pyrazol-4-yl)methyl)-1H-pyrazolo[4,3-b]pyridin-7-amine and 1-(tert-butyl)imidazolidin-2-one.
$^1$H NMR (500 MHz, Chloroform-d) δ 7.71 (s, 1H), 7.61 (s, 1H), 7.48 (s, 1H), 6.52 (t, J=5.6 Hz, 1H), 5.10-4.94 (m, 1H), 4.25 (d, J=5.6 Hz, 2H), 3.91-3.82 (m, 2H), 3.77 (s, 3H), 3.44 (t, J=7.9 Hz, 2H), 2.34 (s, 3H), 1.48-1.23 (m, 15H). LC-MS (m/z) 425.2 (MH⁺); t_R=1.64 (Method K).

Example 154: 1-[1-isopropyl-3-methyl-7-[(1-methylpyrazol-4-yl)methylamino]pyrazolo[4,3-b]pyridin-5-yl]pyrrolidin-2-one

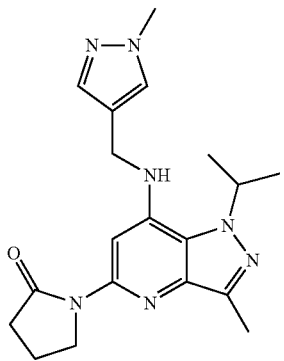 [SMILES: Cc1nn(C(C)C)c2c(NCc3cnn(C)c3)cc(N3CCCC3=O)nc12]

Prepared using the same procedure as described for example 150, from 5-bromo-1-isopropyl-3-methyl-N-((1-methyl-1H-pyrazol-4-yl)methyl)-1H-pyrazolo[4,3-b]pyridin-7-amine and pyrrolidin-2-one.

¹H NMR (600 MHz, DMSO-d6) δ 7.68 (s, 1H), 7.67 (s, 1H), 7.47 (s, 1H), 6.70 (t, J=5.7 Hz, 1H), 5.08 (m, 1H), 4.26 (d, J=5.6 Hz, 2H), 4.06-3.96 (m, 2H), 3.77 (s, 3H), 2.56 (t, J=8.0 Hz, 2H), 2.36 (s, 3H), 2.06-1.94 (m, 2H), 1.39 (d, J=6.3 Hz, 6H). LC-MS (m/z) 368.2 (MH⁺); t_R=1.39 (Method K).

Example 155: 3-[1-isopropyl-3-methyl-7-[(1-methylpyrazol-4-yl)methylamino]pyrazolo[4,3-b]pyridin-5-yl]-4-methyl-oxazolidin-2-one

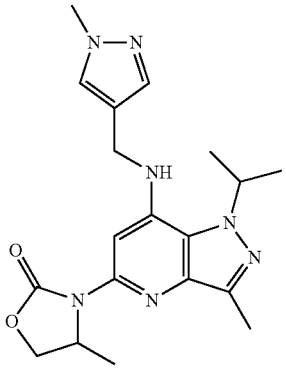 [SMILES: Cc1nn(C(C)C)c2c(NCc3cnn(C)c3)cc(N3C(=O)OCC3C)nc12]

Prepared using the same procedure as described for example 150, from 5-bromo-1-isopropyl-3-methyl-N-((1-methyl-1H-pyrazol-4-yl)methyl)-1H-pyrazolo[4,3-b]pyridin-7-amine and 4-methyloxazolidin-2-one.

¹H NMR (Chloroform-d, 400 MHz): δ=7.55 (d, J=2.4 Hz, 2H), 7.45 (s, 1H), 5.14-5.03 (m, 1H), 4.73-4.64 (m, 1H), 4.62-4.51 (m, 2H), 4.38 (dd, J=5.0, 9.6 Hz, 2H), 4.07 (dd, J=4.5, 8.3 Hz, 1H), 3.92 (s, 3H), 2.51 (s, 3H), 1.56 (dd, J=1.7, 6.5 Hz, 6H), 1.52 (d, J=6.2 Hz, 3H). LC-MS (m/z) 384.1 (MH⁺); t_R=2 (Method B).

Example 156: 4-ethyl-3-[1-isopropyl-3-methyl-7-[(1-methylpyrazol-4-yl)methylamino]pyrazolo[4,3-b]pyridin-5-yl]oxazolidin-2-one

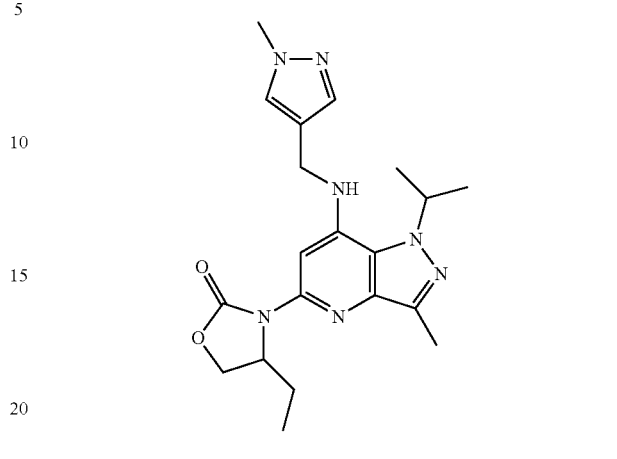

Prepared using the same procedure as described for example 150, from 5-bromo-1-isopropyl-3-methyl-N-((1-methyl-1H-pyrazol-4-yl)methyl)-1H-pyrazolo[4,3-b]pyridin-7-amine and 4-ethyloxazolidin-2-one.

¹H NMR (Chloroform-d, 400 MHz): δ 7.55 (d, J=2.0 Hz, 2H), 7.46 (s, 1H), 5.1-4.98 (m, 1H), 4.70-4.66 (m, 1H), 4.57-4.55 (m, 1H), 4.51 (t, J=8.8 Hz, 1H), 4.40-4.36 (m, 2H), 4.21-4.18 (m, 1H), 3.92 (s, 3H), 2.50 (s, 3H), 2.02-1.79 (m, 2H), 1.55 (d, J=4.8 Hz 6H), 0.93 (t, J=7.6 Hz, 3H). LC-MS (m/z) 398.1 (MH⁺); t_R=1.99 (Method C).

Example 157: N-[[5-(2-ethoxy-3-pyridyl)-1-isopropyl-3-methyl-pyrazolo[4,3-b]pyridin-7-yl]methyl]-5-methoxy-pyridin-3-amine

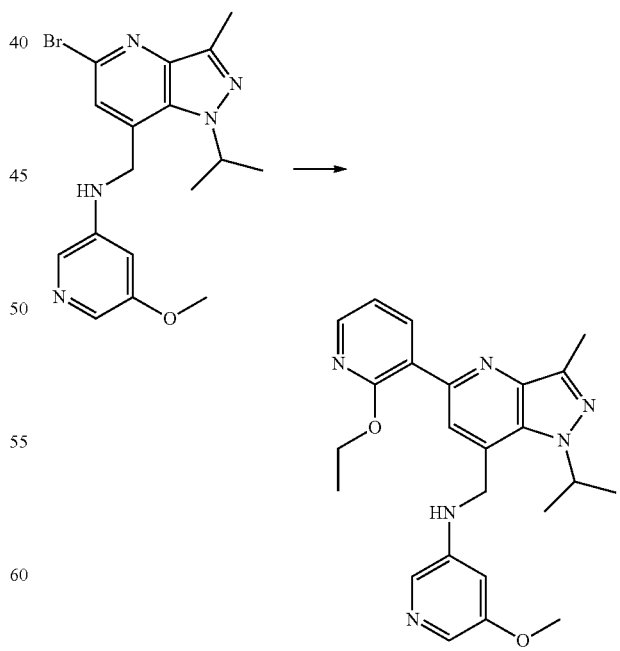

A mixture of N-[(5-bromo-1-isopropyl-3-methyl-pyrazolo[4,3-b]pyridin-7-yl)methyl]-5-methoxy-pyridin-3-amine (69 mg, 0.18 mmol), (2-ethoxy-3-pyridyl)boronic acid (59 mg, 0.35 mmol), Pd(dppf)Cl$_2$ (26 mg, 0.03 mmol), Cs$_2$CO$_3$ (115 mg, 0.35 mmol) in dioxane (3 mL) and water (1 mL) was degassed and purged with N$_2$ 3 times, and then the mixture was stirred at 100° C. for 2 hours under a N$_2$ atmosphere. Water (20 mL) was added and the mixture was extracted with ethyl acetate (30 mL×3). The combined organic layers were washed with brine (20 mL), dried over Na$_2$SO$_4$ and concentrated. The crude mixture was purified by preparative HPLC to give N-[[5-(2-ethoxy-3-pyridyl)-1-isopropyl-3-methyl-pyrazolo[4,3-b]pyridin-7-yl]methyl]-5-methoxy-pyridin-3-amine (48.16 mg).

$^1$H NMR (Chloroform-d, 400 MHz): δ 8.27 (dd, J=2.0, 7.6 Hz, 1H), 8.18 (dd, J=2.0, 4.8 Hz, 1H), 8.00 (s, 1H), 7.81-7.80 (m, 2H), 7.05-7.02 (m, 1H), 6.49-6.48 (m, 1H), 4.90-4.87 (m, 1H), 4.74 (d, J=5.6 Hz, 2H), 4.40 (q, J=7.2 Hz, 2H), 4.18-4.16 (m, 1H), 3.83 (s, 3H), 2.72 (s, 3H), 1.58 (d, J=7.2 Hz, 6H). 1.27 (t, J=7.2 Hz, 3H). LC-MS (m/z) 433.1 (MH$^+$); t$_R$=1.88 (Method A).

Example 158: N-[[5-(2-ethoxy-3-pyridyl)-1-isopropyl-3-methyl-pyrazolo[4,3-b]pyridin-7-yl]methyl]-1-methyl-1,2,4-triazol-3-amine

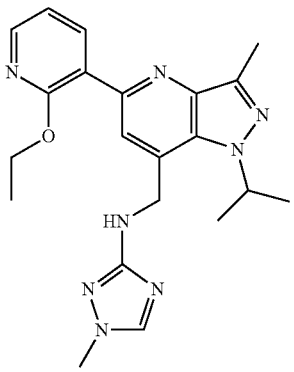 [SMILES: CCOc1ncccc1-c1cc(CNc2ncn(C)n2)c2c(n1)c(C)nn2C(C)C]

Prepared using the same procedure as described for example 157, from N-[(5-bromo-1-isopropyl-3-methyl-pyrazolo[4,3-b]pyridin-7-yl)methyl]-1-methyl-1,2,4-triazol-3-amine and (2-ethoxy-3-pyridyl)boronic acid.

$^1$H NMR (Chloroform-d, 400 MHz): δ 8.24 (dd, J=2.0, 7.6 Hz, 1H), 8.18 (dd, J=2.0, 5.2 Hz, 1H), 7.99 (s, 1H), 7.67 (s, 1H), 7.03 (dd, J=4.8, 7.2 Hz, 1H), 5.01-4.98 (m, 1H), 4.91 (d, J=6.0 Hz, 2H), 4.56 (t, J=6.0 Hz, 1H), 4.45 (q, J=7.2 Hz, 2H), 3.77 (s, 3H), 2.70 (s, 3H), 1.58 (d, J=6.4 Hz, 6H), 1.34 (t, J=7.2 Hz, 3H). LC-MS (m/z) 407.1 (MH$^+$); t$_R$=2.17 (Method C).

Example 159: 5-(2-ethoxy-3-pyridyl)-1-isopropyl-7-[2-(5-methoxy-3-pyridyl)ethyl]-3-methyl-pyrazolo[4,3-b]pyridine

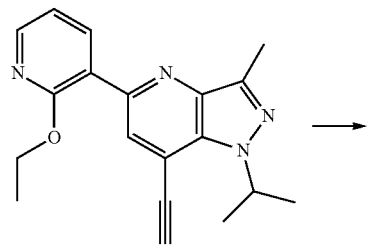

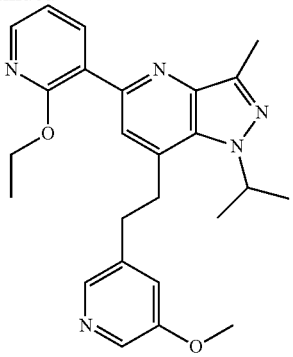

A mixture of 5-(2-ethoxypyridin-3-yl)-7-ethynyl-1-isopropyl-3-methyl-1H-pyrazolo[4,3-b]pyridine (0.05 g, 0.16 mmol), 3-iodo-5-methoxy-pyridine (37 mg, 0.16 mmol), CuI (3 mg, 0.016 mmol), Pd(dppf)Cl$_2$ (11 mg, 0.016 mmol) and Et$_3$N (79 mg, 0.78 mmol) in dioxane (3 mL) was stirred at 100° C. under a N$_2$ atmosphere for 4 hours. The mixture was worked up with 4 other batches (each with same procedure and same amount of starting material). The mixture was concentrated and extracted with ethyl acetate (20 mL×2), dried over Na$_2$SO$_4$, and concentrated to give residue. The mixture was purified by column chromatography (SiO$_2$, Petroleum ether/Ethyl acetate=10/1 to 1/1) to give 5-(2-ethoxypyridin-3-yl)-1-isopropyl-7-((5-methoxypyridin-3-yl)ethynyl)-3-methyl-1H-pyrazolo[4,3-b]pyridine (0.025 g). A mixture of 5-(2-ethoxypyridin-3-yl)-1-isopropyl-7-((5-methoxypyridin-3-yl)ethynyl)-3-methyl-1H-pyrazolo[4,3-b]pyridine (0.02 g, 0.047 mmol), Pd/C (0.005 g, 0.047 mmol, 10%), H$_2$ (15 psi) in ethyl acetate (2 mL) was stirred at room temperature for 0.25 hour. The mixture was filtered and the filtrate was concentrated to give residue. The residue was purified by preparative HPLC to give 5-(2-ethoxypyridin-3-yl)-1-isopropyl-7-(2-(5-methoxypyridin-3-yl)ethyl)-3-methyl-1H-pyrazolo[4,3-b]pyridine (7 mg).

$^1$H NMR (Chloroform-d, 400 MHz): δ=8.27-8.24 (m, 1H), 8.24-8.14 (m, 3H), 7.79 (s, 1H), 7.05 (dd, J=4.8, 7.2 Hz, 1H), 6.96 (t, J=2.0 Hz, 1H), 4.98-4.79 (m, 1H), 4.48 (q, J=7.2 Hz, 2H), 3.81 (s, 3H), 3.43-3.29 (m, 2H), 3.18-3.01 (m, 2H), 2.70 (s, 3H), 1.59 (d, J=6.8 Hz, 6H), 1.41 (t, J=6.8 Hz, 3H). LC-MS (m/z) 432.1 (MH$^+$); t$_R$=1.97 (Method A).

Example 160: 5-(2-ethoxy-3-pyridyl)-1-isopropyl-3-methyl-7-[2-(1-methyl-1,2,4-triazol-3-yl)ethyl]pyrazolo[4,3-b]pyridine

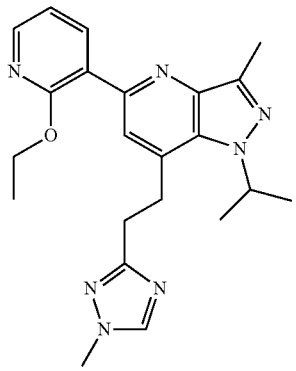 [SMILES: CCOc1ncccc1-c1cc(CCc2ncn(C)n2)c2c(n1)c(C)nn2C(C)C]

Prepared using the same procedure as described for example 159, from 5-(2-ethoxypyridin-3-yl)-7-ethynyl-1-isopropyl-3-methyl-1H-pyrazolo[4,3-b]pyridine and added 3-bromo-1-methyl-1H-1,2,4-triazole.

$^1$H NMR (Chloroform-d, 400 MHz): δ 8.23 (dd, J=2.0, 7.6 Hz, 1H), 8.19 (dd, J=1.6, 4.4 Hz, 1H), 7.99 (s, 1H), 7.81 (s, 1H), 7.04 (dd, J=4.2, 7.6 Hz, 1H), 5.11-5.04 (m, 1H), 4.48 (q, J=7.2 Hz, 2H), 3.90 (s, 3H), 3.55-3.51 (m, 2H), 3.23-3.18 (m, 2H), 2.70 (s, 3H), 1.61 (d, J=6.8 Hz, 6H), 1.43 (t, J=6.8 Hz, 3H). LC-MS (m/z) 406.1 (MH$^+$); $t_R$=2.3 (Method C).

Example 161: 5-(2-ethoxy-3-pyridyl)-1-isopropyl-3-methyl-N-[(2-methyl-1,2,4-triazol-3-yl)methyl]pyrazolo[4,3-b]pyridin-7-amine and Example 162: 5-(2-ethoxy-3-pyridyl)-1-isopropyl-3-methyl-N-[(4-methyl-1,2,4-triazol-3-yl)methyl]pyrazolo[4,3-b]pyridin-7-amine

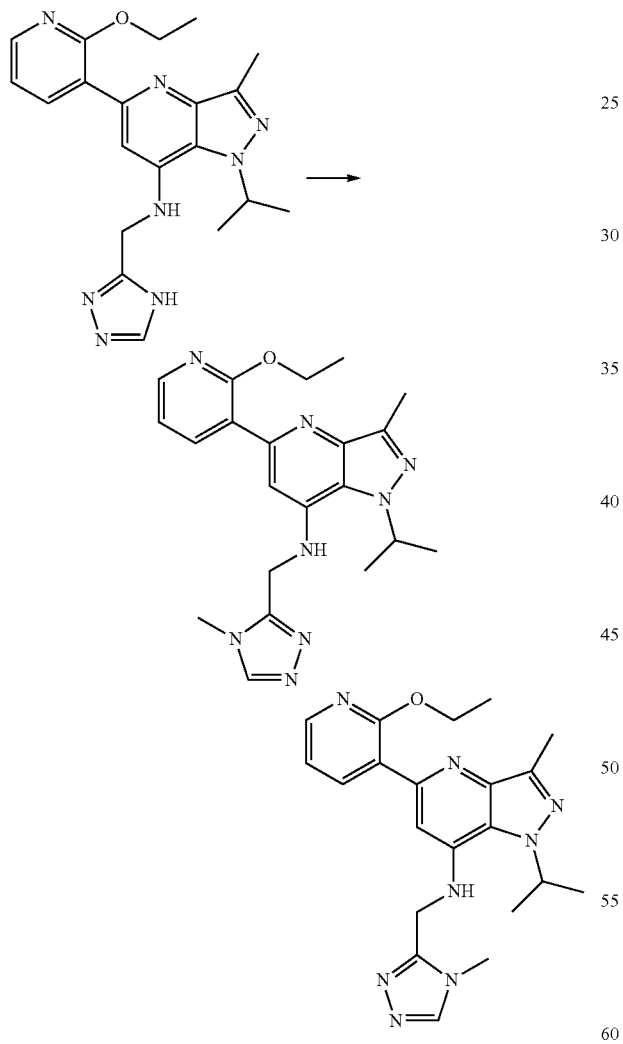

Cs$_2$CO$_3$ (16.6 mg, 0.051 mmol) and iodomethane (510 μl, 0.051 mmol, 100 mM, THF) were added to N-((4H-1,2,4-triazol-3-yl)methyl)-5-(2-ethoxypyridin-3-yl)-1-isopropyl-3-methyl-1H-pyrazolo[4,3-b]pyridin-7-amine (20 mg, 0.051 mmol) in THF (1.3 mL). The reaction mixture was stirred in a sealed vial at 80° C. for 50 minutes. The reaction mixture was concentrated in vacuo. Water was added. The mixture was extracted with ethyl acetate. The organic phase was washed with brine, dried over MgSO4, filtered and concentrated in vacuo. The residue was purified by SFC to give 5-(2-ethoxypyridin-3-yl)-1-isopropyl-3-methyl-N-((1-methyl-1H-1,2,4-triazol-5-yl)methyl)-1H-pyrazolo[4,3-b]pyridin-7-amine (2 mg) and 5-(2-ethoxypyridin-3-yl)-1-isopropyl-3-methyl-N-((4-methyl-4H-1,2,4-triazol-3-yl)methyl)-1H-pyrazolo[4,3-b]pyridin-7-amine (1 mg)

Example 161: 5-(2-ethoxy-3-pyridyl)-1-isopropyl-3-methyl-N-[(2-methyl-1,2,4-triazol-3-yl)methyl]pyrazolo[4,3-b]pyridin-7-amine $^1$H NMR (600 MHz, Chloroform-d) δ 8.28 (dt, J=7.3, 1.4 Hz, 1H), 8.19 (dd, J=4.9, 1.9 Hz, 1H), 7.92 (s, 1H), 7.17 (s, 1H), 7.05 (dd, J=7.3, 4.9 Hz, 1H), 5.72 (s, 1H), 4.98 (hept, J=6.6 Hz, 1H), 4.56 (d, J=4.1 Hz, 2H), 4.49 (q, J=7.0 Hz, 2H), 3.95 (s, 3H), 2.66 (s, 3H), 1.66 (d, J=6.5 Hz, 6H), 1.44 (t, J=7.0 Hz, 3H). LC-MS (m/z) 407.4 (MH$^+$); $t_R$=0.51 (Method D).

Example 162: 5-(2-ethoxy-3-pyridyl)-1-isopropyl-3-methyl-N-[(4-methyl-1,2,4-triazol-3-yl)methyl]pyrazolo[4,3-b]pyridin-7-amine $^1$H NMR (600 MHz, DMSO-d$_6$) δ 8.43 (s, 1H), 8.19 (dd, J=4.9, 1.9 Hz, 1H), 8.12 (dd, J=7.3, 2.0 Hz, 1H), 7.32 (s, 1H), 7.09 (dd, J=7.4, 4.8 Hz, 1H), 6.80 (t, J=5.2 Hz, 1H), 5.17 (hept, J=6.8 Hz, 1H), 4.67 (d, J=5.0 Hz, 2H), 4.42 (q, J=7.0 Hz, 2H), 3.71 (s, 3H), 2.46 (s, 3H), 1.45 (d, J=6.3 Hz, 6H), 1.36 (t, J=7.0 Hz, 3H). LC-MS (m/z) 407.4 (MH$^+$); $t_R$=0.49 (Method D).

Example 163: 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine

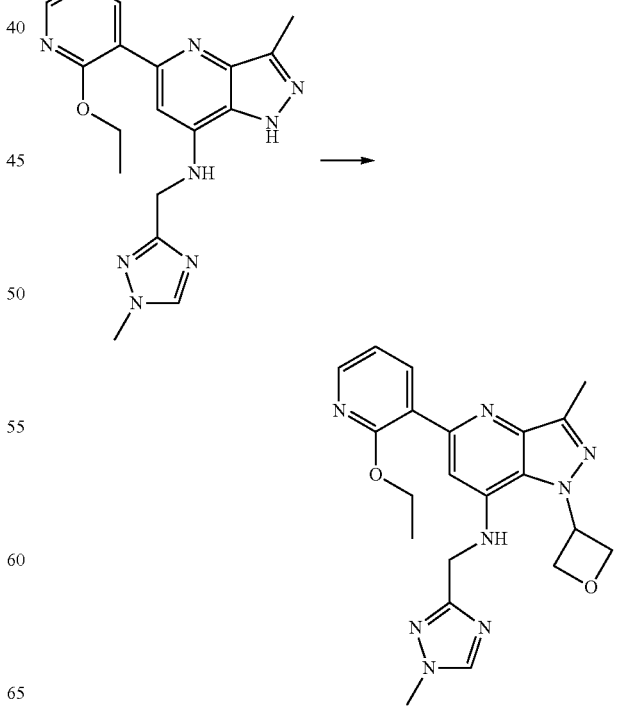

A suspension of 5-(2-ethoxypyridin-3-yl)-3-methyl-N-((1-methyl-1H-1,2,4-triazol-3-yl)methyl)-1H-pyrazolo[4,3-b]pyridin-7-amine (80 mg, 0.22 mmol, prepared using the same procedure as described for example 29, from 5-(2-ethoxypyridin-3-yl)-3-methyl-1H-pyrazolo[4,3-b]pyridin-7-amine and 1-methyl-1,2,4-triazole-3-carbaldehyde), 3-iodooxetane (81 mg, 0.44 mmol) and t-BuOK (215 mg, 1.91 mmol) in DMF (2 mL) was heated to 120° C. for 34 hours. The reaction mixture was cooled to room temperature and concentrated in vacuo. The residue was purified by preparative HPLC twice to give 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine (8 mg).

$^1$H NMR (Chloroform-d, 400 MHz) δ 8.28 (dd, J=2.2, 7.4 Hz, 1H), 8.19 (dd, J=2.0, 4.8 Hz, 1H), 8.06 (s, 1H), 7.26 (s, 1H), 7.03 (dd, J=4.8, 7.4 Hz, 1H), 5.97-5.93 (m, 1H), 5.34 (t, J=6.4 Hz, 2H), 5.19 (t, J=7.2 Hz, 2H), 4.57 (d, J=5.2 Hz, 2H), 4.49 (q, J=6.8 Hz, 2H), 3.96 (s, 3H), 2.67 (s, 3H), 1.44 (t, J=7.2 Hz, 3H). LC-MS (m/z) 421.1 (MH$^+$); $t_R$=2.04 (Method B).

Example 164: 5-(2-ethoxy-3-pyridyl)-1-isopropyl-3-methyl-7-[(1-methylpyrazol-4-yl)methylsulfanyl]pyrazolo[4,3-b]pyridine

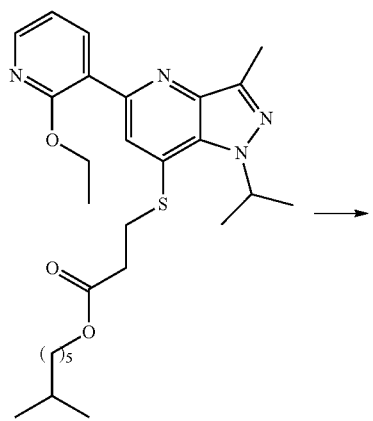

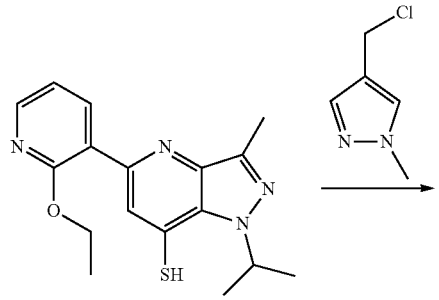

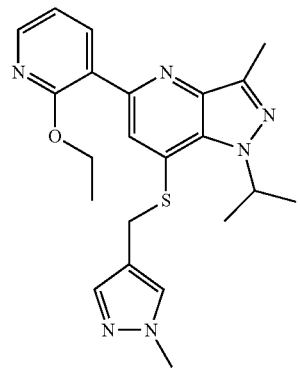

KO$^t$Bu (6.9 mg, 0.06 mmol) was added to a solution of 6-methylheptyl 3-((5-(2-ethoxypyridin-3-yl)-1-isopropyl-3-methyl-1H-pyrazolo[4,3-b]pyridin-7-yl)thio)propanoate (21 mg, 0.04 mmol) in DMF (0.59 mL) at rt. The resulting mixture was stirred at rt over 50 minutes after which 4-(chloromethyl)-1-methyl-1H-pyrazole (13.4 mg, 0.06 mmol) was added in one portion. After stirring at rt over 6 hours the mixture was cooled to ice bath temperature, quenched with a few drops of water and stirred without cooling bath for 5 minutes. Partitioned between ethyl acetate (40 mL) and water (2×15 mL). The org. layer was further washed with brine (10 mL). The combined org. layers were dried (Na$_2$SO$_4$) and concentrated. The crude material was purified by flash chromatography with heptane:ethyl acetate 1:0 to 0:1 to give 5-(2-ethoxypyridin-3-yl)-1-isopropyl-3-methyl-7-(((1-methyl-1H-pyrazol-4-yl)methyl)thio)-1H-pyrazolo[4,3-b]pyridine (8 mg).

$^1$H NMR (DMSO-d$_6$ 600 MHz): δ 8.28-8.22 (m, 2H), 7.94 (s, 1H), 7.76 (s, 1H), 7.47 (s, 1H), 7.16 (dd, J=7.3, 4.9 Hz, 1H), 5.33 (hept, J=6.5 Hz, 1H), 4.44 (q, J=7.0 Hz, 2H), 4.39 (s, 2H), 3.79 (s, 3H), 2.54 (s, 3H), 1.47 (d, J=6.5 Hz, 6H), 1.34 (t, J=7.0 Hz, 3H). LC-MS (m/z) 423.6 (MH$^+$); $t_R$=0.76 (Method D).

Example 165: N-[[1-(difluoromethyl)pyrazol-4-yl]methyl]-5-(2-ethoxy-3-pyridyl)-1-isopropyl-3-methyl-pyrazolo[4,3-b]pyridin-7-amine

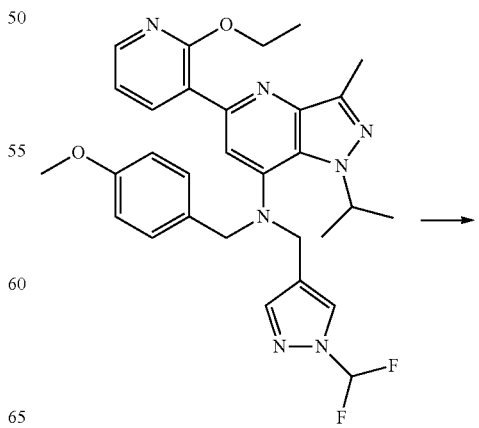

-continued

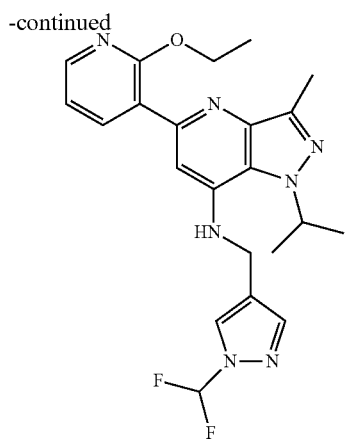

To a solution of N-((1-(difluoromethyl)-1H-pyrazol-4-yl)methyl)-5-(2-ethoxypyridin-3-yl)-1-isopropyl-N-(4-methoxybenzyl)-3-methyl-1H-pyrazolo[4,3-b]pyridin-7-amine (15 mg, 0.027 mmol) in DCM (0.5 mL) was added trifluoro acetic acid (0.5 mL). The mixture was stirred at room temperature for 1 hour. Water (3 mL) was added and the mixture was poured into a saturated, aqueous solution of NaHCO$_3$. The mixture was extracted with ethyl acetate (5 mL×3). The combined organic layers were washed with brine (5 mL), dried over Na$_2$SO$_4$ and concentrated. The crude mixture was purified by flash chromatography with heptane:ethyl acetate=1:0 to 0:1 to give N-((1-(difluoromethyl)-1H-pyrazol-4-yl)methyl)-5-(2-ethoxypyridin-3-yl)-1-isopropyl-3-methyl-1H-pyrazolo[4,3-b]pyridin-7-amine (11 mg, 0.025 mmol, 93% yield).

$^1$H NMR (600 MHz, Chloroform-d) δ 8.26 (dd, J=7.4, 2.0 Hz, 1H), 8.17 (dd, J=4.9, 2.0 Hz, 1H), 7.84 (d, J=2.7 Hz, 1H), 7.20 (s, 1H), 7.17 (t, J=60.7 Hz, 1H), 7.02 (dd, J=7.3, 4.9 Hz, 1H), 6.49 (d, J=2.7 Hz, 1H), 5.24 (s, 1H), 4.91 (hept, J=6.6 Hz, 1H), 4.57 (d, J=4.8 Hz, 2H), 4.47 (q, J=7.0 Hz, 2H), 2.65 (s, 3H), 1.65 (d, J=6.5 Hz, 6H), 1.40 (t, J=7.0 Hz, 3H). LC-MS (m/z) 442.5 (MH$^+$); t$_R$=0.60 minutes (Method D).

Example 166: 5-(2-ethoxypyridin-3-yl)-N-((5-(fluoromethyl)isoxazol-3-yl)methyl)-1-isopropyl-3-methyl-1H-pyrazolo[4,3-b]pyridin-7-amine

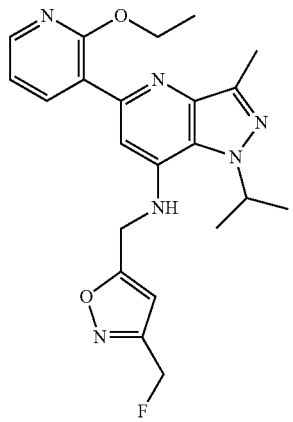 [SMILES: CCOc1ncccc1-c1cc(NCc2cc(CF)no2)c2c(n1)c(C)nn2C(C)C]

Prepared using the same procedure as described for example 165, from 5-(2-ethoxypyridin-3-yl)-N-((5-(fluoromethyl)isoxazol-3-yl)methyl)-1-isopropyl-N-(4-methoxybenzyl)-3-methyl-1H-pyrazolo[4,3-b]pyridin-7-amine $^1$H NMR (600 MHz, Chloroform-d) δ 8.27 (dd, J=7.4, 2.0 Hz, 1H), 8.18 (dd, J=4.9, 2.0 Hz, 1H), 7.22 (s, 1H), 7.02 (dd, J=7.4, 4.9 Hz, 1H), 6.47 (d, J=2.6 Hz, 1H), 5.43 (d, J=47.3 Hz, 2H), 5.22 (s, 1H), 4.89 (hept, J=6.6 Hz, 1H), 4.65 (d, J=5.2 Hz, 2H), 4.47 (q, J=7.0 Hz, 2H), 2.64 (s, 3H), 1.64 (d, J=6.5 Hz, 6H), 1.39 (t, J=7.0 Hz, 3H). LC-MS (m/z) 425.6 (MH$^+$); t$_R$=0.57 minutes (Method D).

Example 167: 5-(2-ethoxypyridin-3-yl)-N-((3-(fluoromethyl)isoxazol-5-yl)methyl)-1-isopropyl-3-methyl-1H-pyrazolo[4,3-b]pyridin-7-amine

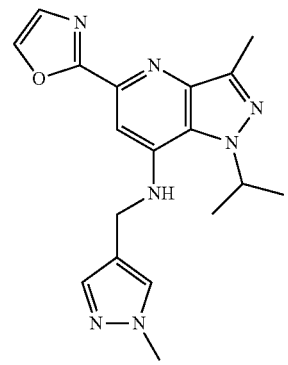 [SMILES: Cc1nn(C(C)C)c2c(NCc3cnn(C)c3)cc(-c3ncco3)nc12]

Prepared using the same procedure as described for example 165, from 5-(2-ethoxypyridin-3-yl)-N-((3-(fluoromethyl)isoxazol-5-yl)methyl)-1-isopropyl-N-(4-methoxybenzyl)-3-methyl-1H-pyrazolo[4,3-b]pyridin-7-amine $^1$H NMR (600 MHz, Chloroform-d) δ 8.28 (dd, J=7.4, 2.0 Hz, 1H), 8.17 (dd, J=4.9, 2.0 Hz, 1H), 7.22 (s, 1H), 7.02 (dd, J=7.4, 4.9 Hz, 1H), 6.41 (s, 1H), 5.44 (d, J=46.9 Hz, 2H), 4.90 (t, J=5.9 Hz, 1H), 4.84 (hept, J=6.6 Hz, 1H), 4.73 (d, J=5.8 Hz, 2H), 4.45 (q, J=7.0 Hz, 2H), 2.65 (s, 3H), 1.64 (d, J=6.5 Hz, 6H), 1.35 (t, J=7.0 Hz, 3H). LC-MS (m/z) 425.6 (MH$^+$); t$_R$=0.55 minutes (Method D).

Example 168: 1-isopropyl-3-methyl-N-[(1-methyl-pyrazol-4-yl)methyl]-5-oxazol-2-yl-pyrazolo[4,3-b]pyridin-7-amine Prepared using the same procedure as described for example 147 from 5-bromo-1-isopropyl-3-methyl-N-((1-methyl-1H-pyrazol-4-yl)methyl)-1H-pyrazolo[4,3-b]pyridin-7-amine and tributyl(oxazol-2-yl)stannane.

$^1$H NMR (Chloroform-d, 400 MHz): δ 7.83 (s, 1H), 7.59 (s, 1H), 7.46 (s, 1H), 7.39 (s, 1H), 7.29 (s, 1H), 4.76-4.70 (m, 1H), 4.58 (brs, 1H), 4.44 (d, J=4.2 Hz, 2H), 3.94 (s, 3H), 2.69 (s, 3H), 1.59 (d, J=6.4 Hz, 6H). LC-MS (m/z) 352 (MH$^+$); t$_R$=1.75 minutes (Method C).

Example 169: 1-isopropyl-3-methyl-N-[(1-methyl-pyrazol-4-yl)methyl]-5-(3-methyltriazol-4-yl)pyrazolo[4,3-b]pyridin-7-amine

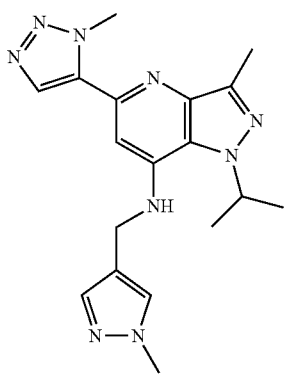 [SMILES: Cc1nn(C(C)C)c2c(NCc3cnn(C)c3)cc(-c3cnnn3C)nc12]

Prepared using the same procedure as described for example 147 from 5-bromo-1-isopropyl-3-methyl-N-((1-methyl-1H-pyrazol-4-yl)methyl)-1H-pyrazolo[4,3-b]pyridin-7-amine and 1-methyl-5-(tributylstannyl)-1H-1,2,3-triazole.

$^1$H NMR (Chloroform-d, 400 MHz): δ 7.93 (s, 1H), 7.57 (s, 1H), 7.45 (s, 1H), 6.70 (s, 1H), 4.76-4.69 (m, 1H), 4.65 (brs, 1H), 4.48 (s, 3H), 4.39 (d, J=4.4 Hz, 2H), 3.95 (s, 3H), 2.62 (s, 3H), 1.60 (d, J=6.4 Hz, 6H). LC-MS (m/z) 366 (MH$^+$); t$_R$=1.69 minutes (Method C).

Example 170: 1-isopropyl-5-(2-methoxy-3-pyridyl)-3-methyl-N-[[2-(trifluoromethyl)-3-pyridyl]methyl]pyrazolo[4,3-b]pyridin-7-amine

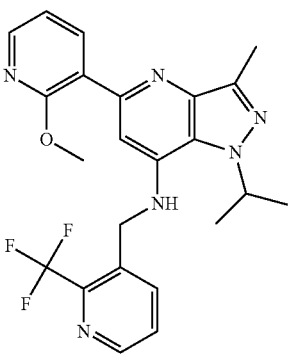 [SMILES: COc1ncccc1-c1cc(NCc2cccnc2C(F)(F)F)c2c(n1)c(C)nn2C(C)C]

Prepared using the same procedure as described for example 1 from [2-(trifluoromethyl)-3-pyridyl]methanamine, (2-methoxypyridin-3-yl)boronic acid and 5,7-dichloro-1-isopropyl-3-methyl-pyrazolo[4,3-b]pyridine.

$^1$H NMR (Chloroform-d, 400 MHz): δ 8.67 (d, J=4.0 Hz 1H), 8.20 (dd, J=1.2, 7.2 Hz 1H), 8.15 (dd, J=2.0, 4.8 Hz 1H), 7.99 (d, J=7.6 Hz 1H), 7.50 (dd, J=4.8, 8.0 Hz 1H), 7.01 (dd, J=5.2, 7.6 Hz 1H), 6.90 (s, 1H), 5.07 (brs, 1H), 4.86-4.89 (m, 3H), 3.74 (s, 3H), 2.65 (s, 3H), 1.66 (d, J=6.8 Hz, 6H). LC-MS (m/z) 457 (MH$^+$); t$_R$=1.89 minutes (Method A).

Example 171: 3-[1-isopropyl-7-[(2-methoxy-3-pyridyl)methylamino]-3-methyl-pyrazolo[4,3-b]pyridin-5-yl]-1H-pyridin-2-one

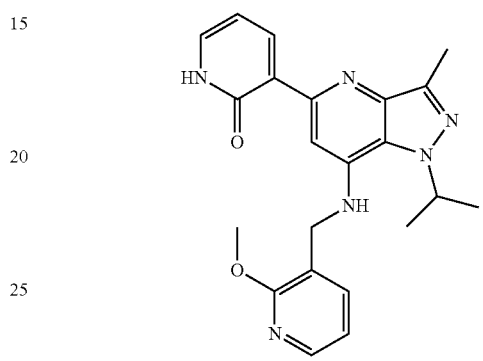

Prepared using the same procedure as described for example 1 from 5,7-dichloro-1-isopropyl-3-methyl-1H-pyrazolo[4,3-b]pyridine, (2-methoxypyridin-3-yl)methanamine and (2-oxo-1,2-dihydropyridin-3-yl)boronic acid.

$^1$H NMR (DMSO-d$_6$, 400 MHz): δ 11.73 (brs, 1H), 8.27 (dd, J=2.0, 7.2 Hz, 1H), 8.01 (d, J=3.6 Hz, 1H), 7.57 (d, J=6.4 Hz, 1H), 7.45-7.35 (m, 1H), 6.88 (dd, J=4.2, 7.2 Hz, 1H), 6.75-6.67 (m, 1H), 6.35-6.25 (m, 1H), 5.20-5.14 (m, 1H), 4.45-4.40 (m, 2H), 3.91 (s, 3H), 2.43 (s, 3H), 1.43 (d, J=6.4 Hz, 6H). LC-MS (m/z) 405 (MH$^+$); t$_R$=1.95 minutes (Method C).

Example 172: 5-(2-ethoxy-3-pyridyl)-1-isopropyl-N-[(3-methoxy-4-pyridyl)methyl]-3-methyl-pyrazolo[4,3-b]pyridin-7-amine

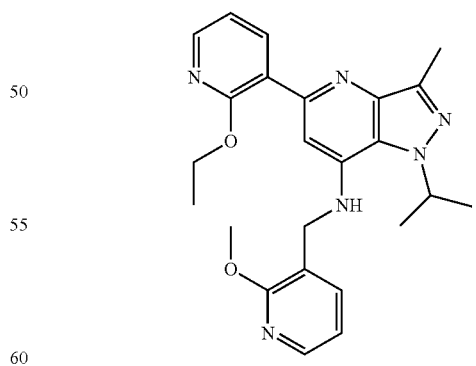

Prepared using the same procedure as described for example 1 from 5,7-dichloro-1-isopropyl-3-methyl-1H-pyrazolo[4,3-b]pyridine, (3-methoxy-4-pyridyl)methanamine and (2-ethoxy-3-pyridyl)boronic acid.

$^1$H NMR (Chloroform-d, 400 MHz): δ 8.32 (s, 1H), 8.26 (d, J=4.8 Hz, 1H), 8.22 (d, J=7.2 Hz, 1H), 8.14 (d, J=4.2 Hz, 1H), 7.30-7.25 (m, 1H), 7.08 (s, 1H), 7.01 (dd, J=4.8, 7.2 Hz, 1H), 5.02 (brs, 1H), 4.91-4.88 (m, 1H), 4.58 (d, J=5.6 Hz, 2H), 4.35 (q, J=7.2 Hz, 2H), 4.01 (s, 3H), 2.65 (s, 3H), 1.66 (d, J=7.2 Hz, 6H), 1.26 (t, J=7.2 Hz, 3H). LC-MS (m/z) 433.1 (MH⁺); $t_R$=1.47 minutes (Method A).

Example 173: 1-isopropyl-5-(2-methoxy-3-pyridyl)-3-methyl-N-[(2-methylthiazol-5-yl)methyl]pyrazolo[4,3-b]pyridin-7-amine

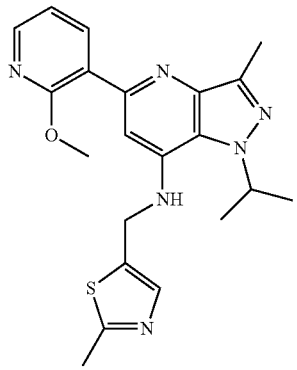 [SMILES: COc1ncccc1-c1cc(NCc2cnc(C)s2)c2c(n1)c(C)nn2C(C)C]

Prepared using the same procedure as described for example 29 from 1-isopropyl-5-(2-methoxypyridin-3-yl)-3-methyl-1H-pyrazolo[4,3-b]pyridin-7-amine and 2-methylthiazole-5-carbaldehyde.

¹H NMR (Chloroform-d, 400 MHz): δ 8.20-8.18 (m, 2H), 7.64 (s, 1H), 7.12 (s, 1H), 7.07-7.04 (m, 1H), 4.88-4.77 (m, 2H), 4.77-4.68 (m, 2H), 4.00 (s, 3H), 2.72 (s, 3H), 2.65 (s, 3H), 1.62 (d, J=6.8 Hz, 6H). LC-MS (m/z) 409 (MH⁺); $t_R$=1.66 minutes (Method A).

Example 174: 5-(2-cyclopropoxypyridin-3-yl)-1-isopropyl-N-((2-methoxypyridin-3-yl)methyl)-3-methyl-1H-pyrazolo[4,3-b]pyridin-7-amine

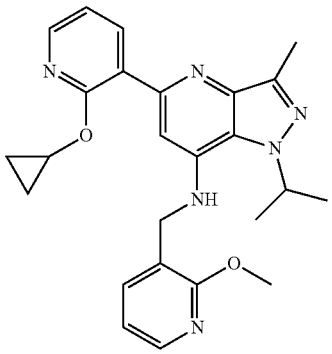 [SMILES: COc1ncccc1CNc1cc(-c2cccnc2OC2CC2)nc2c(C)nn(C(C)C)c12]

Prepared using the same procedure as described for example 1 from 5,7-dibromo-1-isopropyl-3-methyl-1H-pyrazolo[4,3-b]pyridine, (2-methoxypyridin-3-yl)methanamine and 2-cyclopropoxy-3-(4,4,5,5-tetramethyl-1,3,2-dioxaborolan-2-yl)pyridine.

¹H NMR (Chloroform-d, 600 MHz) δ 8.23 (dd, J=4.9, 2.0 Hz, 1H), 8.21 (dd, J=7.4, 2.0 Hz, 1H), 8.14 (dd, J=5.0, 1.9 Hz, 1H), 7.59 (dd, J=7.2, 1.8 Hz, 1H), 7.05 (dd, J=7.4, 4.9 Hz, 1H), 6.97 (s, 1H), 6.90 (dd, J=7.2, 5.0 Hz, 1H), 5.11 (t, J=5.8 Hz, 1H), 4.86 (hept, J=6.5 Hz, 1H), 4.48 (d, J=5.8 Hz, 2H), 4.39-4.34 (m, 1H), 4.04 (s, 3H), 2.63 (s, 3H), 1.63 (d, J=6.6 Hz, 6H), 0.79-0.76 (m, 2H), 0.63-0.60 (m, 2H). LC-MS (m/z) 445.5 (MH⁺); $t_R$=0.6 minutes (Method D).

Example 175: 1-isopropyl-N-((2-methoxypyridin-3-yl)methyl)-3-methyl-5-(1-methyl-1H-pyrazol-5-yl)-1H-pyrazolo[4,3-b]pyridin-7-amine

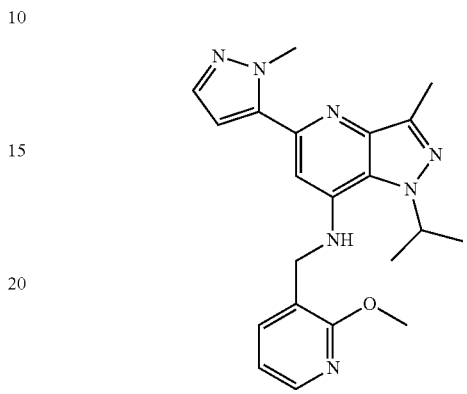

Prepared using the same procedure as described for example 1 from 5,7-dibromo-1-isopropyl-3-methyl-1H-pyrazolo[4,3-b]pyridine, (2-methoxypyridin-3-yl)methanamine and 1-methyl-5-(4,4,5,5-tetramethyl-1,3,2-dioxaborolan-2-yl)-1H-pyrazole.

¹H NMR (Chloroform-d, 600 MHz) δ 8.15 (dd, J=5.1, 1.9 Hz, 1H), 7.60 (dd, J=7.2, 1.8 Hz, 1H), 7.48 (d, J=1.9 Hz, 1H), 6.91 (dd, J=7.2, 5.0 Hz, 1H), 6.64 (s, 1H), 6.44 (d, J=2.0 Hz, 1H), 5.22 (t, J=5.9 Hz, 1H), 4.84 (hept, J=6.6 Hz, 1H), 4.49 (d, J=5.8 Hz, 2H), 4.22 (s, 3H), 4.04 (s, 3H), 2.60 (s, 3H), 1.63 (d, J=6.5 Hz, 6H). LC-MS (m/z) 392.5 (MH⁺); $t_R$=0.49 minutes (Method D).

Example 176: 5-(2-ethoxy-3-pyridyl)-1-isopropyl-N-[(5-methoxypyrimidin-2-yl)methyl]-3-methyl-pyrazolo[4,3-b]pyridin-7-amine

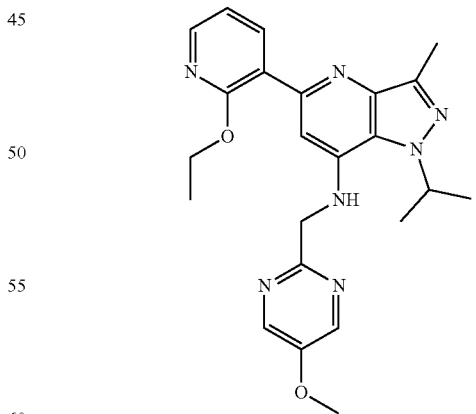

Prepared using the same procedure as described for example 1 from 5,7-dichloro-1-isopropyl-3-methyl-1H-pyrazolo[4,3-b]pyridine, (5-methoxypyrimidin-2-yl)methanamine and (2-ethoxy-3-pyridyl)boronic acid.

¹H NMR (Chloroform-d, 400 MHz): δ 8.48 (s, 2H), 8.27 (d, J=7.6 Hz, 1H), 8.20 (d, J=4.0 Hz, 1H), 7.16 (s, 1H), 7.04

(dd, J=4.8, 6.8 Hz, 1H), 5.15-5.08 (m, 1H), 4.68 (d, J=4.4 Hz, 2H), 4.50 (q, J=7.2 Hz, 2H), 3.98 (s, 3H), 2.70 (s, 3H), 1.71 (d, J=6.4 Hz, 6H), 1.45 (t, J=6.8 Hz, 3H). LC-MS (m/z) 434.1 (MH$^+$); $t_R$=2.15 minutes (Method C).

Example 177: 3-[1-isopropyl-3-methyl-7-[(1-methylpyrazol-4-yl)methylamino]pyrazolo[4,3-b]pyridin-5-yl]-1H-pyridin-2-one

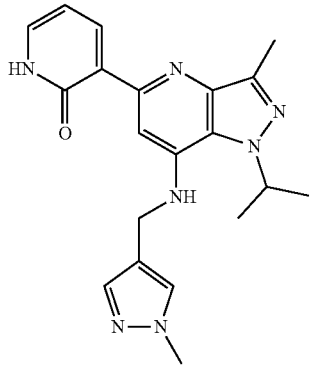 [SMILES: Cc1nn(C(C)C)c2c(NCc3cnn(C)c3)cc(-c3ccc[nH]c3=O)nc12]

Prepared using the same procedure as described for example 1 from 5,7-dichloro-1-isopropyl-3-methyl-1H-pyrazolo[4,3-b]pyridine, (1-methyl-1H-pyrazol-4-yl)methanamine and (2-oxo-1,2-dihydropyridin-3-yl)boronic acid.

$^1$H NMR (Chloroform-d, 400 MHz): δ 8.22 (d, J=6.8 Hz, 1H), 7.90-7.75 (m, 1H), 7.59 (s, 1H), 7.57 (s, 1H), 7.26-7.20 (m, 1H), 6.65-6.63 (m, 1H), 5.47 (brs, 1H), 4.96-4.90 (m, 1H), 4.52 (d, J=4.4 Hz, 2H), 3.92 (s, 3H), 2.60 (s, 3H), 1.59 (d, J=6.4 Hz, 6H). LC-MS (m/z) 378 (MH$^+$); $t_R$=1.71 minutes (Method C).

Example 178: N-[[2-(difluoromethyl)-3-pyridyl]methyl]-5-(2-ethoxy-3-pyridyl)-1-isopropyl-3-methyl-pyrazolo[4,3-b]pyridin-7-amine

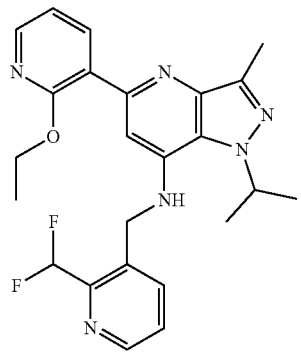 [SMILES: CCOc1ncccc1-c1cc(NCc2cccnc2C(F)F)c2c(n1)c(C)nn2C(C)C]

Prepared using the same procedure as described for example 1 from 5,7-dibromo-1-isopropyl-3-methyl-1H-pyrazolo[4,3-b]pyridine, (2-(difluoromethyl)pyridin-3-yl)methanamine and (2-ethoxy-3-pyridyl)boronic acid.

$^1$H NMR (Chloroform-d, 400 MHz): δ 8.58 (d, J=4.4 Hz, 1H), 8.24 (dd, J=7.6, 2.0 Hz, 1H), 8.14 (dd, J=4.8, 2.0 Hz, 1H), 7.92 (d, J=7.6 Hz, 1H), 7.42 (dd, J=8.0, 5.2 Hz, 1H), 7.13 (s, 1H), 7.00 (dd, J=7.2, 4.8 Hz, 1H), 6.80 (t, J=54.8 Hz, 1H), 4.97-4.82 (m, 4H), 4.33 (q, J=6.8 Hz, 2H), 2.66 (s, 3H), 1.64 (d, J=6.4 Hz, 6H), 1.21 (t, J=6.8 Hz, 3H) LC-MS (m/z) 453.1 (MH$^+$); $t_R$=1.98 minutes (Method A).

Example 179: 5-(2-ethoxy-3-pyridyl)-1-isopropyl-N-[(6-methoxypyrimidin-4-yl)methyl]-3-methyl-pyrazolo[4,3-b]pyridin-7-amine

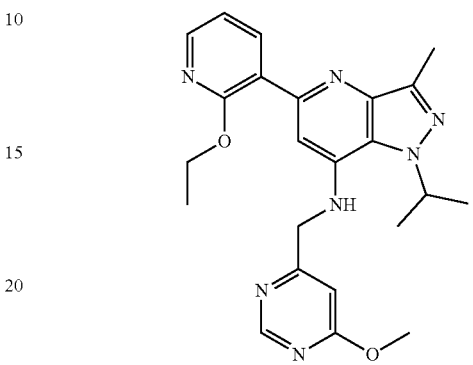

Prepared using the same procedure as described for example 1 from 5,7-dichloro-1-isopropyl-3-methyl-1H-pyrazolo[4,3-b]pyridine, (6-methoxypyrimidin-4-yl)methanamine and (2-ethoxy-3-pyridyl)boronic acid.

$^1$H NMR (Chloroform-d, 400 MHz): δ 8.82 (s, 1H), 8.25 (dd, J=5.2, 7.2 Hz, 1H), 8.17 (dd, J=2.0, 5.2 Hz, 1H), 7.08 (s, 1H), 7.02 (dd, J=4.8, 7.2 Hz, 1H), 6.78 (s, 1H), 6.01 (brs, 1H), 5.06-5.00 (m, 1H), 4.54 (d, J=4.4 Hz, 2H), 4.43 (q, J=6.8 Hz, 2H), 4.01 (s, 3H), 2.66 (s, 3H), 1.69 (d, J=6.8 Hz, 6H), 1.36 (t, J=6.8 Hz, 3H) LC-MS (m/z) 434.1 (MH$^+$); $t_R$=1.9 minutes (Method A).

Example 180: 5-(2-(ethoxy-1,1-d$_2$)pyridin-3-yl)-1-isopropyl-N-((2-methoxypyridin-3-yl)methyl)-3-methyl-1H-pyrazolo[4,3-b]pyridin-7-amine

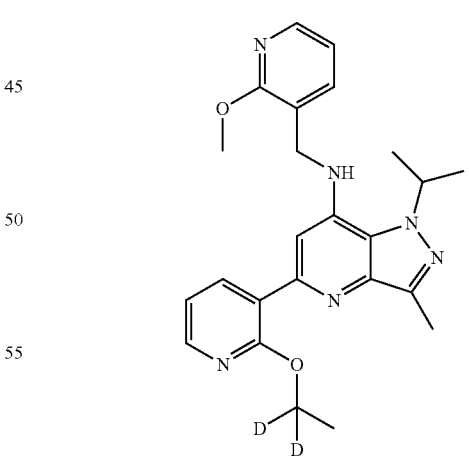

Prepared using the same procedure as described for example 1 from 5-bromo-1-isopropyl-N-((2-methoxypyridin-3-yl)methyl)-3-methyl-1H-pyrazolo[4,3-b]pyridin-7-amine and 2-(ethoxy-1,1-d$_2$)-3-(4,4,5,5-tetramethyl-1,3,2-dioxaboran-2yl)pyridine.

$^1$H NMR (Chloroform-d, 600 MHz) δ 8.24 (dd, J=7.3, 2.0 Hz, 1H), 8.12-8.15 (m, 2H), 7.59 (ddt, J=7.2, 1.8, 0.8 Hz, 1H), 7.14 (s, 1H), 6.99 (dd, J=7.4, 4.9 Hz, 1H), 6.89 (dd, J=7.2, 5.0 Hz, 1H), 5.10 (t, J=5.8 Hz, 1H), 4.87 (hept, J=6.6 Hz, 1H), 4.50 (d, J=5.7 Hz, 2H), 4.03 (s, 3H), 2.64 (s, 3H), 1.63 (d, J=6.5 Hz, 6H), 1.29 (s, 3H). LC-MS (m/z) 435.6 (MH+); t_R=0.61 minutes (Method D).

Example 181: 5-(2-(ethoxy-d_5)pyridin-3-yl)-1-isopropyl-N-((2-methoxypyridin-3-yl)methyl)-3-methyl-1H-pyrazolo[4,3-b]pyridin-7-amine

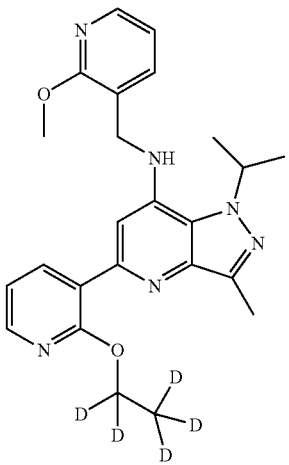 [SMILES: [2H]C([2H])([2H])C([2H])([2H])Oc1ncccc1-c1cc(NCc2cccnc2OC)c2c(n1)c(C)nn2C(C)C]

Prepared using the same procedure as described for example 1 from 5-bromo-1-isopropyl-N-((2-methoxypyridin-3-yl)methyl)-3-methyl-1H-pyrazolo[4,3-b]pyridin-7-amine and 2-(ethoxy-d_5)-3-(4,4,5,5-tetramethyl-1,3,2-dioxaboran-2yl)pyridine.

$^1$H NMR (Chloroform-d, 600 MHz) δ 8.24 (ddd, J=7.4, 2.0, 0.7 Hz, 1H), 8.12-8.15 (m, 2H), 7.61-7.56 (m, 1H), 7.14 (s, 1H), 7.02-6.96 (m, 1H), 6.89 (dd, J=7.2, 5.0 Hz, 1H), 5.10 (t, J=5.8 Hz, 1H), 4.87 (hept, J=6.6 Hz, 1H), 4.50 (d, J=5.7 Hz, 2H), 4.03 (s, 3H), 2.64 (s, 3H), 1.63 (d, J=6.5 Hz, 6H). LC-MS (m/z) 438.6 (MH+); t_R=0.6 minutes (Method D).

Example 182: 5-(2-(ethoxy-2,2,2-d_3)pyridin-3-yl)-1-isopropyl-N-((2-methoxypyridin-3-yl)methyl)-3-methyl-1H-pyrazolo[4,3-b]pyridin-7-amine

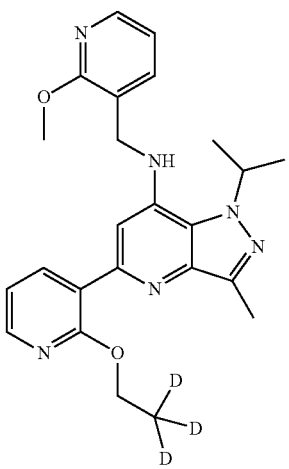 [SMILES: [2H]C([2H])([2H])COc1ncccc1-c1cc(NCc2cccnc2OC)c2c(n1)c(C)nn2C(C)C]

Prepared using the same procedure as described for example 1 from 5-bromo-1-isopropyl-N-((2-methoxypyridin-3-yl)methyl)-3-methyl-1H-pyrazolo[4,3-b]pyridin-7-amine and 2-(ethoxy-2,2,2-d_3)-3-(4,4,5,5-tetramethyl-1,3,2-dioxaboran-2yl)pyridine.

$^1$H NMR (Chloroform-d, 600 MHz) δ 8.24 (dd, J=7.4, 2.0 Hz, 1H), 8.12-8.16 (m, 2H), 7.59 (ddd, J=7.3, 1.9, 0.9 Hz, 1H), 7.14 (s, 1H), 6.99 (dd, J=7.4, 4.9 Hz, 1H), 6.89 (dd, J=7.2, 5.0 Hz, 1H), 5.10 (t, J=5.8 Hz, 1H), 4.87 (hept, J=6.6 Hz, 1H), 4.50 (d, J=5.7 Hz, 2H), 4.38 (s, 2H), 4.03 (s, 3H), 2.64 (s, 3H), 1.63 (d, J=6.5 Hz, 6H). LC-MS (m/z) 436.6 (MH+); t_R=0.6 minutes (Method D).

Example 183: 1-isopropyl-N-((2-methoxypyridin-3-yl)methyl)-3-methyl-5-(2-(trifluoromethyl)pyridin-3-yl)-1H-pyrazolo[4,3-b]pyridin-7-amine

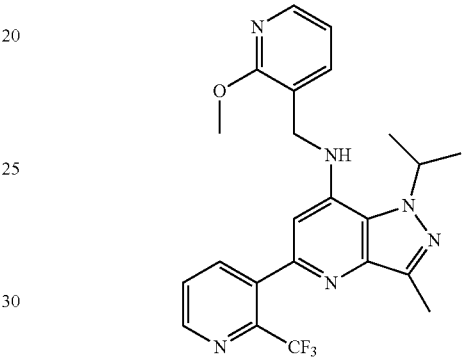

Prepared using the same procedure as described for example 1 from 5-bromo-1-isopropyl-N-((2-methoxypyridin-3-yl)methyl)-3-methyl-1H-pyrazolo[4,3-b]pyridin-7-amine and (2-(trifluoromethyl)pyridin-3-yl)boronic acid.

$^1$H NMR (Chloroform-d, 600 MHz) δ 8.73 (dd, J=4.7, 1.6 Hz, 1H), 8.13 (dd, J=5.1, 1.9 Hz, 1H), 7.94 (dd, J=7.9, 1.6 Hz, 1H), 7.57-7.52 (m, 2H), 6.89 (dd, J=7.2, 5.1 Hz, 1H), 6.49 (s, 1H), 5.29 (t, J=5.8 Hz, 1H), 4.87 (hept, J=6.6 Hz, 1H), 4.45 (d, J=5.8 Hz, 2H), 4.01 (s, 3H), 2.61 (s, 3H), 1.66 (d, J=6.5 Hz, 6H). LC-MS (m/z) 457.5 (MH+); t_R=0.56 minutes (Method D).

Example 184: 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine

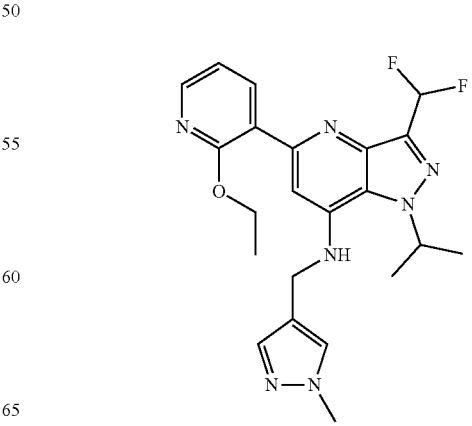

A solution of 7-chloro-3-(difluoromethyl)-5-(2-ethoxy-pyridin-3-yl)-1-isopropyl-1H-pyrazolo[4,3-b]pyridine (3.0 mg, 6.5 μmol), (1-methyl-1H-pyrazol-4-yl)methanamine (29.0 mg, 0.26 mmol) in NMP (0.22 ml) in a sealed vial was inserted in an oil bath at 155° C. and stirred for 16 hours The mixture was partitioned between ethyl acetate (20 ml) and water (2×15 ml). The organic layer was washed with brine (10 ml), dried (Na$_2$SO$_4$) and concentrated. Flash chromatography on silica gel (elution gradient from heptane to ethyl acetate) delivered 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine.

$^1$H NMR (Chloroform-d, 600 MHz) δ 8.33 (dd, J=7.4, 2.0 Hz, 1H), 8.18 (dd, J=4.9, 2.0 Hz, 1H), 7.57 (s, 1H), 7.44 (s, 1H), 7.35 (s, 1H), 7.16 (t, J=54.1 Hz, 1H), 7.03 (dd, J=7.4, 4.9 Hz, 1H), 4.82 (hept, J=6.5 Hz, 1H), 4.57 (t, J=5.0 Hz, 1H), 4.47 (q, J=7.0 Hz, 2H), 4.40 (d, J=4.8 Hz, 2H), 3.93 (s, 3H), 1.64 (d, J=6.5 Hz, 6H), 1.39 (t, J=7.0 Hz, 3H). LC-MS (m/z) 442.6 (MH$^+$); t$_R$=0.55 minutes (Method D).

Example 185: 1-isopropyl-3-methyl-N-((1-methyl-1H-pyrazol-4-yl)methyl)-5-(1H-1,2,4-triazol-1-yl)-1H-pyrazolo[4,3-b]pyridin-7-amine

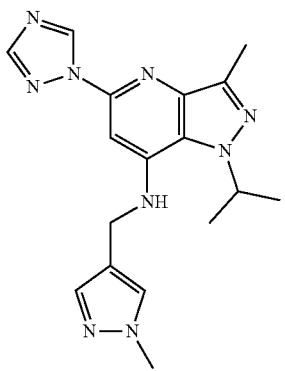 [SMILES: Cc1nn(C(C)C)c2c(NCc3cnn(C)c3)cc(-n3cncn3)nc12]

A mixture of 5-bromo-1-isopropyl-3-methyl-N-((1-methyl-1H-pyrazol-4-yl)methyl)-1H-pyrazolo[4,3-b]pyridin-7-amine (50 mg, 0.14 mmol), 1H-1,2,4-triazole (19 mg, 0.28 mmol), Cs$_2$CO$_3$ (135 mg, 0.41 mmol) N$_1$,N$_2$-dimethylethane-1,2-diamine (2 mg, 0.028 mmol), iodocopper; tetrabutylammonium; diiodide (30 mg, 0.027 mmol) in dimethylacetamide (2 mL) was stirred at 110° C. for 16 hours in a glove box. After a filtration, the filtrate was concentrated and purified by preparative HPLC to give 1-isopropyl-3-methyl-N-((1-methyl-1H-pyrazol-4-yl)methyl)-5-(1H-1,2,4-triazol-1-yl)-1H-pyrazolo[4,3-b]pyridin-7-amine.

$^1$H NMR (Chloroform-d, 400 MHz): δ 9.24 (s, 1H), 8.08 (s, 1H), 7.58 (s, 1H), 7.47 (s, 1H), 7.13 (s, 1H), 4.76-4.73 (m, 1H), 4.73-4.64 (m, 1H), 4.45 (d, J=4.8 Hz, 2H), 3.95 (s, 3H), 2.59 (s, 3H), 1.59 (d, J=6.4 Hz, 6H). LC-MS: t$_R$=1.88 min (Method B), m/z=352.1 [M+H]$^+$.

Example 186: 3-[1-isopropyl-3-methyl-7-[(1-methyl-1,2,4-triazol-3-yl)methylamino]pyrazolo[4,3-b]pyridin-5-yl]-1H-pyridin-2-one

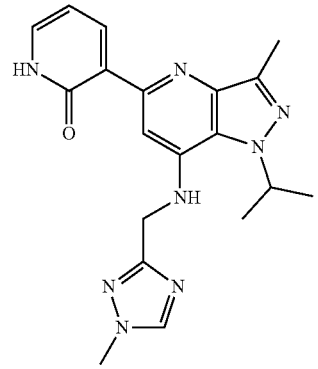 [SMILES: Cc1nn(C(C)C)c2c(NCc3ncn(C)n3)cc(-c3ccc[nH]c3=O)nc12]

Prepared using the same procedure as described for example 29 from 3-(7-amino-1-isopropyl-3-methyl-1H-pyrazolo[4,3-b]pyridin-5-yl)pyridin-2(1H)-one and 1-methyl-1H-1,2,4-triazole-3-carbaldehyde.

$^1$H NMR (Chloroform-d, 400 MHz): δ 8.24-8.22 (m, 1H), 8.05 (s, 1H), 8.02-7.98 (m, 1H), 7.21 (s, 1H), 6.79-6.74 (m, 1H), 6.00-5.94 (m, 1H), 5.03-4.97 (m, 1H), 4.70 (d, J=4.4 Hz, 2H), 3.95 (s, 3H), 2.62 (s, 3H), 1.65 (d, J=6.8 Hz, 6H). LC-MS (m/z) 379.1 (MH$^+$); t$_R$=1.56 minutes (Method B).

Example 187: 3-[1-isopropyl-3-methyl-7-(1H-pyrazol-3-ylmethylamino)pyrazolo[4,3-b]pyridin-5-yl]-1H-pyridin-2-one

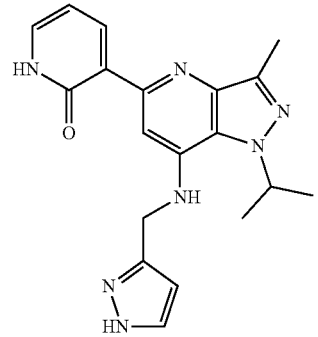 [SMILES: Cc1nn(C(C)C)c2c(NCc3cc[nH]n3)cc(-c3ccc[nH]c3=O)nc12]

Prepared using the same procedure as described for example 29 from 3-(7-amino-1-isopropyl-3-methyl-1H-pyrazolo[4,3-b]pyridin-5-yl)pyridin-2(1H)-one and 1H-pyrazole-3-carbaldehyde.

$^1$H NMR (DMSO-d$_6$, 400 MHz): δ 12.63 (brs, 1H), 11.73 (brs, 1H), 8.30-8.28 (m, 1H), 7.82-7.47 (m, 3H), 6.62-6.51 (m, 1H), 6.32-6.21 (m, 2H), 5.16-5.13 (m, 1H), 4.57-4.39 (m, 2H), 2.46 (s, 3H), 1.43 (d, J=6.4 Hz, 6H). LC-MS (m/z) 364 (MH$^+$); t$_R$=1.79 minutes (Method C).

Example 188: 5-[2-(difluoromethoxy)-3-pyridyl]-1-isopropyl-N-[(2-methoxy-3-pyridyl)methyl]-3-methyl-pyrazolo[4,3-b]pyridin-7-amine

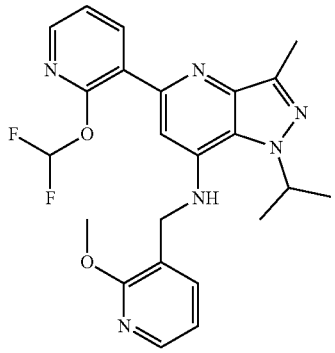 [SMILES: COc1ncccc1CNc1cc(-c2cccnc2OC(F)F)nc2c(C)nn(C(C)C)c12]

Prepared using the same procedure as described for example 1 from 5,7-dibromo-1-isopropyl-3-methyl-1H-pyrazolo[4,3-b]pyridine, (2-methoxypyridin-3-yl)methanamine and (2-(difluoromethoxy)pyridin-3-yl)boronic acid. $^1$H NMR (Chloroform-d, 600 MHz) δ 8.38 (dd, J=7.5, 2.0 Hz, 1H), 8.19 (dd, J=4.8, 2.0 Hz, 1H), 8.12 (dd, J=5.1, 1.9 Hz, 1H), 7.64 (dd, J=7.2, 1.7 Hz, 1H), 7.60 (t, J=73.1 Hz, 1H), 7.24 (dd, J=7.5, 4.8 Hz, 1H), 7.05 (s, 1H), 6.90 (dd, J=7.2, 5.0 Hz, 1H), 5.27 (t, J=6.0 Hz, 1H), 4.87 (hept, J=6.5 Hz, 1H), 4.51 (d, J=5.9 Hz, 2H), 4.03 (s, 3H), 2.62 (s, 3H), 1.64 (d, J=6.6 Hz, 6H). LC-MS (m/z) 455.6 (MH$^+$); $t_R$=0.57 minutes (Method D).

Example 189: 5-(2-ethoxy-3-pyridyl)-1-isopropyl-N-[(4-methoxypyrimidin-2-yl)methyl]-3-methyl-pyrazolo[4,3-b]pyridin-7-amine

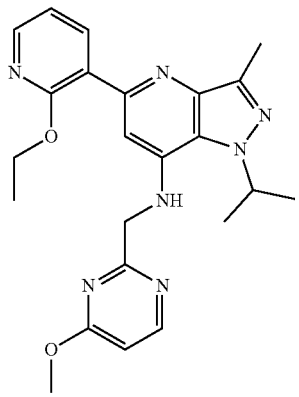 [SMILES: CCOc1ncccc1-c1cc(NCc2nccc(OC)n2)c2c(n1)c(C)nn2C(C)C]

Prepared using the same procedure as described for example 1 from 5,7-dichloro-1-isopropyl-3-methyl-1H-pyrazolo[4,3-b]pyridine, (4-methoxypyrimidin-2-yl)methanamine and (2-ethoxy-3-pyridyl)boronic acid.

$^1$H NMR (Chloroform-d, 400 MHz): δ 8.47 (d, J=5.6 Hz, 1H), 8.26 (dd, J=2.0, 7.6 Hz, 1H), 8.19 (dd, J=2.0, 4.8 Hz, 1H), 7.17 (s, 1H), 7.03 (dd, J=4.8, 7.2 Hz, 1H), 6.71 (d, J=6.0 Hz, 1H), 6.35 (brs, 1H), 5.16-5.10 (m, 1H), 4.62 (d, J=4.4 Hz, 2H), 4.50 (q, J=6.8 Hz, 2H), 4.04 (s, 3H), 2.67 (s, 3H), 1.69 (d, J=6.4 Hz, 6H), 1.46 (t, J=6.8 Hz, 3H) LC-MS (m/z) 434.2 (MH$^+$); $t_R$=1.75 minutes (Method A).

Example 190: 5-(2-ethoxy-3-pyridyl)-1-isopropyl-N-[(4-methoxypyrimidin-5-yl)methyl]-3-methyl-pyrazolo[4,3-b]pyridin-7-amine

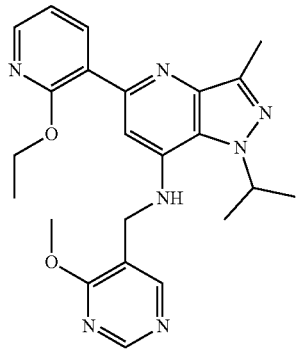 [SMILES: CCOc1ncccc1-c1cc(NCc2cncnc2OC)c2c(n1)c(C)nn2C(C)C]

Prepared using the same procedure as described for example 165 from 5-(2-ethoxypyridin-3-yl)-1-isopropyl-N-(4-methoxybenzyl)-3-methyl-1H-pyrazolo[4,3-b]pyridin-7-amine and 5-(bromomethyl)-4-methoxypyrimidine.

$^1$H NMR (Chloroform-d, 400 MHz): δ 8.77 (s, 1H), 8.49 (s, 1H), 8.24 (dd, J=2.0, 7.2 Hz, 1H), 8.17 (dd, J=2.0, 4.8 Hz, 1H), 7.16 (s, 1H), 7.02 (dd, J=4.8, 7.2 Hz, 1H), 4.97-4.94 (m, 1H), 4.88-4.84 (m, 1H), 4.52 (d, J=5.6 Hz, 2H), 4.44 (q, J=7.2 Hz, 2H), 4.09 (s, 3H), 2.65 (s, 3H), 1.64 (d, J=6.8 Hz, 6H), 1.34 (t, J=6.8 Hz, 3H). LC-MS (m/z) 434.1 (MH$^+$); $t_R$=1.57 minutes (Method A).

Example 191: 5-(2-ethoxy-3-pyridyl)-N-[(2-ethoxy-3-pyridyl)methyl]-1-isopropyl-3-methyl-pyrazolo[4,3-b]pyridin-7-amine

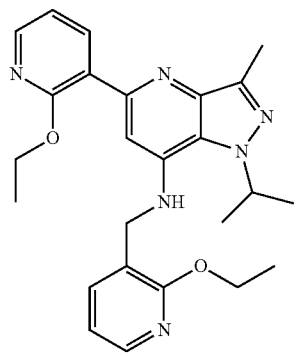 [SMILES: CCOc1ncccc1CNc1cc(-c2cccnc2OCC)nc2c(C)nn(C(C)C)c12]

Prepared using the same procedure as described for example 1 from 5,7-dichloro-1-isopropyl-3-methyl-1H-pyrazolo[4,3-b]pyridine, (2-ethoxypyridin-3-yl)methanamine and (2-ethoxy-3-pyridyl)boronic acid.

$^1$H NMR (Chloroform-d, 400 MHz): δ 8.26-8.24 (m, 1H), 8.17-8.16 (m, 1H), 8.12-8.11 (m, 1H), 7.60-7.59 (m, 1H), 7.17 (s, 1H), 7.03-7.00 (m, 1H), 6.88-6.87 (m, 1H), 5.08 (brs, 1H), 4.89-4.86 (m, 1H), 4.53-4.45 (m, 4H), 4.41 (q, J=6.8 Hz, 2H), 2.65 (s, 3H), 1.64 (d, J=6.4 Hz, 6H), 1.43 (t, J=7.2 Hz, 3H), 1.32 (t, J=7.2 Hz, 3H). LC-MS (m/z) 447.2 (MH$^+$); $t_R$=1.9 minutes (Method A).

Example 192: 5-[2-(dimethylamino)-3-pyridyl]-1-isopropyl-N-[(4-methoxyphenyl)methyl]-3-methyl-pyrazolo[4,3-b]pyridin-7-amine

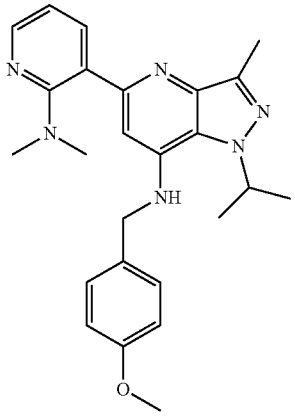 [SMILES: COc1ccc(CNc2cc(-c3cccnc3N(C)C)nc3c(C)nn(C(C)C)c23)cc1]

To a solution of NaH (183 mg, 4.59 mmol, 60% w/w) in THF (4 mL) was added 5-(2-fluoropyridin-3-yl)-1-isopropyl-N-(4-methoxybenzyl)-3-methyl-1H-pyrazolo[4,3-b]pyridin-7-amine (310 mg, 0.77 mmol) at 0° C. Dimethylamine hydrochloride (156 mg, 1.91 mmol) was added and the resulting mixture was stirred at 70° C. for 16 hours. Water (3 mL) was added and the mixture was poured into a saturated, aqueous solution of NaHCO$_3$. The mixture was extracted with ethyl acetate (20 mL×3). The combined organic layers were washed with brine (20 mL), dried over Na$_2$SO$_4$ and concentrated. The crude mixture was purified by flash chromatography with heptane:ethyl acetate=1:0 to 0:1 to give 5-(2-(dimethylamino)pyridin-3-yl)-1-isopropyl-N-(4-methoxybenzyl)-3-methyl-1H-pyrazolo[4,3-b]pyridin-7-amine $^1$H NMR (Chloroform-d, 600 MHz) δ 8.19 (dd, J=4.8, 1.9 Hz, 1H), 7.82 (dd, J=7.4, 1.9 Hz, 1H), 7.32 (d, J=8.6 Hz, 2H), 6.93 (d, J=8.7 Hz, 2H), 6.82 (dd, J=7.4, 4.8 Hz, 1H), 6.79 (s, 1H), 4.87-4.83 (m, 1H), 4.83-4.79 (m, 1H), 4.42 (d, J=5.1 Hz, 2H), 3.83 (s, 3H), 2.64 (s, 3H), 2.61 (s, 6H), 1.64 (d, J=6.6 Hz, 6H). LC-MS (m/z) 431.2 (MH$^+$); t$_R$=0.42 minutes (Method D).

Example 193: 3-[1-isopropyl-3-methyl-7-[[2-(trifluoromethyl)-3-pyridyl]methylamino]pyrazolo[4,3-b]pyridin-5-yl]-1H-pyridin-2-one

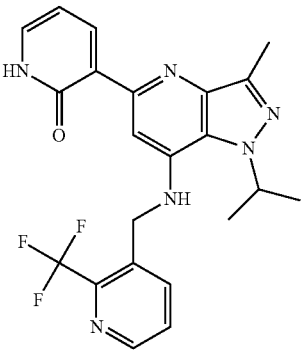 [SMILES: Cc1nn(C(C)C)c2c(NCc3cccnc3C(F)(F)F)cc(-c3ccc[nH]c3=O)nc12]

Prepared using the same procedure as described for example 1 from 5,7-dichloro-1-isopropyl-3-methyl-1H-pyrazolo[4,3-b]pyridine, (2-(trifluoromethyl)pyridin-3-yl)methanamine and (2-oxo-1,2-dihydropyridin-3-yl)boronic acid.

$^1$H NMR (Chloroform-d, 400 MHz): δ 8.64 (d, J=4.4 Hz, 1H), 8.08 (d, J=8.0 Hz, 2H), 7.69 (m, 1H), 7.50-7.47 (m, 1H), 7.07 (m, 1H), 6.59-6.56 (m, 1H), 6.06 (brs, 1H), 5.08 (m, 1H), 4.91 (s, 2H), 2.58 (s, 3H), 1.63 (d, J=6.4 Hz, 6H). LC-MS (m/z) 443 (MH$^+$); t$_R$=1.87 minutes (Method C).

Example 194: 1-isopropyl-3-methyl-5-(3-methylisoxazol-4-yl)-N-[(1-methylpyrazol-4-yl)methyl]pyrazolo[4,3-b]pyridin-7-amine

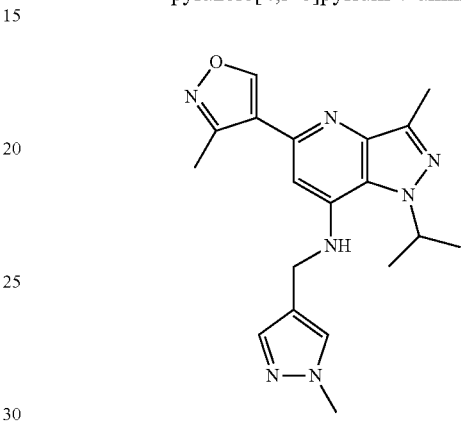

Prepared using the same procedure as described for example 1 from 5-bromo-1-isopropyl-3-methyl-N-((1-methyl-1H-pyrazol-4-yl)methyl)-1H-pyrazolo[4,3-b]pyridin-7-amine and 3-methyl-4-(4,4,5,5-tetramethyl-1,3,2-dioxaborolan-2-yl)isoxazole.

$^1$H NMR (Chloroform-d, 400 MHz): δ=8.67 (s, 1H), 7.56 (s, 1H), 7.43 (s, 1H), 6.54 (s, 1H), 4.79-4.66 (m, 1H), 4.60 (brs, 1H), 4.38 (d, J=4.8 Hz, 2H), 3.94 (s, 3H), 2.61 (s, 6H), 1.59 (d, J=6.4 Hz, 6H). LC-MS (m/z) 366.1 (MH$^+$); t$_R$=1.61 minutes (Method C).

Example 195: 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine

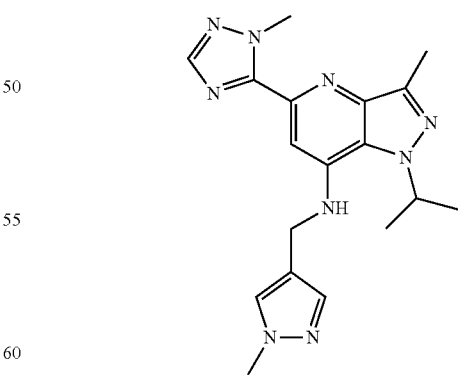

A mixture of 5-bromo-1-isopropyl-3-methyl-N-((1-methyl-1H-pyrazol-4-yl)methyl)-1H-pyrazolo[4,3-b]pyridin-7-amine (0.15 g, 0.41 mmol), 1-methyl-1H-1,2,4-triazole (103 mg, 1.24 mmol), Pd(OAc)$_2$ (5 mg, 0.021 mmol), Ru-Phos (2-dicyclohexylphosphino-2',6'-diisopropoxybiphenyl) (19 mg, 0.041 mmol), K₂CO₃ (171 mg, 1.24 mmol) and 2,2-dimethylpropanoic acid (21 mg, 0.21 mmol) in xylene (15 mL) was stirred at 140° C. for 12 hours under N₂. The mixture was concentrated under vacuum. The residue was purified by preparative TLC (SiO₂, ethyl acetate/MeOH=10:1) and preparative HPLC to afford 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine.

¹H NMR (Chloroform-d; 400 MHz): δ 7.92 (s, 1H), 7.57 (s, 1H), 7.46 (s, 1H), 7.42 (s, 1H), 4.76-4.70 (m, 1H), 4.59-4.56 (m, 1H), 4.47 (s, 3H), 4.44 (d, J=4.4 Hz, 2H), 3.93 (s, 3H), 2.62 (s, 3H), 1.59 (d, J=6.4 Hz, 6H). LC-MS (m/z) 366.1 (MH⁺); $t_R$=1.72 minutes (Method C).

Example 196: 1-isopropyl-3-methyl-5-(2-propoxy-3-pyridyl)-N-(1H-pyrazol-4-ylmethyl)pyrazolo[4,3-b]pyridin-7-amine

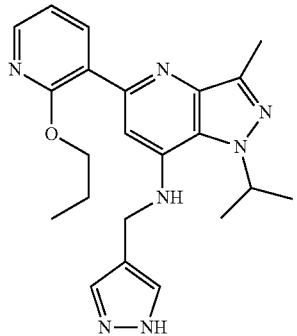 [SMILES: CCCOc1ncccc1-c1cc(NCc2cn[nH]c2)c2c(n1)c(C)nn2C(C)C]

Prepared using the same procedure as described for example 29 from 1-isopropyl-3-methyl-5-(2-propoxypyridin-3-yl)-1H-pyrazolo[4,3-b]pyridin-7-amine and 1-trityl-1H-pyrazole-4-carbaldehyde.

¹H NMR (DMSO-d₆, 400 MHz): δ8.27 (dd, J=7.2, 2.0 Hz, 1H), 8.18 (dd, J=4.8, 2.0 Hz, 1H), 7.70 (s, 2H), 7.24 (s, 1H), 7.03 (dd, J=7.6, 5.2 Hz, 1H), 4.82-4.72 (m, 1H), 4.52 (brs, 1H), 4.45 (d, J=4.8 Hz, 2H), 4.37 (t, J=6.4 Hz, 2H), 2.65 (s, 3H), 1.86-1.77 (m, 2H), 1.6 (d, J=6.4 Hz, 6H), 1.04 (t, J=7.6 Hz, 3H). LC-MS (m/z) 406.1 (MH⁺); $t_R$=1.66 minutes (Method A).

Example 197: 5-(2-ethoxy-3-pyridyl)-N-[(2-methoxy-3-pyridyl)methyl]-3-methyl-1-(oxetan-3-yl)pyrazolo[4,3-b]pyridin-7-amine

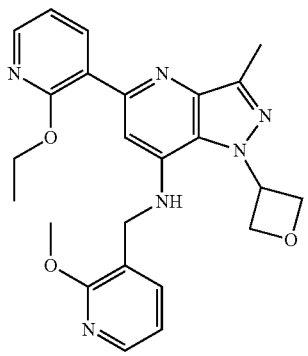 [SMILES: CCOc1ncccc1-c1cc(NCc2cccnc2OC)c2c(n1)c(C)nn2C1COC1]

Prepared using the same procedure as described for example 1 from 5,7-dibromo-3-methyl-1-(oxetan-3-yl)pyra-zolo[4,3-b]pyridine, (2-methoxy-3-pyridyl)methanamine and (2-ethoxy-3-pyridyl)boronic acid.

¹H NMR (Chloroform-d, 400 MHz): δ 8.27 (dd, J=2.0, 7.6 Hz, 1H), 8.19-8.16 (m, 1H), 8.15-8.12 (m, 1H), 7.59 (d, J=6.4 Hz 1H), 7.23 (s, 1H), 7.04-7.01 (m, 1H), 6.91-6.88 (m, 1H), 6.15 (brs, 1H), 5.90-5.86 (m, 1H), 5.26-5.22 (m, 2H), 5.18-5.15 (m, 2H), 4.53 (d, J=5.6 Hz, 2H), 4.42 (q, J=6.8 Hz, 2H) 4.03 (s, 3H), 2.64 (s, 3H), 1.32 (t, J=6.8 Hz, 3H). LC-MS (m/z) 447 (MH⁺); $t_R$=1.89 minutes (Method C).

Example 198: 5-(2-(ethyl(methyl)amino)pyridin-3-yl)-1-isopropyl-N-(4-methoxybenzyl)-3-methyl-1H-pyrazolo[4,3-b]pyridin-7-amine

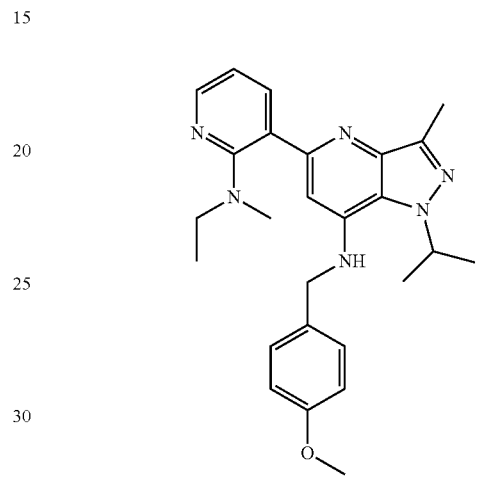

Prepared using the same procedure as described for example 192 from 5-(2-fluoropyridin-3-yl)-1-isopropyl-N-(4-methoxybenzyl)-3-methyl-1H-pyrazolo[4,3-b]pyridin-7-amine and methylethanamine.

¹H NMR (Chloroform-d, 600 MHz) δ 8.20 (dd, J=4.8, 1.9 Hz, 1H), 7.80 (dd, J=7.4, 1.9 Hz, 1H), 7.32 (d, J=8.7 Hz, 2H), 6.93 (d, J=8.6 Hz, 2H), 6.84-6.80 (m, 2H), 4.79 (hept, J=6.6 Hz, 1H), 4.72 (t, J=5.2 Hz, 1H), 4.40 (d, J=5.1 Hz, 2H), 3.83 (s, 3H), 3.08 (q, J=7.0 Hz, 2H), 2.65 (s, 3H), 2.64 (s, 3H), 1.62 (d, J=6.5 Hz, 6H), 0.93 (t, J=7.0 Hz, 3H). LC-MS (m/z) 445.6 (MH⁺); $t_R$=0.53 minutes (Method D).

Example 199: 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine

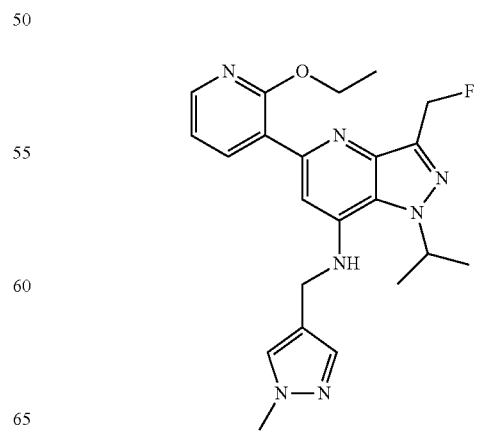

A solution of 7-chloro-5-(2-ethoxypyridin-3-yl)-3-(fluoromethyl)-1-isopropyl-1H-pyrazolo[4,3-b]pyridine (2.0 mg, 5.7 μmol), (1-methyl-1H-pyrazol-4-yl)methanamine (30.0 mg, 0.27 mmol) in NMP (0.2 ml) in a sealed vial was inserted in an oil bath at 155° C. After 20 hours (1-methyl-1H-pyrazol-4-yl)methanamine (30.0 mg, 0.27 mmol) was added and the solution was heated at 155° C. for 15 hours. The mixture was partitioned between ethyl acetate (25 ml) and water (3×20 ml). The organic layer was washed with brine (25 ml), dried (Na$_2$SO$_4$) and concentrated. The residue was purified by flash chromatography on silica gel (heptane/ethyl acetate) to give 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine.

$^1$H NMR (DMSO-d$_6$, 600 MHz) δ 8.21-8.15 (m, 2H), 7.61 (s, 1H), 7.42 (s, 1H), 7.14 (s, 1H), 7.10 (dd, J=7.4, 4.9 Hz, 1H), 6.84 (t, J=5.6 Hz, 1H), 5.67 (d, J=49.2 Hz, 2H), 5.28 (hept, J=6.4 Hz, 1H), 4.41-4.33 (m, 4H), 3.77 (s, 3H), 1.51 (d, J=6.5 Hz, 6H), 1.24 (t, J=6.9 Hz, 3H). LC-MS (m/z) 424.6 (MH$^+$); t$_R$=0.5 minutes (Method D).

Example 200: 1-isopropyl-3-methyl-N-((1-methyl-1H-pyrazol-4-yl)methyl)-5-(4-methyloxazol-5-yl)-1H-pyrazolo[4,3-b]pyridin-7-amine

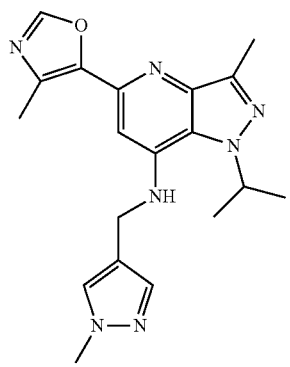 [SMILES: Cc1ncoc1-c1cc(NCc2cnn(C)c2)c2c(n1)c(C)nn2C(C)C]

A mixture of 5-bromo-1-isopropyl-3-methyl-N-((1-methyl-1H-pyrazol-4-yl)methyl)-1H-pyrazolo[4,3-b]pyridin-7-amine (0.15 g, 0.41 mmol), 4-methyloxazole (103 mg, 1.2 mmol), Pd(OAc)$_2$ (5 mg, 0.021 mmol), Ru-Phos (19 mg, 0.041 mmol), K$_2$CO$_3$ (171 mg, 1.2 mmol) and 2,2-dimethylpropanoic acid (17 mg, 0.17 mmol) in toluene (15 mL) was stirred at 110° C. for 12 hours. The mixture was concentrated under vacuum. The residue was purified by preparative TLC (SiO$_2$, petroleum ether/ethyl acetate=0:1) and preparative HPLC to afford 1-isopropyl-3-methyl-N-((1-methyl-1H-pyrazol-4-yl)methyl)-5-(4-methyloxazol-5-yl)-1H-pyrazolo[4,3-b]pyridin-7-amine.

$^1$H NMR (Chloroform-d; 400 MHz): δ 7.85 (s, 1H), 7.58 (s, 1H), 7.45 (s, 1H), 6.84 (s, 1H), 4.78-4.72 (m, 2H), 4.43 (d, J=4.4 Hz, 2H), 3.94 (s, 3H), 2.68 (s, 3H), 2.62 (s, 3H), 1.58 (d, J=6.4 Hz, 6H). LC-MS (m/z) 366 (MH$^+$); t$_R$=1.6 minutes (Method C).

Example 201: 5-[2-(dimethylamino)-3-pyridyl]-1-isopropyl-3-methyl-N-[(1-methylpyrazol-4-yl)methyl]pyrazolo[4,3-b]pyridin-7-amine

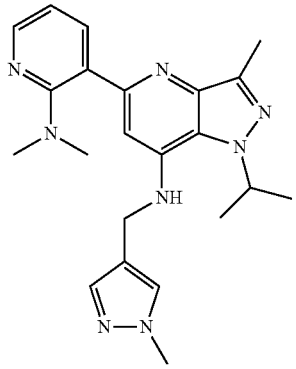 [SMILES: Cc1nn(C(C)C)c2c(NCc3cnn(C)c3)cc(-c3cccnc3N(C)C)nc12]

Prepared using the same procedure as described for example 29 from 5-(2-(dimethylamino)pyridin-3-yl)-1-isopropyl-3-methyl-1H-pyrazolo[4,3-b]pyridin-7-amine and 1-methyl-1H-pyrazole-4-carbaldehyde. $^1$H NMR (Chloroform-d, 600 MHz) δ 8.22 (dd, J=4.8, 1.9 Hz, 1H), 7.83 (dd, J=7.3, 1.9 Hz, 1H), 7.54 (s, 1H), 7.40 (s, 1H), 6.87-6.82 (m, 2H), 4.77 (hept, J=6.6 Hz, 1H), 4.58 (t, J=4.7 Hz, 1H), 4.33 (d, J=5.0 Hz, 2H), 3.93 (s, 3H), 2.73 (s, 6H), 2.64 (s, 3H), 1.61 (d, J=6.6 Hz, 6H).

LC-MS (m/z) 405.6 (MH$^+$); t$_R$=0.34 minutes (Method D).

Example 202: 1-isopropyl-3-methyl-N-((1-methyl-1H-pyrazol-4-yl)methyl)-5-(4-methyloxazol-2-yl)-1H-pyrazolo[4,3-b]pyridin-7-amine

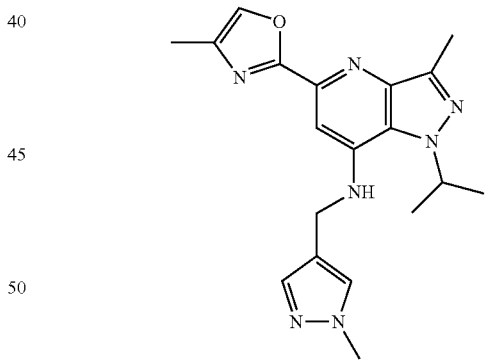

A mixture of 5-bromo-1-isopropyl-3-methyl-N-((1-methyl-1H-pyrazol-4-yl)methyl)-1H-pyrazolo[4,3-b]pyridin-7-amine (100 mg, 0.28 mmol), 4-methyloxazole (46 mg, 0.55 mmol), XPHOS-Pd-G3 ((2-dicyclohexylphosphino-2',4',6'-triisopropyl-1,1'-biphenyl)[2-(2'-amino-1,1'-biphenyl)]palladium(II) methanesulfonate) (12 mg, 0.014 mmol), t-BuOK (93 mg, 0.83 mmol) in dimethylacetamide (5 mL) was stirred at 100° C. for 12 hours under N$_2$. The mixture was concentrated under vacuum. The residue was purified by preparative TLC (SiO$_2$, Petroleum ether/ethyl acetate=0:1) and preparative HPLC to afford 1-isopropyl-3-methyl-N-((1-methyl-1H-pyrazol-4-yl)methyl)-5-(4-methyloxazol-2-yl)-1H-pyrazolo[4,3-b]pyridin-7-amine.

¹H NMR (Chloroform-d; 400 MHz): δ 7.58 (s, 1H), 7.53 (s, 1H), 7.45 (s, 1H), 7.34 (s, 1H), 4.77-4.67 (m, 1H), 4.58 (brs, 1H), 4.44 (d, J=4.8 Hz, 2H), 3.94 (s, 3H), 2.68 (s, 3H), 2.29 (s, 3H), 1.58 (d, J=6.8 Hz, 6H). LC-MS (m/z) 366.1 (MH$^+$); $t_R$=1.74 minutes (Method C).

Example 203: 1-isopropyl-3-methyl-N-[(1-methyl-pyrazol-4-yl)methyl]-5-(4-methyl-1,2,4-triazol-3-yl)pyrazolo[4,3-b]pyridin-7-amine

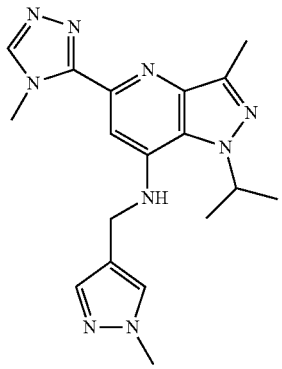 [SMILES: Cc1nn(C(C)C)c2c(NCc3cnn(C)c3)cc(-c3nncn3C)nc12]

Prepared using the same procedure as described for example 195 from 5-bromo-1-isopropyl-3-methyl-N-((1-methyl-1H-pyrazol-4-yl)methyl)-1H-pyrazolo[4,3-b]pyridin-7-amine and 4-methyl-4H-1,2,4-triazole.

¹H NMR (CDCl₃ 400 MHz): δ 8.18 (s, 1H), 7.56 (s, 1H), 7.55 (s, 1H), 7.48 (s, 1H), 4.78-4.71 (m, 1H), 4.60 (brs, 1H), 4.44 (d, J=4.4 Hz, 2H), 4.23 (s, 3H), 3.93 (s, 3H), 2.60 (s, 3H), 1.59 (d, J=6.4 Hz, 6H). LC-MS (m/z) 366.1 (MH$^+$); $t_R$=1.65 minutes (Method B).

In Vitro Testing
PDE1 Inhibition Assay

PDE1A, PDE1B and PDE1C assays were performed as follows: the assays was performed in 60 μL samples containing a fixed amount of the PDE1 enzyme (sufficient to convert 20-25% of the cyclic nucleotide substrate), a buffer (50 mM HEPES pH 7.6; 10 mM MgCl₂; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 hr at room temperature before being terminated through mixing with 20 μL (0.2 mg) yttrium silicate SPA beads (PerkinElmer). The beads were allowed to settle for 1 hr in the dark before the plates were counted in a Wallac 1450 Microbeta counter. The measured signals were converted to activity relative to an uninhibited control (100%) and IC$_{50}$ values were calculated using XIFit (model 205, IDBS).

What is claimed is:
1. A compound according to formula (I):

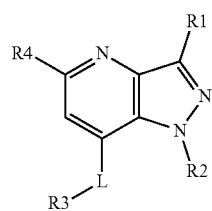

(I)

or a pharmaceutically acceptable salt thereof;

wherein:
L is selected from the group consisting of NH, CH₂, S and O;
R1 is selected from the group consisting of hydrogen, linear or branched C₁-C₅ alkyl, C₁-C₅ fluoroalkyl and saturated monocyclic C₃-C₅ cycloalkyl;
R2 is selected from the group consisting of linear or branched C₁-C₈ alkyl, saturated monocyclic C₃-C₈ cycloalkyl, oxetanyl, tetrahydrofuranyl, and tetrahydropyranyl; all of which can be optionally substituted one or more times with one or more substituents selected from the group consisting of methyl, fluorine, hydroxy, cyano and methoxy;
R3 is methyl substituted with phenyl, pyridonyl, pyridinyl, pyrimidinyl or pyrazinyl all of which can be optionally substituted one or more times with one or more substituents selected from the group consisting of halogen, cyano, C₁-C₃ alkyl, C₁-C₃ fluoroalkyl, C₁-C₃ fluoroalkoxy and C₁-C₃ alkoxy; or
R3 is methyl substituted with a 5-membered heteroaryl which is optionally substituted with one or more substituents selected from halogen, cyano, C₁-C₃ alkyl, C₁-C₃ fluoroalkyl, C₁-C₃ fluoroalkoxy and C₁-C₃ alkoxy; or
R3 is ethyl substituted with phenyl, pyridonyl, pyridinyl, pyrimidinyl or pyrazinyl all of which can be optionally substituted one or more times with one or more substituents selected from the group consisting of halogen, cyano, C₁-C₃ alkyl, C₁-C₃ fluoroalkyl, C₁-C₃ fluoroalkoxy and C₁-C₃ alkoxy; or
R3 is ethyl substituted with a 5-membered heteroaryl which is optionally substituted with one or more substituents selected from halogen, cyano, C₁-C₃ alkyl, C₁-C₃ fluoroalkyl, C₁-C₃ fluoroalkoxy and C₁-C₃ alkoxy; or
L is CH₂ and R3 is NH which is substituted with phenyl, pyridonyl, pyridinyl, pyrimidinyl or pyrazinyl all of which can be optionally substituted one or more times with one or more substituents selected from the group consisting of halogen, cyano, C₁-C₃ alkyl, C₁-C₃ fluoroalkyl, C₁-C₃ fluoroalkoxy and C₁-C₃ alkoxy; or
L is CH₂ and R3 is NH which is substituted with a 5-membered heteroaryl which is optionally substituted with one or more substituents selected from halogen, cyano, C₁-C₃ alkyl, C₁-C₃ fluoroalkyl, C₁-C₃ fluoroalkoxy and C₁-C₃ alkoxy;
and
R4 is phenyl, pyridinyl or pyridonyl all of which can be optionally substituted one or more times with one or more substituents selected from the group consisting of halogen, cyano, C₁-C₄ alkyl, C₁-C₄ fluoroalkyl, C₁-C₄ deutereoalkyl, C₁-C₃ fluoroalkoxy, cyclopropyloxy, C₁-C₃ alkoxy, C₁-C₃ deutereoalkoxy and —N—R5R6 wherein R5 and R6 are each independently selected from H, C₁-C₃ alkyl and C₁-C₃ deutereoalkyl; or
R4 is a 5-membered heteroaryl which is optionally substituted with one or more substituents selected from halogen, cyano, C₁-C₄ alkyl, C₁-C₄ fluoroalkyl, C₁-C₄ deutereoalkyl, C₁-C₃ fluoroalkoxy, cyclopropyloxy, C₁-C₃ alkoxy, C₁-C₃ deutereoalkoxy and —N—R5R6 wherein R5 and R6 are each independently selected from H, C₁-C₃ alkyl and C₁-C₃ deutereoalkyl; or
R4 is a 4, 5 or 6 membered saturated heterocycle all of which can be optionally substituted with one or more substituents selected from oxo, C₁-C₄ alkyl and C₁-C₄ fluoroalkyl.

2. A compound or a pharmaceutically acceptable salt thereof, wherein the compound is selected from the group consisting of:

2: 5-(2-ethoxy-3-pyridyl)-1-isopropyl-3-methyl-N-[(5-methylthiazol-2-yl)methyl]pyrazolo[4,3-b]pyridin-7-amine;
3: 5-(2-ethoxy-3-pyridyl)-1-isopropyl-3-methyl-N-[(5-methylisoxazol-3-yl)methyl]pyrazolo[4,3-b]pyridin-7-amine;
6: 5-(2-ethoxy-3-pyridyl)-1-isopropyl-3-methyl-N-[(1-methyltriazol-4-yl)methyl]pyrazolo[4,3-b]pyridin-7-amine;
8: 5-(2-ethoxy-3-pyridyl)-1-isopropyl-3-methyl-N-[(2-methyltetrazol-5-yl)methyl]pyrazolo[4,3-b]pyridin-7-amine;
9: 5-(2-ethoxypyridin-3-yl)-1-isopropyl-3-methyl-N-((1-methyl-1H-pyrazol-4-yl)methyl)-1H-pyrazolo[4,3-b]pyridin-7-amine;
10: 5-(2-ethoxy-3-pyridyl)-1-isopropyl-3-methyl-N-[(3-methylisoxazol-5-yl)methyl]pyrazolo[4,3-b]pyridin-7-amine;
21: 5-(2-ethoxy-3-pyridyl)-1-isopropyl-N-[(1-methylimidazol-4-yl)methyl]pyrazolo[4,3-b]pyridin-7-amine;
31: 5-(2-ethoxy-3-pyridyl)-1-isopropyl-3-methyl-N-[(1-methyl-1,2,4-triazol-3-yl)methyl]pyrazolo[4,3-b]pyridin-7-amine;
32: 5-(2-ethoxy-3-pyridyl)-1-isopropyl-3-methyl-N-[(2-methylthiazol-5-yl)methyl]pyrazolo[4,3-b]pyridin-7-amine;
33: 5-(2-ethoxy-3-pyridyl)-1-isopropyl-3-methyl-N-[(5-methyl-1,3,4-thiadiazol-2-yl)methyl]pyrazolo[4,3-b]pyridin-7-amine;
37: 5-(2-ethoxy-3-pyridyl)-1-isopropyl-3-methyl-N-[(2-methyloxazol-4-yl)methyl]pyrazolo[4,3-b]pyridin-7-amine;
38: 5-(2-ethoxy-3-pyridyl)-1-isopropyl-3-methyl-N-[(5-methyloxazol-2-yl)methyl]pyrazolo[4,3-b]pyridin-7-amine;
39: 5-(2-ethoxy-3-pyridyl)-1-isopropyl-3-methyl-N-(1H-pyrazol-3-ylmethyl)pyrazolo[4,3-b]pyridin-7-amine;
46: 5-(2-ethoxypyridin-3-yl)-1-isopropyl-3-methyl-N-((2-methyl-1H-imidazol-4-yl)methyl)-1H-pyrazolo[4,3-b]pyridin-7-amine;
47: 5-(2-ethoxypyridin-3-yl)-1-isopropyl-3-methyl-N-((5-methyl-1H-pyrazol-3-yl)methyl)-1H-pyrazolo[4,3-b]pyridin-7-amine;
52: 5-(2-ethoxy-3-pyridyl)-1-isopropyl-3-methyl-N-[(5-methyl-1,2,4-oxadiazol-3-yl)methyl]pyrazolo[4,3-b]pyridin-7-amine;
54: N-[(1,5-dimethylpyrazol-3-yl)methyl]-5-(2-ethoxy-3-pyridyl)-1-isopropyl-3-methyl-pyrazolo[4,3-b]pyridin-7-amine;
58: 5-(2-ethoxypyridin-3-yl)-1-isopropyl-3-methyl-N-((1-methyl-1H-imidazol-4-yl)methyl)-1H-pyrazolo[4,3-b]pyridin-7-amine 2,2,2-trifluoroacetate;
68a: (R)-3-methyl-1-[1-methylpropyl]-N-[(2-methyltetrazol-5-yl)methyl]-5-(2-propoxy-3-pyridyl)pyrazolo[4,3-b]pyridin-7-amine;
68b: (S)-3-methyl-1-[1-methylpropyl]-N-[(2-methyltetrazol-5-yl)methyl]-5-(2-propoxy-3-pyridyl)pyrazolo[4,3-b]pyridin-7-amine;
74: 5-(2-ethoxy-3-pyridyl)-1-isopropyl-3-methyl-N-(pyrimidin-2-ylmethyl)pyrazolo[4,3-b]pyridin-7-amine;
77: 5-(2-ethoxy-3-pyridyl)-1-isopropyl-3-methyl-N-[[2-(trifluoromethyl)-3-pyridyl]methyl]pyrazolo[4,3-b]pyridin-7-amine;
81: 5-(2-ethoxy-3-pyridyl)-1-isopropyl-N-[(4-methoxy-2-pyridyl)methyl]-3-methyl-pyrazolo[4,3-b]pyridin-7-amine;
85: 5-(2-ethoxy-3-pyridyl)-N-[(2-fluoro-3-pyridyl)methyl]-1-isopropyl-3-methyl-pyrazolo[4,3-b]pyridin-7-amine;
86: 5-(2-ethoxy-3-pyridyl)-1-isopropyl-N-[(2-methoxy-3-pyridyl)methyl]-3-methyl-pyrazolo[4,3-b]pyridin-7-amine;
94: 1-isopropyl-3-methyl-N-[(1-methylpyrazol-4-yl)methyl]-5-(2-propoxy-3-pyridyl)pyrazolo[4,3-b]pyridin-7-amine;
99: 5-(2-ethoxy-3-pyridyl)-1-isopropyl-3-methyl-N-(2H-tetrazol-5-ylmethyl)pyrazolo[4,3-b]pyridin-7-amine;
100: 5-(2-ethoxy-3-pyridyl)-1-isopropyl-3-methyl-N-(2-pyridylmethyl)pyrazolo[4,3-b]pyridin-7-amine;
104: 5-(2-ethoxy-3-pyridyl)-1-isopropyl-N-[(2-methoxy-4-pyridyl)methyl]-3-methyl-pyrazolo[4,3-b]pyridin-7-amine;
106: 5-(2-ethoxy-3-pyridyl)-1-isopropyl-N-[(5-methoxy-3-pyridyl)methyl]-3-methyl-pyrazolo[4,3-b]pyridin-7-amine;
108: 3-[[[5-(2-ethoxy-3-pyridyl)-1-isopropyl-3-methyl-pyrazolo[4,3-b]pyridin-7-yl]amino]methyl]-1-methyl-pyridin-2-one;
118: 5-(2-ethoxy-3-pyridyl)-1-isopropyl-N-[(3-methoxy-2-pyridyl)methyl]-3-methyl-pyrazolo[4,3-b]pyridin-7-amine;
120: (R)-5-(2-ethoxy-3-pyridyl)-3-methyl-1-[1-methylpropyl]-N-(1H-pyrazol-3-ylmethyl)pyrazolo[4,3-b]pyridin-7-amine or (S)-5-(2-ethoxy-3-pyridyl)-3-methyl-1-[1-methylpropyl]-N-(1H-pyrazol-3-ylmethyl)pyrazolo[4,3-b]pyridin-7-amine;
121: (R)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine;
122: (R)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine or (S)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine;
125a: (R)-5-(2-ethoxy-3-pyridyl)-N-[(5-methoxy-3-pyridyl)methyl]-3-methyl-1-[1-methylpropyl]pyrazolo[4,3-b]pyridin-7-amine;
125b: (S)-5-(2-ethoxy-3-pyridyl)-N-[(5-methoxy-3-pyridyl)methyl]-3-methyl-1-[1-methylpropyl]pyrazolo[4,3-b]pyridin-7-amine;
127a: (R)-5-(2-ethoxy-3-pyridyl)-3-methyl-1-[1-methylpropyl]-N-[(2-methyltetrazol-5-yl)methyl]pyrazolo[4,3-b]pyridin-7-amine;
127b: (S)-5-(2-ethoxy-3-pyridyl)-3-methyl-1-[1-methylpropyl]-N-[(2-methyltetrazol-5-yl)methyl]pyrazolo[4,3-b]pyridin-7-amine;
128a: (R)-5-(2-ethoxy-3-pyridyl)-3-methyl-N-[(5-methyl-1,2,4-oxadiazol-3-yl)methyl]-1-[1-methylpropyl]pyrazolo[4,3-b]pyridin-7-amine;
128b: (S)-5-(2-ethoxy-3-pyridyl)-3-methyl-N-[(5-methyl-1,2,4-oxadiazol-3-yl)methyl]-1-[1-methylpropyl]pyrazolo[4,3-b]pyridin-7-amine;
131a: (R)-5-(2-ethoxy-3-pyridyl)-3-methyl-1-[1-methylpropyl]-N-[(5-methyl-1H-pyrazol-3-yl)methyl]pyrazolo[4,3-b]pyridin-7-amine;

131b: (S)-5-(2-ethoxy-3-pyridyl)-3-methyl-1-[1-methylpropyl]-N-[(5-methyl-1H-pyrazol-3-yl)methyl]pyrazolo[4,3-b]pyridin-7-amine;

132a: (R)-5-(2-ethoxy-3-pyridyl)-3-methyl-N-[(1-methylimidazol-4-yl)methyl]-1-[1-methylpropyl]pyrazolo[4,3-b]pyridin-7-amine;

132b: (S)-5-(2-ethoxy-3-pyridyl)-3-methyl-N-[(1-methylimidazol-4-yl)methyl]-1-[1-methylpropyl]pyrazolo[4,3-b]pyridin-7-amine;

134a: (R)-3-methyl-1-[1-methylpropyl]-N-[(1-methyl-1,2,4-triazol-3-yl)methyl]-5-(2-propoxy-3-pyridyl)pyrazolo[4,3-b]pyridin-7-amine;

134b: (S)-3-methyl-1-[1-methylpropyl]-N-[(1-methyl-1,2,4-triazol-3-yl)methyl]-5-(2-propoxy-3-pyridyl)pyrazolo[4,3-b]pyridin-7-amine;

135a: (R)-3-methyl-1-[1-methylpropyl]-5-(2-propoxy-3-pyridyl)-N-(1H-pyrazol-3-ylmethyl)pyrazolo[4,3-b]pyridin-7-amine;

135b: (S)-3-methyl-1-[1-methylpropyl]-5-(2-propoxy-3-pyridyl)-N-(1H-pyrazol-3-ylmethyl)pyrazolo[4,3-b]pyridin-7-amine;

142: 1-isopropyl-3-methyl-N-[(1-methylimidazol-4-yl)methyl]-5-(2-propoxy-3-pyridyl)pyrazolo[4,3-b]pyridin-7-amine;

143: 1-isopropyl-3-methyl-5-(2-propoxy-3-pyridyl)-N-(1H-pyrazol-3-ylmethyl)pyrazolo[4,3-b]pyridin-7-amine;

145: 1-isopropyl-3-methyl-N-[(1-methyl-1,2,4-triazol-3-yl)methyl]-5-(2-propoxy-3-pyridyl)pyrazolo[4,3-b]pyridin-7-amine;

166: 5-(2-ethoxy-3-pyridyl)-N-[[5-(fluoromethyl)isoxazol-3-yl]methyl]-1-isopropyl-3-methyl-pyrazolo[4,3-b]pyridin-7-amine;

189: 5-(2-ethoxy-3-pyridyl)-1-isopropyl-N-[(4-methoxypyrimidin-2-yl)methyl]-3-methyl-pyrazolo[4,3-b]pyridin-7-amine.

3. A pharmaceutical composition comprising a therapeutically effective amount of the compound or pharmaceutically acceptable salt thereof of claim 2 and one or more pharmaceutically acceptable carriers, diluents and excipients.

4. The compound or a pharmaceutically acceptable salt thereof according to claim 2, wherein the compound is
5-(2-ethoxy-3-pyridyl)-1-isopropyl-3-methyl-N-[(5-methylthiazol-2-yl)methyl]pyrazolo[4,3-b]pyridin-7-amine.

5. The compound or a pharmaceutically acceptable salt thereof according to claim 2, wherein the compound is
5-(2-ethoxy-3-pyridyl)-1-isopropyl-3-methyl-N-[(5-methylisoxazol-3-yl)methyl]pyrazolo[4,3-b]pyridin-7-amine.

6. The compound or a pharmaceutically acceptable salt thereof according to claim 2, wherein the compound is
5-(2-ethoxy-3-pyridyl)-1-isopropyl-3-methyl-N-[(1-methyl-1,2,4-triazol-3-yl)methyl]pyrazolo[4,3-b]pyridin-7-amine.

7. The compound or a pharmaceutically acceptable salt thereof according to claim 2, wherein the compound is
5-(2-ethoxy-3-pyridyl)-1-isopropyl-3-methyl-N-[(2-methylthiazol-5-yl)methyl]pyrazolo[4,3-b]pyridin-7-amine.

8. The compound or a pharmaceutically acceptable salt thereof according to claim 2, wherein the compound is
5-(2-ethoxypyridin-3-yl)-1-isopropyl-3-methyl-N-((5-methyl-1H-pyrazol-3-yl)methyl)-1H-pyrazolo[4,3-b]pyridin-7-amine.

9. The compound or a pharmaceutically acceptable salt thereof according to claim 2, wherein the compound is
5-(2-ethoxy-3-pyridyl)-1-isopropyl-3-methyl-N-[(5-methyl-1,2,4-oxadiazol-3-yl)methyl]pyrazolo[4,3-b]pyridin-7-amine.

10. The compound or a pharmaceutically acceptable salt thereof according to claim 2, wherein the compound is
N-[(1,5-dimethylpyrazol-3-yl)methyl]-5-(2-ethoxy-3-pyridyl)-1-isopropyl-3-methyl-pyrazolo[4,3-b]pyridin-7-amine.

11. The compound or a pharmaceutically acceptable salt thereof according to claim 2, wherein the compound is
5-(2-ethoxypyridin-3-yl)-1-isopropyl-3-methyl-N-((1-methyl-1H-imidazol-4-yl)methyl)-1H-pyrazolo[4,3-b]pyridin-7-amine 2,2,2-trifluoroacetate.

12. The compound or a pharmaceutically acceptable salt thereof according to claim 2, wherein the compound is
(R)-3-methyl-1-[1-methylpropyl]-N-[(2-methyltetrazol-5-yl)methyl]-5-(2-propoxy-3-pyridyl)pyrazolo[4,3-b]pyridin-7-amine.

13. The compound or a pharmaceutically acceptable salt thereof according to claim 2, wherein the compound is
(S)-3-methyl-1-[1-methylpropyl]-N-[(2-methyltetrazol-5-yl)methyl]-5-(2-propoxy-3-pyridyl)pyrazolo[4,3-b]pyridin-7-amine.

14. The compound or a pharmaceutically acceptable salt thereof according to claim 2, wherein the compound is
1-isopropyl-3-methyl-N-[(1-methylpyrazol-4-yl)methyl]-5-(2-propoxy-3-pyridyl)pyrazolo[4,3-b]pyridin-7-amine.

15. The compound or a pharmaceutically acceptable salt thereof according to claim 2, wherein the compound is
5-(2-ethoxy-3-pyridyl)-1-isopropyl-N-[(2-methoxy-4-pyridyl)methyl]-3-methyl-pyrazolo[4,3-b]pyridin-7-amine.

16. The compound or a pharmaceutically acceptable salt thereof according to claim 2, wherein the compound is
(R)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine.

17. The compound or a pharmaceutically acceptable salt thereof according to claim 2, wherein the compound is
(S)-5-(2-ethoxy-3-pyridyl)-3-methyl-1-[1-methylpropyl]-N-[(1-methyl-1,2,4-triazol-3-yl)methyl]pyrazolo[4,3-b]pyridin-7-amine.

18. The compound or a pharmaceutically acceptable salt thereof according to claim 2, wherein the compound is
(R)-5-(2-ethoxy-3-pyridyl)-3-methyl-1-[1-methylpropyl]-N-[(5-methyl-1H-pyrazol-3-yl)methyl]pyrazolo[4,3-b]pyridin-7-amine.

19. The compound or a pharmaceutically acceptable salt thereof according to claim 2, wherein the compound is
(S)-5-(2-ethoxy-3-pyridyl)-3-methyl-1-[1-methylpropyl]-N-[(5-methyl-1H-pyrazol-3-yl)methyl]pyrazolo[4,3-b]pyridin-7-amine.

20. The compound or a pharmaceutically acceptable salt thereof according to claim 2, wherein the compound is
(R)-5-(2-ethoxy-3-pyridyl)-3-methyl-N-[(1-methylimidazol-4-yl)methyl]-1-[1-methylpropyl]pyrazolo[4,3-b]pyridin-7-amine.

21. The compound or a pharmaceutically acceptable salt thereof according to claim 2, wherein the compound is
(S)-5-(2-ethoxy-3-pyridyl)-3-methyl-N-[(1-methylimidazol-4-yl)methyl]-1-[1-methylpropyl]pyrazolo[4,3-b]pyridin-7-amine.

22. The compound or a pharmaceutically acceptable salt thereof according to claim 2, wherein is (R)-3-methyl-1-[1-methylpropyl]-N-[(1-methyl-1,2,4-triazol-3-yl)methyl]-5-(2-propoxy-3-pyridyl)pyrazolo[4,3-b]pyridin-7-amine.

23. The compound or a pharmaceutically acceptable salt thereof according to claim 2, wherein the compound is
(S)-3-methyl-1-[1-methylpropyl]-N-[(1-methyl-1,2,4-triazol-3-yl)methyl]-5-(2-propoxy-3-pyridyl)pyrazolo[4,3-b]pyridin-7-amine.

24. The compound or a pharmaceutically acceptable salt thereof according to claim 2, wherein the compound is
(R)-3-methyl-1-[1-methylpropyl]-5-(2-propoxy-3-pyridyl)-N-(1H-pyrazol-3-ylmethyl)pyrazolo[4,3-b]pyridin-7-amine.

25. The compound or a pharmaceutically acceptable salt thereof according to claim 2, wherein the compound is
(S)-3-methyl-1-[1-methylpropyl]-5-(2-propoxy-3-pyridyl)-N-(1H-pyrazol-3-ylmethyl)pyrazolo[4,3-b]pyridin-7-amine.

26. The compound or a pharmaceutically acceptable salt thereof according to claim 2, wherein the compound is
1-isopropyl-3-methyl-N-[(1-methylimidazol-4-yl)methyl]-5-(2-propoxy-3-pyridyl)pyrazolo[4,3-b]pyridin-7-amine.

27. The compound or a pharmaceutically acceptable salt thereof according to claim 2, wherein the compound is
1-isopropyl-3-methyl-N-[(1-methyl-1,2,4-triazol-3-yl)methyl]-5-(2-propoxy-3-pyridyl)pyrazolo[4,3-b]pyridin-7-amine.

28. The compound or a pharmaceutically acceptable salt thereof according to claim 2, wherein the compound is
5-(2-ethoxy-3-pyridyl)-N-[[5-(fluoromethyl)isoxazol-3-yl]methyl]-1-isopropyl-3-methyl-pyrazolo[4,3-b]pyridin-7-amine.

\* \* \* \* \*